United States Patent

Korte et al.

Patent Number: 5,877,119
Date of Patent: Mar. 2, 1999

[54] SUBSTITUTED PYRIDINE COMPOUNDS

[75] Inventors: Donald Edwin Korte, St. Louis; Len Fang Lee, St. Charles, both of Mo.

[73] Assignee: Rohm and Haas Company, Philadelphia, Pa.

[21] Appl. No.: 471,784

[22] Filed: Jun. 6, 1995

Related U.S. Application Data

[62] Division of Ser. No. 339,994, Nov. 15, 1994, Pat. No. 5,512,536, which is a division of Ser. No. 45,154, Apr. 12, 1993, Pat. No. 5,391,540, which is a division of Ser. No. 871,525, Apr. 20, 1992, Pat. No. 5,228,897, which is a division of Ser. No. 660,480, Feb. 25, 1991, Pat. No. 5,125,956.

[51] Int. Cl.[6] .................. A01N 43/50; C07D 401/06
[52] U.S. Cl. .................. 504/219; 504/221; 504/225; 504/230; 504/252; 504/253; 544/58.4; 544/124; 544/130; 540/597; 540/598; 546/275.4; 546/272.7; 546/279.1; 546/268.1; 546/270.4; 546/272.1
[58] Field of Search .................. 546/275.4, 272.7, 546/279.1, 193, 268.1, 270.4, 272.1; 540/597, 598; 544/58.4, 130, 124; 504/219, 221, 225, 230, 248, 252, 253

[56] References Cited

U.S. PATENT DOCUMENTS

| | | | |
|---|---|---|---|
| 4,609,399 | 9/1986 | Lee | 546/296 |
| 4,692,184 | 9/1987 | Lee | 544/333 |
| 4,698,093 | 10/1987 | Lee et al. | 546/278 |
| 4,789,395 | 12/1988 | Lee et al. | 546/298 |
| 4,835,279 | 5/1989 | Lee et al. | 546/313 |
| 4,988,384 | 1/1991 | Sing et al. | 546/283 |
| 5,114,465 | 5/1992 | Bryant et al. | 546/261 |

*Primary Examiner*—Jane Fan
*Attorney, Agent, or Firm*—Thomas D. Rogerson

[57] ABSTRACT

Disclosed herein are herbicidal pyridine compounds substituted at the 2- or 6-position with an $OR_2$ moiety where $R_2$ is hydrogen, lower alkyl, halomethyl, lower cyanoalkyl, alkenyl or alkynyl, as well as herbicidal compositions and herbicidal use of these compounds.

12 Claims, No Drawings

SUBSTITUTED PYRIDINE COMPOUNDS

This is a divisional of application Ser. No. 08/339,994, filed Nov. 15, 1994 now U.S. Pat. No. 5,512,536, which is a divisional of U.S. Ser. No. 08/045,154, filed Apr. 12, 1993, now U.S. Pat. No. 5,391,540; which is a divisional of U.S. Ser. No. 07/871,525, filed Apr. 20, 1992, now U.S. Pat. No. 5,228,897; which is a divisional of U.S. Ser. No. 07/660,480, filed Feb. 25, 1991, now U.S. Pat. No. 5,125,956.

This invention relates to a new class of substituted pyridinecarboxylic acid derivatives having a wide range of activity as herbicides.

Pyridine derivatives have, for many years, been investigated for use in biological sciences. For example, 2,6-bis (trifluoromethyl)-4-pyridinols have been found useful as herbicides and fungicides as disclosed in U.S. Pat. No. 3,748,334. Such compounds are characterized by substitution in the 4-position by a hydroxy radical. In addition to the hydroxy radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO patent 44,262 there are disclosed 2,6-dialkyl-3-phenylcarbamyl-5-pyridinecarboxylates and 5-cyano-compounds useful as herbicides. There is no disclosure of the 2-haloalkyl radicals or any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4-position is occupied by a silver salt, U.S. Pat. No. 1,944,412 discloses that such compounds have been utilized in the production of X-ray pictures with intravenous injection of such compounds.

Pyridinedicarboxylate compounds useful as herbicides are described in U.S. Pat. No. 4,692,184. These compounds have fluorinated methyl groups at the 2- and 6-positions and carboxylic acid derivative at the 3- and 5-positions.

Other pyridinedicarboxylate compounds including pyrazole amides are disclosed in U.S. Pat. No. 4,698,093. U.S. Pat. Nos. 4,066,438 and 4,180,395 disclose various herbicidal polyhalo substituted pyridyloxy compounds.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

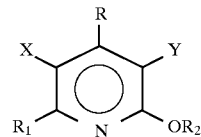

wherein:

$R_1$ is fluorinated methyl, chlorofluorinated methyl or fluorinated ethyl;

$R_2$ is hydrogen, lower alkyl, trichloromethyl, lower cyanoalkyl, alkenyl, or alkynyl;

R is $C_1$–$C_6$ straight or branched alkyl, haloalkyl, alkylthioalkyl, alkoxyalkyl, carboxyalkyl, $C_3$–$C_4$ cycloalkyl, or cyclopropylmethyl;

X and Y are independently selected from a)

where $Z_1$ is oxygen or $NR_3$ where $R_3$ is lower alkyl and where Z is hydrogen; halogen; hydroxy; alkynyloxy; haloalkoxy; alkynoxy; alkylthio; $NR_4R_5$ where $R_4$ and $R_5$ are independently hydrogen or lower alkyl; acetylamino; hydroxyalkyl; haloalkyl; 1-pyrazolyl; 1-imidazolyl; 1,2,4-triazolyl; 1-pyrrolidinyl; 1-piperidinyl; 1-azetidinyl; 4-morpholinyl; 4-thiomorpholinyl; 3-thiazolidinyl; 1-aziridinyl; hexahydro-1-azepinyl; alkoxymethyleneamino; and 2-isoxazolidinyl; or b) 1-pyrrolyl; cyano; 4,5-dihydro-2-oxazolyl; $NR_6R_7$ where $R_6$ and $R_7$ are independently hydrogen or hydroxyalkyl; 4,5-dihydro-2-thiazolyl; alkoxymethyleneamino; dialkylaminomethyleneamino; alkylthiomethyleneamino; tetrahydro-4-methylene-5-oxo-2-furanyl; 1,3-dioxolan-2-yl; 1,3-dithian-2-yl; (2-hydroxyalkyl)iminomethyl; halo-2-(haloalkyl) iminomethyl; 5,6-dihydro-4H-1,3-thiazin-2-yl; 5,6-dihydro-4H-1,3-oxazin-2-yl; 1,3,4-oxadiazol-2-yl; 1,3-dioxan-2-yl; 5-oxazolyl; hydroxyalkyl; 2-oxazolyl; halo-1-oxoalkylamino; (dihydro-2(3H)furanylidene) amino; 1,3-oxathiolan-2-yl; 4-oxo-1,3-dioxolan-2-yl; 3-oxathiolan-2-yl; 3,3-dioxo-1,3-oxathiolan-2-yl; and 2-thiazolyl; or c) the above-mentioned heterocycles substituted by one or more substituents selected from lower alkyl; halo; nitro; acetylamino; amino; and cyano.

The term "lower" used herein for lower alkyl, lower alkoxy or like group means a group containing 1–7 carbon atoms in straight or branched chain form. Specifically, the lower alkyl group may be methyl, ethyl, propyl, isopropyl, butyl, isobutyl, pentyl, isopentyl or hexyl; the lower alkoxy group may be methoxy, ethoxy, propoxy, isopropoxy; the lower alkylthio group may be methylthio, ethylthio, propylthio, isopropylthio, butylthio or pentylthio. The lower alkynyl or lower alknyl group have 3 to 7 carbon atoms and may be vinyl, allyl, isopropenyl, 2-butenyl, 1,3 butadienyl, 2-pentenyl, 1,4-pentadienyl, 1,6-heptadienyl, 1-hexenyl, ethynyl, 2-propynyl, etc.

The term "halo" or cognates thereof include chlorine, bromine, fluorine and iodine.

Examples of "cycloalkyl" as used herein include cyclopropyl, cyclobutyl, cyclopentyl, and cyclohexyl.

Examples of "lower haloalkyl" as used herein include chloromethyl, bromomethyl, dichloromethyl, dibromomethyl, trifluoromethyl and the like.

Examples of "lower alkoxyalkyl" as used herein include methoxymethyl, ethoxymethyl, propoxymethyl, butoxymethyl and the like.

Examples of "lower alkylthioalkyl" as used herein include methylthiomethyl, ethylthiomethyl, methylthioethyl, ethylthioethyl and the like.

The term "cycloalkylalkyl" means a $C_1$–$C_2$ alkyl group substituted with a $C_3$–$C_6$ cycloalkyl group, such as cyclopropylmethyl, cyclopropylethyl, cyclobutylmethyl, cyclopentylethyl, and so forth.

The terms "fluorinated methyl", "chlorinated methyl", and "chlorofluorinated methyl" mean methyl radicals wherein one or more of the three hydrogen atoms have been replaced by a fluorine atom, a chlorine atom, or a fluorine atom and a chlorine atom, respectively.

DETAILED DESCRIPTION OF THE INVENTION

The novel herbicidal derivative and their compounds of this invention are readily prepared by reaction as illustrated in the following working examples.

As used throughout the specification, including the examples, the following abbreviations have the following meanings:

THF—tetrahydrofuran
HPLC—high pressure liquid chromatography
RT—room temperature
DBU—1,8-diazabicyclo-[5.4.0]-undec-7-ene
EtOAc—ethyl acetate
DME—dimethoxyethane
t-BuOK—potassium t-butoxide
DMF—N,N-dimethylformamide
RBF—round bottom flask
GC—gas chromatography
d—day(s)
nD—index of refraction at 25° C.
v/v—volume/volume
kp—kiloPascal(s)
c—cyclo
Me—methyl
Et—ethyl
Ac—acetyl
TFAA—trifluoroacetic anhydride
HMPA—hexamethylphosphoric triamide The present invention is merely illustrated by the following working examples but obviously is not limited thereto. All percentages are given on a weight/weight basis unless otherwise indicated.

In some examples, the reaction of selected ketoesters, aldehydes, and cyanoacetamide in the presence of a base was used to form several dihydropyridone precursors as illustrated in the following scheme.

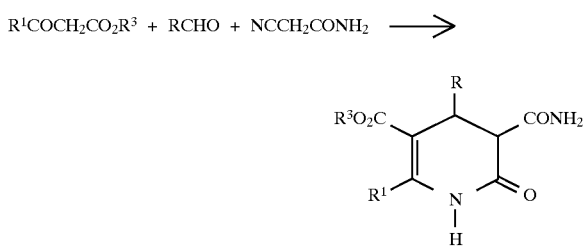

In some other examples, the reaction of an aldehyde with cyanacetamide was used to form an alkylidene which was further reacted with a ketoester to give-additional dihydropyridine precursors as illustrated in the following scheme.

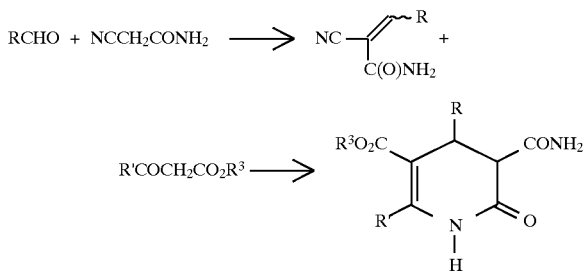

EXAMPLE 1

This example illustrates the preparation of 5-pyridinecarboxylic acid, 3-(aminocarbonyl)-1,2,3,4-tetrahydro-4-(2-methylpropyl)-2-oxo-6-(trifluoromethyl)-, methyl ester.

Methyl trifluoroacetoacetate (170 g, 1.0 mol), isovaleraldehyde (86 g, 1.0 mol) and cyanoacetamide (84 g, 1.0 mol) were placed in a 3-liter round bottom flask fitted with a thermometer and water condenser. To this mixture was added 500 mL ethanol followed by 20 mL piperidine, and the resulting mixture was heated at reflux for 4 h after which time all the cyanoacetamide had dissolved. The reaction mixture was cooled to room temperature, 50 mL concentrated hydrochloric acid added, and the volatiles removed by rotary evaporator until a thick slurry formed. This slurry was filtered through a Buchner funnel overnight (without a solvent wash) to separate the solid product from an oily impurity. The crude product was dampened with ether to facilitate its removal from the funnel, then mechanically stirred with 200 mL ether until a uniform thick slurry was obtained. The slurry was filtered through a Buchner funnel and the filter cake washed with a minimum amount of cold ether, broken into fine pieces and dried in air. Yield was 175 g (54%) of the intermediate as a white solid.

mp 153°–155° C.

Anal: Calcd for $C_{13}H_{17}F_3N_2O_4$: C, 48.45; H, 5.32; N, 8.69. Found: C, 48.58; H, 5.35; N, 8.69.

EXAMPLE 2

This example illustrates the preparation of 5-pyridinecarboxylic acid, 3-(aminocarbonyl)-1,2,3,4-tetrahydro-4-(2-methylpropyl)-2-oxo-6-(pentafluoroethyl)-, ethyl ester.

A mixture of ethyl pentafluoropropionylacetate (234 g, 1.0 mol), isovaleraldehyde (86 g, 1.0 mol), cyanoacetamide (84 g, 1.0 mol) and piperidine (20 mL) were heated at reflux in 500 mL ethanol for 20 h, after which time the reaction mixture was cooled in an ice bath and the solid product filtered and washed with a minimum amount of ether. On drying, 232 g (60%) of the product was obtained as a white solid, mp 154°–157° C.

EXAMPLE 3

This example illustrates the preparation of 5-pyridinecarboxylic acid, 3-(aminocarbonyl)-1,2,3,4-tetrahydro-4-(cyclopropylmethyl)-2-oxo-6-trifluoromethyl-, methyl ester, was prepared as follows. A mixture of cyclopropylacetaldehyde (2.52 g, 30 mmol), methyl trifluoroacetoacetate (5.10 g, 30 mmol), cyanoacetamide (2.52 g, 30 mmol) and piperidine (0.6 g) was heated at reflux in 30 mL 1,2-dichloroethane for 3.5 h, after which time the reaction mixture was cooled to room temperature and volatiles removed via rotory evaporator. The residue was purified by chromatotron, eluting with 8:1 hexane: ethyl acetate to remove impurities, followed by ethyl acetate to elute the product. Yield of the product was 4.4 g (46%) of a white sticky solid.

EXAMPLE 4

This example illustrates the preparation of butenamide, 2-cyano.

A mixture of cyanoacetamide (84 g, 1.0 mol), acetaldehyde (44 g, 1.0 mol) and piperidine (3 mL) was stirred in glacial acetic acid (150 mL) at room temperature for 21 h. The reaction mixture was then poured into 1000 mL water and extracted with three 300 mL portions of ethyl acetate. The combined ethyl acetate extracts were dried with anhydrous magnesium sulfate, filtered and solvent removed. To the residue was added ether (50 mL) and the resulting slurry was filtered to give 22.8 g (21 %) of product as a white solid. A portion was recrystallized from methanol to give a white solid, mp 114°–146° C.

EXAMPLE 5

This example illustrates the preparation of 2-hexenamide, 2-cyano-5-methyl.

To a 22-L round bottomed flask was added 2.9 L of glacial acetic acid, cyanoacetamide (2229 g, 26.51 mol) and isovaleraldehyde (2387 g, 27.72 mol). The solution was stirred while a mixture of piperidine (72.3 g) in 600 ml of glacial acetic acid was added over the course of 3 h. The reaction temperature, initially at 19° C., rose to 26° C. during the course of the addition with no external cooling. The reaction mixture was allowed to stand at RT overnight, during which time a small amount of white solid formed in solution. The reaction mixture was split in half, and each half was extracted by adding 6 L of $H_2O$ and 5 L of $CH_2Cl_2$. The layers were separated, and the aqueous layer was extracted an additional time with 2 L of $CH_2Cl_2$. The combined organic layers were extracted with 6 L of $H_2O$, separated and dried over $MgSO_4$ then the solvents were removed by rotary evaporation to yield a yellow solid. The yellow solid was placed in a bucket and stirred with ether followed by filtration to yield 2954 g (73%) of a white solid. The filtrate was reduced in volume by ⅓, then placed in a freezer to crystallize an additional 194 g (5%) of the desired product (total yield: 78%) as an uncharacterized mixture of E/Z isomers: mp 97°–98° C.

EXAMPLE 6

This example illustrates the preparation of butenamide, 2-cyano-4-cyclopropyl.

A mixture of cyclopropylacetaldehyde (1.75 g, 20.8 mmol), cyanoacetamide (1.68 g, 20 mmol), and 5 drops piperidine was stirred in 25 mL glacial acetic acid at room temperature for 5 d, after which time a stream of nitrogen was passed over the resulting solution overnight. The solid yellow residue was dissolved in 100 mL ethyl acetate, washed with three 50-mL portions of water, dried with anhydrous magnesium sulfate, filtered, and solvent removed to give a yellow solid which was used without further purification. Yield of product was 2.0 g (67%).

EXAMPLE 7

This example illustrates the preparation of Compound 86, namely, 3,5-pyridinedicarboxylic acid, 2-methoxy-4-methyl-6-(trifluoromethyl)-, dimethyl ester. A mixture of the product of Example 4 (55 g, 0.5 mol), methyl trifluoroacetoacetate (85 g, 0.5 mol), and 10 mL piperidine in 300 mL 1,2-dichloroethane was refluxed for 22 h. The resulting solution was cooled in an ice bath to precipitate the product, which was filtered and washed with a small portion of cold 1,2-dichloroethane. Additional product was obtained by treating the filtrate with ether. Total yield was 80.1 g (57%) of white solid. To a solution of this material (14 g, 50 mmol) in 75% sulfuric acid (100 mL) cooled in an ice bath was added sodium nitrite (20 g, 290 mmol) in water (20 mL) over 20 min. After the addition was complete, the reaction mixture was stirred for an additional 20 min, after which time 500 g ice was added and the resulting mixture stirred at ambient temperature for 2 h. The crude acid pyridone was filtered and dried in air to give 6.8 g of a yellow solid. This material was dissolved in DMF (50 mL) and stirred with potassium carbonate (10 g, 72 mmol) and methyl iodide (10 mL, 161 mmol) at room temperature for 40 h. The resulting mixture was poured into 100 mL water and extracted with two 100 mL portions of ether. The combined ether extracts were dried with anhydrous magnesium sulfate, filtered and solvent removed to give the crude product which was purified by chromatotron, eluting with 8:1 hexane:ethyl acetate. Yield was 5.6 g (37%) of a clear oil which solidified on standing, mp 36°–37° C.

EXAMPLE 8

This example illustrates another route for the preparation of the product of Example 1.

To a 22-L RBF was added product of Example 5 (2738 g, 17.99 mol), methyl trifluoroacetoacetate (3059.8 g, 17.99 mol) and 12.5 L of 1,2-dichloroethane. To the reaction mixture, which was stirring at RT, piperidine (270 g) was added dropwise over the course of 40 min. After all of the piperidine was added, a small exotherm was noted that raised the reaction temperature from 29° C. to 55° C. in 30 minutes. At this point the reaction was gently refluxed for 4 h and then stirred at room temperature overnight. The following morning, a white solid had precipitated from the yellow reaction mixture. The solid was collected by filtration, washed with portions of ether and then dried to yield 4885 g (84%) of a white solid: mp 154°–157° C.

The following additional four compounds were prepared in the manner of the foregoing examples with the indicated yields.
1. 5-pyridinecarboxylic acid, 3-(aminocarbonyl)-1,2,3,4-tetrahydro-4-(1-methylethyl)-2-oxo-6-(trifluoromethyl)-, methyl ester (41% yield).
2. 5-pyridinecarboxylic acid, 3-aminocarbonyl)-1,2,3,4-tetrahydro-4-cyclopropyl-2-oxo-6-(trifluoromethyl)-, methyl ester (74% yield).
3. 5-pyridinecarboxylic acid, 3-aminocarbonyl)-1,2,3,4-tetrahydro-4-cyclobutyl-2-oxo-6-(trifluoromethyl)-, methyl ester (62% yield).

4. 5-pyridinecarboxylic acid, 3-aminocarbonyl-1,2,3,4-tetrahydro-4-(2-methylpropyl)-2-oxo-6-(trifluoromethyl)-, ethyl ester (65% yield).

The reaction of dihydropyridones with nitrous acid was used to form hydroxypyridines in accordance with the following scheme:

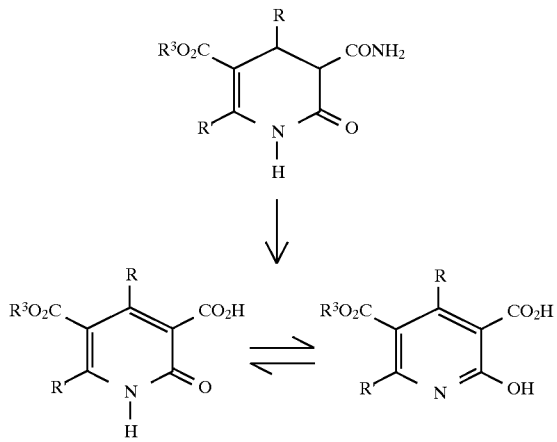

EXAMPLE 9

This example illustrates the preparation of 3,5-pyridinedicarboxylic acid, 2-hydroxy-4-(2-methyl propyl)-6-(trifluoromethyl)-, 5-methyl ester.

To a 22-L round bottomed flask, equipped for cooling, was added water (1667 mL) and concentrated sulfuric acid (5 L). After the aqueous acid had cooled to 23° C., the product of Example 1 (1.0 kg, 3.1 mol) was added to the flask. After several minutes of stirring an even suspension of material formed. To the reaction mixture was added, dropwise over the course of 3 h, a solution of sodium nitrite (875 g, 12.68 mol) in 2.0 L of water. Cooling was applied as needed to maintain the reaction temperature below 50° C. Large volumes of a brown gas (nitrous oxide) were evolved and a large amount of foam was formed during the reaction. A white solid formed in solution after stirring at RT overnight. To the flask was added 10 L of water, cooling was applied to maintain the temperature below 20° C. The reaction mixture was filtered and the collected solid was washed with large amounts of water in a Buchner funnel. The product was dried to yield 927 g (93%) of a white solid: mp 131°–133° C.

EXAMPLE 10

This example illustrates the preparation of 3,5-pyridinedicarboxylic acid, 2-hydroxy-4-(2-methylpropyl)-6-(pentafluoroethyl)-, 5-ethyl ester and 3,5-pyridinedicarboxylic acid, 2-methoxy-4-(2-methylpropyl)-6-(pentafluoroethyl)-, 5-ethyl 3-methyl ester, the latter compound being Compound 11.

To a mechanically stirred solution of product of Example 2 (232 g, 0.60 mol) in 1500 mL 75% v/v sulfuric acid was added sodium nitrite (250 g, 3.62 mol) in 700 mL water over 3 h. The sodium nitrite solution was introduced below the surface of the reaction medium. Vigorous gas evolution occurred. Stirring was continued for 1 h after the addition was complete, after which time the reaction mixture was diluted with an equal volume of ice, filtered, and the crude product was washed with water. On drying, 217 g (94%) of a yellow solid was obtained.

A mixture of the thus-produced material (217 g), methyl iodide (120 mL), and potassium carbonate (240 g) was mechanically stirred in 1000 mL DMF at room temperature overnight. The reaction mixture was diluted with two volumes of water and extracted into a total of 3 L ether. The ether extracts were washed with 4N hydrochloric acid, dried with anhydrous magnesium sulfate, filtered and solvent removed to give the crude product, which was purified by column chromatography ($SiO_2$), eluting with 8:1 hexane: ethyl acetate. Yield of Compound 11 was 200 g (81%) of a light reddish-brown oil.

The reaction of pyridine acids with alcohols in the presence of acid was used to give certain esters.

EXAMPLE 11

This example illustrates the preparation of Compound 1, namely, dimethyl 2-hydroxy-4-(2-methylpropyl)-6-(trifluoromethyl)-3,5-pyridine dicarboxylate. A two liter round bottom flask was charged with 247 g (0.77 mole) of the product of Example 9 and one liter of methanol. Three drops of concentrated sulfuric acid were added and the solution was heated at reflux for 48 hours. The methanol was removed by rotary evaporation and the solid mass was dissolved in methylene chloride and washed with saturated aqueous sodium bicarbonate. The solution was dried with magnesium sulfate and the solvent was removed by rotary evaporation to give 119.63 g (50.5%) of an off-white solid, mp 80°–85° C.

Anal: Calcd for $C_{14}H_{16}N_1O_5F_3$: C, 50.15; H, 4.81; N, 4.18. Found: C, 49.88; H, 4.73; N, 4.18.

The reaction of pyridines with alkyl halides in the presence of base was used to give certain pyridines of the present invention.

EXAMPLE 12

This example illustrates the preparation of Compound 2.

To a 22-L RBF was added the product of Example 9 (2368 g, 7.37 mol), 9 L of DMF and potassium carbonate (2230.3 g, 16.14 mol). The reaction mixture was cooled to 4° C. then iodomethane (935 mL, 15.47 mol) was added dropwise over the course of 3 h while maintaining the reaction temperature below 6° C. After the addition was complete the reaction was stirred at RT for 48 h. The reaction was split in half and each half was treated with 7 L of $H_2O$ and 3.5 L of $CH_2Cl_2$. The aqueous layer was extracted a second time with 3 L of $CH_2Cl_2$ and 1 L of $H_2O$. The combined organic layers were dried over $MgSO_4$, filtered and removed by rotory evaporation to yield a red oil (2097.4 g) which by GC consisted of Compound 2 (81%), the N-methyl-2-pyridone (15.6%) and the starting acid (0.3%). The more mobile Compound 2 was separated from the N-methylated by-product by applying 1 kg of the reaction mixture to 1.5 kg of silica gel and eluting with hexane or 1% EtOAc/hexane. Compound 2 (1677 g, 65% yield, 99% pure) was isolated as a yellow oil.

EXAMPLES 13–16

The general procedure for the preparation of Compounds 9, 44, 48 and 63 was used as follows.

A mixture of the appropriate pyridone (1 eq), potassium carbonate (4 eq), and methyl iodide (2.2 eq) in DMF was mechanically stirred at room temperature for 16 h. The reaction mixture was diluted with water and the product extracted with ether (3×), dried ($MgSO_4$), filtered, and concentrated. The crude product was chromatographed eluting with 10% ethyl acetate in hexane to afford the desired product.

Compound 9: yellow solid (17%) mp 96°–97° C.

Compound 44: colorless oil (48%) nD: 1.4618.

Compound 48: yellow oil (27%) nD: 1.4809.

Compound 63: colorless oil (28%) nD: 1.4623.

The reaction of an imidate with an alkylidene in the presence of base, followed by aromatization was used to give compounds of the present invention.

EXAMPLE 17

This example illustrates the preparation of propenoic acid, 3-amino-3-methoxy-, methyl ester, used in preparation of compounds of the present invention. Hydrogen chloride was bubbled into a solution of methyl cyanoacetate (54.0 g, 0.54 mol), ether (21 g), and methanol (21.0 g, 0.60 mol) cooled in an ice/salt water bath. When the exotherm ceased, the cloudy reaction mixture was stoppered and placed in the refrigerator overnight. A viscous oil formed, which was dissolved in ether (200 mL) and vigorously stirred at 0° C. The solid precipitate was filtered and added to a mixture of saturated $NaHCO_3$ (150 mL) and ether (150 mL) vigorously stirred. The layers were separated and the aqueous layer was washed with ether (3×100 mL). The combined ether extracts were washed with water (1×100 mL), dried over magnesium sulfate, filtered and concentrated to a colorless oil. Vacuum distillation 45°–70° C. afforded 27.1 g (38%) of the desired product, mixed with starting material (61:39).

EXAMPLE 18

This example illustrates the preparation of Compound 3, namely, 3,5-pyridinedicarboxylic acid, 2-ethoxy-4-(2-methylpropyl)-6-(trifluoromethyl)-, 3-ethyl, 5-methyl ester, hydrate (1:0.4), used in the preparation of compounds of the present invention. Propenoic acid, 3-amino-3-ethoxy-, ethyl ester (100 g, 0.51 mol) was added to 2-hexenoic acid, 5-methy-2-(trifluoroacetyl)-, methyl ester (122.2 g, 0.51 mol) in 450 mL chloroform; an exotherm was observed. Triethylamine (catalytic amount) was added and the reaction mixture heated to reflux for 1 h, then concentrated to an oil (200 g). The crude product was heated to reflux in 400 mL trifluoroacetic anhydride overnight, then concentrated and washed with saturated $NaHCO_3$ (1×500 mL). The product was extracted with ether (3×200 mL), dried over magnesium sulfate, filtered and concentrated to an oil (220 g). The crude product (150 g, 0.40 mol) was refluxed in thionyl chloride (380 mL) for 3 h, then cooled, carefully added to ice water and extracted into ether (3×200 mL). The organic layer was dried over magnesium sulfate, filtered and concentrated. The resulting oil was purified by HPLC, eluting with 10% ethyl acetate in hexane to give 48 g (32%) of Compound 3 as a light yellow oil. The flush (EtOAc) was recovered to give 80 g (45%) 3-ethyl 5-methyl 2-hydroxy-4-(2-methylpropyl)-6-(trifluoromethyl)-3,5-pyridinedicarboxylate.

EXAMPLES 19–22

The general procedure for the preparation of Compounds 4, 5, 7 and 23 was used as follows. The appropriate alkyl halide (1 eq) was added to a slurry of 3-ethyl 5-methyl 2-hydroxy-4-(2-methylpropyl)-6-(trifluoromethyl)-3,5-pyridinedicarboxylate (1 eq) and silver carbonate (0.5 equivalent) in hexane with stirring at room temperature in the dark. The reaction mixture was heated to reflux overnight, cooled, and filtered. The mother liquor was washed with saturated $NaHCO_3$ (1×), water (2×), dried over magnesium sulfate, filtered, and concentrated. The crude material was chromatographed to give the desired product.

EXAMPLES 23–26

Compounds 26, 29, 30 and 31 were prepared in accordance with the following scheme.

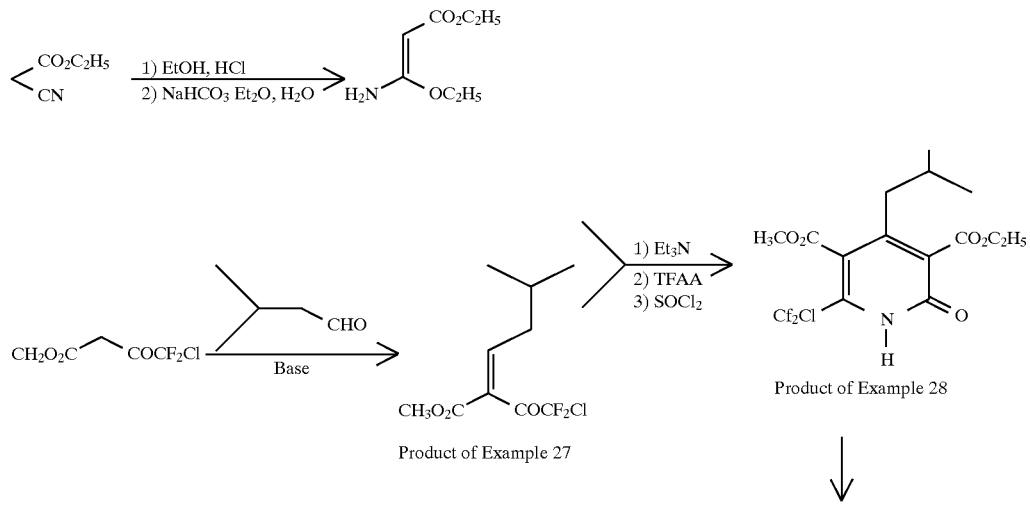

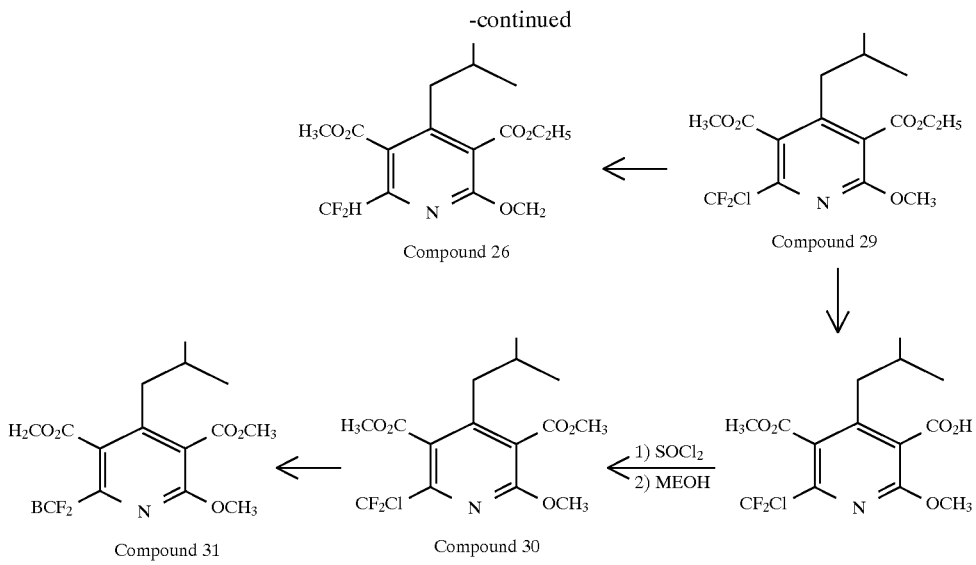

EXAMPLE 27

2-Hexenoic acid, 5-methyl-2-(chlorodifluoroacetyl)-, methyl ester, was prepared as follows. To a solution of methyl chlorodifluoroacetoacetate (200 g, 1.07 mol) and isovaleraldehyde (108.5 g, 1.26 mol) in 125 mL benzene was added 13.8 g glacial acetic acid and 3.91 g piperidine, resulting in an exotherm to ca 80° C. The reaction mixture was heated at reflux for 2.5 h with azeotropic removal of water, after which time solvent was distilled at atmospheric pressure and remaining volatiles removed by pumping at 1 torr (0.2 kp). Yield of product was 278 g (100%) of a clear red oil which was 88% pure by gas chromatographic analysis.

EXAMPLE 28

3,5-Pyridinedicarboxylic acid, 1,2-dihydro-6-(chlorodifluoromethyl)-4-(2-methylpropyl)-2-oxo-, 3-ethyl 5-methyl ester, was prepared as follows. To a solution of the product of Example 27 (67.3 g, 208 mmol) and ethyl 3-amino-3-ethoxypropenoate (30.1 g, 189 mmol) in 50 mL chloroform was added 5 mL triethylamine and the resulting mixture refluxed for 1 hour. The reaction mixture was cooled to room temperature, washed with 100 mL of 4N hydrochloric acid, and the organic layer dried with anhydrous magnesium sulfate, filtered and concentrated. To this residue was added 275 mL trifluoroacetic anhydride and the mixture heated at reflux for 21 h, after which time volatiles were removed via rotary evaporator. To the residue was added 250 mL thionyl chloride and the mixture heated at reflux for 16 h. The reaction mixture was cooled to room temperature, slowly poured onto 1000 mL ice, and extracted with two 500-mL portions of ether. The combined ether extracts were dried with anhydrous magnesium sulfate, filtered and concentrated to give a crude product which was purified by HPLC (10% hexane:ethyl acetate). Yield of product was 31.2 g (45%) as a yellow oil.

EXAMPLE 29

This example illustrates the preparation of Compound 29, namely, 3,5-pyridinedicarboxylic acid, 2-(chlorodifluoromethyl)-6-methoxy-4-(2-methylpropyl)-, 5-ethyl 3-methyl ester. A mixture of the product of Example 28 (31 g, 85 mmol), methyl iodide (5.3 mL, 85 mmol) and silver carbonate (17.53 g, 64 mmol) in 250 mL hexane was refluxed for 5 h in the dark. The reaction mixture was cooled to room temperature, filtered and the filtrate successively washed with saturated aqueous sodium bicarbonate (1×100 mL) and water (2×100 mL). The organic layer was dried with anhydrous magnesium sulfate, filtered, and concentrated to give the crude product which was purified by HPLC (5:1 hexane:ethyl acetate). Yield of Compound 29 was 22.2 g (69%) of colorless oil.

EXAMPLE 30

This example illustrates the preparation of 3-pyridinecarboxylic acid, 5-(chlorocarbonyl)-2-(chlorodifluoromethyl)-6-methoxy-4-(2-methylpropyl)-, methyl ester. Selective hydrolysis of Compound 29 was accomplished using the method described in Example 50. Acidification and extraction of the reaction mixture yielded a solid, which was washed with hot petroleum ether/ether solution to afford a 56% yield of product. Treatment of the crude monoacid with an equimolar amount of phosphorous pentachloride gave the desired acid chloride product in 85% yield.

EXAMPLE 31

This example illustrates the preparation of Compound 30, namely, 3,5-pyridinedicarboxylic acid, 2-(chlorodifluoromethyl)-6-methoxy-4-(2-methylpropyl)-, dimethyl ester. Product of Example 30 (8.0 g, 0.021 mol) was stirred in methanol (25 mL) overnight at room temperature, then concentrated, dissolved in ether (100 mL), and washed with water (3×100 mL). The organic phase was dried over magnesium sulfate filtered, and concentrated to an oil. Purification via HPLC, eluting with 2% ethyl acetate in hexane afforded 5.25 g (66%) Compound 30 as a yellow oil. nD: 1.4812

EXAMPLES 32 AND 33

This illustrates the preparation of Compounds 26 and 31. 5% Palladium on carbon was placed in the reaction flask. Under a nitrogen atmosphere, the chlorodifluoropyridine (Compound 29 or Compound 30) (1 eq) in ethanol was carefully added, followed by triethylamine (1.1 eq). The reaction flask was placed on a Parr hydrogenator and heated at 60° C. overnight. The reaction mixture was filtered, and the mother liquor concentrated, dissolved in ether and washed with water (3×). The organic layer was dried over magnesium sulfate, filtered, and concentrated. The crude material was chromatographed to yield the desired difluoromethylpyridine.

EXAMPLE 34

This example illustrates the preparation of 3,5-pyridinedicarboxylic acid, 2-methoxy-4-(2-methyl propyl)-6-(trifluoromethyl). Compound 2 (70.9 g, 0.20 mol) was heated at reflux in 25% NaOH (500 mL) and methanol (250 mL) overnight, then cooled and concentrated. The residue was diluted with water (200 mL) and washed with ether (2×100 mL), which was discarded. The aqueous layer was acidified with concentrated HCl and extracted with ether (3×200 mL). The organic layer was dried over magnesium sulfate, filtered, and concentrated to give 60 g (93%) of the dicarboxylic acid product as a solid.

EXAMPLE 35

This example illustrates the preparation of 3,5-pyridinedicarbonyl chloride, 2-methoxy-4-(2-methyl propyl)-6-(trifluoromethyl). Phosphorus pentachloride (85.6 g, 0.40 mol) was added to the product of Example 34 (60.0 g, 0.19 mol) in carbon tetrachloride (450 mL) at 0° C. The reaction mixture was stirred at 0° C. for 1 h, then at room temperature overnight before concentrating to give 70 g (100%) of product as an oil.

EXAMPLE 36

This example illustrates the preparation of Compound 84, namely, 3-pyridinecarboxylic acid, 5-(chlorocarbonyl)-2-methoxy-4-(2-methylpropyl)-6-(trifluoromethyl)-methyl ester.

The product of Example 35 (70 g, 0.19 mol) was dissolved in THF (150 mL) and methanol (70 mL) and the solution was allowed to sit without stirring at room temperature. After 28 h, the solution was concentrated and kugelrohr distilled (135°–120° C. at 0.2 kp) to give 51.3 g (74%) of product as a colorless oil.

Calcd for $C_{14}H_{15}Cl_1F_3N_1O_4$: C, 47.54; H, 4.27; N, 3.96; Cl, 10.02. Found: C, 47.47; H, 4.28; N, 3.92; Cl, 9.99.

EXAMPLE 37

This example illustrates the preparation of 3-pyridinecarboxylic acid, 5-(chlorocarbonyl)-2-methoxy-4-cyclopropylmethyl-6-(trifluoromethyl)-, methyl ester. A mixture of Compound 92 (44.6 g, 129 mmol) and 200 mL of 25% aqueous sodium hydroxide was heated at reflux in 200 mL methanol for 23.5 h. The reaction mixture was cooled to room temperature, diluted with two volumes of ice, and washed with three 300-mL portions of ether. The aqueous layer was acidified with concentrated hydrochloric acid (external ice cooling), and extracted with three 500-mL portions of ether. The combined ether extracts were dried with anhydrous magnesium sulfate, filtered, and solvent removed to give the diacid as a light tan solid. The above diacid (47.0 g of material containing ether by $^1$H NMR) was stirred with 32.1 g phosphorous pentachloride in 400 mL carbon tetrachloride at ambient temperature for 17 h. Solvent was removed at reduced pressure and the residue diluted with 1000 mL hexane and filtered through a column of silica. On removal of solvent, 42.2 g of the diacid chloride was obtained as a yellow oil. This material was stirred at ambient temperature with 50 mL methanol in 100 mL ether for 30 h, after which time volatiles were removed at reduced pressure and the residue was dissolved in 500 mL hexane and filtered through a column of silica. The column was then washed with 3.5 L hexane and the filtrate concentrated to give 35.2 g (78% from Compound 92) of product as a clear oil.

EXAMPLE 38

This example illustrates the preparation of 3,5-pyridinedicarboxylic acid, 2-ethoxy-4-(2-methylpropyl)-6-(trifluoromethyl)-, dimethyl ester.

A mixture of Compound 3 (100 g, 0.26 mol) and 25% NaOH (600 mL) was heated at reflux in 350 mL ethanol overnight, after which time the resulting solution was cooled to room temperature and concentrated. The residue was washed twice with ether to remove impurities and the aqueous layer acidified with concentrated hydrochloric acid. The product was extracted with three portions of ether, dried with anhydrous magnesium sulfate, filtered and solvent removed to give 48.3 g (55%) of the diacid as a dark solid. To this material (48.3 g, 0.14 mol) in 300 mL carbon tetrachloride at 0° C. was added phosphorous pentachloride (66.0 g, 0.32 mol) and the resulting mixture stirred in an ice bath for 1 h, warmed to room temperature and the heated at ca 50° C. for 3.5 h. The reaction mixture was then filtered, concentrated, and the residue kugelrohr distilled at 130° C. at 1.1 kp to give the diacid chloride as a dark oil. Yield was 34 g (65%). To this material (34 g, 0.09 mol) was added methanol (35 mL) and THF (40 mL), and the resulting mixture stirred until homogeneous, then allowed to sit at room temperature overnight. The reaction mixture was concentrated and the residue kugelrohr-distilled at 143° C. at 1.1 kp to give 27 g (81%) of the product as a yellow oil.

The conversion of pyridyl acids to pyridyl amines was used to prepare compounds of the present invention.

EXAMPLE 39

This example illustrates the preparation of Compound 32, namely, 3-pyridinecarboxylic acid, 5-amino-6-methoxy-4-(2-methylpropyl-2-(trifluoromethyl)-, methyl ester. Product of Example 51 (20.10 g, 0.057 mol) in 30 mL acetone was added at room temperature to a vigorously stirring mixture of sodium azide (8.13 g, 0.125 mol) in 45 mL acetone and 15 mL water. An exotherm to 50° C. was observed and the reaction mixture was stirred overnight at room temperature. The reaction mixture was diluted with 100 mL water and extracted with ether (3×100 mL). The combined organic layers were dried over magnesium sulfate, filtered, and concentrated to a solid. Recrystallization from ether/petroleum ether afforded 6.23 g of Compound 32. The mother liquor was chromatographed eluting with 10% ethyl acetate in hexane to give a total product recovery of 15.17 g (86%) Compound 32 as a white solid.

EXAMPLE 40

This example illustrates the preparation of Compound 36, namely, 3-pyridinecarboxylic acid, 5-amino-2-methoxy-4-(2-methylpropyl)-6-(trifluoromethyl)-, methyl ester.

To a stirred slurry of sodium azide (9.62 g, 150 mmol) in 50 mL acetone and 15 mL water was added Compound 84 (23.8 g, 67 mmol). A temperature rise to 35° C. was observed, so external cooling (cold water bath) was applied. The reaction mixture was then stirred at room temperature overnight. The mixture was then diluted with water and extracted with three portions of ether. The combined ether extracts were dried with anhydrous magnesium sulfate, filtered and concentrated to give the crude product, 20.1 g (98%), as a yellow oil. A portion was purified via chromatotron, eluting with 5:1 hexane:ethyl acetate to give an analytical sample.

The conversion of pyridyl acid chlorides to pyridyl aldehydes was used to prepare compounds of the present invention in accordance with the following general scheme.

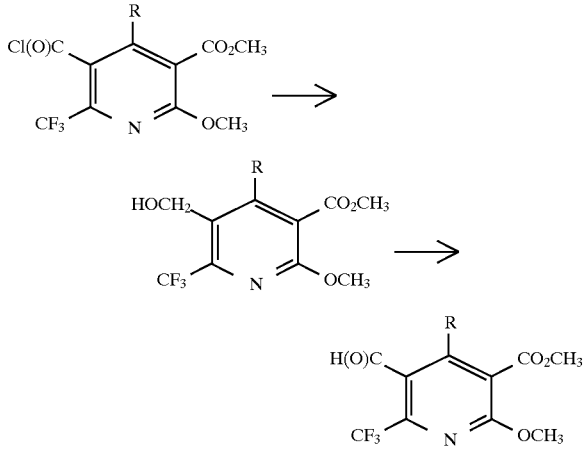

EXAMPLE 41

This example illustrates the preparation of Compound 40, namely, 3-pyridinecarboxylic acid, 5-hydroxymethyl-2-methoxy-4-(2-methylpropyl)-6-trifluoromethyl)-, methyl ester.

To a stirred slurry of sodium borohydride (86 g, 2.25 mol) in 2000 mL diglyme was added Compound 84 (419 g, 1.12 mol) in 800 mL diglyme at a rate keeping the temperature ca 10° C. The resulting mixture was allowed to warm to room temperature, whereupon it was stirred for an additional 3 h. The reaction mixture was cooled in an ice bath and to it was slowly added 450 mL concentrated hydrochloric acid, followed by 8 L of water. To this was added 3000 mL methylene chloride with stirring. The aqueous layer was discarded and the organic layer washed with two 10-L portions of 5% sodium chloride solution. The organic layer was concentrated and the residue distilled at 165° C. at 0.05 kp to afford the desired product as a yellow oil. Yield of Compound 40 was 292 g (74%).

EXAMPLE 42

This example illustrates the preparation of Compound 79, namely, 3-pyridinecarboxylic acid, 5-formyl-2-methoxy-4-(2-methylpropyl)-6-(trifluoromethyl)-, methyl ester.

A solution of 3.21 g (10 mmol) of Compound 40 in 25 mL methylene chloride was added slowly at 0° C. to a mixture of Celite (2.37 g), pyridinium chlorochromate (2.37 g, 11 mmol), and 25 mL methylene chloride at 0° C. with vigorous mechanical stirring. The mixture was stirred overnight at room temperature, then filtered and the filter cake rinsed well with methylene chloride. The filtrate was refiltered through a silica gel column, and the resulting solution concentrated by rotary evaporation. The crude product was dissolved in 2% ethyl acetate: 98% cyclohexane and filtered to remove solid impurities. The purified product was obtained by rotary evaporation of the solvent giving 2.41 g (75.4%) of a clear faint green oil. nD: 1.4774.

EXAMPLE 43

This example illustrates the preparation of Compound 117, namely, 3-pyridinecarboxylic acid, 4-(cyclopropylmethyl)-5-(hydroxymethyl)-2-methoxy-6-(trifluoromethyl)-, methyl ester.

To a slurry of sodium borohydride (2.26 g, 60 mmol) in 50 mL THF cooled in an ice bath was added the product of Example 37 (10.55 g, 30 mmol) in 50 mL THF and the resulting mixture stirred overnight, warming to room temperature in the process. The reaction mixture was cooled in an ice bath and quenched by careful addition of 4N hydrochloric acid. The resulting mixture was extracted with three 200 mL portions of ether, dried with anhydrous magnesium sulfate, filtered, and solvent removed to afford the crude product which was found to still contain some unreacted starting material. This material was stirred with an additional 2.26 g sodium borohydride in 100 mL THF at ambient temperature overnight. On workup as above, there was obtained the crude alcohol which was purified by HPLC (8:1 hexane:ethyl acetate) to give 8.1 g (85%) of Compound 117 as an off-white solid, mp 76°–77° C. Calcd for $C_{14}H_{16}F_3N_1O_4$: C, 52.67; H, 5.05; N, 4.39. Found: C, 52.79; H, 5.08; N, 4.36.

EXAMPLE 44

This example illustrates the preparation of Compound 115, namely, 3-pyridinecarboxylic acid, 4-(cyclopropylmethyl)-5-formyl-2-methoxy-6-(trifluoromethyl)-, methyl ester.

To a stirred slurry of pyridinium chlorochromate (5.62 g, 26 mmol) and 5 g Celite in 100 mL methylene chloride was added Compound 17 (7.6 g, 23.8 mmol) in 50 mL methylene chloride and the resulting mixture stirred at ambient temperature for 3 h. The reaction mixture was diluted with 400 mL hexane and filtered through a silica column, which was washed with an additional 500 mL hexane. The eluent was concentrated to give 7.2 g (95%) of Compound 115 as a clear oil, nD; 1.4911.

Calcd for $C_{14}H_{14}F_3N_1O_4$: C, 53.00; H, 4.45; N, 4.42. Found: C, 53.05; H, 4.48; N. 4.42.

EXAMPLE 45

This example illustrates another preparation of Compound 2.

The product of Example 9 (330 g, 1.03 mol) from above was mechanically stirred with 195 g $K_2CO_3$ in 1500 mL DMF, and to this mixture was added methyl iodide (65 mL, 1034 mmol). The reaction mix was stirred at room temperature for 18 h, then poured into a large excess of water and extracted (3×) with ether. The combined ether layers were washed with 1.2N hydrochloric acid, dried with anhydrous magnesium sulfate, filtered and concentrated to give a crude product which was purified by HPLC (7:1 hexane:ethyl acetate) (or better, by elution with hexane through a silica gel gravity column) to give Compound 2 (70 g, 20%) as a nearly colorless oil.

Calcd for $C_{15}H_{18}F_3N_1O_5$: C, 51.58; H, 5.19; N, 4.01. Found: C, 51.44; H, 5.21; N, 3.99.

EXAMPLE 46

This example illustrates the preparation of Compound 80, namely, dimethyl 2-(cyanomethoxy)-4-(2-methylpropyl)-6-(trifluoromethyl)-3,5-pyridine-dicarboxylate. A solution of 6.38 g (0.019 mol) of dimethyl 2-hydroxy-4-(2- methylpropyl)-6-(trifluoromethyl)-3,5-pyridinedicarboxylate (Compound 1) in 50 mL of dimethylformamide was prepared and to it was added 7.2 g (0.06 mol) of bromoacetonitrile and 8.3 g (0.06 mol) of anhydrous potassium carbonate. The mixture was stirred at room temperature overnight then suction filtered. The filtrate was diluted with 400 mL of water and extracted with four 50 mL portions of methylene chloride. The combined extracts were dried with magnesium sulfate and the solvent was removed by rotary evaporation giving 7.09 g (98.9% yield) of a dark amber oil. Silica gel chromatography with 10% ethyl acetate, 90% cyclohexane gave 3.51 g (49%) of Compound 80 as a clear colorless oil.

Calcd for $C_{16}H_{17}N_2O_5F_3$: C, 51.34; H, 4.58; N, 7.48. Found: C, 51.26; H, 4.61; N, 7.43.

EXAMPLE 47

This example illustrates the preparation of Compound 22, namely, 3-pyridinecarboxylic acid, 5-cyano-1,6-dihydro-4-(2-methylpropyl)-6-oxo-2-(trifluoromethyl)-, methyl ester.

Product of Example 1 (107 g) was dissolved in thionyl chloride (150 mL). An exotherm to reflux was observed upon the addition of DMF (8 mL). The reaction mixture was heated to reflux for 3 h before cooling and carefully adding to ice water. The product was extracted into ether (3×300 mL), dried over magnesium sulfate, filtered and concentrated to a sticky solid. The crude product was suspended in hot petroleum ether and the solid filtered from the hot solution. Compound 22 was obtained in 82% yield (82 g) as a white solid, MP 159°–163° C.

Calcd for $C_{13}H_{13}F_3N_2O_3$: C, 51.66; H, 4.34; N, 9.27. Found: C, 51.60; H, 4.37; N, 8.99.

EXAMPLE 48

This example illustrates the preparation of 3-pyridinecarboxylic acid, 6-chloro-5-cyano-4-(2-methylpropyl)-2-(trifluoromethyl)-, methyl ester. Compound 22 (11.50 g, 38.05 mmol) and phosphorus pentachloride (7.92 g, 38.05 mmol) were heated neat at 140° C. in an oil bath for 2 h. Upon cooling, the reaction mixture was carefully added to ice water and the product extracted into ether (3×100 mL) dried over magnesium sulfate, filtered and concentrated to a dark oil. Purification via HPLC, eluting with 10:1 hexane-:ethyl acetate afforded 4.30 g (35%) of product.

EXAMPLE 49

This example illustrates the preparation of Compound 20, namely, 3-pyridinecarboxylic acid, 5-cyano-6-methoxy-4-(2-methylpropyl)-2-(trifluoromethyl)-, methyl ester. Sodium methoxide (16.17 g, 0.074 mol) was added to the product of Example 48 (24.0 g, 0.074 mol) in methanol (50 mL). The reaction mixture was heated at reflux for 1 h, cooled, diluted with water (150 mL), extracted into ether (3×150 mL), dried over magnesium sulfate, filtered and concentrated to 21.00 g (88%) of an orange oil. Purification via HPLC eluting with 10% ethyl acetate in hexane gave Compound 20 as a colorless oil. $n_D$: 1.4723.

Calcd for $C_{14}H_{15}F_3N_2O_3$: C, 53.17; H, 4.78; N, 8.86. Found: C, 53.09; H, 4.82; N, 8.80.

Conversion of pyridyl esters to pyridyl acid chlorides attained in accordance with the following general scheme:

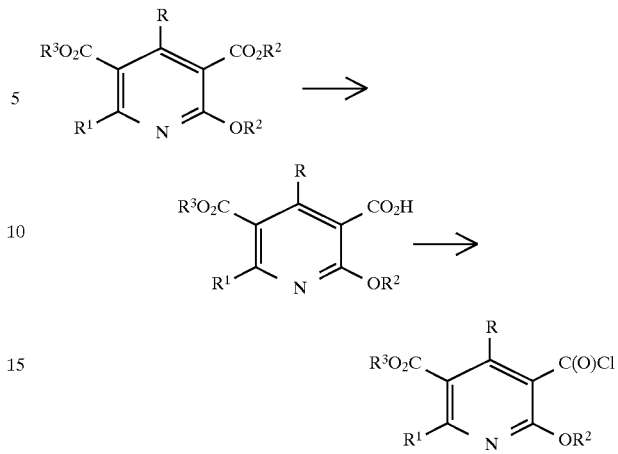

EXAMPLE 50

This example illustrates the preparation of 3,5-pyridine dicarboxylic acid, 2-methoxy-4-(2-methylpropyl)-6-(trifluoromethyl)-, 5-methyl ester.

Compound 2 (104.7 g,300 mmol) was heated at reflux in 600 mL of 25% sodium hydroxide and 300 mL methanol for 1 h, then cooled. The residue was diluted with water and washed with ether (3×300 ml), dried over magnesium sulfate, filtered and concentrated to a solid. Yield was 86.2 g (86%).

EXAMPLE 51

This example illustrates the preparation of 5-pyridinecarboxylic acid, 2-methoxy-3-chlorocarbonyl-4-(2-methylpropyl)-6-(trifluoromethyl)-, methyl ester. Product of Example 50 (86.2 g, 257 mmol) was heated at reflux in 170 mL thionyl chloride for 5 h. The reaction mixture was cooled to room temperature, concentrated by rotary evaporator, and eluted through silica gel with hexane. Concentration of the eluent afforded the acid chloride as an oil, sufficiently pure for further derivation. Yield of product was 50.4 g (55.5%).

EXAMPLE 52

This illustrates the preparation of Compound 13, namely, 3,5-pyridinedicarboxylic acid, 4-(carboxymethyl)-2-methoxy-6-(trifluoromethyl)-, dimethyl ester.

To a solution of Compound 86 (20.2 g, 66 mmol) in 100 mL THF at −30° C. was added lithium bis(trimethylsilyl) amide (75 mL of a 1.0M solution in THF, 75 mmol) at a rate maintaining the reaction temperature between −30° C. and −35° C. The reaction mixture was then poured onto 500 cc dry ice and the resulting mixture stirred at ambient temperature until most of the dry ice had dissipated. Water (1 L) was then carefully added to the reaction mixture and the resulting solution was washed with two 300 mL portions of ether. The combined ether extracts were washed with water (300 mL) and the combined aqueous layers cooled in an ice bath and acidified with 4N hydrochloric acid (700 mL). The product was filtered and dried in air to give 20.8 g (91%) of a white solid, mp 167°–168° C.

EXAMPLE 53

This example illustrates the preparation of Compound 87, namely, 3,5-pyridinedicarboxylic acid, 4-(bromomethyl)-2- methoxy-6-(trifluoromethyl)-, dimethyl ester. Compound 13 (98 g, 279 mmol) and red mercuric oxide (50 g, 240 mmol) were stirred in 1:1 carbon tetrachloride:1,2-dichloroethane (500 mL) and heated to near reflux. A 150-watt floodlight was then turned on and bromine (25 mL) in 200 mL of the above solvent mixture was added over 20 minutes. After the addition was complete, the reaction mixture was refluxed for 1 h under illumination, then stirred at ambient temperature without illumination overnight. The reaction mixture was then poured into aqueous saturated sodium sulfite (500 mL), shaken, the layers separated, and the aqueous layer washed with 300 mL of the mixed solvent. The combined organic layers were dried with anhydrous magnesium sulfate, filtered, and solvent removed to give the crude product which was purified by elution down a silica gel column with 16:1 hexane:ethyl acetate. Yield of product was 70.5 g (66%) of a white solid, mp 65°–66° C.

EXAMPLE 54

This example illustrates the preparation of Compound 88, namely, 3,5-pyridinedicarboxylic acid, 2-methoxy-4-(methoxymethyl)-6-(trifluoromethyl)-, dimethyl ester.

To a solution of Compound 87 (2.2 g, 5.7 mmol) in 20 mL methanol and 20 mL THF was added sodium methoxide (2.65 g of a 25% solution in methanol, 12 mmol) and the resulting solution stirred at ambient temperature for 3 d, after which time it was poured into 100 mL of 1.3N hydrochloric acid and extracted with three 50 mL portions of ether. The combined ether extracts were dried with anhydrous magnesium sulfate, filtered, and solvent removed to give the crude product which was purified by chromatotron, eluting with 8:1 hexane:ethyl acetate. Yield was 1.1 g (57%) of a yellow oil.

EXAMPLE 55

This example illustrates the preparation of Compound 89, namely, 3,5-pyridinedicarboxylic acid, 2-methoxy-4-[(methylthio)methyl]-6-(trifluoromethyl)-, dimethyl ester. A mixture of Compound 87 (2.2 g, 5.7 mmol) and sodium methanethiolate (0.84 g, 12 mmol) in 20 mL THF and 50 mL DMF was stirred at ambient temperature for 10 d, after which time the reaction mixture was poured into 4N hydrochloric acid (100 mL), extracted with three 100 mL portions of ether. The combined ether extracts were washed with three 100 mL portions of 4N hydrochloric acid, dried with anhydrous magnesium sulfate, filtered and solvent removed to give the crude product which was purified by chromatotron, eluting with 8:1 hexane:ethyl acetate. Yield was 1.4 g (70%) of a colorless oil.

EXAMPLE 56

This example illustrates the preparation of Compound 91, namely, 3,5-pyridinedicarboxylic acid, 2-methoxy-4-propyl-6-(trifluoromethyl)-, dimethyl ester.

To a solution of Compound 86, (6.2 g, 20 mmol) in 20 mL THF at −25° C. was added lithium bis(trimethylsilyl)amide (22 mL of a 1.0M solution in THF, 22 mmol) at a rate keeping the temperature below −20° C. The reaction mixture was then stirred at −20° to −30° C. for 30 min, after which time it was added over 15 min to a solution of ethyl iodide (3.43 g, 22 mmol) in 20 mL THF maintained at −25° C. The reaction then was stirred at −25° C. for 30 min, warmed to room temperature over 30 min, and then poured into 100 mL of 4N hydrochloric acid. The resulting mixture was extracted with three 100 mL portions of ether, dried (MgSO$_4$), filtered and solvent removed to give the crude product which was purified by chromatotron, eluting with 8:1 hexane:ethyl acetate. Purified yield was 2.7 g (40%) of a yellow oil which partially solidified on standing.

EXAMPLE 57

This example illustrates the preparation of Compound 92, namely, 3,5-pyridinedicarboxylic acid, 4-cyclopropylmethyl-2-methoxy-6-(trifluoromethyl)-, dimethyl ester.

To a solution of bromocyclopropane (18.3 g, 150 mmol) in 100 mL THF under nitrogen and previously cooled to −78° C. was added s-butyllithium (100 mL of a 1.5M solution in cyclohexane, 150 mmol) and the resulting mixture stirred at −78° C. for 2 h. This solution was then added over 20 min to a slurry of copper (I) bromide-dimethyl sulfide complex (16.2 g, 79 mmol) in 200 mL THF under nitrogen and previously cooled to −78° C. The resulting mixture was stirred for an additional 30 min, after which time a solution of Compound 87 (10.3 g, 25 mmol) in 100 mL THF was added at a rate keeping the reaction temperature below −60° C. Stirring was continued overnight, during which time the reaction mixture warmed to room temperature. The reaction product was isolated by quenching the reaction mixture with aqueous ammonium chloride at 0° C. followed by extraction with three 500-mL portions of ether. The combined ether extracts were dried with anhydrous magnesium sulfate, filtered, and solvent removed to give the crude product which was purified by chromatotron, eluting with 16:1 hexane:ethyl acetate. Compound 92 (1.2 g, 14%) was obtained as a light yellow oil.

EXAMPLES 58–60

Compound 12, 47 and 65 were prepared by the following general procedure. Sodium methanethiolate (2.5–8 eq) was added to a solution of the requisite diacid chloride prepared in a manner similar to the product of Example 35 (1 eq) in THF at 0° C. or methylene chloride at room temperature (for Compound 12). The reaction mixture was stirred at room temperature for 2–4 h, or for 5 days (for Compound 12), then added to 1N HCl, extracted with ether (3×), dried (MgSO$_4$), filtered, and concentrated. Recrystallization in methanol/water for Compound 47, or ether/petroleum ether for Compound 65, or hexane at −78° C. for Compound 12 gave the desired product.

Compound 12: white solid (75%) mp: 82°–84° C.
Compound 47: white solid (79%) mp: 81°–83° C.
Compound 65: white solid (66%) mp: 118°–120° C.

EXAMPLE 61

This illustrates the preparation of Compound 59, namely, 4-cyclobutyl-2-methoxy-3,5-bis(1H-pyrazol-1-ylcarbonyl)-6-(trifluoromethyl)-pyridine. A solution of 4-cyclobutyl-2-methoxy-6-(trifluoromethyl)-3,5-pyridinedicarbonyl chloride (7.00 g, 0.019 mol) and pyrazole (3.85 g, 0.056 mol) in 50 mL THF was stirred at room temperature for 16 h. The reaction mixture was added to 100 mL 1N HCl and extracted with ether (3×100 mL), dried (MgSO$_4$), filtered, and concentrated. The crude product was chromatographed, eluting with 10% ethyl acetate in hexane to afford 0.70 g (8%) of Compound 59 as a white solid, mp 111°–113° C.

EXAMPLES 62–64

Compounds 41, 46 and 55 were prepared by the following general procedures.

Phosphorous pentachloride (1 eq) was added to a solution of the requisite methyl amide (1 eq) in carbon tetrachloride and heated at 40°–55° C. for 3–16 h. The reaction mixture was cooled and concentrated to an oil. Sodium methanethiolate (1.1–5 eq) was added to a solution of the crude oil in THF and stirred at room temperature for 3 h for Compound 55, 72 h for Compound 41, and 36 h for Compound 46. The reaction mixture was added to 1N HCl and extracted with ether (3×), dried (MgSO$_4$), filtered, and concentrated. The crude product was chromatographed eluting with 5–10% ethyl acetate in hexane to afford the desired product.

Compound 41: pale yellow oil (21%) nD: 1.5020.
Compound 46: colorless oil (21%) nD: 1.4967.
Compound 55: white solid (39%) mp: 88°–90° C.

EXAMPLES 65–87

Twenty-three additional compounds having the following general structure were prepared by reacting the appropriate monoacid chloride with ZH as defined in Table 1 below except Compounds 104, 107 and 108 which were prepared in accordance with Examples 145–147. The prepared compounds are set out in Table 1 wherein Z is given.

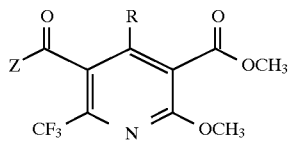

TABLE 1

| Cmpd | R | Z |
|---|---|---|
| 105 | i-butyl | NH2 |
| 102 | i-butyl | 3-F-Pyrazole |
| 101 | i-butyl | 4-NO$_2$-Pyrazole |
| 108 | i-butyl | 4-NH$_2$-Pyrazole |
| 104 | i-butyl | 4-Cl-Pyrazole |
| 107 | i-butyl | 4-AcNH-Pyrazole |
| 111 | i-butyl | 4-CN-Pyrazole |
| 97 | i-butyl | NH(CH$_2$)$_3$Br |
| 60 | i-butyl | triazole |
| 51 | i-butyl | 3-Me-pyrazole |
| 44 | i-butyl | OC$_2$H$_5$ |
| 53 | i-butyl | SC$_2$H$_5$ |
| 81 | i-butyl | OCH$_2$CH$_2$F |
| 82 | i-butyl | OCH$_2$C≡CH |
| 66 | i-butyl | 1-pyrrolidine |
| 67 | i-butyl | 1-piperidine |
| 16 | i-butyl | OC$_4$H$_9$ |
| 68 | i-butyl | 1-azetidine |
| 69 | i-butyl | 4-morpholino |
| 72 | i-butyl | 2-Me-aziridine |
| 52 | c-butyl | 1-pyrazole |
| 119 | c-propylmethyl | SCH$_3$ |
| 116 | c-propylmethyl | 1-pyrazole |
| 71 | i-butyl | 3-thiazolidine |

EXAMPLE 88

This example illustrates the preparation of Compound 45, namely, 3-pyridinecarboxylic acid, 2-ethoxy-4-methylpropyl)-5-[(methylthio)carbonyl]-6-(trifluoromethyl)-, methyl ester. Sodium mathanethiolate (1.07 g, 15 mmol) was added to a solution of 3-pyridinecarboxylic acid-2-ethoxy-4(2-methylpropyl)-5-(chlorocarbonyl)-6-(trifluoromethyl)-, methyl ester (5.11 g, 14 mmol) in 30 mL THF at 5° C. The methyl ester (5.11 g, 14 mmol) in 30 mL THF at 5° C. The reaction mixture was stirred at 5° C. for 0.5 h, at room temperature for 60 h, then added to 1N HCl (100 mL) and extracted with ether (3×100 mL), dried (MgSO$_4$), filtered, and concentrated. The crude product was chromatographed eluting with 1% ethyl acetate in hexane to give 1.48 g (28%) of Compound 45 as a colorless oil, which solidified upon standing at RT. mp: 35°–38° C.

EXAMPLE 89

This example illustrates the preparation of Compound 60, namely, 3-pyridinecarboxylic acid, 2-methoxy-4-(2-methylpropyl)-5-(1H-1,2,4-triazol-1-yl carbonyl)-6-(trifluoromethyl)-, methyl ester.

Triazole, sodium salt (1.42 g, 0.015 mmol) was added to Compound 84 (5.00 g, 0.014 mmol) in 50 mL THF, and the reaction mixture was heated at ref lux for 16 h. The reaction mixture was added to 1N HCl (100 mL) and extracted with ether (3×100 mL), dried over MgSO$_4$, filtered, and concentrated. The crude product was chromatographed eluting with 8% ethyl acetate in hexane to afford 2.85 g (53%) of the desired product as an oil which solidified on standing to a white solid. mp: 64°–66° C.

Calcd for C$_{16}$H$_{17}$N$_4$O$_4$F$_3$: C, 49.74; H, 4.43; N, 14.50. Found: C, 50.03; H, 4.60; N, 14.50.

EXAMPLE 90

This example illustrates the preparation of Compound 66.

Pyrrolidine (3.3 eq) was added to a solution of Compound 84 (1 eq) in ether at 0° C. The reaction mixture was stirred at 0° C. for 0.5 h, then at room temperature for 1 h before acidification with 1N HCl. The product was extracted with ether (3×), dried over MgSO$_4$, filtered, and concentrated. The crude product was chromatographed, eluting with 5:1 hexane:ethyl acetate, to afford the desired product in 57% yield as a colorless oil, nD: 1.4905.

Calcd for C$_{18}$H$_{23}$N$_2$O$_4$F$_3$: C, 55.66; H, 5.97; N, 7.21. Found: C, 55.76; H, 6.01; N, 7.18.

EXAMPLE 91

This example illustrates the preparation of Compound 42.

A solution of pyrazole (3–5 eq) and Compound 84 in THF was heated at reflux for 16 h. The reaction mixture was added to 1N HCl and extracted with ether (3×), dried over MgSO$_4$, filtered, and concentrated. The crude product was chromatographed, eluting with 5–10% ethyl acetate in hexane to afford the desired product in 51% yield as a colorless oil, nD: 1.4973.

Calcd for C$_{17}$H$_{18}$N$_3$O$_4$F$_3$: C, 52.99; H, 4.71; N, 10.90. Found: C, 53.10; H, 4.73; N, 10.84.

EXAMPLE 92

This example illustrates the preparation of Compound 51, namely, 3-pyridinecarboxylic acid, 2-methoxy-4-(2-methylpropyl)-5-[(3-methyl-1H-pyrazol-1-yl)carbonyl]-6-(trifluoromethyl)-, methyl ester. 3-Methylpyrazole (3.58 mL, 0.044 mol) was added to a solution of Compound 84 (5.15 g, 0.014 mmol) in 50 mL dichloromethane at 0° C. The reaction mixture was stirred at 0° C. for 0.5 h, then heated at reflux for 16 h. The reaction mixture was then added to 1N HCl (100 mL) and extracted with dichloromethane (3×100 mL), dried over MgSO$_4$, filtered, and concentrated. The crude product was chromatographed eluting with 10% ethyl acetate in hexane to afford 2.67 g (48%) of product as a yellow oil, nD: 1.4958.

Calcd for C$_{18}$H$_{20}$N$_3$O$_4$F$_3$: C, 54.14; H, 5.05; N, 10.52. Found: C, 54.71; H, 5.21; N, 10.20.

EXAMPLE 93

This example illustrates the preparation of Compound 53, namely, 3-pyridinecarboxylic acid, 5-[(ethylthio)carbonyl]-2-methoxy-4-(2-methylpropyl)-6-(trifluoromethyl)-, methyl ester.

Ethanethiol (1.26 mL, 0.017 mol) was added to a suspension of sodium hydride (0.41 g, 0.017 mol) in 35 mL THF at 0° C. The reaction mixture was stirred at room temperature for 1 h, then Compound 84 (5.49 g, 0.016 mmol) in 15 mL THF was added to the reaction mixture. An exotherm was observed, and an ice bath was used to cool the mixture. After 3 h at room temperature, the reaction mixture was acidified with 1N HCl and extracted with ether (3×100 mL), dried over $MgSO_4$, filtered, and concentrated. Purification via chromatograph eluting with 1% ethyl acetate in hexane afforded 3.65 g (60%) of product as a white solid, mp: 43°–47° C.

Calcd for $C_{16}H_{20}N_1O_4S_1F_3$: C, 50.65; H, 5.31; N, 3.69; S, 8.45. Found: C, 50.71; H, 5.34; N, 3.67; S, 8.50.

EXAMPLE 94

This example illustrates the preparation of Compound 16, namely, 3,5-pyridinedicarboxylic acid, 2-methoxy-4-(2-methylpropyl)-6-(trifluoromethyl)-, 5-butyl, 3-methyl diester. Compound 84 (3.54 g, 10 mmol) was heated at reflux in 20 mL n-butanol for 30 h, after which time the reaction mixture was cooled to room temperature, diluted with 300 mL water and extracted with three 200 mL portions of ether. The combined ether extracts were dried over anhydrous $MgSO_4$, filtered, and solvent was removed to give the crude product which was purified via chromatotron to give the product as a colorless oil. Yield was 2.9 g (74%).

Calcd for $C_{18}H_{24}F_3N_1O_5$: C, 55.24; H, 6.18; N, 3.58. Found: C, 55.32; H, 6.19; N, 3.54.

EXAMPLES 95–100

Compounds 97, 100, 101, 102, 105 and 111 were prepared by the following general procedure.

A solution of Compound 84 (10.61 g, 30 mmol) in 100 mL ether was added to a stirred solution of either excess amine or a stoichiometric amount of the requisite amine and excess triethylamine in ether. The resulting stirred at ambient overnight, after which time the reaction mixture was partitioned between ether and water. The ether layer was washed with dilute hydrochloric acid, dried with magnesium chloride, filtered and solvent removed to afford the crude product which was purified as outlined below.

Compound 97: recrystallized from 10% ethyl acetate/90% hexane, 55% of a white powder, mp: 133°–134° C. Calcd for $C_{18}H_{22}BrF_3N_2O_4$: C, 44.85; H, 4.87; N, 6.15; Br, 17.55. Found: C, 44.91; H, 4.92; N, 6.13; Br, 17.54.

Compound 100: recrystallized from ether, 41% of a white powder, mp: 224°–225° C. Calcd for $C_{16}H_{20}F_3N_3O_5$: C, 49.10; H, 5.15; N, 10.74. Found: C, 49.00; H, 5.19; N, 10.71.

Compound 101: recrystallized from ether; 82% of white powder, mp: 113°–114° C. Calcd for $C_{17}H_{17}F_3N_4O_6$: C, 47.45; H, 3.98; N, 13.02. Found: C, 47.29; H, 4.00; N, 12.97.

Compound 102: HPLC (2% ethyl acetate/98% hexane); 48% of colorless oil; nD=1.4925. Calcd for $C_{17}H_{17}F_4N_3O_4$: C, 50.63; H, 4.25; N, 10.42. Found: C, 50.74; H, 4.31; N, 10.37.

Compound 105: recrystallized from ether giving 85% yield of white powder, mp: 175°–176° C. Calcd for $C_{14}H_{17}F_3N_2O_4$: C, 50.30; H, 5.13; N, 8.38. Found: C, 50.27; H, 5.16; N, 8.37.

Compound 111: HPLC (4% ethyl acetate/96% hexane); 57% of a viscous pale yellow oil, nD=1.5705. Calcd for $C_{18}H_{17}F_3N_4O_4$: C, 52.70; H, 4.18; N, 13.60. Found: C, 53.00; H, 4.43; N, 13.00.

EXAMPLE 101

This example illustrates the preparation of Compound 112, namely, 3,5-pyridinedicarboxylic acid, 2-methoxy-4-(2-methylpropyl)-6-(trifluoromethyl)-, 3-methyl 5-(2,2,2-trifluoroethyl)ester. This material was prepared as in Example 94 to yield 1.8 g (43%) of a colorless oil. nD: 1.5705. Calcd for $C_{16}H_{17}F_6N_1O_5$: C, 46.05; H, 4.11; N, 3.36. Found: C, 46.09; H, 4.14; N, 3.36.

EXAMPLE 102

This example illustrates the preparation of Compound 116, namely, 3-pyridinecarboxylic acid, 4-(cyclopropylmethyl)-2-methoxy-5-(1H-pyrazol-1-ylcarbonyl)-6-(trifluoromethyl)-, methyl ester.

To a solution of the product of Example 37 (2.50 g, 7.1 mmol) in 15 mL THF was added pyrazole (1.93 g, 28.4 mmol) and the resulting mixture stirred at room temperature for 24 h, after which time it was diluted with 50 mL 4N hydrochloric acid and extracted with two 100-mL portions of ether. The combined ether extracts were dried with anhydrous magnesium sulfate, filtered through a column of silica, and the eluent concentrated to give 1.2 g (44%) of product as a white solid. Calcd for $C_{17}H_{16}F_3N_3O_4$: C, 53.27; H, 4.21; N, 10.96. Found: C, 53.24; H, 4.25; N, 10.93.

EXAMPLES 103–104

Compounds 129 and 130 were prepared by the following general procedure.

A mixture of the appropriate dihydro heterocycle (Compound 43 or 54) and 3 eq nickel peroxide was heated at reflux in cyclohexane for 5 days, after which time the reaction mixture was cooled to room temperature and filtered. The filtrate was concentrated to give the crude product, which was separated from unreacted starting material by careful HPLC (5% ethyl acetate/hexane).

Compound 129: 21% of white solid, mp 75°–76° C. Calcd for $C_{16}H_{17}N_2O_3S_1F_3$: C, 51.33; H, 4.58; N, 7.48; S, 8.56. Found: C, 51.50; H, 4.64; N, 7.41; S, 8.49.

Compound 130: 12% of white solid, mp 88°–89.5° C. Calcd for $C_{16}H_{17}N_2O_4F_3$: C, 53.63; H, 4.78; N, 7.82. Found: C, 53.77; H, 4.88; N, 7.67.

EXAMPLE 105–106

Compounds 81 and 82 were prepared by the following general procedure.

Compound 84 (3.54 g, 10 mmol) and the requisite alcohol (50 mmol) was stirred overnight at room temperature in 20 mL THF (for Compound 82) or neat (for Compound 81), after which time 10 mmol triethylamine was added and stirring continued overnight. For Compound 81, an additional 5.0 g of the alcohol was added and stirring continued overnight. In each case, on completion of the reaction, the reaction mixture was filtered to remove amine hydrochloride and the filtrate diluted with 100 mL methylene chloride. The organic layer was sequentially washed with dilute hydrochloric acid, water, and aqueous sodium bicarbonate, then dried with anhydrous magnesium sulfate, filtered, and solvent removed to give the crude product, which was purified via chromatotron, eluting with 2% ethyl acetate in cyclohexane.

Compound 81: colorless oil (45%) nD: 1.4619.

Compound 82: colorless oil (67%) nD: 1.4748.

EXAMPLES 107–114

Compounds 66–73 were prepared by the following general procedure.

The requisite amine (3.3 eq) was added to a solution of Compound 84 (1 eq) in ether at 0° C. The reaction mixture was stirred at 0° C. for 0.5 h, then at room temperature for 1–16 h before acidification with 1N HCl. The product was extracted with ether (3×), dried (MgSO$_4$), filtered, and concentrated. The crude product was chromatographed, eluting with 5:1 hexane:ethyl acetate, to afford the desired product.

Compound 66: colorless oil (57%) nD: 1.4905.

Compound 67: colorless oil (48%) nD: 1.4939.

Compound 68: white solid (54%) mp: 78°–81° C.

Compound 69: white solid (25%) mp: 96°–98° C.

Compound 70: white solid (38%) mp: 104°–106° C.

Compound 71: colorless oil (55%) nD: 1.5110.

Compound 72: colorless oil (45%) nD: 1.4805.

Compound 73: white solid (58%) mp: 58°–62° C.

EXAMPLES 115–117

Compounds 42, 49 and 52 were prepared by the following general procedure.

A solution of pyrazole (3–5 eq) and requisite acid chloride (1 eq) in THF was stirred at room temperature for Compound 52 for 16 h, or heated at reflux for Compounds 42 and 49 for 16 h. The reaction mixture was added to 1N HCl and extracted with ether (3×), dried (MgSO$_4$), filtered, and concentrated. The crude product was chromatographed, eluting with 5–10% ethyl acetate in hexane to afford the desired product. Compound 42: colorless oil (51%) nD: 1.4973.

Compound 49: colorless oil (31%) nD: 1.4920.

Compound 52: white solid (9%) mp: 86°–88° C.

EXAMPLE 118

This example illustrates the preparation of Compound 103, namely, 3-pyridinecarboxylic acid, 2-methoxy-5-(5-methyl-1,3,4-oxadiazol-2-yl)-4-(2-methylpropyl)-6-(trifluoromethyl)-, methyl ester.

A mixture of Compound 84 (9.2 g, 26 mmol), acethydrazide (3.8 g, 51.3 mmol), and methylene chloride (75 mL) was heated at reflux for six days. The slurry was filtered after cooling and the filtrate was washed with water then dried with MgSO$_4$. Rotary evaporation gave a crude white solid which was recrystallized from ether to give 4.15 g (41%) of the pyridineacethydrazide. A portion (3.91 g, 10 mmol) of this material was mixed with phosphorus oxychloride (7.3 mL) and phosphorus pentachloride (2.57 g, 12 mmol) and heated at reflux for four hours. The mixture was quenched into ice and extracted with methylene chloride and the organic layer was dried with MgSO4. After rotary evaporation, the residue was purified by silica gel chromatography with 2% ethyl acetate:hexane to give 1.5 g (40%) of Compound 103 as white crystals, mp: 65°–66° C. Anal: Calcd for C$_{16}$H$_{18}$F$_3$N$_3$O$_4$: C, 51.48; H, 4.86; N, 11.26. Found: C, 51.47; H, 4.84; N, 11.27.

EXAMPLE 119

This example illustrates the preparation of Compound 108, namely, 3-pyridinecarboxylic acid, 5-[(4-amino-1H-pyrazol-1-yl)carbonyl]-2-methoxy-4-(2-methylpropyl)-6-(trifluoromethyl)-, methyl ester.

A solution of 4-nitropyrazole (22.62 g, 200 mmol) in THF (100 mL) was cooled to 0° C., then sodium bis (trimethylsilyl)amide (204.3 mmol) in THF solution was added dropwise. A solution of Compound 84 (70.75 g, 200 mmol) in THF (100 mL) was then added dropwise at 0° C., then the pot was stirred at 25° C. for 30 minutes. The reaction mixture was then poured into 5% hydrochloric acid and extracted with dichloromethane. The organic layer was dried with MgSO$_4$ and the solvent removed by rotary evaporation. The residue was purified by silica gel chromatography (5% ethyl acetate:hexane) to give 70.14 g (82%) of the pyrazole amide (Compound 101).

A portion of the above pyrazole amide (51.84 g, 120 mmol) was dissolved in 500 mL methanol. After adding 5 g of 5% Pd/C catalyst, the mixture was placed on a Parr shaker overnight at 50 (385 kp) psig hydrogen, 25° C. The material was filtered, solvent evaporated, and the crude product purified by silica gel chromatography (10% ethyl acetate:hexane) to give 34.34 g (71%) of Compound 108 as a glassy solid. A small amount was kugelrohr distilled at 165°–170° C., 0.12 Torr (0.02 kp) to give analytically pure material which was still a glassy solid. Anal: Calcd for C$_{17}$H$_{19}$F$_3$N$_4$O$_4$: C, 51.00; H, 4.78; N, 13.99. Found: C, 51.05; H, 4.80; N, 13.90.

EXAMPLE 120

This example illustrates the preparation of Compound 104, namely, 3-pyridinecarboxylic acid, 5-[(4-chloro-1H-pyrazol-1-yl)carbonyl]-2-methoxy-4-(2-methylpropyl)-6-(trifluoromethyl)-, methyl ester.

To a solution of Compound 108 (4.00 g, 10 mmol), anhydrous cupric chloride (1.61 g, 12 mmol) in acetonitrile (20 mL) was added t-butyl nitrite (1.55 g, 15 mmol) at a rate maintaining the temperature below 30° C. After the addition was complete, the resulting solution was heated at 50°–60° C. for one hour. The solvent was removed by rotary evaporation and the residue was mixed with 50 mL water and 15 mL of concentrated hydrochloric acid. Extraction with methylene chloride followed by HPLC (2% ethyl acetate hexane) gave 0.9 g (21%) of Compound 104 as a yellow oil. Anal: Calcd for C$_{17}$H$_{17}$F$_3$Cl$_1$N$_3$O$_4$: C, 48.64; H, 4.08; N, 10.01; Cl, 8.44. Found: C, 48.71; H, 4.10; N, 9.99; Cl, 8.48.

EXAMPLE 121

This example illustrates the preparation of Compound 107, namely, 3-pyridinecarboxylic acid, 5-[[(4-(acetylamino)-1H-pyrazol-1-yl)carbonyl]-2-methoxy-4-(2-methylpropyl)-6-(trifluoromethyl)-, methyl ester.

A mixture of Compound 108 (2.38 g, 5.94 mmol) and acetic anhydride (25 mL) was stirred overnight at room temperature and then the volatiles were removed by rotary evaporation. The residue was recrystallized from hot methylcyclohexane to give 2.13 g (81%) of Compound 107 as fine white crystals, mp: 145°–146° C.

Anal: Calcd for C$_{19}$H$_{21}$F$_3$N$_4$O$_5$: C, 51.58; H, 4.78; N, 12.66. Found: C, 51.57; H, 4.81; N, 12.65.

EXAMPLE 122

Compound 83 was prepared by the following general procedure. To a solution of Compound 1 in DMF (2 mL solvent per mmol of Compound 1) under nitrogen was added 3 eq of the requisite alkyl halide and 6 eq of anhydrous potassium carbonate. The resulting mixture was stirred at room temperature overnight, then diluted with 15–20 volumes of water. This solution was extracted with methylene chloride, the resulting extracts dried with anhydrous magnesium sulfate, filtered and solvent removed to give the crude product which was purified by silica gel column chromatography.

Compound 83: colorless oil (54%), bp 95°–101° C. at 0.004 kp.

EXAMPLE 123

This example illustrates the preparation of Compound 43, namely, 3-pyridinecarboxylic acid, 5-(4,5-dihydro-2-oxazolyl)-2-methoxy-4-(2-methylpropyl)-6-(trifluoromethyl)-, methyl ester.

Compound 38 (5.70 g, 15 mmol) was stirred at room temperature in 25 mL thionyl chloride for 3 h. On removal of volatiles by rotary evaporation, 5.2 g (87%) of the chloroethyl amide was obtained as a white solid. A solution of this material in THF was stirred at room temperature overnight with sodium hydride (0.35 g, 14 mmol), after which time the reaction was heated at reflux overnight, then kept at room temperature for two days. The reaction mixture was then diluted with 1N hydrochloric acid and extracted with ether. The combined ether extracts were dried with anhydrous magnesium sulfate, filtered, and solvent removed to give the crude product which was purified by chromatotron, followed by recrystallization from methanol/water. Yield of product was 2.01 g (42% overall yield) of a white solid, mp 59°–61° C.

EXAMPLES 124–126

Compounds 50, 64 and 75 were prepared by the following general procedure.

A mechanically stirred mixture of the requisite hydroxyamide, e.g., Compound 38 or its methylated and dimethylated analogues, (1 eq) and phosphorous pentasulfide (1 eq) in xylene was heated at 100°–135° C. for 2–5 h. The reaction mixture was added to a saturated solution of sodium bicarbonate, extracted with ether (3×), dried (MgSO$_4$), filtered, and concentrated. The excess xylene was removed via kugelrohr distillation and the crude product was chromatographed eluting with 5–10% ethyl acetate in hexane to afford the desired product.

Compound 50: yellow solid (31%) mp: 59°–62° C.

Compound 64: pale orange oil (26%) nD: 1.5085.

Compound 75: pink oil (46%) nD: 1.5043.

EXAMPLE 127

This example illustrates the preparation of Compound 74, namely, 3-pyridinecarboxylic acid, 5-(4,5-dihydro-4-methyl-2-thiazolyl)-2-methoxy-4-(2-methylpropyl)-6-(trifluoromethyl)-, methyl ester.

A mixture of lithium sulfide (0.86 g, 0.018 mol) and the product from the reaction of methyl 5-[[(2-hydroxy-2-propyl)amino]carbony]-2-methoxy-4-(2-methypropyl)-6-(trifluoromethyl)-3-pyridinecarboxylate and phosphorus pentachloride (5.04 g, 0.012 mol) in 75 mL THF was stirred at room temperature for 4 days. The reaction mixture was filtered, concentrated, added to water (100 mL) and extracted with ether (3×100 mL), dried (MgSO4), filtered, and concentrated. The crude product was chromatographed, eluting with 7:1 petroleum ether:ethyl acetate to afford 2.77 g, (60%) of Compound 74 as a pale yellow oil. nD: 1.4999.

EXAMPLE 128

This example illustrates the preparation of Compound 54, namely, 3-pyridinecarbothioic acid, 5-(4,5-dihydro-2-thiazolyl)-2-methoxy-4-(2-methylpropyl)-6-(trifluoromethyl)-, S-methyl ester.

A solution of Compound 50 (2.53 g, 6.72 mmol) and 25% sodium hydroxide (50 mL) was heated at reflux for 1 h. The reaction mixture was cooled, diluted with water (50 mL), then washed with ether (2×50 mL). The aqueous phase was acidified with concentrated HCl and extracted with ether (3×50 mL), dried (MgSO$_4$), filtered, and concentrated to 1.90 g (5.24 mmol, 78%) of the desired carboxylic acid. A mixture of phosphorous pentachloride (1.10 g, 5.24 mmol) and this crude product was heated at 75° C. in 25 mL carbon tetrachloride for 3 h. The reaction mixture was cooled and concentrated to 2.00 g (100%) of the desired acid chloride. A solution of sodium methanethiolate (0.37 g, 5.24 mmol) and the crude acid chloride was stirred in 20 mL THF at room temperature for 72 h. The reaction mixture was added to 1N HCl (100 mL), extracted with ether (3×100 mL), dried (MgSO$_4$), filtered, and concentrated. The crude product was chromatographed eluting with 10% ethyl acetate in hexane to give 1.25 g (47%) Compound 54 as an oil which solidified to a yellow solid on standing. mp: 58°–64° C.

EXAMPLE 129

This example illustrates the preparation of Compound 98, namely, 3-pyridinecarboxylic acid, 5-(5,6-dihydro-4H-1,3-thiazin-2-yl)-2-methoxy-4-(2-methylpropyl)-6-(trifluoromethyl)-, methyl ester.

A mixture of Compound 84 (12 g, 33.92 mmol), 3-bromopropylamine hydrobromide (8.17 g, 37.32 mmol), triethylamine (7.59 g, 75 mmol), and 75 mL methylene chloride was refluxed for 90 minutes. After cooling, the mixture was washed with 5% hydrochloric acid, saturated NaHCO$_3$, and brine then dried with MgSO$_4$. Rotary evaporation gave 8.57 g (55%) of the bromoamide as a white powder which was used for the next step. A portion (4.55 g, 10 mmol) of the bromoamide was mixed with P$_2$S$_5$ (2.4 g, 10.8 mmol) in 30 mL xylene and heated to 120°–130° C., for 30 minutes. After cooling, 100 mL methylene chloride was added and the resulting solution was washed first with water and then with saturated NaHCO$_3$. The organic layer was dried with MgSO$_4$ and the solvent removed by rotary evaporation to give 2.75 g (70%) of Compound 98 as an amber oil. Anal: Calcd for $C_{17}H_{21}F_3N_2O_3S_1$: C, 52.30; H, 5.42; N, 7.18. Found: C, 50.83; H, 5.37; N, 6.80.

EXAMPLE 130

This example illustrates the preparation of Compound 99, namely, 3-pyridinecarboxylic acid, 5-(5,6-dihydro-4H-1,2-oxazin-2-yl)-2-methoxy-4-(2-methylpropyl)-6-(trifluoromethyl)-, methyl ester.

A portion (4.55 g, 10 mmol) of the bromo amide used for Compound 98 was dissolved in 20 mL methylene chloride and benzyltriethylammonium chloride (1.00 g) was added. A 20 mL portion of 50% NaOH was added and the mixture was stirred vigorously for two hours. The layers were separated and the organic layer was washed with brine then dried with MgSO$_4$ and the solvent rotary evaporated to give 3.61 g (96%) of Compound 99 as a pale yellow oil. n$_D$: 1.4855. Anal: Calcd for $C_{17}H_{21}F_3N_2O_4$: C, 54.54; H, 5.65; N, 7.48. Found: C, 54.56; H, 5.66; N, 7.48.

EXAMPLE 131

This example illustrates the preparation of Compound 106, namely, 3-pyridinecarboxylic acid, 5-cyano-2-methoxy-4-(2-methylpropyl)-6-(trifluoromethyl)-, methyl ester.

A flask was charged with 150 mL THF and saturated with ammonia at 0° C. While maintaining a slow flow of ammonia, a solution of Compound 84 (25 g, 70.7 mmol) in 50 mL THF was added dropwise at 0° C. After stirring for one hour at 0° C., the mixture was filtered and the filtrate rotary evaporated. The residue was dissolved in ether then washed with 5% hydrochloric acid, saturated $NaHCO_3$, and brine. The ether was dried with $MgSO_4$ then slowly evaporated under reduced pressure to give 19.74 g (84%) of the amide as a fine white powder, mp: 175°–176° C. A portion of this amide (5.01 g, 15 mmol) was mixed with toluene (50 mL) and chlorocarbonylsulfenyl chloride (10 g, 75 mmol) and heated at 100° C., overnight. The volatiles were removed by rotary evaporation and the residue was purified by HPLC (5% ethyl acetate:hexane) to give 3.46 g (59%) of Compound 106 as a yellow oil. Anal: Calcd for $C_{14}H_{15}F_3N_2O_3$: C, 53.17; H 4.78; N, 8.86. Found: C, 53.36; H, 4.72; N, 8.84.

EXAMPLE 132

This example illustrates the preparation of Compound 90, namely, 3-pyridinecarboxylic acid, 5-(tetrahydro-4-methylene-5-oxo-2-furanyl)-2-methoxy-4-(2-methylpropyl)-6-(trifluoromethyl)-, methyl ester.

A mixture of Compound 79 (7.66 g, 24 mmol), 2-bromomethylacrylic acid (3.96 g, 24 mmol), tin (II) chloride (4.55 g, 24 mmol), 2 mL glacial acetic acid, 4 mL water, and 7.5 mL DME was heated at reflux for 4 h. The reaction mixture was cooled to room temperature, diluted with 100 mL water and made basic with excess solid sodium bicarbonate. The resulting solution was extracted with two 100-mL portions of ether and the ether extracts dried with anhydrous magnesium sulfate, filtered, and solvent removed to afford the crude product which was purified by HPLC (8:1 hexane:ethyl acetate). The yield of Compound 90 was 4.3 g (46%) of a white solid, mp 107°–108° C.

Calcd for $C_{18}H_{20}F_3N_1O_5$: C, 55.81; H, 5.20; N, 3.62. Found: C, 55.76; H, 5.21; N, 3.58.

EXAMPLES 133–134

Compounds 93 and 94 were prepared by the following general procedure.

To a solution of Compound 79 (3.2 g, 10 mmol) and either ethanedithiol (1 mL) or propanedithiol (1.2 mL) in 50 mL methylene chloride previously cooled in an ice bath was added titanium tetrachloride (0.4 mL for Compound 93; 0.6 mL for Compound 94) under nitrogen. The resulting mixture was stirred overnight, warming to room temperature in the process. The reaction mixture was then washed with 100 mL water. The layers were separated and the aqueous layer was washed with 100 mL methylene chloride. The combined organic extracts were dried with anhydrous magnesium sulfate and filtered through a short silica gel column. The filtrate was concentrated and purified as described below.

Compound 93: HPLC (16:1 hexane:ethyl acetate); 96% pale yellow solid; mp 74°–75° C. Calcd for $C_{16}H_{20}F_3N_1O_3S_2$: C, 48.60; H, 5.10; N, 3.53; S, 16.22. Found: C, 48.65; H, 3.54; N, 3.53; N, 16.11.

Compound 94: HPLC (16:1 hexane:ethyl acetate); 61% colorless solid; mp 98°–100° C. Calcd for $C_{17}H_{22}F_3N_1O_3S_2$: C, 49.86; H, 5.42; N, 3.42; S, 15.66. Found: C, 49.91; H, 5.45; N, 3.38; S, 15.73.

EXAMPLES 135–136

Compounds 109 and 110 were prepared by the following general procedure.

A mixture of Compound 79 (1 eq) and either bis(trimethylsiloxy)ethane or bis(trimethylsiloxy)propane (2 eq) with a trace (approximately 1 mole%) of trimethylsilyltriflate was stirred at room temperature overnight under nitrogen. Pyridine (1 eq) was added and the pot was diluted with ether. The ether was silica gel filtered then evaporated. The crude product was purified by HPLC.(1–5% ethyl acetate:hexane).

Compound 109: white powder (59%) mp: 57°–58° C. Calcd for $C_{16}H_{20}F_3N_1O_5$: C, 52.89; H, 5.55; N, 3.86. Found: C, 52.71; H, 5.63; N, 3.72.

Compound 110: white solid (93%) mp: 77°–79° C. Calcd for $C_{17}H_{22}F_3N_1O_5$: C, 54.11; H, 5.88; N, 3.71. Found: C, 54.13; H, 5.89; N, 3.71.

EXAMPLES 137

This example illustrates the preparation of Compound 114, 3-pyridinecarboxylic acid, 2-methoxy-4-(2-methylpropyl)-5-(5-oxazolyl)-6-(trifluoromethyl)-, methyl ester.

Compound 79 (3.19 g, 10 mmol), tosylmethyl isocyanide (1.95 g, 10 mmol), and potassium carbonate (1.38 g, 10 mmol) were heated at reflux in 50 mL methanol for 19 h, after which time the reaction mixture was cooled to room temperature and solvent removed at reduced pressure. The residue was partitioned between ether and water, and the ether layer dried with anhydrous magnesium sulfate, filtered, and solvent removed to afford the crude product. Purification using HPLC (16:1 hexane:ethyl acetate) gave 2.05 g (57%) of Compound 114 as a clear oil, nD: 1.4909. Calcd for $C_{16}H_{17}F_3N_2O_4$: C, 53.63; H, 4.78; N, 7.82. Found: C, 53.79; H, 4.84; N, 7.77.

EXAMPLE 138

This example illustrates the preparation of Compound 118, namely, 3-pyridinecarboxylic acid, 4-cyclopropylmethyl-5-(1,3-dioxolan-2-yl)-2-methoxy-6-(trifluoromethyl)-, methyl ester.

To a mixture of Compound 115 (2.54 g, 8 mmol) and 1,2-bis(trimethylsilyloxy)ethane (3.30 g, 16 mmol) was added 2 drops trimethylsilyl triflate and the resulting solution stirred at room temperature for 25 h, after which time 1 mL pyridine was added. The mixture was diluted with 50 mL hexane and filtered through a column of silica gel. The eluent was concentrated to give a clear oil which was purified by HPLC (18:1 hexane:ethyl acetate) to give 1.63 g (56%) of product as an off-white solid, mp 64°–65° C. Calcd for $C_{16}H_{18}F_3N_1O_5$: C, 53.19; H, 5.02; N, 3.88. Found: C, 53.36; H, 5.04; N, 3.85.

EXAMPLE 139

This example illustrates the preparation of Compound 122, namely, 3-pyridinecarboxylic acid, 2-methoxy-4-(2-methylpropyl)-5-(1,3-oxathiolan-2-yl)-6-(trifluoromethyl)-, methyl ester.

A mixture of Compound 79 (15.96 g, 50 mmol), 2-mercaptoethanol (4.69 g, 60 mmol), and methylene chloride (125 mL) was cooled to −78° C., and then TiCl4 (2.16 g, 11.4 mmol) was added dropwise by syringe. After 30 minutes, the cooling was removed and the pot was stirred at 25°–C., overnight. The reaction mixture was quenched into iced water, extracted with ether, and then the ether was removed by rotary evaporation. The residue was filtered through silica gel with 2% ethyl acetate:hexane and the solvent evaporated. The product was then recrystallized from hot hexane to give 10.84 g (57%) of Compound 122 as a fine white powder, mp: 79°–81° C. Calcd for $C_{16}H_{20}N_1O_4Si$: C, 50.65; H, 5.31; N, 3.69; S, 8.45. Found: C, 50.70; H, 5.33; N, 3.67; S, 8.45.

EXAMPLE 140

This example illustrates the preparation of Compound 123, namely, 3-pyridinecarboxylic acid, 2-methoxy-4-(2-methylpropyl)-5-(4-oxo-1,3-dioxolan-2-yl)-6-(trifluoromethyl)-, methyl ester.

Trimethylsilyl(trimethylsilyloxy)acetate (6.61 g, 30 mmol) was mixed with Compound 79 (4.79 g, 15 mmol) and then three drops of trimethylsilyl triflate were added. The mixture was stirred overnight at room temperature overnight. Ether (250 mL) and pyridine (2 mL) were added and the mixture was filtered. After evaporating the ether, the residue was purified by silica gel chromatography with 5% ethyl acetate : hexane to give 3.50 g (62%) of Compound 123 as a white solid, mp: 94°–96° C. Calcd for $C_{16}H_{18}F_3N_1O_6$: C, 50.93; H, 4.81; N, 3.71. Found: C, 50.97; H, 4.83; N, 3.70.

EXAMPLES 141–142

Compounds 126 and 127 were prepared by the following general procedure.

A solution of metachloroperbenzoic acid (4.16 g, 20 mmol) in 25 mL methylene chloride was added slowly to a mixture of Compound 122 (7.59 g, 20 mmol) in 25 mL methylene chloride and stirred for two hours at 25° C. The mixture was then washed with 10% sodium sulfite followed by saturated $NaHCO_3$ and brine. The organic layer was dried with $MgSO_4$ and the solvent evaporated. The residue was purified by silica gel chromatography (10% ethyl acetate:hexane) to give 7.64 g (97%) of Compound 126 as a white solid, mp: 67°–69° C. A portion (3.98 g, 10 mmol) of this material was dissolved in 25 mL methylene chloride and a solution of m-chloroperbenzoic acid (2.5 g, 12 mmol) in 25 mL methylene chloride was added and the mixture stirred overnight. A precipitate was filtered off and the filtrate was worked up as before. Silica gel chromatography of the crude material gave 1.61 g (39%) of Compound 127 as a white solid, mp: 117°–120° C.

Compound 126: Calcd for $C_{16}H_{20}F_3N_1O_6S_1$: C, 48.60; H, 5.10; N, 3.54; S, 8.11. Found: C, 48.57; H, 5.10; N, 3.51; S, 8.09.

Compound 127: Calcd for $C_{16}H_{20}F_3N_1O_6S_1$: C, 46.71; H, 4.90; N, 3.40; S, 7.79. Found: C, 46.69; H, 4.91; N, 3.39; S, 7.73.

EXAMPLES 143–144

Compounds 14 and 15 were prepared by the following general procedure.

The requisite aminopyridine Compound 36 or Compound 32 (10 mmol), 2,5-dimethoxytetrahydrofuran (1.45 g, 11 mmol) were heated at 90° C. in 20 mL glacial acetic acid for 1.5–2 h, after which time the reaction mixture was cooled to room temperature and poured into excess aqueous sodium carbonate. The resulting mixture was extracted with three 100-mL portions of ether, dried with anhydrous magnesium sulfate, filtered and solvent removed to give the crude product which was purified by column chromatography or chromatotron, eluting with 10:1 hexane:ethyl acetate.

Compound 14: yellow oil (84%)

Compound 15: white solid (81%), mp 36°–37° C.

EXAMPLES 145–147

Compounds 56, 76 and 61 were prepared by the following general procedure.

A solution of the requisite amine (Compound 32 or Compound 36) (1 eq), trimethyl orthoformate (3 eq), and p-toluenesulfonic acid (0.1 eq) were heated at 90°–106° C. for 3–16 h. The reaction mixture was then cooled, concentrated, and filtered through silica gel. The crude product was chromatographed eluting with 8–10% ethyl acetate:petroleum ether to afford the desired product.

Compound 56: colorless oil (57%) nD: 1.4815.

Compound 76: pale yellow oil (49%) nD: 1.4755.

Compound 61: colorless oil (63%) nD: 1.4742.

EXAMPLES 148–149

Compounds 57 and 62 were prepared by the following general procedure.

A mixture of the requisite amine, Compound 32 or Compound 36, (1 eq), dimethylformamide dimethyl acetal (6 eq), and p-toluenesulfonic acid (0.1 eq) was heated at reflux overnight. Upon cooling, the reaction mixture was concentrated, suspended in ether, filtered, and concentrated. The crude product was filtered through silica gel, and subsequent recrystallization in methanol/water for Compound 37, or purification via chromatography, eluting with 8:1 petroleum ether:ethyl acetate for Compound 62 afforded the desired product.

Compound 57: white solid (62%) mp: 52°–55° C.

Compound 62: colorless oil (80%) nD: 1.4926.

EXAMPLES 150–152

Compounds 58, 77 and 78 were prepared by the following general procedure.

Formic acid (30 eq) was added to acetic anhydride (26 eq) at 0° C. The resulting mixture was allowed to gradually warm to room temperature after which the mixture was heated at 50°–65° C. for 10–15 minutes. The reaction mixture was then cooled to 0° C., and the requisite aminopyridine (Compound 32 or Compound 36) (1 eq) was added thereto. After stirring at room temperature for 16 h, the reaction mixture was concentrated. The residue was dissolved in ether, filtered, and concentrated. Purification via chromatography eluting with 3:1 ethyl acetate:hexane afforded the desired product as a solid.

Lawesson's reagent (0.5 eq) was added to a solution of the above product in HMPA, and the reaction mixture was heated at 100° C. for 3 h. Upon cooling, the reaction mixture was added to water and extracted with ether (3×). The organic phase was washed with water (1×), dried ($MgSO_4$), filtered and concentrated.

A solution of the requisite thioamide, (1 eq), methyl iodide (1 eq), and potassium carbonate (1.5 eq) in DMF was heated at 55°–60° C. for 3–4 h. Upon cooling, the reaction mixture was diluted with water and extracted with ether (3×), dried ($MgSO_4$), filtered and concentrated. The crude product was chromatographed eluting with 8–10% ethyl acetate in hexane to afford the desired product as an oil.

Compound 58: light yellow oil (44%) nD: 1.5169.
Compound 77: colorless oil (75%) nD: 1.5077.
Compound 78: colorless oil (61%) nD: 1.5066.

The following is a listing by number and nomenclature of compounds herein.

| Compound No. | Name |
|---|---|
| 1 | 3,5-pyridinedicarboxylic acid, 2-hydroxy-4-(2-methylpropyl)-6-(trifluoromethyl)-, dimethyl ester |
| 2 | 3,5-pyridinedicarboxylic acid, 2-methoxy-4-(2-methylpropyl)-6-(trifluoromethyl)-, dimethyl ester |
| 3 | 3,5-pyridinedicarboxylic acid, 2-ethoxy-4-(2-methylpropyl)-6-(trifluoromethyl)-, 3-ethyl 5-methyl ester, hydrate (1:0.4) |
| 4 | 3,5-pyridinedicarboxylic acid, 2-methoxy-4-(2-methylpropyl)-6-(trifluoromethyl)-, 3-ethyl 5-methyl ester |
| 5 | 3,5-pyridinedicarboxylic acid, 2-(1-methylethoxy)-4-(2-methylpropyl)-6-(trifluoromethyl)-, 3-ethyl 5-methyl ester |
| 6 | 3,5-pyridinedicarboxylic acid, 2-ethoxy-4-(2-methylpropyl)-6-(trifluoromethyl)-, dimethyl ester |
| 7 | 3,5-pyridinedicarboxylic acid, 4-(2-methylpropyl)-2-propyloxy-6-(trifluoromethyl)-, 3-ethyl 5-methyl ester |
| 8 | 3-pyridinecarboxylic acid, 6-ethoxy-4-(2-methylpropyl)-5-[(methylthio)carbonyl]-2-(trifluoromethyl)-, methyl ester |
| 9 | 3,5-pyridinedicarboxylic acid, 4-cyclopropyl-2-methoxy-6-(trifluoromethyl)-, dimethyl ester |
| 10 | 3-pyridinecarboxylic acid, 5-(aminocarbonyl)-1,2,3,4-tetrahydro-4-(2-methylpropyl)-6-(pentafluoroethyl)-, ethyl ester |
| 11 | 3,5-pyridinedicarboxylic acid, 2-methoxy-4-(2-methylpropyl)-6-(pentafluoroethyl)-, 5-ethyl 3-methyl ester |
| 12 | 3,5-pyridinedicarbothioic acid, 4-cyclopropyl-2-methoxy-6-(trifluoromethyl)-, S,S-dimethyl ester |
| 13 | 3,5-pyridinedicarboxylic acid, 4-(carboxymethyl)-2-methoxy-6-(trifluoromethyl)-, dimethyl ester |
| 14 | 3-pyridinecarboxylic acid, 6-methoxy-4-(2-methylpropyl)-5-(1H-pyrrol-1-yl)-2-(trifluoromethyl)-1 methyl ester |
| 15 | 3-pyridinecarboxylic acid, 2-methoxy-4-(2-methylpropyl)-5-(1H-pyrrol-1-yl)-6-(trifluoromethyl)-, methyl ester |
| 16 | 3,5-pyridinedicarboxylic acid, 2-methoxy-4-(2-methylpropyl)-6-(trifluoromethyl)-,5 butyl 3-methyl ester |
| 17 | 3-pyridinecarboxylic acid, 5-[(dimethylamino)carbony]-6-ethoxy-4-(2-methylpropyl)-2-(trifluoromethyl)-, methyl ester |
| 18 | 3,5-pyridinedicarboxylic acid, 2-ethoxy-4-(2-methylpropyl)-6-(trifluoromethyl)-, 5-methyl ester |
| 19 | 3,5-pyridinedicarbothioic acid, 2-ethoxy-4-(2-methylpropyl)-6-(trifluoromethyl)-, S,S-dimethyl ester |
| 20 | 3-pyridinecarboxylic acid, 5-cyano-6-methoxy-4-(2-methylpropyl)-2-(trifluoromethyl)-, methyl ester |
| 21 | 3-pyridinecarboxylic acid, 6-methoxy-5-[(methylamino)carbonyl]-4-(2-methylpropyl)-2-(trifluoromethyl)-, methyl ester |
| 22 | 3-pyridinecarboxylic acid, 5-cyano-1,6-dihydro-4-(2-methylpropyl)-6-oxo-2-(trifluoromethyl)-, methyl ester |
| 23 | 3,5-pyridinecarboxylic acid, 4-(2-methyl-propyl)-2-(2-propenyloxy)-6-(trifluoromethyl)-, 3-ethyl 5-methyl ester, hydrate (1:0.3) |

-continued

| Compound No. | Name |
|---|---|
| 24 | 3-pyridinecarboxylic acid, 6-methoxy-4-(2-methylpropyl)-5-(1H-pyrazol-1-ylcarbonyl)-2-(trifluoromethyl)-, methyl ester, hydrate (1:0.3) |
| 25 | 3-pyridinecarboxylic acid, 5-[[(2-hydroxyethyl)amino]carbonyl]-6-methoxy-4-(2-methylpropyl)-2-(trifluoromethyl)-, methyl ester, hydrate (1:0.2) |
| 26 | 3,5-pyridinedicarboxylic acid, 2-(difluoromethyl)-6-methoxy-4-(2-methylpropyl)-, 5-ethyl 3-methyl ester |
| 27 | 3-pyridinecarboxylic acid, 5-(4,5-dihydro-2-oxazolyl)-6-methoxy-4-(2-methylpropyl)-2-(trifluoromethyl)-, methyl ester |
| 28 | 3-pyridinecarboxylic acid, 6-methoxy-4-(2-methylpropyl)-5-(1H-imidazol-1-ylcarbonyl)-2-(trifluoromethyl)-, methyl ester |
| 29 | 3,5-pyridinedicarboxylic acid, 2-(chlorodifluoromethyl)-6-methoxy-4-(2-methylpropyl)-, 5-ethyl 3-methyl ester |
| 30 | 3,5-pyridinedicarboxylic acid, 2-(chlorodifluoromethyl)-6-methoxy-4-(2-methylpropyl)-, dimethyl ester |
| 31 | 3,5-pyridinedicarboxylic acid, 2-(difluoromethyl)-6-methoxy-4-(2-methylpropyl)-, dimethyl ester |
| 32 | 3-pyridinecarboxylic acid, 5-amino-6-methoxy-4-(2-methylpropyl)-2-(trifluoromethyl)-, methyl ester |
| 33 | 3-pyridinecarboxylic acid, 6-methoxy-4-(2-methylpropyl)-5-[(methylthio)carbonyl]-2-(trifluoromethyl)-, methyl ester |
| 34 | 3-pyridinecarboxylic acid, 2-methoxy-4-(2-methylpropyl)-5-[(methylthio)carbonyl]-6-(trifluoromethyl)-, methyl ester |
| 35 | 3-pyridinecarboxylic acid, 5-(aminocarbonyl)-1,4,5,6-tetrahydro-4-(2-methylpropyl)-6-oxo-2-(trifluoromethyl)-, ethyl ester |
| 36 | 3-pyridinecarboxylic acid, 5-amino-2-methoxy-4-(2-methylpropyl)-6-(trifluoromethyl)-, methyl ester |
| 37 | 3-pyridinecarboxylic acid, 2-methoxy-5-[(methylamino)carbonyl]-4-(2-methylpropyl)-6-(trifluoromethyl)-, methyl ester |
| 38 | 3-pyridinecarboxylic acid,5-[[(2-hydroxyethyl)amino]carbonyl]-2-methoxy-4-(2-methylpropyl)-6-(trifluoromethyl)-, methyl ester |
| 39 | 3,5-pyridinedicarboxylic acid, 2-ethoxy-4-(2-methylpropyl)-6-(trifluoromethyl)-, diethyl ester |
| 40 | 3-pyridinecarboxylic acid, 5-(hydroxymethyl)-2-methoxy-4-(2-methylpropyl)-6-(trifluoromethyl)-, methyl ester |
| 41 | 3-pyridinecarboxylic acid, 2-methoxy-5-[(methylimino) (methylthio)methyl]-4-(2-methylpropyl)-6-(trifluoromethyl)-, methyl ester |
| 42 | 3-pyridinecarboxylic acid, 2-methoxy-4-(2-methylpropyl)-5-(1H-pyrazol-1-ylcarbonyl)-6-(trifluoromethyl)-, methyl ester |
| 43 | 3-pyridinecarboxylic acid, 5-(4,5-dihydro-2-oxazolyl)-2-methoxy-4-(2-methylpropyl)-6-(trifluoromethyl)-, methyl ester |
| 44 | 3,5-pyridinedicarboxylic acid, 2-methoxy-4-(2-methylpropyl)-6-(trifluoromethyl)-, 5-ethyl 3-methyl ester |
| 45 | 3-pyridinecarboxylic acid, 2-ethoxy-4-(2-methylpropyl)-5-[(methylthio)carbonyl]-6-(trifluoromethyl)-, methyl ester |
| 46 | 3-pyridinecarboxylic acid, 2-ethoxy-5-((methylimino) (methylthio) methyl]-4-(2-methylpropyl)-6-(trifluoromethyl)-, methyl ester |
| 47 | 3,5-pyridinedicarbothioic acid, 2-methoxy-4-(2-methylpropyl)-6-(trifluoromethyl)-, S,S,-dimethyl ester |

| Compound No. | Name |
|---|---|
| 48 | 3,5-pyridinedicarboxylic acid, 4-cyclobutyl-2-methoxy-6-(trifluoromethyl)-, dimethyl ester |
| 49 | 3-pyridinecarboxylic acid, 2-ethoxy-4-(2-methylpropyl)-5-(1H-pyrazol-1-ylcarbonyl)-6-(trifluoromethyl)-, methyl ester |
| 50 | 3-pyridinecarboxylic acid, 5-(4,5-dihydro-2-thiazolyl)-2-methoxy-4-(2-methylpropyl)-6-(trifluoromethyl)-, methyl ester |
| 51 | 3-pyridinecarboxylic acid, 2-methoxy-4-(2-methylpropyl)-5-[(3-methyl-1H-pyrazol-1-yl)carbonyl]-6-(trifluoromethyl)-, methyl ester |
| 52 | 3-pyridinecarboxylic acid, 4-cyclobutyl-2-methoxy-5-(1H-pyrazol-1-ylcarbonyl)-6-(trifluoromethyl)-, methyl ester |
| 53 | 3-pyridinecarboxylic acid, 5-[(ethylthio)carbonyl])-2-methoxy-4-(2-methylpropyl)-6-(trifluoromethyl)-, methyl ester |
| 54 | 3-pyridinecarbothioic acid, 5-(4,5-dihydro-2-thiazolyl)-2-methoxy-4-(2-methylpropyl)-6-(trifluoromethyl)-, S-methyl ester |
| 55 | 3-pyridinecarboxylic acid, 6-methoxy-5-(methylimino) (methylthio) methyl]-4-(2-methylpropyl)-2-(trifluoromethyl)-, methyl ester |
| 56 | 3-pyridinecarboxylic acid, 6-methoxy-5-[(methoxymethylene) amino]-4-(2-methylpropyl)-2-(trifluoromethyl)-, methyl ester |
| 57 | 3-pyridinecarboxylic acid, 5([(dimethylamino)methylene]amino)-6-methoxy-4-(2-methylpropyl)-2-(trifluoromethyl)-, methyl ester |
| 58 | 3-pyridinecarboxylic acid, 6-methoxy-4-(2-methylpropyl)-5-[(methylthiomethylene)]amino-2-(trifluoromethyl)-, methyl ester |
| 59 | 4-cyclobutyl-2-methoxy-3,5-bis(1H-pyrazol-1-ylcarbonyl)-6-(trifluoromethyl)-pyridine |
| 60 | 3-pyridinecarboxylic acid, 2-methoxy-4-(2-methylpropyl)-5-(1H-1,2,4-triazol-1-ylcarbonyl)-6-(trifluoromethyl)-, methyl ester |
| 61 | 3-pyridinecarboxylic acid, 5-[(ethoxymethylene)amino]-2-methoxy-4-(2-methylpropyl)-6-(trifluoromethyl)-, methyl ester |
| 62 | 3-pyridinecarboxylic acid, 5-[[(dimethylamino)methylene]amino]-2-methoxy-4-(2-methylpropyl)-6-(trifluoromethyl)-, methyl ester |
| 63 | 3,5-pyridinedicarboxylic acid, 2-methoxy-4-(1-methylethyl)-6-(trifluoromethyl)-, dimethyl ester |
| 64 | 3-pyridinecarboxylic acid, 5-(4,5-dihydro-5-methyl-2-thiazolyl)-2-methoxy-4-(2-methylpropyl)-6-(trifluoromethyl)-, methyl ester |
| 65 | 3,5 pyridinedicarbothioic acid, 4-cyclobutyl-2-methoxy-6-(trifluoromethyl)-, S,S-dimethyl ester |
| 66 | 3-pyridinecarboxylic acid, 2-methoxy-4-(2-methylpropyl)-5-(1-pyrrolidinylcarbonyl)-6-(trifluoromethyl)-, methyl ester |
| 67 | 3-pyridinecarboxylic acid, 2-methoxy-4-(2-methylpropyl)-5-(1-piperidinylcarbonyl)-6-(trifluoromethyl)-, methyl ester |
| 68 | 3-pyridinecarboxylic acid, 5-(1-azetidinylcarbonyl)-2-methoxy-4-(2-methylpropyl)-6-(trifluoromethyl)-, methyl ester |
| 69 | 3-pyridinecarboxylic acid, 2-methoxy-4-(2-methylpropyl)-5-(4-morpholinyl) carbonyl-6-(trifluoromethyl)-, methyl ester |
| 70 | 3-pyridinecarboxylic acid, 2-methoxy-4-(2-methylpropyl)-5-(4-thiomorpholinylcarbonyl)-6-(trifluoromethyl)-, methyl ester |
| 71 | 3-pyridinecarboxylic acid, 2-methoxy-4-(2-methylpropyl)-5-(3-thiazolidinylcarbonyl)-6-(trifluoromethyl)-, methyl ester |
| 72 | 3-pyridinecarboxylic acid,1-methoxy-5-[(2-methyl-1-aziridinyl) carbonyl]-4-(2-methylpropyl)-6-(trifluoromethyl)-, methyl ester |
| 73 | 3-pyridinecarboxylic acid, 5-[(hexahydro-1H-azepin-1-yl) carbonyl]-2-methoxy-4-(2-methylpropyl)-6-(trifluoromethyl)-, methyl ester |
| 74 | 3-pyridinecarboxylic acid, 5-(4,5-dihydro-4-methyl-2-thiazolyl)-2-methoxy-4-(2-methylpropyl)-6-(trifluoromethyl)-, methyl ester |
| 75 | 3-pyridinecarboxylic acid, 5-(4,5-dihydro-4,4-dimethyl-2-thiazolyl)-2-methoxy-4-(2-methylpropyl)-6-(trifluoromethyl)-, methyl ester |
| 76 | 3-pyridinecarboxylic acid, 2-methoxy-5-[(methoxymethylene) amino]-4-(2-methylpropyl)-6-(trifluoromethyl)-, methyl ester |
| 77 | 3-pyridinecarboxylic acid, 2-methoxy-4-(2-methylpropyl)-5-[[(methylthio) methylene]amino]-6-(trifluoromethyl)-, methyl ester |
| 78 | 3-pyridinecarboxylic acid, 5-[[(ethylthio)methylene]amino]-2-methoxy-4-(2-methylpropyl)-6-(trifluoromethyl)-, methyl ester |
| 79 | 3-pyridinecarboxylic acid, 5-formyl-2-methoxy-4-(2-methylpropyl)-6-(trifluoromethyl) methyl ester |
| 80 | 3,5-pyridinedicarboxylic acid, 2-(cyanomethoxy)-4-(2-methylpropyl)-6-(trifluoromethyl)-, dimethyl ester |
| 81 | 3,5-pyridinedicarboxylic acid, 2-methoxy-4-(2-methylpropyl)-6-(trifluoromethyl)-, 5-(2-fluoroethyl) 3-methyl ester |
| 82 | 3,5-pyridinedicarboxylic acid, 2-methoxy-4-(2-methylpropyl)-6-(trifluoromethyl)-, 3-methyl 5-(2-propynyl) ester |
| 83 | 3,5-pyridinedicarboxylic acid, 4-(2-methylpropyl)-2-(2-propynyloxy)-6-(trifluoromethyl)-, dimethyl ester |
| 84 | 3-pyridinecarboxylic acid, 5-(chlorocarbonyl)-2-methoxy-4-(2-methylpropyl)-6-(trifluoromethyl)-, methyl ester |
| 85 | 3-pyridinecarboxylic acid, 2-(cyanomethyl)-4-(2-methylpropyl)-5-(1H-pyrazol-1-ylcarbonyl)-6-(trifluoromethyl)-, methyl ester |
| 86 | 3,5-pyridinedicarboxylic acid, 2-methoxy-4-methyl-6-(trifluoromethyl)-, dimethyl ester |
| 87 | 3,5-pyridinedicarboxylic acid, 4-(bromomethyl)-2-methoxy-6-(trifluoromethyl)-, dimethyl ester |
| 88 | 3,5-pyridinedicarboxylic acid, 2-methoxy-4-(methoxymethyl)-6-(trifluoromethyl)-, dimethyl ester |
| 89 | 3,5-pyridinedicarboxylic acid, 2-methoxy-4-[(methylthio)methyl]-6-(trif1uoromethyl)-, dimethyl ester |
| 90 | 3-pyridinecarboxylic acid, 5-(tetrahydro-4-methylene-5-oxo-2-furanyl)-2-methoxy-4-(2-methylpropyl)-6-(trifluoromethyl)-, methyl ester |
| 91 | 3,5-pyridinedicarboxylic acid, 2-methoxy-4-propyl-6-(trifluoromethyl)-, dimethyl ester |
| 92 | 3,5-pyridinedicarboxylic acid, 4-(cyclopropylmethyl)-2-methoxy-6-(trifluoromethyl)-, dimethyl ester |
| 93 | 3-pyridinecarboxylic acid, 5-(1,3-dithiolan-2-yl)-2-methoxy-4-(2-methylpropyl)-6-(trifluoromethyl)-, methyl ester |
| 94 | 3-pyridinecarboxylic acid, 5-(1,3-dithian-2-yl)-2-methoxy-4-(2-methylpropyl)-6-(trifluoromethyl)-, methyl ester |
| 95 | 3-pyridinecarboxylic acid, 5-[[chloro[2-chloroethyl)imino]methyl]-2-methoxy-4-(2-methylpropyl)-6-(trifluoromethyl)-, methyl ester |

| Compound No. | Name |
|---|---|
| 96 | 3,5-pyridinedicarboxylic acid, 4-(2-methylpropyl)-2-(trichloromethoxy)-6-(trifluoromethyl)-, dimethyl ester |
| 97 | 3-pyridinecarboxylic acid, 5-[[(3-bromopropyl)amino]carbonyl]-2-methoxy-4-(2-methylpropyl)-6-(trifluoromethyl)-, methyl ester |
| 98 | 3-pyridinecarboxylic acid, 5-(5,6-dihydro-4H-1,3-thiazin-2-yl)-2-methoxy-4-(2-methylpropyl)-6-(trifluoromethyl)-, methyl ester |
| 99 | 3-pyridinecarboxylic acid, 5-(5,6-dihydro-4H-1,2-oxazin-2-yl)-2-methoxy-4-(2-methylpropyl)-6-(trifluoromethyl)-, methyl ester |
| 100 | 3,5-pyridinedicarboxylic acid, 2-methoxy-4-(2-methylpropyl)-6-(trifluotomethyl)-, 3-methyl ester 5-(2-acetylhydrazide) |
| 101 | 3-pyridinecarboxylic acid, 2-methoxy-4-(2-methylpropyl)-5-[(4-nitro-1H-pyrazol-1-yl)carbonyl]-6-(trifluoromethyl)-, methyl ester |
| 102 | 3-pyridinecarboxylic acid, 5-[(3-fluoro-1H-pyrazol-1-yl)carbonyl]-2-methoxy-4-(2-methylpropyl)-6-(trifluoromethyl)-, methyl ester |
| 103 | 3-pyridinecarboxylic acid, 2-methoxy-5-(5-methyl-1,3,4-oxadiazol-2-yl)-4-(2-methylpropyl)-6-(trifluoromethyl)-, methyl ester |
| 104 | 3-pyridinecarboxylic acid, 5-[(4-chloro-1H-pyrazol-1-yl)carbonyl]-2-methoxy-4-(2-methylpropyl)-6-(trifluoromethyl)-, methyl ester |
| 105 | 3-pyridinecarboxylic acid, 5-(aminocarbonyl)-2-methoxy-4-(2-methylpropyl)-6-(trifluoromethyl)-, methyl ester |
| 106 | 3-pyridinecarboxylic acid, 5-cyano-2-methoxy-4-(2-methylpropyl)-6-(trifluoromethyl)-, methyl ester |
| 107 | 3-pyridinecarboxylic acid, 5-[[4-(acetylamino)-1H-pyrazol-1-yl]carbonyl]-2-methoxy-4-(2-methylpropyl)-6-(trifluoromethyl)-, methyl ester |
| 108 | 3-pyridinecarboxylic acid, 5-[(4-amino-1H-pyrazol-1-yl)carbonyl]-2-methoxy-4-(2-methylpropyl)-6-(trifluoromethyl)-, methyl ester |
| 109 | 3-pyridinecarboxylic acid, 5-(1,3-dioxolan-2-yl)-2-methoxy-4-(2-methylpropyl)-6-(trifluoromethyl)-, methyl ester |
| 110 | 3-pyridinecarboxylic acid, 5-(1,3-dioxan-2-yl)-2-methoxy-4-(2-methylpropyl)-6-(trifluoromethyl)-, methyl ester |
| 111 | 3-pyridinecarboxylic acid, 5-[(4-cyano-1H-pyrazol-1-yl)carbonyl]-2-methoxy-4-(2-methylpropyl)-6-(trifluoromethyl)-, methyl ester |
| 112 | 3,5-pyridinedicarboxylic acid, 2-methoxy-4-(2-methylpropyl)-6-(trifluoromethyl)-, 3-methyl 5-(2,2,2-trifluoroethyl) ester |
| 113 | 3-pyridinecarboxylic acid, 5-(chlorocarbonyl)-4-(cyclopropylmethyl)-2-methoxy-6-(trifluoromethyl)-, methyl ester |
| 114 | 3-pyridinecarboxylic acid, 2-methoxy-4-(2-methylpropyl)-5-(5-oxyazolyl)-6-(trifluoromethyl)-, methyl ester |
| 115 | 3-pyridinecarboxylic acid, 4-(cyclopropylmethyl)-5-formyl-2-methoxy-6-(trifluoromethyl)-, methyl ester |
| 116 | 3-pyridinecarboxylic acid, 4-(cyclopropylmethyl)-2-methoxy-5-(1H-pyrazol-1-ylcarbonyl)-6-(trifluoromethyl)-, methyl ester |
| 117 | 3-pyridinecarboxylic acid, 4-(cyclopropylmethyl)-5-(hydroxymethyl)-2-methoxy-6-(trifluoromethyl)-, methyl ester |
| 118 | 3-pyridinecarboxylic acid, 4-(cylcoproylmethyl)-5-(1,3-dioxolan-2-yl)-2-methoxy-6-(trifluoromethyl)-, methyl ester |
| 119 | 3-pyridinecarboxylic acid, 4-(cylcopropylmethyl)-2-methoxy-5-[(methylthio)carbonyl]-6-(trifluoromethyl)-, methyl ester |
| 120 | 3-pyridinecarboxylic acid, 5-[(4-bromo-1-oxobutyl)amino]-2-methoxy-4-(2-methylpropyl)-6-(trifluoromethyl)-, methyl ester |
| 121 | 3-pyridinecarboxylic acid, 5-[(dihydro-2(3H)-furanylidene)amino]-2-methoxy-4-(2-methylpropyl)-6-(trifluoromethyl)-, methyl ester |
| 122 | 3-pyridinecarboxylic acid, 2-methoxy-4-(2-methylpropyl)-5-(1,3-oxathiolan-2-yl)-6-(trifluoromethyl)-, methyl ester |
| 123 | 3-pyridinecarboxylic acid, 2-methoxy-4-(2-methylpropyl)-5-(4-oxo-1,3-dioxolan-2-yl)-6-(trifluoromethyl)-, methyl ester |
| 124 | 3,5-pyridinedicarboxylic acid, 2-methoxy-4-(2-methylpropyl)-6-(trifluoromethyl)-, 3-methyl ester,5-(ethoxymethylene)hydrazide |
| 125 | 3-pyridinecarboxylic acid, 2-methoxy-4-(2-methylpropyl)-5-(1,3,4-oxadiazol-2-yl)-6-(trifluoromethyl)-, methyl ester |
| 126 | 3-pyridinecarboxylic acid, 2-methoxy-4-(2-methylpropyl)-5-(1,3-oxathiolan-2-yl)-6-(trifluoromethyl)-, methyl ester, S-oxide |
| 127 | 3-pyridinecarboxylic acid, 2-methoxy-4-(2-methylpropyl)-5-(3,3-dioxo-1,3-oxathiolan-2-yl)-6-(trifluoromethyl)-, methyl ester |
| 128 | 3-pyridinecarboxylic acid, 5-[[2-hydroxyethyl)imino]methyl]-2-methoxy-4-(2-methylpropyl)-6-(trifluoromethyl)-, methyl ester |
| 129 | 3-pyridinecarboxylic acid, 2-methoxy-4-(2-methylpropyl)-5-(2-thizaolyl)-6-(trifluoromethyl)-, methyl ester |
| 130 | 3-pyridinecarboxylic acid, 2-methoxy-4-(2-methylpropyl)-5-(2-oxazolyl)-6-(trifluoromethyl)-, methyl ester |
| 131 | 3-pyridinacarbothioic acid, 2-methoxy-4-(2-methylpropyl)-5-(1H-pyrazol-1-ylcarbonyl)-6-(trifluoromethyl)-, S-methyl ester |
| 132 | 3-pyridinecarboxylic acid, 5-(2-isoxazolidinecarbonyl)-2-methoxy-4-(2-methy-propyl)-6-(trifluornmethyl)-, methyl ester |
| 133 | 3-pyridinecarbothioic acid, 5-(chlorocarbonyl)-2-methoxy-4-(2-methylpropyl)-6-(trifluoromethyl)-, S-methyl ester |
| 134 | 3-pyridinecarbothioic acid, 5-(hydroxymethyl)-2-methoxy-4-(2-methylpropyl)-6-(trifluoromethyl)-, S-methyl ester |
| 135 | 3-pyridinecarbothioic acid, 5-formyl-2-methoxy-4-(2-methylpropyl)-6-(trifluoromethyl)-, S-methyl ester |
| 136 | 3-pyridinecarbothioic acid, 5-(13,-dioxan-2-yl)-2-methoxy-4-(2-methylpropyl)-6-(trifluormethyl)-, S-methyl ester |
| 137 | 3-pyridinecarboxylic acid, 4-cyclobutyl-2-methyoxy-5-[(methylthio)-carbonyl]-6-(trifluoromethyl)-, methyl ester |
| 138 | 3-pyridinecarboxylic acid, 5-(chlorocarbonyl)-4-cyclobutyl-2-methoxy-6-(trifluoromethyl)-, methyl ester |
| 139 | 3-pyridinecarboyxlic acid, 4-cylcobutyl-5-formyl-2-methoxy-6-(trifluoromethyl)-, methyl ester |
| 140 | 3-pyridinecarboxylic acid, 4-cyclobutyl-5-[(3-fluoro-1H-pyrazol-1-yl)carbonyl]-2-methoxy-6-(trifluoromethyl)-, methyl ester |
| 141 | 3-pyridinecarboxylic acid, 4-cyclobutyl-2-methoxy-5-(1H-1,2,4-triazol-1-ylcarbonyl-6-(trifluoromethyl)-, methyl ester |

PRE-EMERGENT ACTIVITY ON PLANTS

As noted above, compounds of this invention have been found to be effective as herbicides, particularly pre-emergent herbicides. Tables A and B summarize results of tests conducted to determine the pre-emergent herbicidal activity of the compounds of this invention. The herbicidal ratings used in Tables A and B were assigned according to a scale based on the percent inhibition of each plant species. The herbicide rating symbols in Tables A and B are defined as follows:

| % Inhibition | Rating |
|---|---|
| 0–24 | 0 |
| 25–49 | 1 |
| 50–74 | 2 |
| 75–100 | 3 |
| Not planted | — or a blank |
| Species planted, no data | N |

One set of pre-emergent tests was conducted as follows:

Topsoil was placed in a pan and compacted to a depth of 0.95 to 1.27 cm. from the top or the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.2 kilograms/hectare (kg/ha). After treatment, the pans were moved to a greenhouse bench where they were watered as needed to give adequate moisture for germination and growth.

Approximately 10–14 days (usually 11 days) after planting and treating, the plants were observed and the results recorded.

The plant species usually regarded as weeds which were utilized in one set of pre-emergent activity tests, the data for which are shown in Table A, are identified by letter headings printed vertically above the columns according to the following legend:

CATH—Canada thistle*
RHQG—Quackgrass*
COBU—Cocklebur
RHJG—Rhizome Johnsongrass*
VELE—Velvetleaf
DOBR—Downy Brome
MOGL—Morningglory
BYGR—Barnyardgrass
COLQ—Common Lambsquarters
ANBG—Annual Bluegrass
PESW—Pennsylvania Smartweed
SEJG—Seedling Johnsongrass
YENS—Yellow Nutsedge*
INMU—Indian Mustard
WIBW—Wild Buckwheat

* Grown from vegetative propagules

TABLE A

| Compound No. | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|
| 1 | 0 | — | — | 0 | 0 | 0 | 0 | 0 | — | — | 0 | 0 | 0 | 0 | 0 |
| 2 | 3 | — | — | 3 | 3 | 3 | 3 | 3 | — | — | 3 | 3 | 3 | 3 | 3 |
| 3 | 1 | — | — | 3 | 3 | 2 | 0 | 0 | — | — | 3 | 3 | 2 | 3 | 0 |
| 4 | 1 | — | — | 3 | 3 | 3 | 0 | 3 | — | — | 3 | 3 | 3 | 3 | 3 |
| 5 | 0 | — | — | 3 | 3 | 0 | 0 | 0 | — | — | 0 | 3 | 1 | 2 | 3 |
| 6 | 1 | — | — | — | 3 | 3 | 1 | 3 | — | — | 3 | 3 | 3 | 3 | 3 |
| 7 | 0 | — | — | — | 3 | 0 | 0 | 0 | — | — | 0 | 3 | 1 | 0 | 0 |
| 8 | 0 | — | — | — | 3 | 3 | 0 | 3 | — | — | 0 | 3 | 3 | 3 | 0 |
| 9 | 3 | — | — | 3 | 3 | 3 | 0 | 3 | — | — | 3 | 3 | 3 | 3 | 3 |
| 10 | 0 | — | — | 0 | 0 | 0 | 0 | 0 | — | — | 0 | 0 | 0 | 0 | 0 |
| 11 | 3 | — | — | 3 | 3 | 2 | 0 | 1 | — | — | 1 | 3 | 3 | 3 | 0 |
| 12 | 1 | — | — | 3 | 3 | 3 | 1 | 3 | — | — | 1 | 3 | 3 | 3 | 0 |
| 13 | 0 | — | — | 0 | 0 | 0 | 0 | 0 | — | — | 0 | 0 | N | 0 | 0 |
| 14 | 0 | — | — | 3 | 3 | 3 | 0 | 3 | — | — | 3 | 3 | 3 | 2 | 3 |
| 15 | 1 | — | — | 3 | 3 | 3 | 0 | 3 | — | — | 3 | 3 | 3 | 3 | 3 |
| 16 | 0 | — | — | 3 | 3 | 3 | 0 | 3 | — | — | 2 | 3 | 3 | 3 | 0 |
| 17 | 0 | — | — | — | 3 | 0 | 0 | 0 | — | — | 0 | 2 | 0 | 0 | 0 |
| 18 | 0 | — | — | — | 0 | 0 | 1 | 0 | — | — | 0 | 2 | 0 | 0 | 0 |
| 19 | 0 | — | — | — | 3 | 2 | 1 | 3 | — | — | 1 | 3 | 3 | 3 | 0 |
| 20 | 0 | — | — | 3 | 3 | 2 | 0 | 0 | — | — | 0 | 3 | 1 | 3 | 3 |
| 21 | 0 | — | — | 3 | 3 | 0 | 0 | 0 | — | — | 0 | 3 | 0 | 3 | 0 |
| 22 | 0 | — | — | 0 | 0 | 0 | 0 | 0 | — | — | 0 | 0 | 0 | 0 | 0 |
| 23 | 0 | — | — | 3 | 3 | 1 | 0 | 1 | — | — | 0 | 3 | 3 | 1 | 3 |
| 24 | 0 | — | — | 3 | 3 | 3 | 0 | 3 | — | — | 1 | 3 | 3 | 3 | 3 |
| 25 | 0 | — | — | 0 | 0 | 0 | 0 | 0 | — | — | 0 | 0 | 0 | 0 | 0 |
| 26 | 0 | — | — | 3 | 3 | 3 | 0 | 3 | — | — | 3 | 3 | 3 | 3 | 3 |
| 27 | 2 | — | — | 3 | 3 | 3 | 1 | 3 | — | — | 3 | 3 | 3 | 3 | 0 |
| 28 | 0 | — | — | 3 | 3 | 2 | 3 | 1 | — | — | 0 | 3 | 2 | 0 | 0 |
| 29 | 1 | — | — | 3 | 3 | 3 | 0 | 3 | — | — | 0 | 3 | 3 | 3 | 1 |
| 30 | 2 | — | — | 3 | 3 | 3 | 1 | 3 | — | — | 3 | 3 | 3 | 3 | 3 |
| 31 | 2 | — | — | 3 | 3 | 3 | 0 | 3 | — | — | 0 | 3 | 3 | 3 | 3 |
| 32 | 0 | — | — | 0 | 3 | 0 | 0 | 0 | — | — | 0 | 3 | 2 | 0 | N |
| 33 | 2 | — | — | 3 | 3 | 3 | 1 | 3 | — | — | 2 | 3 | 3 | 3 | 3 |
| 34 | 3 | — | — | 3 | 3 | 3 | 3 | 2 | — | — | 3 | 3 | 3 | 3 | 3 |

TABLE A-continued

| Compound No. | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|
| 35 | 0 | — | — | 0 | 0 | 0 | 0 | 0 | — | — | 0 | 0 | 0 | 0 | 0 |
| 36 | 0 | — | — | 3 | 3 | 2 | 0 | 2 | — | — | 1 | 3 | 3 | 3 | 3 |
| 37 | 0 | — | — | 0 | 0 | 0 | 0 | 0 | — | — | 0 | 3 | 0 | 0 | 0 |
| 38 | 0 | — | — | 0 | 0 | 0 | 0 | 0 | — | — | 0 | 0 | 0 | 0 | 0 |
| 39 | 0 | — | — | 3 | 3 | 1 | 0 | 2 | — | — | 0 | 3 | 3 | 0 | 0 |
| 40 | 0 | — | — | 3 | 3 | 0 | 0 | 1 | — | — | 0 | 3 | 3 | 3 | 0 |
| 41 | 0 | — | — | 3 | 3 | 3 | 1 | 3 | — | — | 3 | 3 | 3 | 3 | 0 |
| 42 | 2 | — | — | 3 | 3 | 3 | 3 | 3 | — | — | 3 | 3 | 3 | 3 | 2 |
| 43 | 3 | — | — | 3 | 3 | 3 | 2 | 3 | — | — | 3 | 3 | 3 | 3 | 3 |
| 44 | 3 | — | — | 3 | 3 | 3 | 1 | 3 | — | — | 3 | 3 | 3 | 3 | 3 |
| 45 | 3 | — | — | 3 | 3 | 3 | 0 | 3 | — | — | 3 | 3 | 3 | 3 | 3 |
| 46 | 0 | — | — | 3 | 3 | 3 | 0 | 2 | — | — | 3 | 3 | 3 | 3 | 0 |
| 47 | 3 | — | — | 3 | 3 | 3 | 1 | 3 | — | — | 3 | 3 | 3 | 3 | 3 |
| 48 | 3 | — | — | 3 | 3 | 3 | 3 | 3 | — | — | 3 | 3 | 3 | 3 | 3 |
| 49 | 3 | — | — | 3 | 3 | 3 | 1 | 3 | — | — | 3 | 3 | 3 | 3 | 2 |
| 50 | 3 | — | — | 3 | 3 | 3 | 3 | 3 | — | — | 3 | 3 | 3 | 3 | 3 |
| 51 | 1 | — | — | 3 | 3 | 3 | 1 | 3 | — | — | 3 | 3 | 3 | 3 | 3 |
| 52 | 3 | — | — | 3 | 3 | 3 | 3 | 3 | — | — | 3 | 3 | 3 | 3 | 0 |
| 53 | 0 | — | — | 3 | 3 | 3 | 3 | 3 | — | — | 0 | 3 | 3 | 3 | 0 |
| 54 | 0 | — | — | 3 | 3 | 3 | 1 | 3 | — | — | 3 | 3 | 3 | 3 | 0 |
| 55 | 0 | — | — | 3 | 3 | 1 | 0 | 1 | — | — | 0 | 3 | 3 | 3 | 0 |
| 56 | 0 | — | — | 3 | 3 | 0 | 0 | 0 | — | — | 0 | 3 | 0 | 0 | 0 |
| 57 | 0 | — | — | 3 | 3 | 2 | 0 | 2 | — | — | 0 | 3 | 0 | 3 | 3 |
| 58 | 0 | — | — | 3 | 3 | 1 | 0 | 1 | — | — | 0 | 3 | 3 | 3 | 0 |
| 59 | 0 | — | — | 3 | 3 | 3 | 0 | 2 | — | — | 0 | 3 | 3 | 3 | 0 |
| 60 | 0 | — | — | 3 | 3 | 3 | 1 | 3 | — | — | 3 | 3 | 3 | 3 | 3 |
| 61 | 0 | — | — | 3 | 3 | 3 | 1 | 3 | — | — | 2 | 3 | 3 | 3 | 3 |
| 62 | 1 | — | — | 3 | 3 | 3 | 1 | 3 | — | — | 3 | 3 | 3 | 3 | 2 |
| 63 | 3 | — | — | 3 | 3 | 3 | 0 | 3 | — | — | 2 | 3 | 3 | 3 | 3 |
| 64 | 0 | — | — | 3 | 3 | 3 | 3 | 3 | — | — | 3 | 3 | 3 | 2 | 0 |
| 65 | 1 | — | — | 3 | 3 | 3 | 1 | 3 | — | — | 3 | 3 | 3 | 2 | 0 |
| 66 | 0 | — | — | 3 | 3 | 2 | 0 | 1 | — | — | 3 | 3 | 1 | 3 | 0 |
| 67 | 0 | — | — | 3 | 3 | 3 | 0 | 2 | — | — | 3 | 3 | 3 | 3 | 0 |
| 68 | 0 | — | — | 3 | 3 | 2 | 0 | 0 | — | — | 1 | 3 | 1 | 3 | 1 |
| 69 | 0 | — | — | 1 | 3 | 1 | Q | 0 | — | — | 2 | 3 | 0 | 3 | 2 |
| 70 | 1 | — | — | 2 | 3 | 2 | 0 | 0 | — | — | 2 | 3 | 0 | 2 | 0 |
| 71 | 0 | — | — | 3 | 3 | 2 | 0 | 1 | — | — | 1 | 3 | 2 | 2 | 0 |
| 72 | 0 | — | — | 3 | 3 | 1 | 0 | 1 | — | — | 0 | 3 | 1 | 0 | 0 |
| 73 | 0 | — | — | 3 | 3 | 2 | 0 | 1 | — | — | 3 | 3 | 3 | 3 | 3 |
| 74 | 1 | — | — | 3 | 3 | 3 | 3 | 3 | — | — | 3 | 3 | 3 | 3 | 3 |
| 75 | 3 | — | — | 3 | 3 | 3 | 2 | 3 | — | — | 3 | 3 | 3 | 3 | 1 |
| 76 | 2 | — | — | 3 | 3 | 3 | 0 | 3 | — | — | 3 | 3 | 3 | 3 | 2 |
| 77 | 3 | — | — | 3 | 3 | 3 | 2 | 3 | — | — | 3 | 3 | 3 | 3 | 3 |
| 78 | 0 | — | — | 3 | 3 | 3 | 0 | 3 | — | — | 3 | 3 | 3 | 2 | 0 |
| 79 | 0 | — | — | 3 | 3 | 2 | 0 | 2 | — | — | 3 | 3 | 3 | 3 | — |
| 80 | 2 | — | — | 3 | 3 | 3 | 1 | 3 | — | — | 3 | 3 | 3 | 1 | — |
| 81 | 3 | — | — | 3 | 3 | 3 | 3 | 3 | — | — | 3 | 3 | 3 | 3 | — |
| 82 | 1 | — | — | 3 | 3 | 3 | 2 | 3 | — | — | 3 | 3 | 3 | 2 | — |
| 83 | 0 | — | — | 3 | 3 | 3 | 0 | 3 | — | — | 1 | 3 | 3 | 3 | 1 |
| 84 | 0 | — | — | 3 | 3 | 1 | 0 | 0 | — | — | 3 | 3 | N | 0 | 0 |
| 85 | 0 | 3 | 3 | 3 | 3 | 3 | 0 | 3 | 3 | 2 | — | — | — | — | — |
| 86 | 0 | — | — | 3 | 3 | 3 | 0 | 2 | — | — | 0 | 3 | 2 | 3 | 3 |
| 87 | 0 | — | — | 0 | 0 | 0 | 0 | 0 | — | — | 0 | 2 | N | 0 | 0 |
| 88 | 0 | — | — | 1 | 3 | 1 | 0 | 1 | — | — | 0 | 2 | N | 0 | 0 |
| 89 | 0 | — | — | 1 | 3 | 3 | 1 | 3 | — | — | 3 | 3 | 3 | 1 | 0 |
| 90 | 0 | 3 | 1 | 2 | 2 | 0 | 0 | 0 | 0 | 0 | — | — | — | — | — |
| 91 | 3 | — | — | 3 | 3 | 3 | 1 | 3 | — | — | 3 | 3 | 3 | 3 | 3 |
| 92 | 3 | — | — | 3 | 3 | 3 | 2 | 3 | — | — | 3 | 3 | 3 | 3 | 0 |
| 93 | 0 | 3 | 3 | 3 | 3 | 3 | 0 | 3 | 3 | 3 | — | — | — | — | — |
| 94 | 0 | 3 | 3 | 2 | 3 | 3 | 1 | 3 | 3 | 3 | — | — | — | — | — |
| 95 | 0 | 3 | 3 | 1 | 3 | 0 | 0 | 2 | 2 | 3 | — | — | — | — | — |
| 96 | 0 | 3 | 3 | 2 | 3 | 3 | 0 | 3 | 3 | 3 | — | — | — | — | — |
| 97 | 0 | 3 | 3 | 2 | 3 | 2 | 0 | 2 | 3 | 2 | — | — | — | — | — |
| 98 | 0 | 3 | 3 | 3 | 3 | 3 | 0 | 3 | 3 | 3 | — | — | — | — | — |
| 99 | 0 | 3 | 3 | 3 | 3 | 2 | 0 | 3 | 3 | 1 | — | — | — | — | — |
| 100 | 0 | 3 | 0 | 0 | 0 | 0 | 0 | 0 | 0 | 0 | — | — | — | — | — |
| 101 | 0 | 3 | 3 | 2 | 3 | 2 | 1 | 2 | 3 | 3 | — | — | — | — | — |
| 102 | 3 | 3 | 3 | 3 | 3 | 3 | 3 | 3 | 3 | 3 | — | — | — | — | — |
| 103 | 0 | 3 | 3 | 2 | 3 | 3 | 0 | 3 | 3 | 3 | — | — | — | — | — |
| 104 | 0 | 3 | 3 | 2 | 3 | 2 | 0 | 2 | 3 | 2 | — | — | — | — | — |
| 105 | 0 | 3 | 3 | 0 | 3 | 0 | 0 | 0 | 0 | 1 | — | — | — | — | — |
| 106 | 0 | 3 | 0 | 3 | 3 | 2 | 0 | 0 | 3 | 3 | — | — | — | — | — |
| 107 | 0 | 3 | 3 | 0 | 3 | 3 | 0 | 3 | 3 | 2 | — | — | — | — | — |
| 108 | 0 | 3 | 2 | 0 | 3 | 0 | 0 | 2 | 3 | 3 | — | — | — | — | — |

TABLE A-continued

| Compound No. | Yens | Anbg | Sejg | Dobr | Bygr | Mogl | Cobu | Vele | Inmu | Wibw | Cathq | Colq | Pesw | Rhqg | Rhjg |
|---|---|---|---|---|---|---|---|---|---|---|---|---|---|---|---|
| 109 | 3 | 3 | 3 | 3 | 3 | 3 | 3 | 3 | 3 | 3 | — | — | — | — | — |
| 110 | 2 | 3 | 3 | 3 | 3 | 3 | 3 | 3 | 3 | 3 | — | — | — | — | — |
| 111 | 0 | 3 | 3 | 2 | 3 | 3 | 0 | 3 | 3 | 3 | — | — | — | — | — |
| 112 | 0 | 3 | 3 | 3 | 3 | 2 | 0 | 3 | 3 | 3 | — | — | — | — | — |
| 113 | 0 | 3 | 3 | 3 | 3 | 1 | 0 | 1 | 0 | 1 | — | — | — | — | — |
| 114 | 1 | 3 | 3 | 3 | 3 | 2 | 0 | 3 | 3 | 3 | — | — | — | — | — |
| 115 | 1 | 3 | 3 | 3 | 3 | 2 | 0 | 2 | 3 | 2 | — | — | — | — | — |
| 116 | 3 | 3 | 3 | 3 | 3 | 3 | 2 | 3 | 3 | 3 | — | — | — | — | — |
| 117 | 0 | 3 | 3 | 0 | 3 | 0 | 0 | 1 | 2 | 2 | — | — | — | — | — |
| 118 | 3 | 3 | 3 | 3 | 3 | 3 | 0 | 3 | 3 | 3 | — | — | — | — | — |
| 119 | 3 | 3 | 3 | 3 | 3 | 3 | 2 | 3 | 3 | 3 | — | — | — | — | — |
| 120 | 2 | 3 | 3 | 3 | 3 | 3 | 3 | 3 | N | N | — | — | — | — | — |
| 121 | 2 | 3 | 3 | 3 | 3 | 2 | 3 | 3 | 3 | 3 | — | — | — | — | — |
| 122 | 2 | 3 | 3 | 3 | 3 | 3 | 0 | 3 | 3 | 3 | — | — | — | — | — |
| 123 | 0 | 3 | 3 | 3 | 3 | 1 | 0 | 1 | 3 | 3 | — | — | — | — | — |
| 124 | 0 | 0 | 0 | 0 | 0 | 0 | 0 | 0 | 0 | 0 | — | — | — | — | — |
| 125 | 0 | 3 | 3 | 3 | 3 | 3 | 0 | 3 | 3 | 3 | — | — | — | — | — |
| 126 | 0 | 3 | 3 | 3 | 3 | 3 | 1 | 3 | 3 | 3 | — | — | — | — | — |
| 127 | 0 | 3 | 3 | 3 | 3 | 1 | 0 | 1 | 2 | 2 | — | — | — | — | — |
| 128 | 0 | 3 | 3 | 3 | 3 | 2 | 0 | 1 | 3 | 2 | — | — | — | — | — |
| 129 | 3 | 3 | 3 | 3 | 3 | 3 | 2 | 3 | 3 | 3 | — | — | — | — | — |
| 130 | 3 | 3 | 3 | 3 | 3 | 3 | 1 | 3 | 3 | 3 | — | — | — | — | — |
| 131 | 3 | 3 | 3 | 3 | 3 | 3 | 2 | 3 | 3 | 3 | — | — | — | — | — |
| 132 | 0 | 3 | 3 | 3 | 3 | 2 | 0 | 3 | 3 | 3 | — | — | — | — | — |
| 133 | 0 | 0 | 0 | 0 | 0 | 0 | 0 | 0 | 1 | 0 | — | — | — | — | — |
| 134 | 0 | 3 | 0 | 0 | 3 | 0 | 0 | 2 | 1 | 0 | — | — | — | — | — |
| 135 | 0 | 3 | 2 | 3 | 3 | 0 | 0 | 2 | 3 | 1 | — | — | — | — | — |
| 136 | 1 | 3 | 3 | 3 | 3 | 2 | 2 | 2 | 3 | 3 | — | — | — | — | — |
| 137 | 3 | 3 | 3 | 3 | 3 | 3 | 3 | 3 | 3 | 3 | — | — | — | — | — |
| 138 | 0 | 0 | 0 | 0 | 0 | 0 | 0 | 0 | 0 | 0 | — | — | — | — | — |
| 139 | 0 | 3 | 3 | 3 | 3 | 2 | 0 | 3 | 3 | 3 | — | — | — | — | — |
| 140 | 0 | 3 | 3 | 3 | 3 | 3 | 0 | 3 | 3 | 3 | — | — | — | — | — |
| 141 | 2 | 3 | 3 | 3 | 3 | 3 | 0 | 3 | 3 | 3 | — | — | — | — | - |

In another set of tests, the pre-emergence activity of compounds of this invention was tested on weeds in the presence of crop plants. In these tests the following procedure was used:

Topsoil was sieved to pass through a 1.27 cm screen. Fertilizer was added to the topsoil in some of the tests, while in testing other compounds the fertilizer was omitted. The mixture was then sterilized by exposure to methyl bromide or by heating.

The topsoil mixture was placed in individual aluminum pans and compacted to a depth of about 1.27 cm. from the top of the pan. A predetermined number of seeds of each of several monocotyledonous and dicotyledonous plant species and, where noted, vegetative propagules of various perennial plant species were slanted in the pans. The soil required to level fill a pan after seeding or adding vegetative propagules was weighed into another pan. A known amount of the test compound was dissolved or suspended in acetone or a suitable organic solvent as a 1% solution or suspension and applied to the cover soil using a sprayer at the desired rate. The spray was thoroughly mixed with this cover soil, and the herbicide/soil mixture was used as a cover layer for the previously prepared pan. Untreated soil was used as a cover layer for control pans. In Table B below the amount of active ingredient applied is shown. After treatment, the pans were moved to a greenhouse bench. Moisture was supplied to each pan as needed for germination and growth. Growth of each species was observed and corrective measures (greenhouse fumigation, insecticide treatment, and the like) were applied as needed. Approximately 10–14 days (usually 11 days) after planting and treating, the plants were observed and the results recorded.

The pre-emergence data for weeds in the presence of crop plants are shown in the following Table B. In these tests, the plants are identified according to the following column headings.

| | |
|---|---|
| SOBE - Soybean | VELE - Velvetleaf |
| SUBE - Sugarbeet | DOBR - Downy Brome |
| WHEZ - Wheat | PRMI - Proso Millet |
| RICE - Rice | BYGR - Barnyardgrass |
| GRSO - Grain Sorghum | LACG - Large Crabgrass |
| COBU - Cocklebur | GRFT - Green Foxtail |
| WIBW - Wild Buckwheat | CORN - Corn |
| MOGL - Morningglory | COTZ - Cotton |
| HESE - Hemp Sesbania | RAPE - Oilseed Rape |
| COLQ - Common Lambsquarters | JIWE - Jimsonweed |
| PESW - Pennsylvania Smartweed | COCW - Common Chickweed |
| ANBG - Annual Bluegrass | RUTH - Russian Thistle |
| BARZ - Barley | SEJG - Seedling |
| WIOA - Wild Oats | Johnsongrass |

TABLE B

| Compound No. | Rate kg/ha | Sobe | Cotz | Rape | Cobu | Wibw | Mogl | Kese | Jiwe | Vele | Whez | Rice | Grso | Corn | Dbri | Prmi | Bygr | Larg | Grft | Sube | Colq | Pscw | Cocw | Anbg | Brbz | Rujh | Sejg | Wioa |
|---|---|---|---|---|---|---|---|---|---|---|---|---|---|---|---|---|---|---|---|---|---|---|---|---|---|---|---|---|
| 2 | 5.6050 | 3 | — | — | 2 | 3 | 3 | 3 | — | 3 | 3 | 3 | 3 | — | 3 | 3 | 3 | 3 | — | 3 | 3 | 3 | — | — | — | — | — | — |
|   | 5.6050 | 3 | 2 | 3 | 0 | 3 | 3 | 3 | 3 | 3 | 3 | 3 | 3 | 3 | 3 | 3 | 3 | 3 | 3 | — | — | — | — | — | — | — | — | — |
|   | 1.1210 | 2 | 0 | 2 | N | 3 | 2 | 1 | 2 | 2 | 3 | 3 | 3 | 3 | 3 | 3 | 3 | 3 | 3 | — | — | — | — | — | — | — | — | — |
|   | 1.1210 | 3 | — | — | 1 | 3 | 3 | 2 | — | 2 | 3 | 3 | 3 | — | 3 | 3 | 3 | 3 | — | 3 | 3 | 3 | — | — | — | — | — | — |
|   | 0.5605 | 1 | — | — | 0 | 2 | 2 | 2 | — | 1 | 3 | 2 | 3 | — | 3 | 3 | 3 | 3 | — | 3 | 1 | 3 | — | — | — | — | — | — |
|   | 0.2803 | 0 | — | — | 0 | 2 | 2 | 1 | — | 2 | 3 | 2 | 3 | — | 3 | 3 | 3 | 3 | — | 3 | 3 | 3 | — | — | — | — | — | — |
|   | 0.2803 | 0 | 0 | 0 | 0 | 1 | 1 | 1 | 1 | 1 | 3 | 3 | 3 | 1 | 3 | 3 | 3 | 3 | 3 | — | — | — | — | — | — | — | — | — |
|   | 0.1401 | 0 | — | — | 0 | 2 | 1 | 0 | — | 1 | 1 | 2 | 0 | — | 3 | 3 | 3 | 3 | — | 3 | 0 | 2 | — | — | — | — | — | — |
|   | 0.0701 | 0 | — | — | 1 | 0 | 0 | — | 0 | 2 | 0 | 0 | — | 1 | 2 | 3 | 3 | — | 2 | 0 | 2 | — | — | — | — | — | — | — |
|   | 0.0701 | 0 | 0 | 0 | 0 | 1 | 0 | 0 | 0 | 0 | 1 | 1 | 3 | 1 | 3 | 3 | 3 | 3 | 3 | — | — | — | — | — | — | — | — | — |
|   | 0.0350 | 0 | — | — | 0 | 1 | 0 | 0 | — | 0 | 1 | 0 | 0 | — | 0 | 1 | 3 | 2 | — | 1 | 0 | 1 | — | — | — | — | — | — |
|   | 0.0175 | 0 | — | — | 0 | 0 | 0 | 0 | — | 1 | 1 | 0 | 0 | — | 0 | 0 | 1 | 1 | — | 1 | 1 | 1 | — | — | — | — | — | — |
|   | 0.0175 | 0 | 0 | 0 | 0 | 0 | 0 | 0 | 0 | 0 | 0 | 2 | 0 | 1 | 1 | 2 | 0 | 2 | 0 | — | — | — | — | — | — | — | — | — |
|   | 0.0087 | 0 | 0 | 0 | 0 | 0 | 0 | 0 | 0 | 0 | 0 | 0 | 0 | 0 | 0 | 0 | 0 | 0 | 0 | — | — | — | — | — | — | — | — | — |
|   | 0.0087 | 0 | — | — | 0 | 0 | 0 | 0 | — | 0 | 1 | 0 | 0 | — | 0 | 0 | 0 | 2 | — | 1 | 0 | 0 | — | — | — | — | — | — |
| 3 | 5.6050 | 0 | — | — | 0 | 3 | 3 | 20 | — | 1 | 3 | 3 | 3 | 1 | 3 | 3 | 3 | 3 | 3 | 1 | 3 | 3 | — | — | — | — | — | — |
|   | 1.1210 | 0 | — | — | 0 | 0 | 0 | — | 0 | 1 | 0 | 0 | 0 | 1 | 3 | 3 | 3 | 3 | 0 | 0 | 1 | — | — | — | — | — | — | — |
|   | 0.5605 | 0 | — | — | 0 | 0 | 0 | — | 0 | 0 | 0 | 0 | 0 | 0 | 0 | 0 | 0 | 0 | 1 | 0 | 0 | 0 | — | — | — | — | — | — |
|   | 0.2803 | 0 | — | — | 0 | 0 | 0 | 0 | — | 0 | 0 | 0 | 0 | — | 0 | 0 | 0 | 0 | — | 0 | 0 | 0 | — | — | — | — | — | — |
|   | 0.1401 | 0 | — | — | 0 | 0 | 0 | 0 | — | 0 | 0 | 0 | 0 | — | 0 | 0 | 0 | 0 | — | 0 | 0 | 0 | — | — | — | — | — | — |
|   | 0.0701 | 0 | — | — | 0 | 0 | 0 | 0 | — | 0 | 0 | 0 | 0 | — | 0 | 0 | 0 | 0 | — | 0 | 0 | 0 | — | — | — | — | — | — |
|   | 0.0350 | 0 | — | — | 0 | 0 | 0 | 0 | — | 0 | 0 | 0 | 0 | — | 0 | 0 | 0 | 0 | — | 0 | 0 | 0 | — | — | — | — | — | — |
| 4 | 5.6050 | 2 | — | — | 0 | 3 | 3 | 3 | — | 3 | 3 | 3 | 3 | 3 | — | 3 | 3 | 3 | 3 | 3 | 3 | 3 | — | — | — | — | — | — |
|   | 1.1210 | 0 | — | — | 0 | 1 | 0 | 1 | — | 1 | 3 | 2 | 3 | 1 | — | 3 | 3 | 3 | 3 | 2 | 2 | 3 | — | — | — | — | — | — |
|   | 0.5605 | 0 | — | — | 0 | 1 | 0 | 0 | — | 1 | 3 | 2 | 3 | 1 | — | 3 | 3 | 3 | 3 | 1 | 3 | 3 | — | — | — | — | — | — |
|   | 0.2803 | 0 | — | — | 0 | 0 | 0 | 0 | — | 0 | 1 | 1 | 1 | 0 | — | 3 | 1 | 3 | 3 | 0 | 0 | 2 | — | — | — | — | — | — |
|   | 0.1401 | 0 | — | — | 0 | 0 | 0 | 0 | — | 0 | 0 | 0 | 1 | 0 | — | 2 | 2 | 1 | 3 | 0 | 0 | 1 | — | — | — | — | — | — |
|   | 0.0701 | 0 | — | — | 0 | 0 | 0 | — | 0 | 0 | 0 | 0 | 0 | — | 0 | 0 | 0 | 1 | 0 | 0 | 0 | — | — | — | — | — | — | — |
|   | 0.0350 | 0 | — | — | 0 | 0 | 0 | 0 | — | 0 | 0 | 0 | 0 | — | 0 | 0 | 0 | 0 | — | 0 | 0 | 0 | — | — | — | — | — | — |
|   | 0.0175 | 0 | — | — | 0 | 0 | 0 | — | 0 | 0 | 0 | 0 | 0 | — | 0 | 0 | 0 | 0 | 0 | 0 | 0 | — | — | — | — | — | — | — |
| 5 | 5.6050 | 0 | — | — | 0 | 3 | 0 | 0 | — | 1 | 2 | 0 | 2 | 0 | 2 | 2 | 3 | 3 | 0 | 3 | 2 | — | — | — | — | — | — | — |
|   | 1.1210 | 0 | — | — | 0 | 2 | 0 | 0 | — | 0 | 0 | 0 | 0 | 0 | 0 | 0 | 2 | 1 | 0 | 1 | 0 | — | — | — | — | — | — | — |
|   | 0.5605 | 0 | — | — | 0 | 0 | 0 | — | 0 | 0 | 0 | 0 | 0 | — | 0 | 0 | 0 | 0 | — | 0 | 0 | 0 | — | — | — | — | — | — |
|   | 0.2803 | 0 | — | — | 0 | 0 | 0 | — | 0 | 0 | 0 | 0 | 0 | — | 0 | 0 | 0 | 0 | — | 0 | 0 | 0 | — | — | — | — | — | — |
|   | 0.1401 | 0 | — | — | 0 | 0 | 0 | — | 0 | 0 | 0 | 0 | 0 | — | 0 | 1 | 0 | 0 | — | 0 | 0 | 0 | — | — | — | — | — | — |
| 6 | 5.6050 | 0 | — | — | 0 | 3 | 1 | 2 | — | 1 | 3 | 2 | 3 | 2 | 3 | 3 | 3 | 3 | 3 | 3 | 3 | 3 | — | — | — | — | — | — |

TABLE B-continued

| Compound No. | Rate kg/ha | Sobe | Cotz | Rape | Cobu | Wibw | Mogl | Kese | Jiwe | Vele | Whez | Rice | Gron | Cobr | Dormi | Pymgr | Bygr | Lacft | Grft | Sube | Colq | Pscw | Ccbw | Anbg | Abrz | Brth | Rejg | Wioa |
|---|---|---|---|---|---|---|---|---|---|---|---|---|---|---|---|---|---|---|---|---|---|---|---|---|---|---|---|---|
|  | 1.1210 | 0 | — | — | 0 | 1 | 0 | 0 | — | 0 | 3 | 0 | 0 | 0 | 3 | 3 | 3 | 3 | 3 | 2 | 2 | 1 | — | — | — | — | — | — |
|  | 0.5605 | 0 | — | — | 0 | 0 | 0 | 0 | — | 0 | 0 | 0 | 0 | 0 | 1 | 2 | 2 | 3 | 3 | 1 | 1 | 0 | — | — | — | — | — | — |
|  | 0.2803 | 0 | — | — | 0 | 0 | 0 | 0 | — | 0 | 0 | 0 | 0 | 0 | 0 | 0 | 0 | 0 | 3 | 0 | 0 | 0 | — | — | — | — | — | — |
|  | 0.1401 | 0 | — | — | 0 | 0 | 0 | 0 | — | 0 | 0 | 0 | 0 | 0 | 0 | 0 | 0 | 0 | 1 | 0 | 0 | 0 | — | — | — | — | — | — |
|  | 0.0701 | 0 | — | — | 0 | 0 | 0 | 0 | — | 0 | 0 | 0 | 0 | 0 | 0 | 0 | 0 | 0 | 1 | 0 | 0 | 0 | — | — | — | — | — | — |
|  | 0.0350 | 0 | — | — | 0 | 0 | 0 | 0 | — | 0 | 0 | 0 | 0 | 0 | 0 | 0 | 0 | 0 | 2 | 0 | 0 | 0 | — | — | — | — | — | — |
|  | 0.0175 | 0 | — | — | 0 | 0 | 0 | 0 | — | 0 | 0 | 0 | 0 | 0 | 0 | 0 | 0 | 0 | 1 | 0 | 0 | N | 0 | — | — | — | — | — |
|  | 0.0087 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 7 | 5.6050 | 0 | — | — | 0 | 0 | 0 | 0 | — | 0 | 0 | 0 | 0 | 0 | 1 | 1 | 1 | 3 | 3 | 1 | 1 | 0 | — | — | — | — | — | — |
|  | 1.1210 | 0 | — | — | 0 | 0 | 0 | 0 | — | 0 | 0 | 0 | 0 | 0 | 0 | 0 | 0 | 2 | 2 | 1 | 0 | 0 | — | — | — | — | — | — |
|  | 0.5605 | 0 | — | — | 0 | 0 | 0 | 0 | — | 0 | 0 | 0 | 0 | 0 | 0 | 0 | 0 | 2 | 1 | 0 | 0 | 0 | — | — | — | — | — | — |
|  | 0.2803 | 0 | — | — | 0 | 0 | 0 | 0 | — | 0 | 0 | 0 | 0 | 0 | 0 | 0 | 0 | 1 | 0 | 0 | 0 | 0 | — | — | — | — | — | — |
| 8 | 5.6050 | 1 | — | — | 0 | 3 | 2 | 3 | — | 3 | 3 | 3 | 3 | 2 | 3 | 3 | 3 | 3 | 3 | 3 | 3 | 3 | — | — | — | — | — | — |
|  | 1.1210 | 0 | — | — | 0 | 0 | 0 | 1 | — | 0 | 2 | 2 | 0 | 3 | 3 | 3 | 3 | 3 | 0 | 1 | 1 | — | — | — | — | — | — | — |
|  | 0.5605 | 0 | — | — | 0 | 1 | 0 | 0 | — | 0 | 1 | 0 | 2 | 0 | 2 | 3 | 3 | 3 | 3 | 0 | 0 | 0 | — | — | — | — | — | — |
|  | 0.2803 | 0 | — | — | 0 | 0 | 0 | 0 | — | 0 | 0 | 0 | 1 | 0 | 2 | 2 | 2 | 2 | 0 | 0 | 0 | — | — | — | — | — | — | — |
|  | 0.1401 | 0 | — | — | 0 | 0 | 0 | 0 | — | 0 | 0 | 0 | 0 | 0 | 0 | 0 | 2 | 1 | 0 | 0 | 0 | — | — | — | — | — | — | — |
|  | 0.0701 | 0 | — | — | 0 | 0 | 0 | 0 | — | 0 | 0 | 0 | 0 | 0 | 0 | 0 | 0 | 0 | 0 | 0 | 0 | — | — | — | — | — | — | — |
|  | 0.0350 | 0 | — | — | 0 | 0 | 0 | 0 | — | 0 | 0 | 0 | 0 | 0 | 0 | 0 | 0 | 0 | 0 | 1 | 0 | — | — | — | — | — | — | — |
| 9 | 5.6050 | 3 | — | — | 0 | 3 | 2 | 3 | — | 3 | 3 | 3 | 3 | 3 | 3 | 3 | 3 | 3 | 3 | 3 | 3 | 3 | — | — | — | — | — | — |
|  | 5.6050 | 3 | — | — | 1 | 2 | 3 | 3 | — | 3 | 3 | 3 | 3 | 3 | 3 | 3 | 3 | 3 | 3 | 3 | 3 | 3 | — | — | — | — | — | — |
|  | 1.1210 | 2 | — | — | 1 | 3 | 2 | 3 | — | 3 | 3 | 3 | 3 | 3 | 3 | 3 | 3 | 3 | 3 | 3 | 3 | 3 | — | — | — | — | — | — |
|  | 1.1210 | 1 | — | — | 0 | 1 | 2 | 2 | — | 3 | 2 | 3 | 3 | 2 | 3 | 3 | 3 | 3 | 3 | 3 | 3 | 3 | — | — | — | — | — | — |
|  | 0.5605 | N | — | — | 2 | 1 | 1 | 0 | — | 0 | 0 | 3 | 3 | 0 | 3 | 3 | 3 | 3 | 0 | 2 | 3 | — | — | — | — | — | — | — |
|  | 0.5605 | 1 | — | — | 1 | 3 | 2 | 2 | — | 3 | 3 | 3 | 3 | 3 | 3 | 3 | 3 | 3 | 2 | 3 | 3 | — | — | — | — | — | — | — |
|  | 0.2803 | 0 | — | — | 0 | 1 | 1 | 0 | — | 0 | 1 | 3 | 3 | 0 | 1 | 0 | 3 | 3 | 3 | 0 | 1 | 1 | — | — | — | — | — | — |
|  | 0.2803 | 1 | — | — | 0 | 0 | 1 | 0 | — | 2 | 1 | 3 | 3 | 2 | 3 | 3 | 3 | 3 | 3 | 1 | 3 | 2 | — | — | — | — | — | — |
|  | 0.1401 | 0 | — | — | 0 | N | 0 | 0 | — | 1 | 0 | 3 | 3 | 0 | 2 | 3 | 3 | 3 | 3 | 0 | 3 | N | — | — | — | — | — | — |
|  | 0.1401 | N | — | — | 0 | 0 | 0 | 0 | — | 0 | 0 | 3 | 0 | 0 | 1 | 2 | 2 | 3 | 3 | N | 0 | 2 | — | — | — | — | — | — |
|  | 0.0701 | 0 | — | — | 0 | 0 | 0 | 0 | — | 0 | 0 | 2 | 3 | 0 | 3 | 1 | 3 | 3 | 3 | 0 | 0 | 0 | — | — | — | — | — | — |
|  | 0.0701 | N | — | — | 1 | 0 | 0 | 0 | — | 0 | 0 | 1 | 0 | 0 | 0 | 0 | 1 | 3 | 3 | 0 | 0 | 0 | — | — | — | — | — | — |
|  | 0.0350 | 0 | — | — | 0 | 0 | 0 | 0 | — | 0 | 02 | 0 | N | 0 | 0 | 0 | 1 | 0 | 0 | 0 | 0 | — | — | — | — | — | — | — |
|  | 0.0350 | 0 | — | — | 0 | 0 | 0 | 0 | — | 0 | 0 | 0 | 0 | 0 | 0 | 0 | 2 | 1 | 3 | 0 | N | 0 | — | — | — | — | — | — |
|  | 0.0175 | 0 | — | — | 0 | 0 | 0 | 0 | — | 0 | 6 | 0 | 0 | 0 | 2 | 0 | 0 | 1 | 0 | 0 | 0 | 0 | — | — | — | — | — | — |
|  | 0.0175 | 0 | — | — | 0 | 0 | 0 | 0 | — | 0 | 0 | 0 | 0 | 0 | 0 | 0 | 1 | 1 | 2 | 0 | N | 0 | — | — | — | — | — | — |
|  | 0.0087 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |

TABLE B-continued

| Compound No. | Rate kg/ha | Sobe | Cotz | Rape | Cbu | Wibw | Mogl | Kese | Jiwe | Vele | Whez | Rice | Gron | Cbnr | Dbmi | Prygr | Bact | Larft | Gube | Scolq | Cosww | Pebcw | Conbg | Anauz | Baurh | Retjg | Sejga | Wioa |
|---|---|---|---|---|---|---|---|---|---|---|---|---|---|---|---|---|---|---|---|---|---|---|---|---|---|---|---|---|
|  | 0.0087 | 0 | — | — | 0 | 0 | 0 | 0 | — | 0 | 0 | 0 | 0 | 0 | 0 | 1 | 0 | 0 | 0 | 0 | 0 | 0 | — | — | — | — | — | — |
| 11 | 5.6050 | 0 | — | — | 1 | 3 | 0 | 1 | — | 0 | 3 | 2 | 1 | 1 | 3 | 3 | 3 | 3 | 3 | 1 | 3 | 1 | — | — | — | — | — | — |
|  | 1.1210 | 0 | — | — | 0 | 3 | 0 | 0 | — | 0 | 1 | 1 | 0 | 0 | 3 | 3 | 3 | 3 | 3 | N | 3 | N | — | — | — | — | — | — |
|  | 0.5605 | 0 | — | — | 0 | 2 | 0 | 0 | — | 0 | 0 | 1 | 0 | 0 | 0 | 0 | 0 | 3 | 0 | 0 | 3 | N | — | — | — | — | — | — |
|  | 0.2803 | 0 | — | — | 0 | 3 | 0 | 1 | — | 0 | 0 | 0 | 0 | 0 | N | 0 | 0 | N | N | N | 3 | N | — | — | — | — | — | — |
|  | 0.1401 | 0 | — | — | 0 | 1 | 0 | 0 | — | 0 | 0 | 0 | 0 | 0 | N | 0 | 0 | N | 0 | 0 | 3 | 0 | — | — | — | — | — | — |
|  | 0.0701 | 0 | — | — | N | N | 0 | N | — | 0 | 0 | 0 | 0 | 0 | 1 | 0 | 0 | N | 0 | N | N | N | — | — | — | — | — | — |
|  | 0.0350 | 0 | — | — | 1 | N | 0 | 0 | — | 0 | 0 | 0 | 0 | 0 | 0 | 0 | 0 | 2 | 0 | N | N | N | — | — | — | — | — | — |
|  | 0.0175 | 0 | — | — | 0 | 0 | 0 | 0 | — | 0 | 0 | 1 | 0 | 0 | 0 | 0 | 0 | 0 | 0 | 2 | 0 | 0 | — | — | — | — | — | — |
| 12 | 5.6050 | 0 | — | — | 0 | 3 | 2 | 3 | — | 3 | 3 | 3 | 3 | 3 | 3 | 3 | 3 | 3 | 3 | 3 | 3 | 3 | — | — | — | — | — | — |
|  | 5.6050 | 3 | — | — | 2 | 3 | 3 | 3 | — | 3 | 2 | 3 | 3 | 3 | 3 | 3 | 3 | 3 | 3 | 3 | 3 | 3 | — | — | — | — | — | — |
|  | 1.1210 | 0 | — | — | 0 | 0 | 3 | 0 | — | 0 | 2 | 3 | 3 | 0 | 3 | 3 | 3 | 3 | 3 | 3 | 2 | 3 | — | — | — | — | — | — |
|  | 1.1210 | 0 | — | — | 1 | 0 | 3 | 3 | — | 3 | 2 | 3 | 3 | 3 | 3 | 3 | 3 | 3 | 3 | 3 | 3 | 3 | — | — | — | — | — | — |
|  | 0.5605 | 0 | — | — | 1 | 1 | 1 | 0 | — | 0 | 0 | 3 | 1 | 0 | 2 | 3 | 3 | 2 | 3 | 3 | 3 | 3 | — | — | — | — | — | — |
|  | 0.5605 | 0 | — | — | 0 | 2 | 3 | 1 | — | 2 | 3 | 3 | 3 | 1 | 3 | 3 | 3 | 3 | 3 | 3 | 3 | 3 | — | — | — | — | — | — |
|  | 0.2803 | 0 | — | — | 0 | 1 | 1 | 0 | — | 0 | 0 | 3 | 1 | 0 | 3 | 3 | 3 | 3 | 3 | 3 | 3 | 3 | — | — | — | — | — | — |
|  | 0.2803 | N | — | — | 0 | 1 | 1 | 1 | — | 0 | 1 | 3 | 3 | 0 | 3 | 3 | 3 | 3 | 3 | 3 | 3 | 3 | — | — | — | — | — | — |
|  | 0.1401 | 1 | — | — | 0 | 1 | 2 | 0 | — | 0 | 0 | 0 | 1 | 0 | 3 | 0 | 1 | 3 | 2 | 3 | 3 | 2 | — | — | — | — | — | — |
|  | 0.1401 | N | — | — | 0 | 2 | 0 | 1 | — | 0 | 2 | 3 | 3 | 1 | 1 | 3 | 3 | 3 | 3 | 0 | 3 | 3 | — | — | — | — | — | — |
|  | 0.0701 | 0 | — | — | 0 | 1 | 0 | 0 | — | 0 | 0 | 1 | 0 | 0 | 1 | 0 | 1 | 3 | 0 | 0 | 0 | 0 | — | — | — | — | — | — |
|  | 0.0701 | 0 | — | — | 0 | 1 | 0 | 0 | — | 0 | 0 | 1 | 2 | 0 | 0 | 1 | 3 | 2 | 0 | 0 | 1 | 0 | — | — | — | — | — | — |
|  | 0.0350 | N | — | — | 0 | 1 | 0 | 0 | — | 0 | 0 | 0 | 0 | 0 | 0 | 0 | 0 | 0 | 0 | 1 | 1 | 1 | — | — | — | — | — | — |
|  | 0.0350 | 0 | — | — | 0 | 0 | 0 | 1 | — | 0 | 0 | N | 2 | 0 | 1 | 1 | 1 | N | 0 | 0 | 0 | 0 | — | — | — | — | — | — |
|  | 0.0175 | 1 | — | — | 0 | 0 | 0 | 1 | — | 0 | 0 | 1 | 0 | 0 | 0 | 0 | 0 | 3 | 0 | N | 0 | 0 | — | — | — | — | — | — |
|  | 0.0087 | 0 | — | — | 0 | 1 | 0 | 0 | — | 0 | 0 | 0 | 0 | 0 | 0 | 0 | 0 | 0 | 0 | 2 | 1 | 3 | — | — | — | — | — | — |
| 14 | 5.6050 | 3 | — | — | 0 | 0 | 3 | 2 | — | 0 | 3 | 3 | 3 | 3 | 3 | 3 | 3 | 3 | 3 | 3 | 3 | 3 | — | — | — | — | — | — |
|  | 1.1210 | 1 | — | — | N | N | 3 | N | — | 1 | 2 | 3 | 3 | 2 | 3 | 3 | 3 | 3 | 3 | 3 | 3 | 3 | — | — | — | — | — | — |
|  | 0.5605 | 0 | — | — | N | 0 | 3 | 0 | — | 1 | 1 | 3 | 3 | 0 | 1 | 3 | 3 | 2 | 3 | 0 | 1 | 1 | — | — | — | — | — | — |
|  | 0.2803 | 0 | — | — | N | 0 | N | 1 | — | 0 | 0 | 0 | 0 | 0 | 0 | 3 | 0 | 2 | 1 | 0 | 0 | 0 | — | — | — | — | — | — |
|  | 0.1401 | 1 | — | — | N | 1 | N | 0 | — | 0 | 0 | 0 | 1 | 0 | 0 | 0 | 0 | 1 | 0 | 0 | 0 | 1 | — | — | — | — | — | — |
|  | 0.0701 | 1 | — | — | N | 0 | N | 0 | — | 0 | 0 | 0 | 1 | 1 | 0 | 0 | 1 | 0 | 1 | 0 | 0 | 0 | — | — | — | — | — | — |
|  | 0.0350 | 0 | — | — | N | 0 | N | 0 | — | 0 | 0 | 0 | 1 | 1 | 0 | 0 | 0 | 0 | 0 | 0 | 0 | 1 | — | — | — | — | — | — |
|  | 0.0175 | N | — | — | N | 1 | N | 1 | — | 0 | 0 | 0 | N | N | 0 | 0 | N | 0 | N | 0 | 0 | 0 | — | — | — | — | — | — |
| 15 | 5.6050 | 3 | — | — | 1 | 1 | 3 | 1 | — | 1 | 3 | 3 | 3 | 3 | 3 | 3 | 3 | 3 | 3 | 3 | 3 | 3 | — | — | — | — | — | — |
|  | 1.1210 | 2 | — | — | N | 0 | 3 | 3 | — | 0 | 3 | 3 | 3 | 2 | 3 | N | 3 | 3 | 3 | 0 | 3 | 3 | — | — | — | — | — | — |
|  | 0.5605 | 0 | — | — | 2 | 0 | 3 | 1 | — | 0 | 3 | 3 | 3 | 2 | 3 | 3 | 3 | 3 | 3 | 1 | 1 | 2 | — | — | — | — | — | — |

TABLE B-continued

| Compound No. | Rate kg/ha | Sobe | Cotz | Rape | Cobu | Wibw | Mogl | Kese | Jiwe | Vele | Whez | Rice | Gron | Cobr | Dormi | Prygr | Bact | Larg | Grft | Suble | Colqw | Pesw | Ccbw | Anbg | Babz | Ruth | Sejg | Wioa |
|---|---|---|---|---|---|---|---|---|---|---|---|---|---|---|---|---|---|---|---|---|---|---|---|---|---|---|---|---|
| | 0.2803 | 1 | — | — | 1 | 0 | 3 | 2 | — | 0 | 1 | 3 | 3 | 1 | 2 | 3 | 3 | 3 | 3 | 3 | 1 | 2 | 1 | — | — | — | — | — |
| | 0.1401 | 0 | — | — | N | 1 | N | 0 | — | 1 | 0 | 1 | 1 | 1 | 0 | 0 | 3 | 3 | 3 | N | 0 | 0 | — | — | — | — | — | — |
| | 0.0701 | N | — | — | N | 0 | N | 2 | — | 1 | 0 | 0 | 2 | 1 | 0 | 1 | 1 | 3 | 1 | 1 | 0 | 2 | — | — | — | — | — | — |
| | 0.0350 | 0 | — | — | N | 0 | N | 1 | — | 0 | 0 | 0 | 1 | 0 | 0 | 0 | 0 | 2 | 3 | N | 1 | 0 | — | — | — | — | — | — |
| | 0.0175 | 1 | — | — | N | 0 | N | 1 | — | 0 | 0 | 0 | 1 | 0 | 0 | 1 | 0 | 1 | 0 | N | N | 1 | — | — | — | — | — | — |
| | 0.0087 | 0 | — | — | N | 1 | N | 0 | — | 0 | 0 | 0 | 0 | 0 | 0 | 0 | 0 | 3 | 0 | 1 | N | 0 | — | — | — | — | — | — |
| 16 | 5.6050 | 1 | — | — | 0 | 0 | 0 | 1 | — | 0 | 3 | 3 | 3 | 3 | 3 | 3 | 3 | 3 | 3 | 3 | 3 | — | — | — | — | — | — | — |
| | 1.1210 | 0 | — | — | N | 0 | N | 1 | — | 0 | 0 | 1 | 1 | 0 | 0 | 1 | 3 | 1 | 3 | 3 | 0 | 2 | — | — | — | — | — | — |
| | 0.5605 | 0 | — | — | N | 0 | N | 2 | — | 0 | 0 | N | 2 | 0 | 1 | N | 3 | 1 | 3 | 1 | 1 | 1 | — | — | — | — | — | — |
| | 0.2803 | 1 | — | — | N | 0 | N | 1 | — | 1 | 0 | 0 | 2 | 1 | 0 | 1 | 3 | 2 | 3 | 0 | 0 | 0 | — | — | — | — | — | — |
| | 0.1401 | 0 | — | — | N | 0 | N | 1 | — | 0 | 0 | 0 | 1 | 0 | 1 | 1 | 0 | 2 | 1 | 0 | 0 | 0 | — | — | — | — | — | — |
| | 0.0701 | 0 | — | — | N | 0 | N | 1 | — | 1 | 0 | 0 | 1 | 0 | 0 | 1 | 1 | 0 | 1 | 0 | 0 | 0 | — | — | — | — | — | — |
| | 0.0350 | N | — | — | N | 0 | N | N | — | N | 0 | 0 | 1 | 0 | 0 | 1 | 0 | 1 | 0 | 0 | 0 | 0 | — | — | — | — | — | — |
| | 0.0175 | N | — | — | N | 0 | N | N | — | 0 | 0 | N | N | 1 | 0 | N | N | 1 | N | N | 0 | 0 | — | — | — | — | — | — |
| 17 | 5.6050 | 0 | — | — | 0 | 2 | 0 | 0 | — | 1 | 2 | 2 | 2 | 0 | 0 | 3 | 3 | 3 | 3 | 2 | 3 | 3 | — | — | — | — | — | — |
| | 1.1210 | 0 | — | — | 0 | 1 | 0 | 0 | — | 0 | 0 | 0 | 0 | 0 | 0 | 0 | 1 | 0 | 0 | 1 | 1 | — | — | — | — | — | — | — |
| | 0.5605 | 0 | — | — | 0 | 1 | 0 | 0 | — | 0 | 0 | 0 | 0 | 0 | 0 | 0 | 0 | 0 | 0 | 0 | 0 | — | — | — | — | — | — | — |
| | 0.2803 | 0 | — | — | 0 | 0 | 0 | 0 | — | 0 | 0 | 0 | 0 | 0 | 0 | 0 | 0 | 0 | 0 | 0 | 0 | — | — | — | — | — | — | — |
| 19 | 5.6050 | 1 | — | — | 1 | 3 | 3 | 3 | — | 3 | 3 | 3 | 3 | 2 | 3 | 3 | 3 | 3 | 3 | 3 | 3 | — | — | — | — | — | — | — |
| | 1.1210 | 0 | — | — | 1 | 3 | 2 | 2 | — | 2 | 3 | 3 | 3 | 1 | 3 | 3 | 3 | 3 | 3 | 3 | 3 | — | — | — | — | — | — | — |
| | 0.5605 | 0 | — | — | 0 | 2 | 1 | 2 | — | 1 | 2 | 1 | 3 | 1 | 3 | 3 | 3 | 3 | 3 | 3 | 3 | — | — | — | — | — | — | — |
| | 0.2803 | 0 | — | — | 0 | 1 | 1 | 1 | — | 0 | 1 | 0 | 1 | 1 | 3 | 3 | 2 | 3 | 2 | 3 | 2 | — | — | — | — | — | — | — |
| | 0.1401 | 0 | — | — | 0 | 1 | 1 | 0 | — | 0 | 0 | 0 | 0 | 0 | 2 | 2 | 2 | 3 | 3 | 1 | 2 | 2 | — | — | — | — | — | — |
| | 0.0701 | 0 | — | — | 0 | 0 | 0 | 0 | — | 0 | 0 | 0 | 0 | 0 | 1 | 1 | 1 | 3 | 3 | 0 | 2 | 0 | — | — | — | — | — | — |
| | 0.0350 | 0 | — | — | 0 | 0 | 0 | 0 | — | 0 | 0 | 0 | 0 | 0 | 0 | 0 | 0 | 2 | 1 | 0 | 2 | 0 | — | — | — | — | — | — |
| | 0.0175 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 20 | 5.6050 | 0 | — | — | 1 | 1 | 1 | 1 | — | 2 | 2 | 0 | 2 | 0 | 2 | 2 | 3 | 3 | 3 | 1 | 3 | 2 | — | — | — | — | — | — |
| | 1.1210 | 0 | — | — | 0 | 1 | 0 | 0 | — | 0 | 0 | 0 | 1 | 0 | 0 | 1 | 0 | 1 | 2 | 0 | 0 | 0 | — | — | — | — | — | — |
| | 0.5605 | 0 | — | — | 0 | 0 | 0 | 0 | — | 0 | 0 | 0 | 0 | 0 | 0 | 0 | 0 | 0 | 0 | 0 | 0 | N | 0 | — | — | — | — | — |
| | 0.2603 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.1401 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.0701 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.0350 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 21 | 5.6050 | 0 | — | — | 0 | 2 | 0 | 0 | — | 0 | 1 | 1 | 1 | 0 | 0 | 2 | 1 | 3 | 2 | 0 | 3 | 1 | — | — | — | — | — | — |
| | 1.1210 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.5605 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |

TABLE B-continued

| Compound No. | Rate kg/ha | Sobe | Cotz | Rape | Cobu | Wibw | Mogl | Kese | Jiwe | Vele | Whez | Rice | Groon | Cobr | Drmi | Pygr | Bact | Larg | Grft | Sube | Colq | Pscw | Cocw | Anbg | Babrz | Ruth | Sejg | Wioa |
|---|---|---|---|---|---|---|---|---|---|---|---|---|---|---|---|---|---|---|---|---|---|---|---|---|---|---|---|---|
| | 0.2803 | 0 | — | — | 0 | 1 | 0 | 0 | — | 0 | 0 | 0 | 0 | 0 | 0 | 0 | 0 | 0 | 0 | 0 | N | N | 0 | — | — | — | — | — |
| | 0.1401 | 0 | — | — | 0 | 0 | 0 | 0 | — | 0 | 0 | 0 | 0 | 0 | 0 | 0 | 0 | 0 | 0 | 0 | 0 | 0 | 0 | — | — | — | — | — |
| | 0.0701 | 0 | — | — | 0 | 0 | 0 | 0 | — | 0 | 0 | 0 | 0 | 0 | 0 | 0 | 0 | 0 | 0 | 0 | 0 | 0 | 0 | — | — | — | — | — |
| 23 | 5.6050 | 0 | — | — | 0 | 2 | 1 | 1 | — | 0 | 2 | 0 | 1 | 1 | 3 | 3 | 2 | 3 | 3 | 1 | 0 | 0 | — | — | — | — | — | — |
| | 1.1210 | 0 | — | — | 0 | 3 | 0 | 1 | — | 3 | 2 | 2 | 3 | 0 | 3 | 3 | 3 | 3 | 3 | 1 | 3 | 3 | — | — | — | — | — | — |
| | 0.5605 | 0 | — | — | 0 | 0 | 0 | 0 | — | 0 | 0 | 0 | 0 | 0 | 1 | N | 0 | 2 | 3 | 0 | 0 | 3 | — | — | — | — | — | — |
| | 0.2803 | 0 | — | — | 0 | N | 0 | 0 | — | 0 | 0 | 0 | 0 | 0 | 1 | N | 0 | 0 | 1 | 0 | 0 | 0 | — | — | — | — | — | — |
| | 0.1401 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.0701 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 24 | 5.6050 | 2 | — | — | 0 | 3 | 3 | 3 | — | 3 | 3 | 3 | 3 | 2 | 3 | 3 | 3 | 3 | 3 | 3 | 2 | 3 | 3 | — | — | — | — | — |
| | 1.1210 | 0 | — | — | 0 | 3 | 0 | 0 | — | 2 | 2 | 2 | 3 | 1 | 3 | 3 | 3 | 3 | 3 | 2 | 3 | 3 | — | — | — | — | — | — |
| | 0.5605 | N | — | — | 0 | 3 | 0 | 0 | — | 1 | 1 | 1 | 2 | 1 | 2 | 3 | 3 | 3 | 3 | N | N | 3 | — | — | — | — | — | — |
| | 0.2803 | 0 | — | — | 0 | 0 | 0 | 0 | — | 0 | 0 | 1 | 0 | 0 | 2 | 3 | 1 | 2 | 2 | 0 | 3 | 1 | — | — | — | — | — | — |
| | 0.1401 | 0 | — | — | 0 | 1 | 0 | 0 | — | 0 | 0 | 0 | 0 | 0 | 1 | N | 2 | 2 | 3 | 0 | N | 3 | — | — | — | — | — | — |
| | 0.0701 | 0 | — | — | 0 | 0 | 0 | 0 | — | 0 | 0 | 0 | 0 | 1 | 0 | 0 | 0 | 0 | 0 | 0 | 2 | 0 | — | — | — | — | — | — |
| | 0.0350 | 0 | — | — | 0 | 0 | 0 | 0 | — | 0 | 0 | 0 | 0 | 1 | N | 0 | 0 | 0 | 0 | 0 | 2 | | — | — | — | — | — | — |
| | 0.0175 | 0 | — | — | 0 | 0 | 0 | 0 | — | 0 | 0 | 0 | 0 | 0 | N | 0 | 0 | 0 | 0 | 0 | 0 | 0 | — | — | — | — | — | — |
| | 0.0087 | 0 | — | — | 0 | N | 0 | 0 | — | 0 | 0 | 0 | 0 | 0 | 0 | 0 | 0 | 0 | 0 | 0 | N | 1 | — | — | — | — | — | — |
| 25 | 11.2100 | — | — | 0 | — | 0 | — | — | — | — | 0 | — | — | — | 0 | — | — | — | 0 | — | — | — | 0 | 0 | 0 | 0 | — | 0 |
| | 11.2100 | 0 | 0 | — | 0 | — | 0 | — | — | 0 | — | 0 | — | 0 | — | — | 1 | 0 | — | — | — | — | — | — | — | — | 0 | — |
| | 5.6050 | 0 | 0 | — | 0 | — | 0 | — | — | 0 | — | 0 | — | 0 | — | — | 1 | 0 | — | — | — | — | — | — | — | — | 0 | — |
| | 5.6050 | — | — | 0 | — | 0 | — | — | — | — | 0 | — | — | — | 0 | — | — | — | 0 | — | — | — | 0 | 0 | 0 | 0 | — | 0 |
| | 1.1210 | 0 | 0 | — | 0 | — | 0 | — | — | 0 | — | 0 | — | 0 | — | — | 0 | 0 | — | — | — | — | — | — | — | — | 0 | — |
| | 1.1210 | — | — | 0 | — | 0 | — | — | — | — | 0 | — | — | — | 0 | — | — | — | 0 | — | — | — | 0 | 0 | 0 | 0 | — | 0 |
| | 0.2803 | — | — | 0 | — | | — | — | — | — | 0 | — | — | — | 0 | — | — | — | 0 | — | — | — | 0 | 0 | 0 | 0 | — | 0 |
| | 0.2803 | 0 | 0 | — | 0 | — | 0 | — | — | 0 | — | 0 | — | 0 | — | — | 0 | 0 | — | — | — | — | — | — | — | — | 0 | — |
| | 0.0701 | — | — | 0 | — | 0 | — | — | — | — | 0 | — | — | — | 0 | — | — | — | 0 | — | — | — | 0 | 0 | 0 | 0 | — | 0 |
| | 0.0701 | 0 | 0 | — | 0 | — | 0 | — | — | 0 | — | 0 | — | 0 | — | — | 0 | 0 | — | — | — | — | — | — | — | — | 0 | — |
| 26 | 5.6050 | 2 | — | — | 0 | 3 | 3 | 3 | 3 | — | 3 | 2 | 3 | 3 | 3 | 3 | 3 | 3 | 3 | 3 | 3 | 3 | — | — | — | — | — | — |
| | 1.1210 | 0 | — | — | 0 | 1 | 1 | 0 | — | 1 | 1 | 3 | 3 | 1 | 1 | 3 | 3 | 3 | 3 | N | 3 | 3 | — | — | — | — | — | — |
| | 0.5605 | 0 | — | — | 0 | 0 | 0 | 0 | — | 1 | 0 | 2 | 3 | 0 | 1 | 3 | 3 | 3 | 3 | 0 | 2 | 2 | — | — | — | — | — | — |
| | 0.2803 | 0 | — | — | 0 | N | 0 | 0 | — | 0 | 0 | 0 | 0 | 0 | 0 | 1 | 0 | 1 | 1 | N | 1 | 1 | — | — | — | — | — | — |
| | 0.1401 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.0701 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.0350 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.0175 | 0 | — | — | 0 | 0 | 0 | 0 | — | 0 | 0 | 0 | 0 | 0 | N | N | 0 | 0 | 0 | 0 | 0 | 0 | — | — | — | — | — | — |

TABLE B-continued

| Compound No. | Rate kg/ha | Sobe | Cotz | Rape | Cobu | Wibw | Mogl | Kese | Jiwe | Vele | Whez | Rice | Gorn | Cobr | Dobr | Pymi | Bygr | Larg | Grft | Sube | Colq | Pesw | Ccw | Anbg | Brbz | Rjth | Sejg | Wioa |
|---|---|---|---|---|---|---|---|---|---|---|---|---|---|---|---|---|---|---|---|---|---|---|---|---|---|---|---|---|
|  | 0.0087 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 27 | 5.6050 | 3 | — | — | 1 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 1 | — | — | 0 | 3 | 1 | 3 | — | 3 | 3 | 3 | 3 | 2 | 3 | 3 | 3 | 3 | 3 | 3 | 3 | 3 | — | — | — | — | — | — |
|  | 0.5605 | 0 | — | — | 0 | 2 | 2 | 1 | — | 2 | 1 | 3 | 3 | 1 | 2 | 3 | 3 | 3 | 3 | 2 | 3 | 3 | — | — | — | — | — | — |
|  | 0.2803 | 0 | — | — | 0 | 1 | 0 | 0 | — | 1 | 0 | 3 | 1 | 0 | 3 | 2 | 2 | 3 | 1 | 0 | 2 | 3 | — | — | — | — | — | — |
|  | 0.1401 | 0 | — | — | 0 | N | 0 | 1 | — | 2 | 0 | 3 | 3 | 0 | 2 | 3 | 3 | 3 | 3 | 0 | N | 3 | — | — | — | — | — | — |
|  | 0.0701 | 0 | — | — | 0 | 0 | 0 | 0 | — | 1 | 0 | 2 | 0 | 0 | 0 | 1 | 1 | 3 | 1 | 0 | 0 | 2 | — | — | — | — | — | — |
|  | 0.0350 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.0175 | 0 | — | — | 0 | 0 | 0 | 0 | — | 0 | 0 | 0 | 0 | 0 | 0 | N | 0 | 1 | 0 | 0 | 0 | 0 | — | — | — | — | — | — |
|  | 0.0087 | 0 | — | — | 0 | 0 | 0 | 0 | — | 0 | 0 | 0 | 0 | 0 | 0 | 0 | 0 | 0 | 0 | 0 | N | 1 | — | — | — | — | — | — |
| 28 | 5.6050 | 0 | — | — | 0 | 3 | 1 | 2 | — | 2 | 0 | 3 | 1 | 2 | 3 | 3 | 3 | 3 | 2 | 3 | 3 | 3 | — | — | — | — | — | — |
|  | 1.1210 | 0 | — | — | 0 | 2 | 0 | 0 | — | 0 | 0 | 1 | 1 | 0 | 0 | 0 | 0 | 2 | 2 | 0 | 1 | 2 | — | — | — | — | — | — |
|  | 0.5605 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.2803 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.1401 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.0701 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 29 | 5.6050 | 1 | — | — | 0 | 3 | 2 | 3 | — | 3 | 3 | 3 | 3 | 2 | 3 | 3 | 3 | 3 | 3 | 3 | 3 | 3 | — | — | — | — | — | — |
|  | 1.1210 | 0 | — | — | 0 | 3 | 0 | 2 | — | 2 | 2 | 1 | 3 | 1 | 3 | 3 | 3 | 3 | 3 | 1 | 3 | 2 | — | — | — | — | — | — |
|  | 0.5606 | 0 | — | — | 0 | 3 | 0 | 0 | — | 0 | 2 | 2 | 1 | 0 | 3 | 3 | 3 | 3 | 3 | 0 | 2 | 2 | — | — | — | — | — | — |
|  | 0.2803 | 0 | — | — | 0 | 0 | 0 | 0 | — | 0 | 0 | 0 | 1 | 0 | 3 | 1 | 3 | 3 | 3 | 0 | 0 | 1 | — | — | — | — | — | — |
|  | 0.1401 | 0 | — | — | 0 | 0 | 0 | 0 | — | 0 | 0 | 0 | 0 | 0 | 0 | 0 | 1 | 1 | 1 | 0 | 0 | 0 | — | — | — | — | — | — |
|  | 0.0701 | 0 | — | — | 0 | N | 0 | 0 | — | 0 | 0 | 0 | 0 | 0 | 0 | 0 | 0 | 0 | 1 | 0 | N | 0 | — | — | — | — | — | — |
|  | 0.0350 | 0 | — | — | 0 | N | 0 | 0 | — | 0 | 0 | 0 | 0 | 0 | 0 | 0 | 0 | 0 | 0 | 0 | N | 0 | — | — | — | — | — | — |
|  | 0.0175 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 30 | 5.6050 | 3 | — | — | 1 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 1 | — | — | 0 | 3 | 1 | 3 | — | 3 | 3 | 3 | 3 | 2 | 3 | 3 | 3 | 3 | 3 | 3 | 3 | 3 | — | — | — | — | — | — |
|  | 0.5605 | 1 | — | — | 0 | 3 | 2 | 3 | — | 3 | 3 | 3 | 2 | 3 | 3 | 3 | 3 | 3 | 3 | 3 | 3 | 3 | — | — | — | — | — | — |
|  | 0.2603 | 0 | — | — | 0 | 2 | 0 | 1 | — | 2 | 3 | 2 | 3 | 1 | 3 | 3 | 3 | 3 | 3 | 3 | N | 3 | 3 | — | — | — | — | — |
|  | 0.1401 | 0 | — | — | 0 | 1 | 0 | 1 | — | 0 | 1 | 2 | 3 | 1 | 3 | 3 | 3 | 3 | 3 | 0 | 2 | 2 | — | — | — | — | — | — |
|  | 0.0701 | 0 | — | — | 0 | 1 | 0 | 0 | — | 0 | 0 | 0 | 3 | 0 | 3 | 2 | 2 | 3 | 3 | 0 | 0 | 0 | — | — | — | — | — | — |
|  | 0.0350 | 0 | — | — | 0 | 1 | 0 | 0 | — | 0 | 0 | 0 | 1 | 0 | 0 | 0 | 1 | 1 | 3 | 0 | 0 | 0 | — | — | — | — | — | — |
|  | 0.0175 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.0087 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 31 | 5.6050 | 3 | — | — | 0 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 0 | — | — | 0 | 3 | 2 | 2 | — | 3 | 2 | 3 | 3 | 2 | 3 | 3 | 3 | 3 | 3 | 2 | 3 | 3 | — | — | — | — | — | — |
|  | 0.5605 | 0 | — | — | 0 | 3 | 2 | 2 | — | 2 | 1 | 2 | 3 | 2 | 3 | 3 | 3 | 3 | 3 | 1 | 3 | 3 | — | — | — | — | — | — |

TABLE B-continued

| Compound No. | Rate kg/ha | Sobe | Cotz | Rape | Cobu | Wibw | Mogl | Kese | Jiwe | Vele | Whez | Rice | Gron | Cobr | Domi | Pygr | Bact | Larg | Grfe | Sube | Colq | Pesw | Cocw | Anbg | Babz | Ruth | Sejg | Wioa |
|---|---|---|---|---|---|---|---|---|---|---|---|---|---|---|---|---|---|---|---|---|---|---|---|---|---|---|---|---|
|  | 0.2803 | 0 | — | — | 0 | 1 | 1 | 0 | — | 1 | 1 | 2 | 3 | 1 | 2 | 3 | 3 | 3 | 3 | 0 | 1 | 2 | — | — | — | — | — | — |
|  | 0.1401 | 0 | — | — | 0 | 1 | 0 | 0 | — | 1 | 0 | 2 | 2 | 0 | 2 | 3 | 2 | 3 | 3 | 0 | N | N | — | — | — | — | — | — |
|  | 0.0701 | 0 | — | — | 0 | 0 | 0 | 0 | — | 0 | 0 | 0 | 1 | 0 | 0 | 0 | 0 | 2 | 2 | 0 | 0 | 1 | — | — | — | — | — | — |
|  | 0.0350 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.0175 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 32 | 5.6050 | 0 | — | — | 0 | 0 | 1 | 0 | — | 0 | 0 | 0 | 0 | 1 | 1 | 1 | 1 | 3 | 3 | 0 | 1 | 1 | — | — | — | — | — | — |
|  | 1.1210 | 0 | — | — | 0 | 0 | 0 | 0 | — | 0 | 0 | 0 | 0 | 0 | 0 | 0 | 0 | 0 | 1 | 0 | 0 | 1 | — | — | — | — | — | — |
|  | 0.5605 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.2803 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.1401 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 33 | 5.6050 | 2 | — | — | 0 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 0 | — | — | 0 | 3 | 3 | 2 | — | 3 | 3 | 3 | 3 | 1 | 3 | 3 | 3 | 3 | 3 | 2 | 3 | 3 | — | — | — | — | — | — |
|  | 0.5605 | 0 | — | — | 0 | 3 | 1 | 3 | — | 2 | 2 | 3 | 3 | 1 | 3 | 3 | 3 | 3 | 3 | 1 | 3 | 3 | — | — | — | — | — | — |
|  | 0.2803 | 0 | — | — | 0 | 1 | 0 | 1 | — | 2 | 2 | 3 | 3 | 0 | 3 | 3 | 3 | 3 | 3 | 1 | 3 | 3 | — | — | — | — | — | — |
|  | 0.1401 | 0 | — | — | 0 | 1 | 0 | 0 | — | 0 | 0 | 1 | 3 | 0 | 2 | 3 | 3 | 3 | 3 | 0 | 1 | 1 | — | — | — | — | — | — |
|  | 0.0701 | 0 | — | — | 0 | 0 | 0 | 0 | — | 1 | 0 | 1 | 1 | 0 | 3 | 3 | 1 | 3 | 3 | 0 | N | N | — | — | — | — | — | — |
|  | 0.0350 | 0 | — | — | 0 | 0 | 0 | 0 | — | 0 | 0 | 0 | N | 0 | 0 | 1 | 0 | 0 | 0 | 0 | 0 | 0 | — | — | — | — | — | — |
|  | 0.0175 | 0 | — | — | 0 | 0 | 0 | 0 | — | 0 | 0 | 0 | N | 0 | 0 | 0 | 0 | 0 | 0 | 0 | 0 | 0 | — | — | — | — | — | — |
|  | 0.0087 | 0 | — | — | 0 | 0 | 0 | 0 | — | 0 | 0 | 0 | N | 0 | 0 | 0 | 0 | 0 | 0 | 0 | 0 | 0 | — | — | — | — | — | — |
| 34 | 5.6050 | 3 | — | — | 3 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 3 | — | — | 1 | 3 | 2 | 3 | — | 3 | 3 | 3 | 3 | 3 | 3 | 3 | 3 | 3 | 3 | 3 | 3 | 3 | — | — | — | — | — | — |
|  | 0.5605 | 2 | — | — | 0 | 3 | 2 | 3 | — | 3 | 3 | 3 | 3 | 3 | 3 | 3 | 3 | 3 | 3 | 3 | 3 | 3 | — | — | — | — | — | — |
|  | 0.2803 | 0 | — | — | 1 | 3 | 3 | 3 | — | 3 | 3 | 3 | 3 | 1 | 3 | 3 | 3 | 3 | 3 | 3 | 3 | 3 | — | — | — | — | — | — |
|  | 0.1401 | 0 | — | — | 0 | 0 | 1 | 3 | — | 3 | 3 | 2 | 3 | 1 | 3 | 3 | 3 | 3 | 3 | 1 | 3 | 3 | — | — | — | — | — | — |
|  | 0.0701 | 0 | — | — | 1 | 0 | 1 | 0 | — | 1 | 3 | 1 | 1 | 0 | 3 | 3 | 3 | 3 | 3 | 1 | 3 | 1 | — | — | — | — | — | — |
|  | 0.0350 | 0 | — | — | 1 | 0 | 0 | 0 | — | 0 | 1 | 1 | 1 | 0 | 3 | 3 | 3 | 3 | 3 | 0 | 1 | 1 | — | — | — | — | — | — |
|  | 0.0175 | 0 | — | — | 0 | 0 | 0 | 0 | — | 0 | 0 | 0 | 0 | 0 | 1 | 1 | 2 | 1 | 3 | 0 | 1 | 0 | — | — | — | — | — | — |
|  | 0.0087 | 0 | — | — | 0 | 0 | 0 | 0 | — | 0 | 0 | 0 | 1 | 0 | 1 | 0 | 0 | 0 | 1 | 0 | 0 | 0 | — | — | — | — | — | — |
| 36 | 5.6050 | 0 | — | — | 0 | 1 | 1 | 0 | — | 1 | 3 | 3 | 3 | 1 | 3 | 3 | 3 | 3 | 3 | 1 | 3 | 3 | — | — | — | — | — | — |
|  | 1.1210 | 0 | — | — | 1 | 1 | 0 | 0 | — | 1 | 1 | 1 | 1 | 0 | 1 | 3 | 3 | 3 | 3 | 0 | 1 | 0 | — | — | — | — | — | — |
|  | 0.5605 | 0 | — | — | 0 | 0 | 1 | 0 | — | 0 | 0 | 0 | 0 | 0 | 0 | 1 | 2 | 3 | 3 | 0 | 0 | 0 | — | — | — | — | — | — |
|  | 0.2803 | 0 | — | — | 0 | 0 | 0 | 0 | — | 0 | 0 | 0 | 0 | 0 | 0 | 1 | 0 | 0 | 0 | 0 | N | — | — | — | — | — | — | — |
|  | 0.1401 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
|  | 0.0701 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 39 | 5.6050 | 0 | — | — | 1 | 1 | 1 | 1 | — | 2 | 2 | 1 | 2 | 0 | 3 | 2 | 3 | 3 | 3 | 2 | 3 | 2 | — | — | — | — | — | — |
|  | 2.8025 | 0 | — | — | 0 | 1 | 1 | 1 | — | 1 | 1 | 0 | 1 | 0 | 3 | 3 | 3 | 3 | 3 | 0 | 2 | 2 | — | — | — | — | — | — |

TABLE B-continued

| Compound No. | Rate kg/ha | Sobe | Cotz | Rape | Cbuu | Wibw | Mogl | Kese | Jiwe | Vele | Whez | Rico | Gron | Cobr | Domi | Pyrg | Barg | Lact | Grfte | Sublq | Cosw | Pecw | Cnbg | Abuz | Brth | Rejg | Wioa |
|---|---|---|---|---|---|---|---|---|---|---|---|---|---|---|---|---|---|---|---|---|---|---|---|---|---|---|---|
| | 1.1210 | 0 | — | — | 0 | 0 | 0 | 0 | — | 0 | 0 | 0 | 1 | 0 | 1 | 0 | 1 | 1 | 2 | 0 | 0 | 0 | — | — | — | — | — |
| | 0.5605 | 0 | — | — | 0 | 1 | 0 | 0 | — | 0 | 0 | 0 | 0 | 0 | 1 | 0 | 0 | 1 | 2 | 1 | 0 | 0 | — | — | — | — | — |
| | 0.2803 | 0 | — | — | 0 | 0 | 0 | 0 | — | 0 | 0 | 0 | 0 | 0 | 0 | 0 | 0 | 0 | 0 | 0 | 0 | 0 | — | — | — | — | — |
| 40 | 5.6050 | 0 | — | — | 0 | 1 | 0 | 0 | — | 1 | 1 | 1 | 2 | 0 | 0 | 3 | 3 | 0 | 1 | 3 | 0 | 3 | — | — | — | — | — |
| | 1.1210 | 0 | — | — | 1 | 0 | 0 | 0 | — | 0 | 0 | 0 | 0 | 0 | 0 | 0 | 0 | 0 | 0 | 0 | 3 | 1 | — | — | — | — | — |
| | 0.5805 | 0 | — | — | 0 | 0 | 0 | 0 | — | 0 | 0 | 0 | 0 | 0 | 0 | 0 | 0 | 0 | 0 | 0 | 3 | 1 | — | — | — | — | — |
| | 0.2803 | 0 | — | — | 0 | 2 | 0 | 0 | — | 0 | 0 | 0 | 0 | 0 | 0 | 0 | 0 | 0 | 0 | 0 | N | 0 | — | — | — | — | — |
| | 0.1401 | 0 | — | — | 1 | N | 0 | 0 | — | 0 | 0 | 0 | 0 | 0 | 0 | 0 | 0 | N | 0 | 0 | 3 | 0 | — | — | — | — | — |
| | 0.0701 | 0 | — | — | 0 | 1 | 0 | 0 | — | 0 | 0 | 0 | 0 | 0 | 0 | 0 | 0 | 0 | 0 | 0 | 1 | 0 | — | — | — | — | — |
| 41 | 5.6050 | 2 | — | — | 0 | 3 | 3 | 3 | — | 3 | 3 | 3 | 3 | 3 | 3 | 3 | 3 | 3 | 3 | 3 | 3 | 3 | — | — | — | — | — |
| | 1.1210 | 1 | — | — | 0 | 3 | 2 | 1 | — | 3 | 3 | 2 | 3 | 3 | 3 | 3 | 3 | 3 | 2 | 3 | 3 | 3 | — | — | — | — | — |
| | 0.5605 | 0 | — | — | 0 | 2 | 2 | 2 | — | 2 | 2 | 2 | 3 | 1 | 3 | 3 | 3 | 3 | 2 | 3 | 3 | 3 | — | — | — | — | — |
| | 0.2803 | 0 | — | — | 0 | 2 | 2 | 1 | — | 2 | 0 | 2 | 2 | 1 | 2 | 3 | 3 | 3 | 3 | 0 | 3 | 3 | — | — | — | — | — |
| | 0.1401 | 0 | — | — | 0 | 2 | 0 | 0 | — | 0 | 1 | 2 | 2 | 0 | 2 | 2 | 3 | 3 | 3 | 0 | 2 | 3 | — | — | — | — | — |
| | 0.0701 | 1 | — | — | 0 | 2 | 0 | 0 | — | 0 | 0 | 0 | 2 | 0 | 0 | 3 | 3 | 3 | 3 | 1 | 2 | 3 | — | — | — | — | — |
| | 0.0350 | 0 | — | — | 0 | 2 | 1 | 0 | — | 0 | 0 | 0 | 1 | 0 | 1 | 2 | 0 | 2 | 1 | 1 | 1 | 2 | — | — | — | — | — |
| | 0.0175 | 0 | — | — | 0 | 2 | 0 | N | — | 1 | 0 | 0 | 1 | 0 | 1 | 1 | 1 | 0 | 1 | 0 | N | 2 | — | — | — | — | — |
| 42 | 5.6050 | 3 | — | — | 2 | 3 | 3 | 3 | — | 3 | 3 | 3 | 3 | 3 | 3 | 3 | 3 | 3 | 3 | 3 | 3 | 3 | — | — | — | — | — |
| | 1.1210 | 3 | — | — | 0 | 3 | 3 | 3 | — | 3 | 3 | 3 | 3 | 3 | 3 | 3 | 3 | 3 | 3 | 3 | 3 | 3 | — | — | — | — | — |
| | 0.5605 | 3 | — | — | 1 | 3 | 3 | 3 | — | 3 | 3 | 3 | 3 | 3 | 3 | 3 | 3 | 3 | 3 | 3 | 3 | 3 | — | — | — | — | — |
| | 0.2803 | 2 | — | — | 0 | 3 | 2 | 3 | — | 3 | 3 | 3 | 3 | 3 | 3 | 3 | 3 | 3 | 3 | 3 | 3 | 3 | — | — | — | — | — |
| | 0.1401 | 0 | — | — | 0 | 2 | 2 | 3 | — | 2 | 3 | 3 | 3 | 2 | 3 | 3 | 3 | 3 | 2 | 3 | 3 | 3 | — | — | — | — | — |
| | 0.0701 | 0 | — | — | 0 | 2 | 1 | 2 | — | 2 | 1 | 1 | 2 | 0 | 3 | 3 | 3 | 3 | 3 | 2 | 3 | 3 | — | — | — | — | — |
| | 0.0350 | 0 | — | — | 0 | 1 | 0 | 1 | — | 2 | 0 | 1 | 0 | 0 | 2 | 3 | 3 | 3 | 3 | 1 | 3 | 3 | — | — | — | — | — |
| | 0.0175 | 0 | — | — | 0 | 1 | 0 | 0 | — | 0 | 0 | 0 | 2 | 0 | 1 | 3 | 3 | 3 | 3 | 0 | 3 | 2 | — | — | — | — | — |
| | 0.0087 | 0 | — | — | 0 | 0 | 0 | 0 | — | 0 | 0 | 0 | 0 | 0 | 2 | 3 | 2 | 3 | 3 | 0 | 1 | 1 | — | — | — | — | — |
| 43 | 5.6050 | 3 | — | — | 2 | 3 | 3 | 3 | — | 3 | 3 | 3 | 3 | 3 | 3 | 3 | 3 | 3 | 3 | 3 | 3 | 3 | — | — | — | — | — |
| | 1.1210 | 2 | — | — | 0 | 3 | 2 | 3 | — | 3 | 3 | 3 | 3 | 1 | 3 | 3 | 3 | 3 | 3 | 3 | 3 | 3 | — | — | — | — | — |
| | 0.5605 | 2 | — | — | 0 | 3 | 0 | 2 | — | 3 | 3 | 3 | 3 | 1 | 3 | 3 | 3 | 3 | 3 | 3 | 3 | 3 | — | — | — | — | — |
| | 0.2803 | 0 | — | — | 0 | 1 | 0 | 1 | — | 2 | 2 | 1 | 2 | 1 | 3 | 3 | 3 | 3 | 3 | 2 | 3 | 3 | — | — | — | — | — |
| | 0.1401 | 0 | — | — | 0 | 1 | 0 | 0 | — | 2 | 2 | 1 | 2 | 0 | 2 | 3 | 3 | 3 | 3 | 2 | 3 | 3 | — | — | — | — | — |
| | 0.0701 | 0 | — | — | 0 | 0 | 0 | 0 | — | 1 | 1 | 1 | 0 | 0 | 2 | 3 | 3 | 3 | 3 | 1 | 2 | 3 | — | — | — | — | — |
| | 0.0350 | 0 | — | — | 0 | 0 | 0 | 0 | — | 1 | 0 | 0 | 0 | 0 | 0 | 2 | 1 | 3 | 3 | 0 | 1 | 3 | — | — | — | — | — |
| | 0.0175 | 0 | — | — | 0 | 0 | 0 | 0 | — | 0 | 1 | 0 | 1 | 1 | 2 | 2 | 3 | 3 | 3 | 0 | 0 | 0 | — | — | — | — | — |
| | 0.0087 | 0 | — | — | 0 | 0 | 0 | 0 | — | 0 | 0 | 0 | 0 | 0 | 0 | 2 | 0 | 1 | 2 | 0 | 0 | 1 | — | — | — | — | — |
| 44 | 5.6050 | 3 | — | — | 1 | 3 | 3 | 3 | — | 3 | 3 | 3 | 3 | 3 | 3 | 3 | 3 | 3 | 3 | 3 | 3 | 3 | — | — | — | — | — |

TABLE B-continued

| Compound No. | Rate kg/ha | Sobe | Cotz | Rape | Cobu | Wibw | Mogl | Kese | Jewe | Vile | Whez | Rice | Gron | Cobr | Domi | Pygr | Byrg | Larg | Grft | Sube | Colq | Pscw | Cocw | Anbg | Babz | Rurth | Sejg | Wioa |
|---|---|---|---|---|---|---|---|---|---|---|---|---|---|---|---|---|---|---|---|---|---|---|---|---|---|---|---|---|
| | 1.1210 | 1 | — | — | 0 | 3 | 2 | 2 | — | 3 | 3 | 3 | 3 | 2 | 3 | 3 | 3 | 3 | 3 | 3 | 3 | 3 | — | — | — | — | — | — |
| | 0.5605 | 0 | — | — | 0 | 1 | 1 | 1 | — | 2 | 3 | 2 | 2 | 1 | 3 | 3 | 3 | 3 | 3 | 2 | 3 | 3 | — | — | — | — | — | — |
| | 0.2803 | 0 | — | — | 0 | 0 | 1 | 1 | — | 2 | 3 | 2 | 3 | 1 | 3 | 3 | 3 | 3 | 3 | 1 | 3 | 3 | — | — | — | — | — | — |
| | 0.1401 | 0 | — | — | 0 | 0 | 0 | 0 | — | 0 | 1 | 1 | 0 | 0 | 3 | 3 | 3 | 3 | 3 | 0 | 1 | 0 | — | — | — | — | — | — |
| | 0.0701 | 0 | — | — | 0 | 0 | 0 | 0 | — | 0 | 0 | 0 | 0 | 0 | 3 | 3 | 3 | 3 | 3 | 1 | 1 | 0 | — | — | — | — | — | — |
| | 0.0350 | 0 | — | — | 1 | 0 | 0 | 0 | — | 0 | 0 | 0 | 0 | 0 | 2 | 2 | 1 | 1 | 2 | 1 | 0 | 0 | — | — | — | — | — | — |
| | 0.0175 | 0 | — | — | 0 | 0 | 0 | 0 | — | 0 | 0 | 0 | 0 | 0 | 2 | 0 | 1 | 0 | 0 | 1 | 1 | 0 | — | — | — | — | — | — |
| | 0.0087 | 0 | — | — | 0 | 0 | 0 | 0 | — | 0 | 0 | 0 | 0 | 0 | 0 | 0 | 0 | 0 | 0 | 0 | N | 0 | — | — | — | — | — | — |
| 45 | 5.6050 | 1 | — | — | 1 | 3 | 3 | 3 | — | 3 | 3 | 3 | 3 | 3 | 3 | 3 | 3 | 3 | 3 | 3 | 3 | 3 | — | — | — | — | — | — |
| | 1.1210 | 0 | — | — | 1 | 3 | 2 | 2 | — | 3 | 3 | 1 | 1 | 1 | 3 | 3 | 3 | 3 | 3 | 3 | 3 | 3 | — | — | — | — | — | — |
| | 0.5605 | 0 | — | — | 0 | 3 | 1 | 1 | — | 2 | 3 | 1 | 0 | 0 | 3 | 3 | 3 | 3 | 3 | 3 | 3 | 3 | — | — | — | — | — | — |
| | 0.2803 | 0 | — | — | 1 | 1 | 0 | 1 | — | 2 | 1 | 0 | 0 | 0 | 3 | 3 | 3 | 3 | 3 | 2 | 2 | 1 | — | — | — | — | — | — |
| | 0.1401 | 0 | — | — | 0 | 0 | 0 | 0 | — | 0 | 0 | 0 | 0 | 0 | 3 | 3 | 2 | 1 | 3 | 0 | 1 | 0 | — | — | — | — | — | — |
| | 0.0701 | 0 | — | — | 0 | 0 | 0 | 0 | — | 0 | 0 | 0 | 0 | 0 | N | 1 | 1 | 0 | 3 | 0 | 0 | 0 | — | — | — | — | — | — |
| | 0.0350 | 0 | — | — | 0 | 0 | 0 | 0 | — | 0 | 0 | 0 | 0 | 0 | 1 | 0 | 0 | 0 | 2 | 0 | 0 | 0 | — | — | — | — | — | — |
| | 0.0175 | 0 | — | — | 0 | 0 | 0 | 0 | — | 0 | 0 | 0 | 0 | 0 | 2 | 0 | 0 | 0 | 1 | 0 | 0 | 0 | — | — | — | — | — | — |
| | 0.0087 | 0 | — | — | 0 | 0 | 0 | 0 | — | 0 | 0 | 0 | 0 | 0 | 2 | 0 | 0 | 0 | 0 | 0 | 0 | 0 | — | — | — | — | — | — |
| 46 | 5.6050 | 0 | — | — | 0 | 1 | 1 | 2 | — | 3 | 3 | 3 | 3 | 1 | 3 | 3 | 3 | 3 | 3 | 3 | 3 | 3 | — | — | — | — | — | — |
| | 1.1210 | 0 | — | — | 0 | 0 | 1 | 0 | — | 2 | 1 | 0 | 0 | 0 | 3 | 3 | 3 | 3 | 3 | 0 | 2 | 2 | — | — | — | — | — | — |
| | 0.5605 | 0 | — | — | 0 | 1 | 1 | 0 | — | 1 | 2 | 0 | 0 | 0 | 3 | 2 | 3 | 3 | 3 | 1 | 2 | 2 | — | — | — | — | — | — |
| | 0.2803 | 0 | — | — | 0 | 1 | 1 | 1 | — | 1 | 1 | 0 | 0 | 0 | 2 | 1 | 1 | 1 | 3 | 0 | 1 | 0 | — | — | — | — | — | — |
| | 0.1401 | 0 | — | — | 0 | 1 | 0 | 0 | — | 0 | 0 | 0 | 0 | 0 | 2 | 0 | 0 | 0 | 2 | 0 | 1 | 0 | — | — | — | — | — | — |
| | 0.0701 | 0 | — | — | 0 | 1 | 0 | 0 | — | 0 | 1 | 0 | 0 | 0 | 2 | 0 | 0 | 0 | 2 | 0 | 0 | 0 | — | — | — | — | — | — |
| | 0.0350 | 0 | — | — | 1 | 2 | 1 | 1 | — | 1 | 1 | 0 | 0 | 0 | 2 | 0 | 0 | 0 | 2 | 1 | 2 | 2 | — | — | — | — | — | — |
| | 0.0175 | 0 | — | — | 0 | 2 | 1 | 0 | — | 0 | 1 | 0 | 0 | 0 | 1 | 0 | 1 | 0 | 0 | 1 | 0 | 0 | — | — | — | — | — | — |
| 47 | 5.6050 | 3 | — | — | 2 | 3 | 2 | 3 | — | 3 | 3 | 3 | 3 | 3 | 3 | 3 | 3 | 3 | 3 | 3 | 3 | 3 | — | — | — | — | — | — |
| | 5.6050 | 3 | 1 | 3 | 2 | 3 | 3 | 3 | — | 3 | 3 | 3 | 3 | 3 | 3 | 3 | 3 | 3 | 3 | — | — | — | 3 | — | — | — | — | — |
| | 1.1210 | 2 | 1 | 3 | 0 | 3 | 3 | 3 | — | 3 | 3 | 3 | 3 | 3 | 3 | 3 | 3 | 3 | 3 | — | — | — | 3 | — | — | — | — | — |
| | 1.1210 | 1 | — | — | 1 | 3 | 1 | 3 | — | 3 | 3 | 3 | 3 | 2 | 3 | 3 | 3 | 3 | 3 | 3 | 3 | 3 | — | — | — | — | — | — |
| | 0.5605 | 1 | — | — | 0 | 2 | 1 | 2 | — | 2 | 3 | 2 | 3 | 2 | 3 | 3 | 3 | 3 | 3 | 2 | 3 | 3 | — | — | — | — | — | — |
| | 0.2603 | 0 | — | — | 0 | 1 | 0 | 2 | — | 2 | 2 | 2 | 3 | 1 | 3 | 3 | 3 | 3 | 3 | 2 | 3 | 3 | — | — | — | — | — | — |
| | 0.2803 | 0 | 0 | 3 | 0 | 3 | 2 | 2 | — | 2 | 3 | 2 | 3 | 1 | 3 | 3 | 3 | 3 | 3 | — | — | — | 3 | — | — | — | — | — |
| | 0.1401 | 0 | — | — | 0 | 1 | 0 | 1 | — | — | 2 | 2 | 0 | 1 | 0 | 3 | 3 | 3 | 3 | 2 | 3 | 2 | — | — | — | — | — | — |
| | 0.0701 | 0 | — | — | 0 | 1 | 0 | 1 | — | 1 | 1 | 0 | 0 | 0 | 3 | 3 | 2 | 3 | 3 | 2 | 2 | 2 | — | — | — | — | — | — |
| | 0.0701 | 1 | 0 | 0 | 0 | 1 | 0 | 0 | — | 0 | 2 | 0 | 2 | 0 | 3 | 3 | 3 | 3 | 3 | — | — | — | 2 | — | — | — | — | — |
| | 0.0350 | 0 | — | — | 0 | 1 | 0 | 0 | — | 0 | 0 | 0 | 0 | 0 | 3 | 2 | 1 | 3 | 3 | 1 | 0 | 0 | — | — | — | — | — | — |

TABLE B-continued

| Compound No. | Rate kg/ha | Soybee | Cotz | Rape | Cobuw | Wibwl | Moge | Kese | Jiwe | Vele | Whez | Rice | Gron | Corbri | Dmigr | Pyrgr | Barcgt | Lauft | Grsble | Scuq | Colsw | Peecw | Conbw | Anbrz | Barth | Rusejg | Wioa |
|---|---|---|---|---|---|---|---|---|---|---|---|---|---|---|---|---|---|---|---|---|---|---|---|---|---|---|---|
| | 0.0175 | 0 | — | — | 0 | 0 | 0 | 0 | — | 0 | 0 | 0 | 0 | 0 | 2 | 1 | 1 | 0 | 1 | 0 | 0 | 0 | — | — | — | — | — |
| | 0.0175 | 0 | N | 0 | 0 | 0 | 0 | 0 | — | 0 | 0 | 0 | 0 | 0 | 0 | 0 | 0 | 1 | 0 | — | — | 2 | — | — | — | — | — |
| | 0.0087 | 0 | — | — | 0 | 0 | 0 | 0 | — | 0 | 0 | 0 | 0 | 0 | 1 | 0 | 1 | 1 | 1 | 0 | 0 | 0 | — | — | — | — | — |
| 48 | 5.6050 | 3 | — | — | 1 | 3 | 3 | 3 | — | 3 | 3 | 3 | 3 | 3 | 3 | 3 | 3 | 3 | 3 | 3 | 3 | 3 | — | — | — | — | — |
| | 5.6050 | 3 | — | — | 2 | 3 | 3 | 3 | — | 3 | 3 | 3 | 3 | 3 | 3 | 3 | 3 | 3 | 3 | 3 | 3 | 3 | — | — | — | — | — |
| | 1.1210 | 2 | — | — | 1 | 3 | 2 | 1 | — | 3 | 3 | 3 | 3 | 3 | 3 | 3 | 3 | 3 | 3 | 3 | 3 | 3 | — | — | — | — | — |
| | 1.1210 | 2 | — | — | 0 | 3 | 3 | 3 | — | 3 | 3 | 3 | 3 | 3 | 3 | 3 | 3 | 3 | 3 | 3 | 3 | 3 | — | — | — | — | — |
| | 0.5605 | 0 | — | — | 0 | 3 | 2 | 2 | — | 3 | 3 | 3 | 3 | 3 | 3 | 3 | 3 | 3 | 3 | 3 | 3 | 3 | — | — | — | — | — |
| | 0.5605 | 1 | — | — | 0 | 1 | 1 | 2 | — | 2 | 2 | 3 | 2 | 2 | 3 | 3 | 3 | 3 | 3 | 3 | 3 | 3 | — | — | — | — | — |
| | 0.2803 | 0 | — | — | N | 2 | 1 | 3 | — | 3 | 1 | 3 | 3 | 1 | 3 | 3 | 3 | 3 | 3 | 3 | 3 | 3 | — | — | — | — | — |
| | 0.2803 | 0 | — | — | 0 | 3 | 2 | 2 | — | 3 | 3 | 3 | 3 | | 1 | 3 | 3 | 3 | 3 | N | 3 | 3 | — | — | — | — | — |
| | 0.1401 | 0 | — | — | 0 | 2 | 0 | 1 | — | 2 | 1 | 1 | 3 | 1 | 3 | 3 | 3 | 3 | 3 | 1 | 3 | 3 | — | — | — | — | — |
| | 0.1401 | 0 | — | — | 0 | 0 | 0 | 0 | — | 0 | 0 | N | 3 | 0 | 2 | N | 3 | 3 | 3 | 0 | N | 3 | — | — | — | — | — |
| | 0.0701 | 0 | — | — | 0 | 0 | 0 | 0 | — | 0 | 0 | 3 | 0 | 0 | 3 | 3 | 2 | 3 | 2 | 1 | 3 | 1 | — | — | — | — | — |
| | 0.0701 | 0 | — | — | 0 | 0 | 0 | 2 | — | 0 | 0 | 1 | 3 | 0 | 2 | 3 | 3 | 3 | 3 | 0 | 1 | 1 | — | — | — | — | — |
| | 0.0350 | 0 | — | — | 0 | 1 | 0 | 0 | — | 0 | 1 | 0 | 2 | 0 | 3 | 3 | 3 | 3 | 3 | N | N | 0 | — | — | — | — | — |
| | 0.0350 | 0 | — | — | 0 | 0 | 0 | 0 | — | 0 | 0 | 3 | 0 | 0 | 1 | 2 | 0 | 3 | 0 | 0 | 0 | 0 | — | — | — | — | — |
| | 0.0175 | 0 | — | — | 0 | 0 | 2 | 0 | — | 1 | 0 | 2 | 0 | 0 | 0 | 1 | 0 | 3 | 1 | N | 1 | 1 | — | — | — | — | — |
| | 0.0175 | 0 | — | — | 0 | 0 | 0 | 0 | — | 0 | 0 | 0 | 0 | 0 | 2 | 0 | 1 | 2 | 3 | 0 | 1 | 0 | — | — | — | — | — |
| | 0.0087 | 0 | — | — | 0 | 0 | 0 | 0 | — | 0 | 0 | 0 | 0 | 0 | 1 | 0 | 0 | 1 | 1 | 0 | 1 | 0 | — | — | — | — | — |
| | 0.0087 | 0 | — | — | 0 | 1 | 1 | N | — | 0 | 0 | 1 | 0 | 0 | 0 | 0 | 0 | 2 | 0 | 1 | 0 | 2 | — | — | — | — | — |
| | 0.0044 | 0 | — | — | 0 | 0 | 0 | 0 | — | 0 | 0 | 0 | 0 | 0 | 0 | 0 | 0 | 0 | 0 | 0 | 0 | 0 | — | — | — | — | — |
| 49 | 5.6050 | 3 | — | — | 0 | 3 | 3 | 3 | — | 3 | 3 | 3 | 3 | 3 | 3 | 3 | 3 | 3 | 3 | 3 | 3 | 3 | — | — | — | — | — |
| | 1.12101 | 0 | — | — | 0 | 3 | 1 | 2 | — | 2 | 3 | 3 | 1 | 3 | 3 | 3 | 3 | 3 | 3 | 3 | 3 | 3 | — | — | — | — | — |
| | 0.5605 | 0 | — | — | 0 | 3 | 2 | 2 | — | 2 | 2 | 1 | 1 | 1 | 3 | 3 | 3 | 3 | 2 | 3 | 3 | — | — | — | — | — | — |
| | 0.2803 | 0 | — | — | 0 | 3 | 1 | 2 | — | 2 | 0 | 0 | 0 | 3 | 3 | 3 | 3 | 0 | 3 | 3 | — | — | — | — | — | — | — |
| | 0.1401 | 0 | — | — | 0 | 0 | 1 | 1 | — | 1 | 1 | 0 | 0 | 1 | 3 | 3 | 3 | 0 | 2 | 3 | — | — | — | — | — | — | — |
| | 0.0701 | 0 | — | — | 0 | 0 | 0 | 0 | — | 1 | 0 | 0 | 0 | 1 | 3 | 2 | 3 | 3 | 0 | 1 | 2 | — | — | — | — | — | — |
| | 0.0350 | 0 | — | — | 0 | 0 | 0 | 0 | — | 0 | 0 | 0 | 0 | 1 | 1 | 2 | 2 | 3 | 0 | 1 | 2 | — | — | — | — | — | — |
| | 0.0175 | 0 | — | — | 0 | 0 | 0 | 0 | — | 0 | 0 | 0 | 0 | 1 | 0 | 0 | 2 | 0 | 0 | 0 | — | — | — | — | — | — | — |
| | 0.0087 | 0 | — | — | 0 | 0 | 0 | 0 | — | 0 | 0 | 0 | 0 | 0 | 0 | 0 | 0 | 0 | 0 | 0 | — | — | — | — | — | — | — |
| 50 | 5.6050 | 3 | — | — | 2 | 3 | 3 | 3 | — | 3 | 3 | 3 | 3 | 3 | 3 | 3 | 3 | 3 | 3 | 3 | 3 | 3 | — | — | — | — | — |
| | 1.1210 | 2 | — | — | 1 | 3 | 2 | 3 | — | 3 | 3 | 3 | 3 | 3 | 3 | 3 | 3 | 3 | 3 | 3 | 3 | 3 | — | — | — | — | — |
| | 0.5605 | 1 | — | — | 0 | 3 | 1 | 3 | — | 3 | 3 | 3 | 3 | 3 | 3 | 3 | 3 | 3 | 3 | 3 | 3 | 3 | — | — | — | — | — |
| | 0.2803 | 0 | — | — | 0 | 3 | 2 | 2 | — | 3 | 3 | 0 | 2 | 1 | 3 | 3 | 3 | 3 | 3 | 3 | 3 | 3 | — | — | — | — | — |
| | 0.1401 | 0 | — | — | 1 | 2 | 1 | 1 | — | 2 | 2 | 2 | 1 | 1 | 3 | 3 | 3 | 3 | 3 | 3 | 3 | 3 | — | — | — | — | — |

TABLE B-continued

| Compound No. | Rate kg/ha | Sobe | Cotz | Rape | Cobu | Wibw | Mogl | Kese | Jiwe | Vele | Whez | Rice | Gron | Cobr | Dbmi | Pygr | Byrg | Larct | Grft | Sube | Colq | Pecw | Cocw | Anbg | Abrz | Bruth | Rsejg | Wioa |
|---|---|---|---|---|---|---|---|---|---|---|---|---|---|---|---|---|---|---|---|---|---|---|---|---|---|---|---|---|
|  | 0.0701 | 0 | — | — | 0 | 2 | 1 | 1 | — | 2 | 1 | 2 | 1 | 0 | 1 | 3 | 3 | 3 | 3 | N | 3 | 3 | — | — | — | — | — | — |
|  | 0.0350 | 0 | — | — | 0 | 3 | 0 | 1 | — | 2 | 1 | 2 | 0 | 0 | N | 3 | 3 | 3 | 3 | N | 3 | 3 | — | — | — | — | — | — |
|  | 0.0175 | 0 | — | — | 0 | 2 | 0 | 0 | — | 1 | 0 | 0 | 0 | 0 | 1 | 1 | 3 | 3 | 3 | N | 3 | 1 | — | — | — | — | — | — |
|  | 0.0087 | 0 | — | — | 0 | 1 | 0 | 0 | — | 0 | 0 | 0 | 0 | 0 | 0 | 0 | 2 | 3 | 2 | 0 | 1 | 0 | — | — | — | — | — | — |
|  | 0.0044 | 0 | — | — | 0 | 0 | 0 | 0 | — | 1 | 0 | 0 | 0 | 0 | 0 | 1 | 2 | 1 | 1 | 0 | 0 | 0 | — | — | — | — | — | — |
| 51 | 5.6050 | 3 | — | — | 3 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 2 | — | — | 0 | 3 | 3 | 3 | — | 3 | 3 | 3 | 3 | 3 | 3 | 3 | 3 | 3 | 3 | 3 | 3 | 3 | — | — | — | — | — | — |
|  | 0.5605 | 1 | — | — | 0 | 3 | 2 | 2 | — | 3 | 3 | 3 | 3 | 2 | 3 | 3 | 3 | 3 | 3 | 3 | 3 | 3 | — | — | — | — | — | — |
|  | 0.2803 | 0 | — | — | 0 | 3 | 2 | 1 | — | 3 | 1 | 3 | 3 | 0 | 3 | 3 | 3 | 3 | 3 | 3 | 3 | 3 | — | — | — | — | — | — |
|  | 0.1401 | 0 | — | — | 0 | 3 | 0 | 0 | — | 2 | 3 | 3 | 3 | 0 | 3 | 3 | 3 | 3 | 3 | 2 | 3 | 3 | — | — | — | — | — | — |
|  | 0.0701 | 0 | — | — | 0 | N | 0 | 0 | — | 0 | 3 | 3 | 2 | 0 | 3 | 3 | 3 | 3 | 3 | N | 3 | 3 | — | — | — | — | — | — |
|  | 0.0350 | 0 | — | — | 0 | 3 | 0 | 0 | — | 0 | 0 | 1 | 0 | 0 | 3 | 3 | 2 | 3 | 3 | 1 | 3 | 3 | — | — | — | — | — | — |
|  | 0.0175 | 0 | — | — | 0 | 0 | 0 | 0 | — | 0 | 0 | 0 | 0 | 0 | N | 0 | 0 | 3 | 2 | 0 | N | 0 | — | — | — | — | — | — |
|  | 0.0087 | 0 | — | — | 0 | 0 | 0 | 0 | — | 0 | 0 | 0 | 0 | 0 | 3 | 0 | 0 | 2 | 0 | 0 | 3 | 1 | — | — | — | — | — | — |
| 52 | 5.6050 | 3 | — | — | 2 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 3 | — | — | 1 | 3 | 3 | 3 | — | 3 | 3 | 3 | 3 | 3 | 3 | 3 | 3 | 3 | 3 | 3 | 3 | 3 | — | — | — | — | — | — |
|  | 0.5605 | 3 | — | — | 0 | 3 | 2 | 3 | — | 3 | 3 | 3 | 3 | 3 | 3 | 3 | 3 | 3 | 3 | 3 | 3 | 3 | — | — | — | — | — | — |
|  | 0.2803 | 1 | — | — | 0 | 3 | 2 | 2 | — | 3 | 3 | 3 | 3 | 1 | 3 | 3 | 3 | 3 | 3 | 3 | 3 | 3 | — | — | — | — | — | — |
|  | 0.1401 | 1 | — | — | 3 | 3 | 2 | 1 | — | 3 | 2 | 3 | 3 | 1 | 3 | 3 | 3 | 3 | 3 | 2 | 3 | 3 | — | — | — | — | — | — |
|  | 0.0701 | 1 | — | — | 0 | 2 | 2 | 1 | — | 3 | 1 | 3 | 2 | 0 | 3 | 3 | 3 | 3 | 3 | 3 | 3 | 3 | — | — | — | — | — | — |
|  | 0.0350 | 0 | — | — | 0 | N | 0 | 1 | — | 1 | 0 | 2 | 0 | 0 | 3 | 3 | 3 | 3 | 3 | 2 | 3 | 3 | — | — | — | — | — | — |
|  | 0.0175 | 0 | — | — | 0 | N | 0 | 0 | — | 0 | 0 | 1 | 0 | 0 | 2 | 3 | 2 | 3 | 3 | 1 | 3 | 3 | — | — | — | — | — | — |
|  | 0.0087 | 0 | — | — | 0 | 1 | 0 | 0 | — | 0 | 0 | 0 | 0 | 0 | 2 | 0 | 0 | 3 | 2 | 0 | N | 1 | — | — | — | — | — | — |
| 53 | 5.6050 | 3 | — | — | 1 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 1 | — | — | 0 | 3 | 2 | 2 | — | 3 | 3 | 3 | 3 | 2 | 3 | 3 | 3 | 3 | 3 | 3 | 3 | 3 | — | — | — | — | — | — |
|  | 0.5605 | 0 | — | — | 0 | 3 | 1 | 1 | — | 3 | 3 | 3 | 3 | 1 | 3 | 3 | 3 | 3 | 3 | 3 | 3 | 3 | — | — | — | — | — | — |
|  | 0.2803 | 0 | — | — | 0 | 3 | 1 | 1 | — | 1 | 2 | 1 | 1 | 0 | 3 | 3 | 3 | 3 | 3 | 3 | 3 | 3 | — | — | — | — | — | — |
|  | 0.1401 | 1 | — | — | 0 | 2 | 0 | 0 | — | 0 | 1 | 0 | 1 | 0 | 3 | 3 | 3 | 3 | 3 | 1 | 3 | 2 | — | — | — | — | — | — |
|  | 0.0701 | 0 | — | — | 0 | 1 | 0 | 0 | — | 0 | 0 | 0 | 0 | 0 | 3 | 0 | 0 | 3 | 3 | 1 | 2 | 1 | — | — | — | — | — | — |
|  | 0.0350 | 0 | — | — | 0 | 0 | 0 | 0 | — | 0 | 0 | 0 | 0 | 0 | 2 | 0 | 0 | 2 | 1 | 0 | 1 | 0 | — | — | — | — | — | — |
|  | 0.0175 | 0 | — | — | 0 | N | 0 | 0 | — | 0 | 0 | 0 | 0 | 0 | 2 | 0 | 0 | 1 | 0 | 0 | N | 1 | — | — | — | — | — | — |
| 54 | 5.6050 | 3 | — | — | 1 | 3 | 3 | 3 | — | 3 | 3 | 3 | 3 | 3 | 3 | 3 | 3 | 3 | 3 | 3 | 3 | 3 | — | — | — | — | — | — |
|  | 1.1210 | 1 | — | — | 0 | 3 | 3 | 3 | — | 3 | 3 | 3 | 3 | 1 | 3 | 3 | 3 | 3 | 3 | 3 | 3 | 3 | — | — | — | — | — | — |
|  | 0.5605 | 0 | — | — | 0 | 3 | 2 | 3 | — | 2 | 3 | 3 | 3 | 1 | 3 | 3 | 3 | 3 | 3 | 3 | 3 | 3 | — | — | — | — | — | — |
|  | 0.2803 | 0 | — | — | 0 | 3 | 1 | 1 | — | 1 | 2 | 3 | 1 | 0 | 3 | 3 | 3 | 3 | 3 | 3 | 3 | 3 | — | — | — | — | — | — |
|  | 0.1401 | 0 | — | — | 1 | 1 | 0 | 1 | — | 1 | 1 | 2 | 1 | 0 | 2 | 3 | 3 | 3 | 3 | 3 | 3 | 3 | — | — | — | — | — | — |

TABLE B-continued

| Compound No. | Rate kg/ha | Sobe | Cotz | Rape | Cbuu | Wibw | Mogl | Kese | Jiwe | Vele | Whez | Rice | Gron | Cobr | Dmir | Pygr | Bact | Lcft | Gble | Sulq | Coscw | Pecbg | Cnbz | Anth | Abuh | Brrj | Sejg | Wioa |
|---|---|---|---|---|---|---|---|---|---|---|---|---|---|---|---|---|---|---|---|---|---|---|---|---|---|---|---|---|
|  | 0.0701 | 0 | — | — | 0 | 1 | 0 | 0 | — | 0 | 0 | 0 | 0 | 0 | 2 | 2 | 3 | 3 | 3 | 1 | 3 | 3 | — | — | — | — | — | — |
|  | 0.0350 | 0 | — | — | 0 | 0 | 0 | 0 | — | 0 | 0 | 0 | 0 | 0 | 1 | 1 | 2 | 3 | 3 | 0 | 1 | 0 | — | — | — | — | — | — |
|  | 0.0175 | 0 | — | — | 0 | 0 | 0 | 0 | — | 0 | 0 | 0 | 0 | 0 | 2 | 0 | 0 | 3 | 0 | 0 | 1 | 0 | — | — | — | — | — | — |
| 55 | 5.6050 | 1 | — | — | 0 | 3 | 2 | 2 | — | 3 | 3 | 3 | 3 | 3 | 3 | 3 | 3 | 3 | 3 | 3 | 3 | 3 | — | — | — | — | — | — |
|  | 1.1210 | 0 | — | — | 0 | 0 | 0 | 0 | — | 0 | 0 | 2 | 1 | 0 | 2 | 3 | 3 | 3 | 3 | 1 | 2 | 1 | — | — | — | — | — | — |
|  | 0.5605 | 0 | — | — | 0 | 1 | 0 | 0 | — | 0 | 0 | 0 | 0 | 0 | 1 | 1 | 3 | 3 | 3 | 0 | 0 | 0 | — | — | — | — | — | — |
|  | 0.2803 | 0 | — | — | 0 | 0 | 0 | 0 | — | 0 | N | 0 | 0 | 0 | N | 1 | 3 | 3 | 3 | 0 | 0 | 0 | — | — | — | — | — | — |
|  | 0.1401 | 0 | — | — | 0 | 0 | 0 | 0 | — | 0 | 0 | 0 | 0 | 0 | 1 | 0 | 0 | 0 | 0 | 0 | 0 | 0 | — | — | — | — | — | — |
|  | 0.0701 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 56 | 11.2100 | 0 | — | — | 0 | 3 | 0 | 0 | — | 1 | 1 | 0 | 1 | 0 | 3 | 3 | 3 | 3 | 3 | 3 | 3 | 2 | — | — | — | — | — | — |
|  | 5.6050 | 0 | — | — | 0 | 0 | 0 | 0 | — | 0 | 1 | 0 | 0 | 0 | 3 | 3 | 1 | 3 | 1 | 0 | 3 | 0 | — | — | — | — | — | — |
|  | 2.8025 | 0 | — | — | 0 | 0 | 0 | 0 | — | 0 | 0 | 0 | 0 | 0 | 2 | 2 | 0 | 2 | 0 | 0 | 2 | 0 | — | — | — | — | — | — |
|  | 1.1210 | 0 | — | — | 0 | 0 | 0 | 0 | — | 0 | 0 | 0 | 0 | 0 | 1 | 0 | 0 | 0 | 0 | 0 | 0 | 0 | — | — | — | — | — | — |
| 57 | 5.6050 | 0 | — | — | 0 | 3 | 1 | 0 | — | 2 | 2 | 3 | 1 | 0 | 3 | 3 | 3 | 3 | 3 | 3 | 3 | 1 | — | — | — | — | — | — |
|  | 1.1210 | 0 | — | — | 0 | 1 | 0 | 0 | — | 0 | 1 | 0 | 0 | 0 | 3 | 3 | 0 | 3 | 1 | 2 | 3 | 0 | — | — | — | — | — | — |
|  | 0.5605 | 0 | — | — | 0 | 0 | 0 | 0 | — | 0 | 0 | 0 | 0 | 0 | 1 | 0 | 0 | 3 | 0 | 0 | 3 | 0 | — | — | — | — | — | — |
|  | 0.2803 | 0 | — | — | 0 | 0 | 0 | 0 | — | 0 | 0 | 0 | 0 | 0 | 1 | 0 | 0 | 3 | 0 | 1 | 3 | 0 | — | — | — | — | — | — |
|  | 0.1401 | 0 | — | — | 1 | N | 0 | 0 | — | 0 | 0 | 0 | 0 | 0 | N | 0 | 0 | 3 | 0 | N | N | N | — | — | — | — | — | — |
|  | 0.0701 | 0 | — | — | 0 | 0 | 0 | 0 | — | 0 | 0 | 0 | 0 | 0 | 0 | 0 | 0 | 3 | 0 | 0 | 3 | N | — | — | — | — | — | — |
|  | 0.0350 | 0 | — | — | 1 | 0 | 0 | 0 | — | 0 | 0 | 0 | 0 | 0 | 0 | 0 | 0 | 1 | 0 | 0 | 3 | 1 | — | — | — | — | — | — |
| 58 | 5.60 | 0 | — | — | 0 | 3 | 2 | 2 | — | 3 | 3 | 2 | 3 | 2 | 3 | 3 | 3 | 3 | 3 | 3 | 3 | 3 | — | — | — | — | — | — |
|  | 1.12 | 0 | — | — | 0 | 0 | 0 | 0 | — | 1 | 1 | 0 | 0 | 0 | 1 | 3 | 3 | 2 | 3 | 2 | 2 | 2 | — | — | — | — | — | — |
|  | 0.56 | 0 | — | — | 0 | N | 0 | 0 | — | 0 | 0 | 0 | 0 | 0 | 0 | 2 | 1 | N | 3 | 1 | N | 1 | — | — | — | — | — | — |
|  | 0.28 | 0 | — | — | 0 | 0 | 0 | 0 | — | 0 | 0 | 0 | 0 | 0 | 0 | 0 | 0 | 2 | 0 | 0 | 0 | 0 | — | — | — | — | — | — |
|  | 0.14 | 0 | — | — | 0 | 0 | 0 | 0 | — | 0 | 0 | 0 | 0 | 0 | N | 0 | 0 | N | 0 | 0 | N | 0 | — | — | — | — | — | — |
|  | 0.07 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| 59 | 5.60 | 3 | — | — | 0 | 3 | 3 | 3 | — | 3 | 3 | 3 | 3 | 3 | 3 | 3 | 3 | 3 | 3 | 3 | 3 | 3 | — | — | — | — | — | — |
|  | 1.12 | 0 | — | — | 0 | N | 1 | 0 | — | 2 | 1 | 3 | 1 | 0 | 2 | 3 | 3 | 3 | 3 | 3 | 3 | 3 | — | — | — | — | — | — |
|  | 0.56 | 0 | — | — | 0 | 3 | 0 | 0 | — | 0 | 0 | 1 | 1 | 0 | 3 | 3 | 3 | 3 | 3 | 3 | 3 | 3 | — | — | — | — | — | — |
|  | 0.28 | 0 | — | — | 0 | 1 | 0 | 0 | — | 0 | 0 | 0 | 0 | 0 | 2 | 2 | 2 | 3 | 0 | 1 | 3 | 2 | — | — | — | — | — | — |
|  | 0.14 | 0 | — | — | 0 | 0 | 0 | 0 | — | 0 | 0 | 0 | 0 | 0 | 1 | 0 | 3 | 0 | 0 | N | 1 |  | — | — | — | — | — | — |
| 60 | 5.60 | 3 | — | — | 2 | 3 | 3 | 3 | — | 3 | 3 | 3 | 3 | 3 | 3 | 3 | 3 | 3 | 3 | 3 | 3 | 3 | — | — | — | — | — | — |
|  | 1.12 | 3 | — | — | 0 | 3 | 3 | 3 | — | 3 | 3 | 3 | 3 | 3 | 3 | 3 | 3 | 3 | 3 | 3 | 3 | 3 | — | — | — | — | — | — |
|  | 0.56 | 3 | — | — | 0 | 3 | 2 | 2 | — | 3 | 3 | 3 | 3 | 3 | 3 | 3 | 3 | 3 | 3 | 3 | 3 | 3 | — | — | — | — | — | — |
|  | 0.28 | 1 | — | — | 0 | 3 | 1 | 1 | — | 2 | 3 | 3 | 3 | 2 | 3 | 3 | 3 | 3 | 3 | 3 | 3 | 3 | — | — | — | — | — | — |
|  | 0.14 | 0 | — | — | 0 | 3 | 0 | 2 | — | 2 | 2 | 2 | 1 | 0 | 3 | 3 | 3 | 3 | 3 | 3 | 3 | 3 | — | — | — | — | — | — |

5,877,119

TABLE B-continued

| Compound No. | Rate kg/ha | Sobe | Cotz | Rape | Cbu | Wibw | Mogl | Kswe | Jiwe | Vele | Whez | Rice | Gron | Cbmr | Dmi | Pygr | Barg | Lcft | Gble | Sulq | Ccbw | Pnbg | Cabz | Abrh | Brjg | Rutg | Seja | Wioa |
|---|---|---|---|---|---|---|---|---|---|---|---|---|---|---|---|---|---|---|---|---|---|---|---|---|---|---|---|---|
| | 0.07 | N | — | — | 0 | 3 | 1 | 1 | — | 1 | 0 | 1 | 0 | 0 | 3 | 3 | 3 | 3 | 3 | 3 | 2 | 2 | — | — | — | — | — | — |
| | 0.35 | 0 | — | — | 0 | N | 0 | 0 | — | 0 | 0 | 1 | 0 | 0 | 3 | 1 | 3 | 3 | 3 | 1 | N | 3 | — | — | — | — | — | — |
| | 0.018 | 0 | — | — | 0 | 1 | 0 | 0 | — | 0 | 0 | 0 | 0 | 0 | 0 | 0 | 0 | 0 | 0 | 0 | 2 | 1 | — | — | — | — | — | — |
| | 0.009 | 0 | — | — | 0 | N | 0 | 0 | — | 0 | 0 | 0 | 0 | 0 | 0 | 0 | 0 | 0 | 0 | 0 | N | N | — | — | — | — | — | — |
| 61 | 5.60 | 3 | — | — | 0 | 3 | 3 | 3 | — | 3 | 3 | 3 | 3 | 3 | 3 | 3 | 3 | 3 | 3 | 3 | 3 | 3 | — | — | — | — | — | — |
| | 1.12 | 3 | — | — | 0 | 3 | 3 | 3 | — | 3 | 3 | 2 | 3 | 3 | 3 | 3 | 3 | 3 | 3 | 3 | 3 | 3 | — | — | — | — | — | — |
| | 0.56 | 1 | — | — | 0 | 3 | 3 | 2 | — | 2 | 3 | 3 | 3 | 2 | 3 | 3 | 3 | 3 | 3 | 3 | 3 | 3 | — | — | — | — | — | — |
| | 0.28 | 0 | — | — | 0 | 3 | 1 | 1 | — | 1 | 3 | 0 | 3 | 3 | 3 | 3 | 3 | 3 | 3 | 2 | 3 | 2 | — | — | — | — | — | — |
| | 0.14 | 0 | — | — | 0 | 3 | 0 | 1 | — | 0 | 2 | 0 | 3 | 1 | 3 | 3 | 3 | 3 | 1 | 3 | 1 | | — | — | — | — | — | — |
| | 0.07 | 0 | — | — | 0 | 0 | 0 | 0 | — | 0 | 0 | 1 | 3 | 0 | 3 | 0 | 3 | 3 | 3 | 0 | 1 | 0 | — | — | — | — | — | — |
| | 0.035 | 0 | — | — | 0 | 1 | 0 | 0 | — | 0 | 0 | 0 | 0 | 0 | 3 | N | 3 | 3 | 3 | 0 | 0 | 0 | — | — | — | — | — | — |
| | 0.08 | 0 | — | — | 0 | 0 | 0 | 0 | — | 0 | 0 | N | 0 | 0 | 2 | 0 | 0 | 3 | 3 | 0 | 0 | 0 | — | — | — | — | — | — |
| | 0.009 | 0 | — | — | 0 | 0 | 0 | 0 | — | 0 | 0 | 0 | 0 | 0 | 2 | 0 | 0 | 3 | 0 | 0 | 0 | 0 | — | — | — | — | — | — |
| 62 | 5.6 | 3 | — | — | 2 | 3 | 3 | 3 | — | 3 | 3 | 3 | 3 | 3 | 3 | 3 | 3 | 3 | 3 | 3 | 3 | 3 | — | — | — | — | — | — |
| | 1.12 | 2 | — | — | 0 | 3 | 3 | 3 | — | 3 | 3 | 3 | 3 | 3 | 3 | 3 | 3 | 3 | 3 | 3 | 3 | 3 | — | — | — | — | — | — |
| | 0.56 | 0 | — | — | 0 | 0 | 2 | 1 | — | 2 | 3 | 3 | 3 | 3 | 3 | 3 | 3 | 3 | 2 | 3 | 1 | | — | — | — | — | — | — |
| | 0.28 | 0 | — | — | 0 | N | 0 | 2 | — | 2 | 1 | 1 | 3 | 1 | 3 | 3 | 3 | 3 | 3 | 3 | 3 | N | — | — | — | — | — | — |
| | 0.14 | 0 | — | — | 0 | 0 | 2 | 0 | — | 1 | 0 | 0 | 1 | 0 | 3 | 3 | 3 | 3 | 1 | 3 | 0 | | — | — | — | — | — | — |
| | 0.07 | 0 | — | — | 0 | N | 0 | 0 | — | 1 | 0 | 0 | 0 | 0 | 3 | 3 | 2 | 3 | 2 | 1 | 3 | 0 | — | — | — | — | — | — |
| | 0.035 | 0 | — | — | 0 | 1 | 0 | 0 | — | 0 | 0 | 0 | 0 | 0 | 3 | 2 | 0 | 3 | 0 | 1 | 3 | 0 | — | — | — | — | — | — |
| | 0.018 | 0 | — | — | 0 | N | 1 | 1 | — | 0 | 0 | 0 | 0 | 0 | 1 | 0 | 0 | 3 | 0 | N | 3 | N | — | — | — | — | — | — |
| | 0.009 | 0 | — | — | 0 | N | 0 | 0 | — | 0 | 0 | 0 | 0 | 0 | 3 | 0 | 0 | 3 | 0 | N | 3 | 0 | — | — | — | — | — | — |
| 63 | 5.60 | 3 | — | — | 1 | 3 | 3 | 3 | — | 3 | 3 | 3 | 3 | 3 | 3 | 3 | 3 | 3 | 3 | 3 | 3 | 3 | — | — | — | — | — | — |
| | 1.12 | 2 | — | — | 0 | 3 | 3 | 3 | — | 3 | 3 | 3 | 3 | 3 | 3 | 3 | 3 | 3 | 3 | 3 | 3 | 3 | — | — | — | — | — | — |
| | 0.56 | 2 | — | — | 0 | 3 | 3 | 2 | — | 1 | 3 | 2 | 3 | 3 | 3 | 3 | 3 | 3 | 3 | 3 | 3 | 3 | — | — | — | — | — | — |
| | 0.28 | 1 | — | — | 0 | 0 | 1 | 1 | — | 0 | 2 | 3 | 3 | 2 | 3 | 3 | 3 | 3 | 3 | 3 | 3 | 2 | — | — | — | — | — | — |
| | 0.14 | 0 | — | — | N | 0 | 0 | 0 | — | 0 | 0 | 0 | 3 | 1 | 3 | 3 | 3 | 1 | 3 | 0 | 2 | 1 | — | — | — | — | — | — |
| | 0.07 | 0 | — | — | 0 | N | 0 | 1 | — | 0 | 0 | 2 | 3 | 0 | 1 | 3 | 3 | N | 3 | N | N | N | — | — | — | — | — | — |
| | 0.035 | 0 | — | — | 0 | 0 | 0 | 1 | — | 0 | 0 | 1 | 2 | 0 | 0 | 0 | 2 | 0 | 2 | 0 | N | N | — | — | — | — | — | — |
| | 0.18 | 0 | — | — | 0 | 0 | 0 | 0 | — | 0 | 0 | 0 | 0 | 0 | 0 | 0 | 0 | N | 0 | 0 | N | 1 | — | — | — | — | — | — |
| | 0.009 | 0 | — | — | 0 | 0 | 0 | 0 | — | 0 | 0 | 0 | 0 | 0 | 0 | 0 | 0 | 0 | 0 | 0 | 1 | 0 | — | — | — | — | — | — |
| 64 | 5.60 | 1 | — | — | 1 | 3 | 3 | 3 | — | 3 | 3 | 3 | 3 | 3 | 3 | 3 | 3 | 3 | 3 | 3 | 3 | 3 | — | — | — | — | — | — |
| | 1.12 | 1 | — | — | 0 | 1 | 3 | 3 | — | 1 | 3 | 3 | 3 | 2 | 3 | 3 | 3 | 3 | 3 | 0 | 3 | | — | — | — | — | — | — |
| | 0.56 | 0 | — | — | 0 | 1 | 3 | 1 | — | 1 | 3 | 3 | 3 | 2 | 3 | 3 | 3 | 3 | 0 | 0 | 3 | | — | — | — | — | — | — |
| | 0.28 | 0 | — | — | 0 | 2 | 1 | 2 | — | 0 | 0 | 3 | 2 | 0 | 3 | 3 | 3 | 3 | 0 | 0 | 3 | | — | — | — | — | — | — |
| | 0.14 | 0 | — | — | 0 | 2 | 0 | 0 | — | 0 | 1 | 1 | 0 | 0 | 2 | 3 | 3 | 3 | 0 | 0 | 1 | | — | — | — | — | — | — |

TABLE B-continued

| Compound No. | Rate kg/ha | Sobe | Cotz | Rape | Cobu | Wibw | Mogl | Kese | Jiwe | Vele | Whez | Rice | Gron | Cobr | Domi | Pygr | Bact | Lafg | Grft | Sube | Colq | Pesw | Cocw | Anbg | Babz | Ruth | Sejg | Wioa |
|---|---|---|---|---|---|---|---|---|---|---|---|---|---|---|---|---|---|---|---|---|---|---|---|---|---|---|---|---|
| | 0.07 | 0 | — | — | 0 | 0 | 0 | 0 | — | 0 | 1 | 1 | 1 | 0 | 1 | 0 | 2 | 3 | 3 | 0 | N | 1 | — | — | — | — | — | — |
| | 0.035 | 0 | — | — | 0 | 1 | 0 | 1 | — | 0 | 0 | 2 | 0 | 0 | 2 | 1 | 0 | 3 | 0 | 0 | N | N | — | — | — | — | — | — |
| | 0.018 | 0 | — | — | 0 | N | 0 | N | — | 0 | 0 | 1 | 0 | 0 | 1 | 0 | 0 | 3 | 0 | 0 | 1 | 1 | — | — | — | — | — | — |
| | 0.009 | 0 | — | — | 0 | 1 | 0 | 0 | — | 0 | 0 | 0 | 0 | 0 | 0 | N | 0 | 0 | 0 | 0 | 0 | 1 | — | — | — | — | — | — |
| 65 | 5.6050 | 2 | — | — | 2 | 3 | 2 | 3 | — | 3 | 3 | 3 | 3 | 3 | 3 | 3 | 3 | 3 | 3 | 3 | 3 | 3 | — | — | — | — | — | — |
| | 5.6050 | 3 | — | — | 2 | 3 | 3 | 3 | — | 3 | 3 | 3 | 3 | 3 | 3 | 3 | 3 | 3 | 3 | 3 | 3 | 3 | — | — | — | — | — | — |
| | 1.1210 | 2 | — | — | 2 | 3 | 3 | 3 | — | 3 | 3 | 3 | 3 | 3 | 3 | 3 | 3 | 3 | 3 | 3 | 3 | 3 | — | — | — | — | — | — |
| | 1.12 | 0 | — | — | 0 | 3 | 2 | 3 | — | 3 | 2 | 3 | 1 | 1 | 3 | 3 | 3 | 3 | 3 | 3 | 3 | 3 | — | — | — | — | — | — |
| | 0.56 | 0 | — | — | 0 | 0 | 0 | 0 | — | 0 | 1 | N | 0 | 1 | 3 | 3 | 3 | 3 | 3 | 3 | 3 | 3 | — | — | — | — | — | — |
| | 0.56 | 1 | — | — | 2 | 2 | 1 | 3 | — | 3 | 2 | 3 | 3 | 2 | 3 | 3 | 3 | 3 | 3 | 3 | 3 | 3 | — | — | — | — | — | — |
| | 0.28 | 0 | — | — | 1 | 3 | 0 | 2 | — | 2 | 2 | 3 | 3 | 1 | 3 | 3 | 3 | 3 | 3 | 3 | 3 | 3 | — | — | — | — | — | — |
| | 0.28 | 0 | — | — | 0 | 1 | 0 | 0 | — | 0 | 0 | 3 | 0 | 0 | 1 | 3 | 3 | 3 | 3 | 3 | 1 | 3 | — | — | — | — | — | — |
| | 0.14 | 0 | — | — | N | 3 | 1 | 2 | — | 0 | 0 | 3 | 3 | 1 | 1 | 3 | 3 | 3 | 3 | 3 | 3 | 3 | — | — | — | — | — | — |
| | 0.14 | 0 | — | — | 0 | N | N | 1 | — | 0 | 0 | 1 | 0 | 0 | 2 | 1 | 3 | 3 | 3 | 2 | N | N | — | — | — | — | — | — |
| | 0.07 | 0 | — | — | 0 | 0 | 0 | 0 | — | 0 | 0 | 0 | 0 | 0 | 0 | 1 | 0 | 3 | 1 | 0 | 0 | 0 | — | — | — | — | — | — |
| | 0.07 | 0 | — | — | N | 1 | 1 | 1 | — | 1 | 0 | 1 | 2 | 1 | 2 | 2 | 3 | 3 | 3 | 1 | 0 | 3 | — | — | — | — | — | — |
| | 0.35 | 0 | — | — | N | 0 | 0 | 0 | — | 0 | 0 | 0 | 0 | 0 | 0 | 0 | 0 | 0 | 0 | 0 | 0 | 1 | — | — | — | — | — | — |
| | 0.35 | N | — | — | 1 | 1 | 0 | N | — | 1 | 0 | N | 1 | 1 | 1 | 1 | 1 | 3 | 2 | N | N | 3 | — | — | — | — | — | — |
| | 0.018 | N | — | — | N | 0 | 0 | 1 | — | 0 | 0 | 0 | 1 | 0 | 0 | 0 | 0 | 0 | 0 | 0 | 0 | 1 | — | — | — | — | — | — |
| | 0.018 | 0 | — | — | 0 | 0 | 0 | 0 | — | 0 | 0 | 0 | 0 | 0 | 0 | 0 | 0 | 0 | 0 | 0 | 0 | 0 | — | — | — | — | — | — |
| | 0.009 | 0 | — | — | 0 | 0 | 0 | 0 | — | 0 | 0 | 0 | 0 | 0 | 1 | 0 | 0 | 1 | 0 | 0 | 0 | 0 | — | — | — | — | — | — |
| 66 | 5.6 | 0 | — | — | 0 | 3 | 1 | 1 | — | 2 | 2 | 3 | 3 | 2 | 3 | 3 | 3 | 3 | 3 | 2 | 3 | 3 | — | — | — | — | — | — |
| | 1.12 | 0 | — | — | 0 | 3 | 0 | 1 | — | 2 | 0 | 3 | 1 | 3 | 0 | 3 | 3 | 2 | 3 | 3 | 3 | 2 | — | — | — | — | — | — |
| | 0.56 | 0 | — | — | 0 | 2 | 0 | 0 | — | 1 | 0 | 2 | 1 | 1 | 0 | 3 | 3 | 3 | 3 | 1 | 3 | 2 | — | — | — | — | — | — |
| | 0.28 | 0 | — | — | 0 | 2 | 0 | 1 | — | 0 | 0 | 0 | 1 | 1 | N | 3 | 3 | 3 | 3 | 0 | 3 | 3 | — | — | — | — | — | — |
| | 0.14 | 0 | — | — | 0 | 2 | 0 | 1 | — | 0 | 0 | 0 | 0 | 0 | 0 | 0 | 0 | 0 | 0 | N | 2 | 2 | — | — | — | — | — | — |
| | 0.07 | 0 | — | — | 0 | 3 | 0 | N | — | 0 | 0 | 0 | 0 | 0 | 0 | 0 | 0 | 0 | 0 | N | 0 | 0 | — | — | — | — | — | — |
| 67 | 5.6 | 0 | — | — | 0 | 3 | 2 | 3 | — | 3 | 3 | 3 | 1 | 3 | 3 | 3 | 3 | 3 | 3 | 3 | 3 | 3 | — | — | — | — | — | — |
| | 1.12 | 0 | — | — | 0 | 3 | 0 | 3 | — | 3 | 2 | 3 | 3 | 2 | 3 | 3 | 3 | 3 | 3 | 3 | 3 | 3 | — | — | — | — | — | — |
| | 0.5605 | 0 | — | — | 1 | 3 | N | 1 | — | 0 | 2 | 2 | 2 | 0 | 1 | 3 | 3 | 3 | 3 | 2 | 3 | 3 | — | — | — | — | — | — |
| | 0.2803 | 0 | — | — | 0 | 3 | 0 | 1 | — | 0 | 0 | 0 | 0 | 0 | 0 | 3 | 3 | 2 | 2 | 3 | 1 | 3 | — | — | — | — | — | — |
| | 0.1401 | 0 | — | — | 0 | 3 | 0 | N | — | 1 | 0 | 0 | 0 | 0 | 1 | 1 | 0 | 3 | 3 | 3 | 1 | 3 | — | — | — | — | — | — |
| | 0.0701 | 0 | — | — | N | 1 | 0 | 0 | — | 0 | 0 | 0 | 0 | 0 | N | 0 | 2 | N | 3 | 0 | 3 | 0 | — | — | — | — | — | — |
| | 0.0350 | 0 | — | — | 0 | 2 | 0 | 0 | — | 0 | 0 | 0 | 0 | 0 | 0 | 0 | 0 | 0 | 0 | N | 3 | N | — | — | — | — | — | — |
| | 0.0175 | 0 | — | — | 0 | N | 0 | 0 | — | 0 | 0 | 0 | 0 | 0 | 0 | 0 | 0 | 0 | 0 | 0 | 2 | N | — | — | — | — | — | — |
| 68 | 5.6050 | 3 | — | — | 1 | 3 | 3 | 2 | — | 3 | 1 | 3 | 3 | 2 | 3 | 3 | 3 | 3 | 3 | 3 | 3 | 3 | — | — | — | — | — | — |

TABLE B-continued

| Compound No. | Rate kg/ha | Sobe | Cotz | Rape | Cobu | Wibw | Mogl | Kese | Jiwe | Vele | Whez | Rice | Gron | Cobr | Dmbi | Prmg | Byrg | Larct | Grft | Subte | Colq | Pesw | Conw | Anbg | Brbz | Ruth | Sejg | Wioa |
|---|---|---|---|---|---|---|---|---|---|---|---|---|---|---|---|---|---|---|---|---|---|---|---|---|---|---|---|---|
| | 1.1210 | 0 | — | — | 0 | 1 | 2 | 1 | — | 0 | 0 | 2 | 2 | 0 | 2 | 3 | 3 | 1 | 3 | 0 | N | 0 | — | — | — | — | — | — |
| | 0.5605 | 0 | — | — | 0 | N | 0 | 0 | — | 0 | 1 | 2 | 1 | 0 | 0 | 3 | 1 | 0 | 3 | N | 3 | N | — | — | — | — | — | — |
| | 0.2803 | 0 | — | — | 1 | 0 | 1 | 0 | — | 0 | 0 | 0 | 0 | 0 | 2 | 0 | 0 | 1 | 0 | 0 | 3 | 2 | — | — | — | — | — | — |
| | 0.1401 | 0 | — | — | 0 | N | 0 | 0 | — | 0 | 0 | 0 | 0 | 0 | 0 | 0 | 0 | 0 | 1 | 0 | 3 | N | — | — | — | — | — | — |
| | 0.0701 | 0 | — | — | 0 | N | 0 | 0 | — | 0 | 0 | 0 | 0 | 0 | 0 | 0 | 0 | 0 | 0 | 0 | 0 | 0 | — | — | — | — | — | — |
| 69 | 5.6050 | 0 | — | — | 0 | 3 | 1 | 1 | — | 1 | 2 | 3 | 1 | 2 | 3 | 3 | 3 | 3 | 3 | 3 | 3 | 3 | — | — | — | — | — | — |
| | 1.1210 | 0 | — | — | 0 | 3 | 0 | 0 | — | 0 | 0 | 2 | 0 | 0 | 2 | 3 | 2 | 3 | 3 | 1 | 3 | 3 | — | — | — | — | — | — |
| | 0.5605 | 0 | — | — | 0 | 3 | 0 | 0 | — | 0 | 0 | 0 | 0 | 0 | 0 | 1 | 1 | 0 | 1 | 0 | 3 | 1 | — | — | — | — | — | — |
| | 0.2803 | 0 | — | — | 0 | 1 | 0 | N | — | 0 | 0 | 0 | 1 | 0 | 0 | 0 | 0 | 0 | 0 | 1 | 3 | 0 | — | — | — | — | — | — |
| | 0.1401 | 0 | — | — | 1 | 2 | 0 | 0 | — | 0 | 0 | 1 | 0 | 0 | N | 1 | 0 | N | 0 | 0 | 1 | 1 | — | — | — | — | — | — |
| | 0.0701 | 0 | — | — | 0 | N | 0 | 0 | — | N | 0 | 0 | 0 | 0 | N | 0 | 0 | N | 0 | 0 | N | 1 | — | — | — | — | — | — |
| 70 | 5.6050 | 0 | — | — | 0 | 3 | 2 | 1 | — | 0 | 0 | 3 | 0 | 1 | 2 | 3 | 3 | 3 | 3 | 1 | 3 | 3 | — | — | — | — | — | — |
| | 1.1210 | 0 | — | — | 0 | 3 | 1 | 0 | — | 0 | 0 | 2 | 0 | 0 | 0 | 2 | 3 | 0 | 1 | 0 | 3 | 1 | — | — | — | — | — | — |
| | 0.5605 | 0 | — | — | 0 | 2 | 1 | 0 | — | 0 | 0 | 0 | 0 | 0 | N | 0 | 1 | 0 | 0 | 0 | 3 | 1 | — | — | — | — | — | — |
| | 0.2803 | 0 | — | — | 1 | N | 0 | 0 | — | 0 | 0 | N | 0 | 0 | 1 | N | 0 | 0 | 0 | 0 | 3 | N | — | — | — | — | — | — |
| | 0.1401 | 1 | — | — | 0 | N | 0 | N | — | 0 | 0 | 1 | 0 | 0 | 1 | 0 | 0 | 0 | 0 | 0 | N | N | N | — | — | — | — | — |
| | 0.0701 | 0 | — | — | 0 | N | 0 | 0 | — | 0 | 0 | 0 | 0 | 0 | N | N | 0 | N | 0 | 1 | 3 | 1 | — | — | — | — | — | — |
| 71 | 5.6050 | 1 | — | — | 0 | 3 | 1 | 2 | — | 2 | 1 | 3 | 2 | 1 | 3 | 3 | 3 | 3 | 3 | 3 | 3 | 3 | — | — | — | — | — | — |
| | 1.1210 | 0 | — | — | 0 | 1 | 0 | 1 | — | 2 | 0 | 2 | 1 | 0 | 3 | 3 | 3 | 3 | 3 | 1 | 3 | 1 | — | — | — | — | — | — |
| | 0.5605 | 0 | — | — | 0 | N | 0 | 0 | — | 0 | 0 | 0 | 0 | 0 | 0 | 0 | 3 | 0 | 3 | 1 | 2 | 0 | — | — | — | — | — | — |
| | 0.2803 | N | — | — | 0 | 2 | 0 | 0 | — | 0 | 0 | 0 | 0 | 0 | 2 | 0 | 1 | 3 | 0 | 1 | 3 | N | — | — | — | — | — | — |
| | 0.1401 | 0 | — | — | 0 | N | 0 | 0 | — | 0 | 0 | 0 | 0 | 0 | 0 | 0 | 0 | 3 | 0 | 0 | 3 | 1 | — | — | — | — | — | — |
| | 0.0701 | 0 | — | — | 0 | N | 0 | 0 | — | 0 | 0 | N | 0 | 0 | 1 | 0 | 0 | 1 | 0 | N | 3 | 2 | — | — | — | — | — | — |
| 72 | 11.2100 | 2 | — | — | 3 | 3 | 3 | 3 | — | 3 | 3 | 3 | 3 | 3 | 3 | 3 | 3 | 3 | 3 | 3 | 3 | 3 | — | — | — | — | — | — |
| | 5.6050 | 0 | — | — | 0 | 3 | 2 | 2 | — | 1 | 1 | 3 | 3 | 1 | 3 | 3 | 3 | 3 | 3 | 1 | 2 | 2 | — | — | — | — | — | — |
| | 2.8025 | 0 | — | — | 1 | 3 | 1 | 1 | — | 2 | 1 | 3 | 3 | 0 | 1 | 3 | 3 | 3 | 3 | N | N | N | — | — | — | — | — | — |
| | 1.1210 | 0 | — | — | 1 | 2 | 0 | 0 | — | 0 | 0 | 0 | 1 | 0 | 0 | 0 | 2 | 0 | 3 | 0 | 2 | 0 | — | — | — | — | — | — |
| | 0.5605 | 0 | — | — | 1 | 2 | 0 | N | — | 1 | 0 | 0 | 0 | 0 | 1 | 0 | 0 | 0 | 0 | 2 | 3 | N | — | — | — | — | — | — |
| 73 | 5.6050 | 0 | — | — | 0 | 3 | 3 | 1 | — | 0 | 2 | 3 | 3 | 1 | 3 | 3 | 3 | 3 | 3 | 2 | 3 | 3 | — | — | — | — | — | — |
| | 1.1210 | 1 | — | — | 0 | 3 | 1 | 1 | — | 0 | 0 | 1 | 0 | 1 | 3 | 2 | 3 | 3 | 3 | 1 | 3 | 3 | — | — | — | — | — | — |
| | 0.5605 | N | — | — | N | 3 | 2 | 0 | — | 0 | 0 | 0 | 1 | 0 | 1 | 1 | 2 | 1 | 3 | 3 | 0 | 3 | — | — | — | — | — | — |
| | 0.2803 | 0 | — | — | 0 | N | 0 | N | — | N | 0 | N | 0 | 0 | N | 1 | 0 | 1 | 0 | N | N | N | — | — | — | — | — | — |
| | 0.1401 | 0 | — | — | 0 | 3 | 0 | 0 | — | 0 | 0 | 0 | N | 0 | 0 | 0 | 0 | 1 | 1 | 3 | 3 | — | — | — | — | — | — | — |
| | 0.0701 | 0 | — | — | 0 | 0 | 0 | N | — | 0 | 0 | 1 | 0 | 0 | 1 | 0 | 0 | 0 | 0 | 0 | 0 | 1 | — | — | — | — | — | — |
| 74 | 5.6050 | 3 | — | — | 3 | 0 | 3 | 3 | — | 3 | 3 | 3 | 3 | 3 | 3 | 3 | 3 | 3 | 3 | 3 | 3 | 3 | — | — | — | — | — | — |
| | 1.1210 | 1 | — | — | 0 | 3 | 3 | 3 | — | 3 | 3 | 3 | 3 | 3 | 3 | 3 | 3 | 3 | 3 | 3 | 3 | 3 | — | — | — | — | — | — |

TABLE B-continued

| Compound No. | Rate kg/ha | Sobe | Cotz | Rape | Cbu | Wibw | Mogl | Kese | Jiwe | Vele | Whez | Rice | Gron | Cbmr | Dormi | Pygr | Byct | Larft | Grbe | Subq | Colw | Pecw | Cong | Anbz | Brrth | Sejg | Wioa |
|---|---|---|---|---|---|---|---|---|---|---|---|---|---|---|---|---|---|---|---|---|---|---|---|---|---|---|---|
|  | 0.5605 | 1 | — | — | 0 | 3 | 3 | 3 | — | 3 | 3 | 3 | 3 | 2 | 3 | 3 | 3 | 3 | 3 | 3 | 3 | 3 | — | — | — | — | — |
|  | 0.2803 | 0 | — | — | 1 | 3 | 3 | 2 | — | 3 | 2 | 3 | 2 | 0 | 3 | 3 | 3 | 3 | 3 | 1 | 3 | 3 | — | — | — | — | — |
|  | 0.1401 | 0 | — | — | N | 3 | 3 | 1 | — | 0 | 2 | 3 | 3 | 0 | 3 | 3 | 3 | 3 | 3 | 1 | 3 | 3 | — | — | — | — | — |
|  | 0.0701 | 1 | — | — | 0 | 3 | 0 | 0 | — | 0 | 2 | 3 | 1 | 0 | 3 | 3 | 3 | 3 | 3 | 2 | 3 | 2 | — | — | — | — | — |
|  | 0.0350 | 0 | — | — | 0 | 0 | 0 | 0 | — | 0 | 0 | 0 | 0 | 0 | 2 | 0 | 2 | 3 | 3 | 1 | 3 | 3 | — | — | — | — | — |
|  | 0.0175 | 0 | — | — | 0 | 1 | 0 | 0 | — | 0 | 0 | 0 | 0 | 0 | 1 | 0 | 0 | 2 | 2 | 0 | 0 | 1 | — | — | — | — | — |
|  | 0.0087 | 0 | — | — | 0 | N | 0 | 0 | — | 0 | 0 | 0 | 0 | 0 | 0 | 0 | 0 | 1 | 0 | 0 | 0 | 0 | — | — | — | — | — |
| 75 | 5.6050 | 3 | — | — | 1 | 3 | 3 | 2 | — | 3 | 3 | 3 | 1 | 1 | 3 | 3 | 3 | 3 | 3 | 3 | 3 | 3 | — | — | — | — | — |
|  | 1.1210 | 0 | — | — | 0 | 1 | 0 | 3 | — | 3 | 1 | 3 | 0 | 1 | 3 | 3 | 3 | 3 | 3 | 3 | 3 | 3 | — | — | — | — | — |
|  | 0.5605 | 1 | — | — | 1 | 0 | 2 | 0 | — | 0 | 2 | 3 | 0 | 1 | 3 | 3 | 3 | 3 | 3 | 3 | 1 | 2 | — | — | — | — | — |
|  | 0.2803 | 1 | — | — | N | 0 | 0 | 0 | — | 0 | 1 | 3 | 0 | 0 | 3 | 3 | 1 | 3 | 3 | 1 | 0 | 0 | — | — | — | — | — |
|  | 0.1401 | 0 | — | — | 0 | 0 | 0 | 0 | — | 0 | 0 | 3 | 0 | 0 | 3 | 3 | 1 | 3 | 3 | 1 | 0 | 1 | — | — | — | — | — |
|  | 0.0701 | 0 | — | — | 0 | 1 | 0 | 0 | — | 0 | 0 | 0 | 0 | 0 | 0 | 0 | 0 | 0 | 0 | 0 | 0 | 0 | — | — | — | — | — |
|  | 0.0350 | 0 | — | — | 0 | 1 | 0 | 0 | — | 0 | 0 | 0 | 0 | 0 | 1 | 1 | 0 | 1 | 1 | 0 | 0 | 0 | — | — | — | — | — |
|  | 0.0175 | 0 | — | — | 0 | 0 | 0 | 0 | — | 0 | 0 | 0 | 0 | 0 | 0 | 0 | 0 | 0 | 0 | 0 | 0 | 0 | — | — | — | — | — |
| 76 | 0.0087 | 0 | — | — | 0 | 0 | 0 | 0 | — | 0 | 0 | 0 | 0 | 0 | 1 | 0 | 0 | N | 0 | 0 | 0 | 0 | — | — | — | — | — |
|  | 5.6050 | 1 | — | — | 0 | 0 | 0 | 0 | — | 0 | 3 | 3 | 3 | 3 | 3 | 3 | 3 | 3 | 3 | 2 | 3 | 3 | — | — | — | — | — |
|  | 1.1210 | 0 | — | — | 0 | N | N | 0 | — | 0 | N | 0 | 1 | 0 | 3 | 2 | 3 | N | 3 | 0 | 0 | 2 | — | — | — | — | — |
|  | 0.5605 | 0 | — | — | 0 | N | N | 0 | — | 0 | N | 0 | 1 | 0 | 3 | 2 | 3 | N | 3 | 0 | 0 | 2 | — | — | — | — | — |
|  | 0.2803 | N | — | — | N | 1 | 1 | 0 | — | 0 | 0 | 0 | 1 | 0 | 1 | 0 | 0 | 0 | 0 | 0 | 0 | 1 | — | — | — | — | — |
|  | 0.1401 | 0 | — | — | N | 0 | 2 | 0 | — | 0 | 0 | 0 | 0 | 0 | 0 | 0 | 0 | 0 | 0 | 0 | N | 0 | — | — | — | — | — |
|  | 0.0701 | 0 | — | — | N | 0 | N | 0 | — | 0 | 0 | 0 | 0 | 0 | 0 | 0 | 0 | 0 | 0 | 0 | 1 | 0 | — | — | — | — | — |
|  | 0.0350 | 0 | — | — | 1 | 0 | N | 0 | — | 0 | 0 | 0 | 0 | 0 | 0 | 0 | 0 | 0 | 0 | 0 | 0 | 0 | — | — | — | — | — |
|  | 0.0175 | 0 | — | — | 0 | 0 | N | 0 | — | 0 | 0 | 0 | 0 | 0 | 0 | 0 | 0 | 0 | 0 | 0 | 0 | 0 | — | — | — | — | — |
|  | 0.0087 | 0 | — | — | N | 0 | 1 | 0 | — | 0 | 0 | 0 | 0 | 0 | 0 | 0 | 0 | 0 | 0 | 0 | 0 | 0 | — | — | — | — | — |
| 77 | 5.6050 | 3 | — | — | 0 | 3 | 3 | 3 | — | 3 | 3 | 3 | 3 | 3 | 3 | 3 | 3 | 3 | 3 | 3 | 3 | 3 | — | — | — | — | — |
|  | 1.1210 | 2 | — | — | 0 | 0 | 3 | 0 | — | 0 | 3 | 3 | 3 | 3 | 3 | 3 | 3 | 3 | 3 | 3 | 3 | 3 | — | — | — | — | — |
|  | 0.5605 | 2 | — | — | 1 | N | 3 | N | — | N | 3 | 3 | 3 | 3 | 3 | 3 | 3 | 3 | 3 | 3 | 3 | 3 | — | — | — | — | — |
|  | 0.2803 | 0 | — | — | 0 | 0 | 2 | 0 | — | 0 | 3 | 0 | 3 | 3 | 3 | 3 | 3 | 3 | 3 | 3 | 1 | 2 | — | — | — | — | — |
|  | 0.1401 | N | — | — | 0 | 0 | 1 | 0 | — | 0 | 0 | 3 | 1 | 3 | 3 | 3 | 3 | 3 | 3 | 3 | 1 | 3 | — | — | — | — | — |
|  | 0.0701 | 0 | — | — | 0 | 0 | N | 0 | — | 0 | 1 | 0 | 3 | 0 | 3 | 0 | 3 | 3 | 3 | 3 | 0 | 1 | — | — | — | — | — |
|  | 0.0350 | 0 | — | — | N | 0 | N | 0 | — | 0 | 0 | 0 | 0 | 3 | 1 | 3 | 3 | 3 | 1 | 1 | 0 | — | — | — | — | — | — |
|  | 0.0175 | 0 | — | — | 0 | 0 | 0 | 0 | — | 0 | 0 | 0 | 0 | 1 | 0 | 3 | 3 | 3 | 0 | 0 | 1 | — | — | — | — | — | — |
|  | 0.0087 | 0 | — | — | 0 | N | 0 | 0 | — | 0 | 0 | 0 | 0 | 0 | 0 | 0 | 3 | 0 | 0 | 0 | — | — | — | — | — | — | — |
| 78 | 5.6050 | 2 | — | — | 0 | 0 | 3 | 0 | — | 0 | 3 | 3 | 3 | 3 | 3 | 3 | 3 | 3 | 3 | 3 | 3 | 3 | — | — | — | — | — |
|  | 1.1210 | 1 | — | — | N | 1 | 3 | N | — | N | 2 | 3 | 3 | 1 | 3 | 3 | 3 | 3 | 3 | 3 | 3 | 2 | — | — | — | — | — |

TABLE B-continued

| Compound No. | Rate kg/ha | Sobe | Cotz | Rape | Cobu | Wibw | Mogl | Kese | Jiwe | Vele | Whez | Rice | Gron | Cobr | Domi | Pygr | Bact | Lfet | Grbq | Sblq | Coscw | Pecw | Cnbg | Abth | Brrtjz | Rujg | Wioa |
|---|---|---|---|---|---|---|---|---|---|---|---|---|---|---|---|---|---|---|---|---|---|---|---|---|---|---|---|
|  | 0.5605 | 0 | — | — | 0 | 3 | 3 | 2 | — | 1 | 3 | 3 | N | 3 | 3 | 3 | 3 | 3 | 3 | 3 | 3 | N | — | — | — | — | — |
|  | 1.1210 | 0 | — | — | 0 | 0 | 3 | 0 | — | 1 | 2 | 3 | 3 | 2 | 3 | 3 | 3 | 3 | 3 | 3 | 3 | — | — | — | — | — | — |
|  | 1.1210 | 0 | 0 | — | 0 | — | 0 | — | — | 2 | — | 3 | — | 1 | — | — | 3 | 3 | — | — | — | — | — | — | — | 3 | — |
|  | 1.1210 | — | — | 3 | — | 3 | — | — | — | — | 2 | — | — | — | 3 | — | — | — | 3 | — | — | — | 3 | 3 | 0 | 0 | — | 3 |
|  | 0.5605 | 0 | — | — | 0 | 1 | 3 | 0 | — | 1 | 3 | 3 | 3 | 1 | 1 | 3 | 3 | 3 | 2 | 1 | 3 | — | — | — | — | — | — |
|  | 0.2803 | 0 | — | — | 0 | N | 2 | 0 | — | 0 | 2 | 3 | 3 | 1 | 3 | 3 | 3 | 3 | 3 | 1 | 2 | 2 | — | — | — | — | — |
|  | 0.2803 | 0 | 0 | — | 0 | — | 0 | — | — | 0 | — | 1 | — | 0 | — | — | 3 | 3 | — | — | — | — | — | — | — | 3 | — |
|  | 0.2803 | — | — | 1 | — | 0 | — | — | — | — | 0 | — | — | — | 2 | — | — | — | 3 | — | — | — | 2 | 3 | 0 | 0 | — | 2 |
|  | 0.1401 | 0 | — | — | 0 | 0 | 2 | 0 | — | 0 | 2 | 1 | 0 | 0 | 2 | 0 | 0 | 3 | 3 | 1 | 1 | 0 | — | — | — | — | — |
|  | 0.0701 | 0 | — | — | 0 | 2 | 0 | 0 | — | 0 | 0 | 1 | 1 | 0 | 1 | 0 | 1 | 3 | 3 | 0 | 3 | 0 | — | — | — | — | — |
|  | 0.0701 | — | — | 0 | — | 0 | — | — | — | — | 0 | — | — | — | 0 | — | — | — | 2 | — | — | — | 0 | 3 | 0 | 0 | — | 0 |
|  | 0.0701 | 0 | 0 | — | 0 | — | 0 | — | — | 0 | — | 0 | — | 0 | — | — | 2 | 3 | — | — | — | — | — | — | — | 2 | 0 |
|  | 0.0350 | 0 | — | — | 0 | 1 | 0 | 0 | — | 0 | 2 | 0 | 0 | 0 | 0 | 0 | 0 | 1 | 1 | 0 | 3 | 0 | — | — | — | — | — |
|  | 0.0175 | 0 | — | — | 1 | 1 | 0 | 0 | — | 0 | 0 | 0 | 0 | 0 | 2 | 0 | 0 | 0 | 0 | 0 | 1 | 0 | — | — | — | — | — |
|  | 0.0087 | 0 | — | — | 0 | N | 1 | 0 | — | 0 | N | 0 | 0 | 0 | N | N | 0 | N | 1 | 0 | N | 0 | — | — | — | — | — |
| 81 | 5.6050 | 3 | — | — | 2 | 3 | 3 | 3 | — | 3 | 3 | 3 | 3 | 3 | 3 | 3 | 3 | 3 | 3 | 3 | 3 | 3 | — | — | — | — | — |
|  | 1.1210 | 1 | — | — | 0 | 3 | 3 | 1 | — | 2 | 3 | 3 | 3 | 2 | 3 | 3 | 3 | 3 | 3 | 3 | 3 | 3 | — | — | — | — | — |
|  | 0.5605 | 0 | — | — | 0 | N | 3 | 2 | — | 1 | 3 | 3 | 3 | 3 | 3 | 3 | 3 | 3 | 3 | 3 | 3 | N | N | — | — | — | — |
|  | 0.2803 | 0 | — | — | 0 | 0 | 0 | 0 | — | 0 | 3 | 3 | 2 | 1 | 3 | 3 | 3 | 3 | 3 | 1 | 1 | 3 | — | — | — | — | — |
|  | 0.1401 | 0 | — | — | 0 | N | 0 | 1 | — | 0 | 3 | 3 | 2 | 0 | 3 | 3 | 3 | 3 | 3 | 2 | N | 2 | — | — | — | — | — |
|  | 0.0701 | 0 | — | — | 0 | 1 | 0 | 1 | — | 0 | 3 | 2 | 0 | 0 | 3 | 3 | 3 | 3 | 3 | N | N | 1 | — | — | — | — | — |
|  | 0.0350 | 0 | — | — | 0 | 0 | 0 | 0 | — | 0 | 3 | 0 | 0 | 0 | 0 | 0 | 1 | 0 | 3 | 0 | 0 | 1 | — | — | — | — | — |
|  | 0.0175 | 0 | — | — | 0 | 0 | 0 | 0 | — | 0 | 3 | 1 | 0 | 0 | 0 | 0 | 0 | N | 2 | 0 | 0 | 0 | — | — | — | — | — |
|  | 0.0087 | 0 | — | — | 0 | 1 | 0 | 0 | — | 0 | 2 | 0 | 0 | 0 | 0 | 0 | 0 | 0 | 0 | N | 0 | 0 | — | — | — | — | — |
|  | 0.0044 | 0 | — | — | 0 | 0 | 0 | 0 | — | 0 | 3 | 0 | 0 | 0 | 0 | 0 | N | 0 | 0 | 0 | 0 | — | — | — | — | — | — |
| 82 | 5.6050 | 0 | — | — | 0 | 3 | 3 | 1 | — | 2 | 3 | 3 | 3 | 1 | 3 | 3 | 3 | 3 | 3 | 3 | 3 | 3 | — | — | — | — | — |
|  | 1.1210 | 0 | — | — | 0 | 2 | N | 3 | — | 2 | 3 | 3 | 1 | 1 | 3 | 3 | 3 | 3 | 3 | 3 | 3 | 3 | — | — | — | — | — |
|  | 0.5605 | 0 | — | — | 0 | 1 | 3 | 1 | — | 0 | 3 | 3 | 1 | 0 | 3 | 3 | 3 | 3 | 3 | 1 | 3 | 3 | — | — | — | — | — |
|  | 0.2803 | 0 | — | — | 0 | 0 | 0 | 0 | — | 0 | 3 | 0 | 2 | 1 | 2 | 2 | 3 | 3 | 3 | N | 2 | 0 | — | — | — | — | — |
|  | 0.1401 | 0 | — | — | 0 | 0 | 0 | 0 | — | 0 | 2 | 0 | 0 | 0 | 1 | 2 | 1 | 3 | 3 | 0 | 3 | 0 | — | — | — | — | — |
|  | 0.0701 | 0 | — | — | 0 | 0 | 0 | 0 | — | 0 | 1 | 0 | 0 | 0 | 1 | 0 | 0 | 1 | 0 | 1 | 0 | — | — | — | — | — | — |
|  | 0.0350 | 0 | — | — | 0 | 1 | 0 | 0 | — | 0 | N | 0 | 0 | 0 | 2 | 0 | 0 | 2 | 0 | N | 1 | 1 | — | — | — | — | — |
|  | 0.0175 | 0 | — | — | 0 | 0 | 0 | 0 | — | 0 | N | 0 | 0 | 0 | 0 | 0 | 0 | 0 | 0 | 0 | 0 | 0 | — | — | — | — | — |
|  | 0.0087 | 0 | — | — | 0 | 0 | 0 | 0 | — | N | 0 | 0 | 0 | 0 | 0 | 0 | 0 | 0 | 0 | 0 | 0 | — | — | — | — | — | — |
| 83 | 5.6050 | 1 | — | — | 1 | 3 | 0 | 2 | — | 2 | 3 | 3 | 2 | 3 | 3 | 3 | 3 | 3 | 3 | 3 | 3 | — | — | — | — | — | — |
|  | 1.1210 | 1 | — | — | 0 | 2 | 0 | 2 | — | 1 | 1 | 3 | 3 | 1 | 3 | 3 | 3 | 3 | 3 | 1 | 3 | 3 | — | — | — | — | — |

TABLE B-continued

| Compound No. | Rate kg/ha | Sobe | Cotz | Rape | Cbu | Wibw | Mogl | Kese | Jiwe | Vele | Whez | Rice | Gron | Cobr | Dobmr | Prmi | Byrg | Lact | Grft | Sube | Colq | Pcsw | Ccbw | Anbg | Abrz | Brth | Rujg | Sejg |
|---|---|---|---|---|---|---|---|---|---|---|---|---|---|---|---|---|---|---|---|---|---|---|---|---|---|---|---|---|
|  | 5.6050 | 1 | — | — | 0 | 3 | 1 | 1 | — | 0 | 1 | 2 | 1 | 0 | 1 | 1 | 2 | 3 | 3 | 1 | 3 | 3 | — | — | — | — | — | — |
|  | 0.2803 | 0 | — | — | 0 | 1 | N | 1 | — | 0 | 0 | 0 | 0 | 0 | 0 | 0 | 1 | 0 | 1 | 0 | 1 | 0 | — | — | — | — | — | — |
|  | 0.1401 | 0 | — | — | 0 | 0 | 1 | 0 | — | 0 | 0 | 0 | 0 | 0 | 0 | 0 | 0 | 0 | 0 | 0 | 0 | N | — | — | — | — | — | — |
|  | 0.0701 | 0 | — | — | 0 | 0 | 0 | 0 | — | 0 | N | 0 | 0 | 0 | 0 | 0 | 0 | 0 | 0 | 0 | 0 | 0 | — | — | — | — | — | — |
| 84 | 11.2100 | 1 | 0 | 2 | N | 3 | 0 | 2 | 0 | 0 | 3 | 3 | 3 | 2 | 3 | 3 | 3 | N | 3 | — | — | — | — | — | — | — | — | — |
|  | 11.2100 | 3 | 0 | 2 | 2 | 3 | 1 | 0 | 1 | 0 | 3 | 3 | 3 | 1 | 3 | 3 | 3 | 3 | 3 | — | — | — | — | — | — | — | — | — |
|  | 11.2100 | 0 | 0 | 2 | 1 | 1 | 2 | 1 | 0 | 0 | 3 | 3 | 3 | 1 | 3 | 3 | 3 | 3 | 3 | — | — | — | — | — | — | — | — | — |
|  | 5.6050 | 0 | 2 | 0 | 0 | N | 0 | 0 | N | 1 | 1 | 1 | 3 | 0 | 0 | 1 | 3 | 0 | 3 | — | — | — | — | — | — | — | — | — |
|  | 1.1210 | 0 | 0 | 0 | N | 1 | 0 | 0 | 0 | 0 | 0 | 0 | 2 | 0 | 0 | 0 | 1 | 0 | 2 | — | — | — | — | — | — | — | — | — |
| 85 | 5.6050 | 3 | 3 | 3 | 0 | 3 | 3 | 3 | 3 | 3 | 3 | 3 | 3 | 3 | 3 | 3 | 3 | 3 | 3 | — | — | — | — | — | — | — | — | — |
|  | 1.1210 | 2 | 0 | 3 | 0 | 3 | 0 | 3 | 3 | 3 | 2 | 3 | 2 | 1 | 3 | 3 | 3 | 3 | 3 | — | — | — | — | — | — | — | — | — |
|  | 0.2803 | 0 | 1 | 3 | 0 | 3 | 0 | 2 | 2 | 2 | 1 | 2 | 1 | 0 | 3 | 3 | 2 | 3 | 3 | — | — | — | — | — | — | — | — | — |
|  | 0.0701 | 0 | 0 | 0 | 0 | 2 | 0 | 0 | 0 | 0 | 0 | 1 | 0 | 0 | 3 | 1 | 0 | 3 | 2 | — | — | — | — | — | — | — | — | — |
|  | 0.0351 | 0 | 0 | 0 | 0 | N | 0 | 0 | 1 | 0 | 0 | 2 | 0 | 0 | 1 | 0 | 0 | 2 | 1 | — | — | — | — | — | — | — | — | — |
|  | 0.0175 | 0 | N | 0 | 0 | 1 | 0 | 1 | N | 1 | 0 | N | 0 | 0 | N | 0 | 0 | N | 0 | — | — | — | — | — | — | — | — | — |
| 86 | 5.6060 | 1 | — | — | 0 | 3 | 2 | 2 | — | 0 | 3 | 3 | 3 | 3 | 3 | 3 | 3 | 3 | 3 | 3 | 3 | 3 | — | — | — | — | — | — |
|  | 1.1210 | 0 | — | — | N | 0 | 0 | 1 | — | 0 | 0 | 0 | 3 | 0 | 0 | 0 | 3 | 0 | 3 | 0 | 0 | 2 | — | — | — | — | — | — |
|  | 0.5605 | 0 | — | — | N | 0 | 0 | 0 | — | 0 | 0 | 0 | 2 | 0 | 0 | 2 | 3 | 0 | 3 | 0 | N | 0 | — | — | — | — | — | — |
|  | 0.2803 | 0 | — | — | 1 | 0 | 0 | 0 | — | 0 | 0 | 0 | 1 | 0 | 0 | 0 | 0 | 0 | 0 | 0 | 0 | 1 | — | — | — | — | — | — |
|  | 0.1401 | 1 | 1 | — | N | 0 | 0 | 1 | — | 1 | 0 | 0 | 0 | 0 | 0 | 0 | 0 | 0 | 0 | 0 | 0 | 3 | — | — | — | — | — | — |
|  | 0.0701 | 0 | — | — | 1 | 0 | 0 | 0 | — | 0 | 0 | 0 | 0 | 0 | 0 | 0 | 0 | 0 | 0 | 0 | 0 | 1 | — | — | — | — | — | — |
|  | 0.0350 | 0 | — | — | 1 | 0 | 0 | 0 | — | 0 | 0 | 0 | 0 | 0 | 0 | 0 | 0 | 0 | 0 | 0 | 0 | 0 | — | — | — | — | — | — |
|  | 0.0175 | 0 | — | — | N | 0 | 0 | 1 | — | 0 | 0 | 0 | 0 | 0 | 0 | 0 | 0 | 0 | 0 | N | N | — | — | — | — | — | — | — |
| 88 | 11.2100 | 2 | — | — | 1 | 1 | 3 | 3 | — | 3 | 2 | 3 | 3 | 3 | 3 | 3 | 3 | 3 | 3 | 1 | 2 | N | — | — | — | — | — | — |
|  | 5.6050 | 0 | — | — | 0 | 0 | 1 | 1 | — | 1 | 0 | 3 | 3 | 3 | 3 | 3 | 3 | 3 | 3 | 0 | 0 | N | — | — | — | — | — | — |
|  | 1.1210 | 0 | — | — | 1 | 0 | 0 | 0 | — | 0 | 0 | 0 | 0 | 0 | 3 | 0 | 0 | 0 | 1 | 0 | N | — | — | — | — | — | — | — |
| 89 | 5.6050 | 3 | — | — | 0 | 1 | 3 | 3 | — | 3 | 2 | 3 | 3 | 3 | 3 | 3 | 3 | 3 | 3 | 3 | 3 | N | — | — | — | — | — | — |
|  | 1.1210 | 0 | — | — | N | 0 | N | 3 | — | 3 | 0 | 2 | 1 | 0 | 2 | 3 | 3 | 3 | 3 | 3 | 3 | N | — | — | — | — | — | — |
|  | 0.5605 | 0 | — | — | 0 | 1 | 3 | 1 | — | 1 | 0 | 0 | 3 | 0 | 0 | 3 | 3 | 3 | 0 | 0 | 0 | N | — | — | — | — | — | — |
|  | 0.2803 | 0 | — | — | 0 | 1 | 0 | 0 | — | 0 | 0 | 1 | 2 | 0 | N | 0 | 0 | 2 | 0 | N | 0 | N | — | — | — | — | — | — |
|  | 0.1401 | 0 | — | — | 0 | 0 | 0 | 0 | — | 0 | 0 | 0 | 0 | 1 | 0 | 0 | 0 | 0 | 1 | 0 | N | — | — | — | — | — | — | — |
|  | 0.0701 | 0 | — | — | N | 0 | 0 | 0 | — | 0 | 0 | 0 | 0 | 0 | 0 | 0 | 0 | 0 | 0 | 0 | N | — | — | — | — | — | — | — |
|  | 0.0350 | 0 | — | — | 0 | 0 | 0 | 0 | — | 0 | 0 | 0 | 0 | 0 | 0 | 0 | 0 | 0 | 0 | 0 | N | — | — | — | — | — | — | — |
| 90 | 5.6050 | 0 | 1 | 1 | 2 | 2 | 1 | 0 | 1 | 1 | 1 | 0 | 1 | 2 | 1 | 2 | 1 | 3 | 1 | — | — | — | — | — | — | — | — | — |
|  | 1.1210 | N | 0 | 1 | 0 | 0 | 0 | 1 | 1 | 0 | 0 | 1 | 0 | 0 | 0 | 1 | 0 | 0 | 0 | — | — | — | — | — | — | — | — | — |
|  | 0.2803 | 0 | N | 0 | 0 | N | 0 | 0 | 1 | 0 | 0 | 1 | N | 0 | 0 | N | 0 | 0 | 0 | — | — | — | — | — | — | — | — | — |

TABLE B-continued

| Compound No. | Rate kg/ha | Sobe | Cotz | Rape | Cobu | Wibw | Mogl | Kese | Jiwe | Vile | Whez | Rice | Grso | Cobn | Dobr | Prmi | Bygr | Larg | Gcft | Sube | Coleq | Pecw | Cocbw | Anbg | Babrz | Ruth | Sejg | Wioa |
|---|---|---|---|---|---|---|---|---|---|---|---|---|---|---|---|---|---|---|---|---|---|---|---|---|---|---|---|---|
| 91 | 5.6050 | 3 | — | — | 1 | 2 | 3 | 3 | — | 3 | 3 | 3 | 3 | 3 | 3 | 3 | 3 | 3 | 3 | 3 | 3 | N | — | — | — | — | — | — |
|  | 1.1210 | 0 | — | — | 1 | 1 | 3 | 0 | — | 0 | 3 | 3 | 3 | 3 | 3 | 3 | 3 | 3 | 3 | 3 | 3 | N | — | — | — | — | — | — |
|  | 0.5605 | 0 | — | — | 0 | 0 | 0 | 1 | — | 2 | 0 | 3 | 2 | 3 | 3 | 3 | 3 | 3 | 3 | 3 | 3 | N | — | — | — | — | — | — |
|  | 0.2803 | 0 | — | — | 0 | 0 | 0 | 0 | — | 0 | 0 | 3 | 0 | 0 | 3 | 1 | 3 | 3 | 3 | 1 | 1 | N | — | — | — | — | — | — |
|  | 0.1401 | 0 | — | — | 1 | 0 | 0 | 0 | — | 0 | 0 | 3 | N | 0 | 3 | 3 | 1 | 3 | 1 | 0 | 1 | N | — | — | — | — | — | — |
|  | 0.0701 | 0 | — | — | 0 | N | 0 | 1 | — | 1 | 0 | 0 | 0 | 0 | 1 | 0 | 0 | 0 | 1 | N | N | N | — | — | — | — | — | — |
|  | 0.0350 | 0 | — | — | 0 | 0 | 0 | 0 | — | 0 | 0 | 1 | 1 | 0 | 0 | 0 | 0 | 2 | 0 | 0 | 0 | N | — | — | — | — | — | — |
|  | 0.0175 | 0 | — | — | N | 0 | 0 | 0 | — | 0 | 0 | 0 | 0 | 1 | 0 | 0 | 0 | 1 | 0 | 0 | 0 | N | — | — | — | — | — | — |
|  | 0.0087 | 0 | — | — | 0 | N | 0 | 0 | — | 0 | 0 | 0 | 0 | 0 | N | 0 | 0 | 0 | 0 | N | N | N | — | — | — | — | — | — |
| 92 | 5.6050 | 3 | — | — | 3 | 3 | 3 | 3 | — | 3 | 3 | 3 | 3 | 3 | 3 | 3 | 3 | 3 | 3 | 3 | 3 | N | — | — | — | — | — | — |
|  | 1.1210 | 1 | — | — | 0 | 3 | 3 | 0 | — | 1 | 3 | 3 | 3 | 3 | 3 | 3 | 3 | 3 | 3 | 3 | 3 | N | — | — | — | — | — | — |
|  | 0.5605 | 0 | — | — | 0 | 2 | 3 | 0 | — | 1 | 3 | 3 | 3 | 3 | 3 | 3 | 3 | 3 | 3 | 3 | 3 | N | — | — | — | — | — | — |
|  | 0.2803 | 2 | — | — | 0 | 1 | 3 | N | — | N | 0 | 3 | 3 | 3 | 3 | 3 | 3 | 3 | 3 | 3 | 3 | N | — | — | — | — | — | — |
|  | 0.1401 | 0 | — | — | N | 1 | 2 | 2 | — | 1 | 2 | 3 | 3 | 3 | 3 | 3 | 3 | 3 | 3 | 2 | 3 | N | — | — | — | — | — | — |
|  | 0.0701 | 0 | — | — | 1 | 1 | 3 | 1 | — | 0 | 0 | 3 | 3 | 3 | 2 | 3 | 3 | 3 | 1 | 3 | 1 | N | — | — | — | — | — | — |
|  | 0.0350 | 1 | — | — | 1 | 0 | 1 | 1 | — | 0 | 0 | 3 | 3 | 0 | 3 | 1 | 3 | 3 | 3 | 0 | 1 | N | — | — | — | — | — | — |
|  | 0.0175 | 0 | — | — | N | 0 | 0 | 1 | — | 1 | 0 | 3 | 2 | 0 | 0 | 1 | 0 | 3 | 3 | 0 | 2 | N | — | — | — | — | — | — |
|  | 0.0087 | 1 | — | — | N | 0 | 1 | 0 | — | 0 | 0 | 1 | 1 | 1 | 0 | 0 | 1 | 0 | 1 | 0 | 1 | N | — | — | — | — | — | — |
| 93 | 5.6050 | 3 | 1 | 3 | 0 | 3 | 3 | 3 | 3 | 3 | 3 | 3 | 3 | 3 | 3 | 3 | 3 | 3 | 3 | 3 | — | — | — | — | — | — | — | — |
|  | 1.1210 | 2 | 0 | 3 | 0 | 3 | 3 | 3 | 3 | 3 | 3 | 3 | 3 | 2 | 3 | 3 | 3 | 3 | 3 | 3 | — | — | — | — | — | — | — | — |
|  | 0.2803 | 0 | 0 | 1 | 0 | 3 | 0 | 1 | 3 | 0 | 1 | 3 | 1 | 0 | 3 | 3 | 3 | 3 | 3 | 3 | — | — | — | — | — | — | — | — |
|  | 0.0701 | 0 | 1 | 0 | N | 1 | 0 | 0 | 2 | 0 | 0 | 1 | 0 | 0 | 2 | 1 | 0 | 3 | 1 | 1 | — | — | — | — | — | — | — | — |
|  | 0.0175 | 0 | 0 | 0 | 0 | 0 | N | N | N | 0 | 0 | 0 | 0 | 0 | 0 | 0 | 0 | 0 | 0 | 0 | — | — | — | — | — | — | — | — |
| 94 | 5.6050 | 2 | 0 | 3 | 0 | 3 | 3 | 2 | 2 | 3 | 2 | 3 | 3 | 3 | 3 | 3 | 3 | 3 | 3 | 3 | — | — | — | — | — | — | — | — |
|  | 1.1210 | 0 | 0 | 1 | 0 | 1 | 3 | 2 | 2 | 0 | 1 | 3 | 3 | 1 | 2 | 3 | 3 | 3 | 3 | 3 | — | — | — | — | — | — | — | — |
|  | 0.2803 | N | 1 | 1 | N | 0 | 1 | 0 | 1 | 0 | 0 | 2 | 0 | 0 | 2 | 1 | 0 | 3 | 1 | 1 | — | — | — | — | — | — | — | — |
|  | 0.0701 | 0 | 0 | 0 | 0 | 0 | 0 | 0 | 0 | 0 | 0 | 0 | 0 | 0 | 0 | 0 | 0 | 0 | 0 | 0 | — | — | — | — | — | — | — | — |
|  | 0.0175 | 0 | 0 | 0 | N | 0 | 1 | 0 | 0 | 0 | 0 | 0 | 0 | 0 | N | 0 | 0 | 0 | 0 | 0 | — | — | — | — | — | — | — | — |
| 95 | 5.6050 | 3 | 0 | 3 | 0 | 3 | 3 | 3 | 3 | 3 | 3 | 3 | 3 | 3 | 3 | 3 | 3 | 3 | 3 | 3 | — | — | — | — | — | — | — | — |
|  | 1.1210 | 3 | 0 | 3 | 0 | 3 | 3 | 3 | 3 | 3 | 3 | 3 | 3 | 2 | 3 | 3 | 3 | 3 | 3 | 3 | — | — | — | — | — | — | — | — |
|  | 0.2803 | 0 | 0 | 0 | 0 | 3 | 0 | 0 | 2 | 1 | 3 | 3 | 3 | 1 | 0 | 3 | 3 | 3 | 3 | 3 | — | — | — | — | — | — | — | — |
|  | 0.0701 | N | 1 | 0 | 0 | 3 | 1 | 0 | 1 | 1 | 3 | 1 | 1 | 0 | 3 | 2 | 3 | 2 | 3 | 3 | — | — | — | — | — | — | — | — |
|  | 0.0351 | 0 | 0 | 0 | 0 | 0 | 0 | 0 | 0 | 0 | 1 | 0 | 0 | 0 | 1 | 0 | 0 | 3 | 0 | 0 | — | — | — | — | — | — | — | — |
|  | 0.0175 | N | 0 | 1 | 0 | 1 | 0 | 0 | N | 0 | 0 | 0 | 0 | 0 | N | 0 | 0 | N | 0 | 0 | — | — | — | — | — | — | — | — |
|  | 0.0087 | N | N | 0 | N | N | 1 | N | 1 | N | 0 | N | 0 | 0 | N | 1 | 0 | N | 0 | 0 | — | — | — | — | — | — | — | — |
| 96 | 5.6050 | 0 | 0 | 0 | 0 | 2 | 0 | 0 | 0 | 0 | 2 | N | 1 | 0 | 1 | 0 | 3 | N | 2 | — | — | — | — | — | — | — | — | — |

5,877,119

TABLE B-continued

| Compound No. | Rate kg/ha | Sobe | Cotz | Rape | Cobu | Wibw | Mogl | Kese | Jiwe | Vele | Whez | Rice | Grso | Corn | Dobr | Prmi | Bygr | Lacg | Grft | Sube | Coel | Pecq | Cocw | Anbg | Barz | Ruth | Sejg | Wioa |
|---|---|---|---|---|---|---|---|---|---|---|---|---|---|---|---|---|---|---|---|---|---|---|---|---|---|---|---|---|
| | 1.1210 | 1 | N | 0 | N | 1 | 0 | 0 | 0 | 1 | 0 | 1 | 0 | 0 | N | 1 | 0 | 0 | 0 | — | — | — | — | — | — | — | — | — |
| | 0.2803 | 0 | 0 | 0 | 0 | 2 | 0 | 0 | 1 | 1 | 0 | 0 | 0 | 0 | 2 | 0 | 0 | 0 | 0 | — | — | — | — | — | — | — | — | — |
| | 0.0701 | 1 | 0 | 0 | N | 0 | 0 | 0 | 1 | 0 | 0 | N | 0 | 0 | N | 0 | 0 | 0 | 0 | — | — | — | — | — | — | — | — | — |
| 97 | 5.6050 | 1 | 1 | 2 | 0 | 3 | 1 | 1 | 2 | 1 | 2 | 3 | 2 | 1 | 3 | 3 | 3 | 3 | 3 | — | — | — | — | — | — | — | — | — |
| | 1.1210 | 0 | 1 | 1 | 0 | 1 | 0 | 1 | 3 | 1 | 1 | 3 | 1 | 0 | 3 | 3 | 3 | 3 | 3 | — | — | — | — | — | — | — | — | — |
| | 0.2803 | 0 | 1 | 0 | 0 | 0 | 0 | 0 | 2 | 0 | 0 | 0 | 0 | 0 | 1 | 0 | 0 | 3 | 0 | — | — | — | — | — | — | — | — | — |
| | 0.0701 | 0 | 1 | 0 | 0 | 0 | 0 | 0 | 1 | 0 | 0 | 0 | 0 | 0 | 1 | 0 | 0 | 2 | 0 | — | — | — | — | — | — | — | — | — |
| 98 | 5.6050 | 3 | 2 | 3 | 0 | 3 | 3 | 3 | 3 | 3 | 3 | 3 | 3 | 3 | 3 | 3 | 3 | 3 | 3 | — | — | — | — | — | — | — | — | — |
| | 1.1210 | 1 | 2 | 3 | 1 | 3 | 3 | 2 | 2 | 3 | 3 | 3 | 3 | 2 | 3 | 3 | 3 | 3 | 3 | — | — | — | — | — | — | — | — | — |
| | 0.2803 | 1 | 1 | 1 | N | 3 | 1 | 1 | 3 | 0 | 1 | 3 | 0 | 0 | 3 | 3 | 3 | 3 | 3 | — | — | — | — | — | — | — | — | — |
| | 0.0701 | 1 | 0 | 0 | 0 | 3 | 0 | 0 | 1 | 0 | 1 | 0 | 1 | 0 | 2 | 0 | 1 | 3 | 3 | — | — | — | — | — | — | — | — | — |
| 99 | 5.6050 | 2 | 1 | 2 | 1 | 3 | 1 | 3 | 3 | 3 | 3 | 3 | 3 | 2 | 3 | 3 | 3 | 3 | 3 | — | — | — | — | — | — | — | — | — |
| | 1.1210 | 0 | 1 | 1 | 1 | 1 | 0 | 1 | 1 | 1 | 1 | 3 | 0 | 0 | 3 | 3 | 3 | 3 | 2 | — | — | — | — | — | — | — | — | — |
| | 0.2803 | 0 | 1 | 0 | 0 | 1 | 0 | 0 | 0 | 1 | 0 | 1 | 0 | 0 | 1 | 1 | 1 | 3 | 0 | — | — | — | — | — | — | — | — | — |
| | 0.0701 | 0 | 2 | 0 | 0 | 0 | 0 | 0 | 0 | 0 | 0 | 0 | 0 | 0 | 0 | 0 | 0 | 1 | 0 | — | — | — | — | — | — | — | — | — |
| | 0.0175 | N | N | N | N | N | N | N | N | N | N | N | N | N | N | N | N | 1 | N | — | — | — | — | — | — | — | — | — |
| 100 | 11.2100 | 2 | 2 | 0 | 1 | 0 | 1 | 1 | 0 | 1 | 1 | 0 | 1 | 1 | 2 | 0 | 0 | 0 | 0 | — | — | — | — | — | — | — | — | — |
| | 5.6050 | 1 | 1 | 1 | 1 | 0 | 1 | 1 | 0 | 3 | 0 | 0 | 0 | 0 | 1 | 0 | 0 | 0 | 0 | — | — | — | — | — | — | — | — | — |
| 101 | 5.6050 | 2 | 3 | 3 | 1 | 3 | 2 | 3 | 3 | 1 | 3 | 3 | 3 | 1 | 3 | 3 | 3 | 3 | 3 | — | — | — | — | — | — | — | — | — |
| | 1.1210 | 1 | 1 | 1 | N | 3 | 1 | 1 | 3 | 0 | 1 | 2 | 1 | 0 | 3 | 3 | 3 | 3 | 3 | — | — | — | — | — | — | — | — | — |
| | 0.2803 | 0 | 0 | 0 | 0 | 1 | 0 | 0 | 1 | 0 | 0 | 0 | 0 | 0 | 3 | 2 | 0 | 3 | 1 | — | — | — | — | — | — | — | — | — |
| | 0.0701 | 0 | 1 | 0 | 0 | N | 0 | 0 | 1 | 0 | 0 | 0 | 0 | 0 | 0 | 3 | 0 | 2 | 0 | — | — | — | — | — | — | — | — | — |
| 102 | 5.6050 | 3 | 3 | 3 | N | 3 | 3 | 3 | 3 | 3 | 3 | 3 | 3 | 3 | 3 | 3 | 3 | 3 | 3 | — | — | — | — | — | — | — | — | — |
| | 1.1210 | 3 | 2 | 3 | N | 3 | 3 | 3 | 3 | 3 | 3 | 3 | 3 | 3 | 3 | 3 | 3 | 3 | 3 | — | — | — | — | — | — | — | — | — |
| | 0.2803 | 2 | 3 | 3 | N | 3 | 1 | 3 | 3 | 3 | 3 | 3 | 3 | 3 | 3 | 3 | 3 | 3 | 3 | — | — | — | — | — | — | — | — | — |
| | 0.0701 | 2 | 2 | 2 | N | 3 | 1 | 3 | 1 | 3 | 3 | 2 | 3 | 0 | 3 | 3 | 3 | 3 | 3 | — | — | — | — | — | — | — | — | — |
| | 0.0175 | 0 | 2 | 0 | N | 1 | 0 | 0 | 1 | 0 | 1 | 1 | 1 | 0 | 2 | 1 | 3 | 3 | 3 | — | — | — | — | — | — | — | — | — |
| | 0.0087 | 0 | 0 | 0 | N | 0 | 0 | 0 | 0 | 0 | 0 | 0 | 0 | 0 | 0 | 0 | 2 | 0 | — | — | — | — | — | — | — | — | — | — |
| 103 | 5.6050 | 3 | 1 | 2 | N | 3 | 3 | 2 | 3 | 3 | 3 | 3 | 3 | 3 | 3 | 3 | 3 | 3 | 3 | — | — | — | — | — | — | — | — | — |
| | 1.1210 | 0 | 2 | 0 | N | 3 | 0 | 1 | 3 | 1 | 0 | 3 | 1 | 2 | 3 | 3 | 3 | 3 | 3 | — | — | — | — | — | — | — | — | — |
| | 0.2803 | 1 | 1 | 0 | N | 1 | 0 | 0 | 1 | 0 | 0 | 1 | 0 | 0 | 3 | 0 | 1 | 3 | 2 | — | — | — | — | — | — | — | — | — |
| | 0.0701 | 0 | N | 0 | N | 0 | 0 | 0 | 0 | 0 | 0 | 0 | 0 | 1 | 0 | 0 | 0 | 0 | 0 | — | — | — | — | — | — | — | — | — |
| 104 | 5.6050 | 0 | 0 | 3 | N | 3 | 2 | 2 | 3 | 3 | 3 | 3 | 3 | 2 | 3 | 3 | 3 | 3 | 3 | — | — | — | — | — | — | — | — | — |
| | 1.1210 | 0 | 1 | 1 | N | 0 | 0 | 1 | 1 | 1 | 3 | 0 | 2 | 2 | 3 | 3 | 3 | 3 | 3 | — | — | — | — | — | — | — | — | — |
| | 0.2803 | 0 | 1 | 0 | N | 1 | 1 | 1 | 1 | 1 | 0 | 1 | 0 | 0 | 2 | 1 | 0 | 2 | 1 | — | — | — | — | — | — | — | — | — |
| | 0.0701 | 0 | 1 | 0 | N | 1 | 1 | 0 | 0 | 0 | 1 | 0 | 1 | 0 | 0 | 0 | 0 | 0 | 0 | — | — | — | — | — | — | — | — | — |

5,877,119

TABLE B-continued

| Compound No. | Rate kg/ha | Sobe | Cotz | Rape | Cbpu | Wibw | Mogl | Kese | Jiwe | Vlee | Whez | Rice | Gron | Cbnr | Dbri | Pymi | Bygr | Larg | Gcft | Sube | Colq | Ceww | Cncw | Anbg | Bruz | Rthj | Sejg | Wioa |
|---|---|---|---|---|---|---|---|---|---|---|---|---|---|---|---|---|---|---|---|---|---|---|---|---|---|---|---|---|
| 105 | 5.6050 | 0 | 1 | 0 | N | 0 | 0 | 0 | 1 | 0 | 0 | 0 | 0 | 0 | 3 | 0 | 0 | 3 | 0 | — | — | — | — | — | — | — | — | — |
|  | 1.1210 | 0 | N | 0 | N | 0 | 0 | 1 | 0 | 1 | 0 | 0 | 0 | 0 | 0 | 0 | 0 | 0 | 0 | — | — | — | — | — | — | — | — | — |
|  | 0.2803 | 0 | 0 | 0 | N | 0 | 0 | 0 | 1 | 0 | 0 | 1 | 0 | 0 | 0 | 0 | 0 | 0 | 0 | — | — | — | — | — | — | — | — | — |
| 106 | 5.6050 | 2 | 2 | 0 | N | 3 | 1 | 1 | 1 | 0 | 3 | 3 | 3 | 3 | 3 | 3 | 3 | 3 | 3 | — | — | — | — | — | — | — | — | — |
|  | 1.1210 | 0 | 0 | 0 | N | 3 | 0 | 0 | 1 | 0 | 1 | 0 | 1 | 0 | 3 | 1 | 0 | 0 | 0 | — | — | — | — | — | — | — | — | — |
|  | 0.2803 | 0 | 1 | 0 | N | 0 | 0 | 0 | 0 | 0 | 0 | 0 | 0 | 0 | 0 | 0 | 0 | 0 | 0 | — | — | — | — | — | — | — | — | — |
|  | 0.0701 | N | 0 | 0 | N | N | 0 | 0 | N | 0 | 0 | 0 | 0 | 0 | 0 | 0 | 0 | 0 | 0 | — | — | — | — | — | — | — | — | — |
| 107 | 5.6050 | 1 | 1 | 1 | N | 3 | 2 | 3 | 3 | 3 | 2 | 1 | 2 | 1 | 3 | 2 | 2 | 3 | 3 | — | — | — | — | — | — | — | — | — |
|  | 1.1210 | 0 | 1 | 0 | N | 2 | 1 | 1 | 2 | 3 | 0 | 0 | 1 | 0 | 2 | 1 | 0 | 3 | 3 | — | — | — | — | — | — | — | — | — |
|  | 0.2803 | 0 | 0 | 0 | N | 1 | 0 | 0 | 1 | 0 | 0 | 0 | 0 | 0 | 0 | 0 | 0 | 3 | 1 | — | — | — | — | — | — | — | — | — |
|  | 0.0701 | 0 | 0 | 0 | N | 0 | 0 | 0 | 0 | 0 | 0 | 0 | 0 | 0 | 0 | 0 | 0 | 0 | 0 | — | — | — | — | — | — | — | — | — |
| 108 | 5.6050 | 0 | 0 | 0 | N | 0 | 1 | 0 | 1 | 0 | 0 | 0 | 0 | 0 | 1 | 1 | 0 | 2 | 0 | — | — | — | — | — | — | — | — | — |
|  | 1.1210 | 0 | 1 | 0 | N | 1 | 1 | 1 | 0 | 1 | 1 | N | 0 | 0 | 1 | 1 | 0 | 0 | 0 | — | — | — | — | — | — | — | — | — |
|  | 0.2803 | 0 | 1 | 0 | N | 0 | 0 | 0 | N | 0 | 0 | 0 | 1 | 0 | 0 | 0 | 0 | 0 | 0 | — | — | — | — | — | — | — | — | — |
|  | 0.0701 | 0 | 1 | 0 | N | 0 | 0 | 0 | N | N | 0 | 0 | 0 | 0 | 0 | 0 | 0 | 0 | 0 | — | — | — | — | — | — | — | — | — |
| 109 | 5.6050 | 3 | 1 | 3 | N | 3 | 3 | 3 | 3 | 3 | 3 | 3 | 3 | 3 | 3 | 3 | 3 | 3 | 3 | — | — | — | — | — | — | — | — | — |
|  | 1.1210 | 1 | 0 | 3 | 0 | 3 | 2 | 3 | — | 3 | 3 | 3 | 3 | 3 | 3 | 3 | 3 | 3 | 3 | — | — | — | 3 | — | — | — | — | — |
|  | 1.1210 | 3 | 1 | 3 | 0 | 3 | 3 | 3 | — | 3 | 3 | 3 | 3 | 3 | 3 | 3 | 3 | 3 | 3 | — | — | — | 3 | — | — | — | — | — |
|  | 1.1210 | 3 | 0 | 3 | 0 | 3 | 3 | 3 | — | 3 | 3 | 3 | 3 | 3 | 3 | 3 | 3 | 3 | 3 | — | — | — | 3 | — | — | — | — | — |
|  | 1.1210 | 3 | 1 | 3 | 2 | 3 | 3 | 3 | — | 3 | 3 | 3 | 3 | 3 | 3 | 3 | 3 | 3 | 3 | — | — | — | 3 | — | — | — | — | — |
|  | 1.1210 | 3 | 1 | 3 | 0 | 3 | 2 | 3 | — | 3 | 3 | 3 | 3 | 3 | 3 | 3 | 3 | 3 | 3 | — | — | — | 3 | — | — | — | — | — |
|  | 1.1210 | 3 | 0 | 3 | 0 | 3 | 3 | 3 | — | 3 | 3 | 3 | 3 | 3 | 3 | 3 | 3 | 3 | 3 | — | — | — | 3 | — | — | — | — | — |
|  | 1.1210 | 3 | 0 | 3 | 1 | 3 | 3 | 3 | — | 3 | 3 | 3 | 3 | 3 | 3 | 3 | 3 | 3 | 3 | — | — | — | 3 | — | — | — | — | — |
|  | 1.1210 | 3 | 0 | 2 | 1 | 3 | 1 | 3 | — | 3 | 3 | 3 | 3 | 3 | 3 | 3 | 3 | 3 | 3 | — | — | — | 3 | — | — | — | — | — |
|  | 1.1210 | 3 | 1 | 3 | N | 3 | 3 | 3 | 3 | 3 | 3 | 3 | 3 | 3 | 3 | 3 | 3 | 3 | 3 | — | — | — | — | — | — | — | — | — |
|  | 1.1210 | 3 | 1 | 3 | 0 | 3 | 3 | 3 | — | 3 | 3 | 3 | 3 | 3 | 3 | 3 | 3 | 3 | 3 | — | — | — | 3 | — | — | — | — | — |
|  | 1.1210 | 3 | 2 | 3 | 1 | 3 | 3 | 3 | — | 3 | 3 | 3 | 3 | 3 | 3 | 3 | 3 | 3 | 3 | — | — | — | 3 | — | — | — | — | — |
|  | 1.1210 | 3 | 2 | 3 | 1 | 3 | 3 | 3 | — | 3 | 3 | 3 | 3 | 3 | 3 | 3 | 3 | 3 | 3 | — | — | — | 3 | — | — | — | — | — |
|  | 1.1210 | — | — | 3 | — | 3 | — | — | — | — | 3 | — | — | — | 3 | — | — | 3 | — | — | — | — | 3 | 3 | 3 | 2 | — | 3 |
|  | 1.1210 | 2 | 0 | 2 | 0 | 3 | 3 | 2 | — | 3 | 3 | 3 | 3 | 3 | 3 | 3 | 3 | 3 | 3 | — | — | — | 3 | — | — | — | — | — |
|  | 1.1210 | 3 | 2 | — | 0 | — | 3 | — | — | 3 | — | 3 | — | 3 | — | — | 3 | — | 3 | — | — | — | — | — | — | — | 3 | — |
|  | 0.2803 | 0 | 1 | 2 | 0 | 3 | 1 | 0 | — | 1 | 3 | 1 | 3 | 1 | 2 | 3 | 3 | 3 | 3 | — | — | — | 3 | — | — | — | — | — |
|  | 0.2803 | 0 | 0 | — | 0 | — | 2 | — | — | 3 | — | 3 | — | 2 | — | — | 3 | 3 | — | — | — | — | — | — | — | — | 3 | — |
|  | 0.2803 | — | — | 3 | — | 3 | — | — | — | — | 3 | — | — | — | 2 | — | — | 3 | — | — | — | — | 3 | 3 | 2 | 0 | — | 3 |
|  | 0.2803 | 1 | 0 | 2 | 0 | 2 | 2 | 1 | — | 2 | 3 | 3 |   | 3 | 3 | 3 | 3 | 3 | 3 | — | — | — | 3 | — | — | — | — | — |
|  | 0.2803 | 2 | 0 | 0 | 0 | 3 | 0 | 0 | — | 2 | 3 | 3 | 3 | 2 | 3 | 3 | 3 | 3 | 3 | — | — | — | 3 | — | — | — | — | — |

TABLE B-continued

| Compound No. | Rate kg/ha | Sobe | Cotz | Rape | Cbuu | Wibw | Mogl | Kese | Jiwe | Vele | Whez | Rice | Gron | Cbmr | Domi | Pygr | Barg | Lcft | Grbe | Sblq | Cocw | Pesw | Conw | Abng | Brbz | Ruth | Sejg | Wioa |
|---|---|---|---|---|---|---|---|---|---|---|---|---|---|---|---|---|---|---|---|---|---|---|---|---|---|---|---|---|
| | 0.2803 | 1 | 0 | — | 0 | — | 2 | — | — | 3 | — | 3 | — | 3 | — | — | 3 | 3 | — | — | — | — | — | — | — | — | 3 | — |
| | 0.2803 | 0 | 0 | 0 | 0 | 3 | 0 | 0 | — | 2 | 3 | 2 | 3 | 0 | 3 | 3 | 3 | 3 | — | — | — | 3 | — | — | — | — | — | — |
| | 0.2803 | — | — | 3 | — | 3 | — | — | — | 3 | — | — | — | — | 3 | — | — | 3 | — | — | — | 3 | 3 | 0 | 0 | — | 3 |
| | 0.2803 | 1 | N | — | 0 | — | 2 | — | — | 2 | — | 3 | — | 0 | — | — | 3 | 3 | — | — | — | — | — | — | — | — | 3 | — |
| | 0.2803 | — | — | 3 | — | 3 | — | — | — | 3 | — | — | — | — | 3 | — | — | 3 | — | — | — | 3 | 3 | 1 | 2 | — | 2 |
| | 0.2803 | 2 | 0 | 2 | N | 3 | 2 | 3 | 3 | 3 | 3 | 3 | 3 | 3 | 3 | 3 | 3 | 3 | — | — | — | — | — | — | — | — | — | — |
| | 0.2803 | 2 | 1 | 1 | 0 | 2 | 1 | 2 | — | 1 | 3 | 3 | 3 | 2 | 3 | 3 | 3 | 3 | — | — | — | 3 | — | — | — | — | — | — |
| | 0.2803 | 1 | 0 | 3 | 0 | 2 | 2 | 3 | — | 2 | 3 | 3 | 3 | 3 | 3 | 3 | 3 | 3 | — | — | — | 3 | — | — | — | — | — | — |
| | 0.2803 | 0 | N | 0 | 0 | 3 | 0 | 3 | — | 3 | 3 | 3 | 3 | 2 | 3 | 3 | 3 | 3 | — | — | — | 3 | — | — | — | — | — | — |
| | 0.2803 | 3 | 0 | 3 | 0 | 3 | 0 | 2 | — | 1 | 3 | 3 | 3 | 3 | 3 | 3 | 3 | 3 | — | — | — | 3 | — | — | — | — | — | — |
| | 0.2803 | 2 | 0 | 3 | 0 | 3 | 3 | 3 | — | 3 | 3 | 3 | 3 | 3 | 3 | 3 | 3 | 3 | — | — | — | 3 | — | — | — | — | — | — |
| | 0.2803 | 1 | 1 | 0 | 0 | 3 | 1 | 2 | — | 3 | 3 | 3 | 2 | 3 | 3 | 3 | 3 | 3 | — | — | — | 3 | — | — | — | — | — | — |
| | 0.2803 | 0 | 0 | 0 | 0 | 3 | 0 | 1 | — | 1 | 3 | 1 | 3 | 1 | 3 | 3 | 3 | 3 | — | — | — | 3 | — | — | — | — | — | — |
| | 0.2803 | 0 | 0 | 3 | 0 | 3 | 0 | 2 | — | 2 | 3 | 3 | 1 | 3 | 3 | 3 | 3 | 3 | — | — | — | 3 | — | — | — | — | — | — |
| | 0.2803 | 0 | 0 | 3 | 0 | 3 | 2 | 2 | — | 3 | 3 | 3 | 2 | 3 | 3 | 3 | 3 | 3 | — | — | — | 3 | — | — | — | — | — | — |
| | 0.2803 | 1 | 1 | 3 | 1 | 3 | 3 | 3 | — | 2 | 3 | 3 | 3 | 1 | 3 | 3 | 3 | 3 | — | — | — | 3 | — | — | — | — | — | — |
| | 0.2803 | 1 | 1 | 3 | 0 | 3 | 2 | 2 | — | 1 | 3 | 3 | 3 | 3 | 3 | 3 | 3 | 3 | — | — | — | 3 | — | — | — | — | — | — |
| | 0.2803 | 2 | 1 | 2 | 0 | 3 | 3 | 2 | — | 2 | 3 | 3 | 3 | 3 | 3 | 3 | 3 | 3 | — | — | — | 3 | — | — | — | — | — | — |
| | 0.2803 | 2 | 2 | 1 | 1 | 3 | 2 | 3 | — | 3 | 3 | 3 | 3 | 3 | 3 | 3 | 3 | 3 | — | — | — | 3 | — | — | — | — | — | — |
| | 0.2803 | 1 | 0 | 1 | 1 | 3 | 0 | 0 | — | 1 | 3 | 2 | 3 | 2 | 3 | 3 | 3 | 3 | — | — | — | 3 | — | — | — | — | — | — |
| | 0.2803 | 0 | 1 | 1 | 0 | 3 | 0 | 2 | — | 2 | 3 | 3 | 2 | 3 | 3 | 3 | 3 | 3 | — | — | — | 3 | — | — | — | — | — | — |
| | 0.2803 | 0 | 0 | 3 | 0 | 3 | 2 | 3 | — | 2 | 3 | 3 | 3 | 3 | 3 | 3 | 3 | 3 | — | — | — | 3 | — | — | — | — | — | — |
| | 0.2803 | 0 | 1 | 1 | 0 | 3 | 0 | 2 | — | 2 | 3 | 3 | 1 | 3 | 3 | 3 | 3 | 3 | — | — | — | 3 | — | — | — | — | — | — |
| | 0.2803 | 2 | 0 | 1 | 0 | 3 | 3 | 2 | — | 2 | 3 | 3 | 3 | 3 | 3 | 3 | 3 | 3 | — | — | — | 3 | — | — | — | — | — | — |
| | 0.0701 | 0 | 0 | 0 | 0 | 0 | 0 | 0 | — | 0 | 3 | 3 | 3 | 1 | 2 | 3 | 3 | 3 | — | — | — | 1 | — | — | — | — | — | — |
| | 0.0701 | 0 | 0 | 1 | 0 | 2 | 0 | 2 | — | 1 | 2 | 3 | 3 | 1 | 3 | 2 | 3 | 3 | — | — | — | 2 | — | — | — | — | — | — |
| | 0.0701 | 0 | 0 | 0 | 0 | 2 | 0 | 0 | — | 0 | 3 | 1 | 2 | 0 | 3 | 3 | 3 | 3 | — | — | — | 2 | — | — | — | — | — | — |
| | 0.0701 | 1 | N | 0 | 0 | 2 | 1 | 1 | — | 2 | 2 | 3 | 2 | 1 | 3 | 3 | 3 | 3 | — | — | — | 2 | — | — | — | — | — | — |
| | 0.0701 | 0 | 0 | 0 | 0 | 2 | 0 | 0 | — | 1 | 1 | 2 | 3 | 0 | 3 | 3 | 3 | 3 | — | — | — | 3 | — | — | — | — | — | — |
| | 0.0701 | 0 | 0 | 0 | 0 | 2 | 0 | 0 | — | 0 | 3 | 1 | 2 | 0 | 2 | 3 | 3 | 3 | — | — | — | 0 | — | — | — | — | — | — |
| | 0.0701 | 0 | 0 | 0 | 0 | 1 | 0 | 2 | — | 1 | 0 | 0 | 3 | 1 | 2 | 3 | 3 | 3 | — | — | — | 0 | — | — | — | — | — | — |
| | 0.0701 | 0 | 1 | 1 | 0 | 0 | 3 | 1 | — | 1 | 2 | 1 | 2 | 0 | 3 | 3 | 3 | 3 | — | — | — | 3 | — | — | — | — | — | — |
| | 0.0701 | 0 | N | 0 | 0 | 3 | 0 | N | — | 2 | 1 | 2 | 1 | 0 | 2 | 3 | 3 | 3 | — | — | — | 3 | — | — | — | — | — | — |
| | 0.0701 | 0 | 1 | 0 | 0 | 3 | 1 | 3 | — | 1 | 1 | 3 | 3 | 1 | 3 | 3 | 3 | 3 | — | — | — | 1 | — | — | — | — | — | — |
| | 0.0701 | N | 0 | 1 | 0 | 1 | 0 | 2 | — | 2 | 3 | 1 | 2 | 0 | 2 | 3 | 3 | 3 | — | — | — | 2 | — | — | — | — | — | — |
| | 0.0701 | 0 | 1 | 0 | N | 2 | 0 | 2 | 1 | 1 | 1 | 3 | 2 | 0 | 3 | 3 | 3 | 3 | — | — | — | — | — | — | — | — | — | — |

TABLE B-continued

| Compound No. | Rate kg/ha | Sobe | Cotz | Rape | Cbu | Wibw | Mogl | Kese | Jiwe | Vele | Whez | Riceo | Gror | Cobr | Dormi | Pryr | Bygr | Lact | Grufbet | Scbl | Cosw | Pelq | Cocw | Anbg | Brrt | Rujh | Sejg | Wioa |
|---|---|---|---|---|---|---|---|---|---|---|---|---|---|---|---|---|---|---|---|---|---|---|---|---|---|---|---|---|
| | 0.0701 | 1 | 2 | 0 | 0 | 2 | 1 | n | — | 1 | 3 | 3 | 3 | 0 | 2 | 3 | 3 | 3 | 3 | — | — | — | 3 | — | — | — | — | — |
| | 0.0701 | 0 | 1 | 0 | 0 | 1 | 0 | 0 | — | 1 | 2 | 2 | 3 | 1 | 2 | 3 | 3 | 3 | 3 | — | — | — | 0 | — | — | — | — | — |
| | 0.0701 | 1 | 0 | 1 | 1 | 1 | 3 | 1 | — | 2 | 3 | 3 | 3 | 2 | 3 | 3 | 3 | 3 | 3 | — | — | — | 3 | — | — | — | — | — |
| | 0.0701 | 0 | 1 | 0 | 0 | 3 | 0 | 0 | — | 1 | 1 | 2 | 3 | 0 | 3 | 3 | 3 | 3 | 3 | — | — | — | 3 | — | — | — | — | — |
| | 0.0701 | 1 | 0 | 0 | 0 | 0 | 0 | 1 | — | 1 | 3 | 1 | 3 | 1 | 3 | 3 | 3 | 3 | 3 | — | — | — | 0 | — | — | — | — | — |
| | 0.0701 | 1 | 1 | 0 | 0 | 3 | 0 | 1 | — | 1 | 3 | 3 | 3 | 2 | 3 | 3 | 3 | 3 | 3 | — | — | — | 3 | — | — | — | — | — |
| | 0.0701 | 0 | 1 | 0 | 1 | 3 | 1 | 0 | — | 1 | 1 | 3 | 3 | 1 | 3 | 3 | 3 | 3 | 3 | — | — | — | 3 | — | — | — | — | — |
| | 0.0701 | — | — | 1 | — | 1 | — | — | — | — | 3 | — | — | — | 3 | — | — | — | 3 | — | — | — | 3 | 3 | 0 | 0 | — | 3 |
| | 0.0701 | — | — | 2 | — | 3 | — | — | — | — | 3 | — | — | — | 3 | — | — | — | 3 | — | — | — | 3 | 3 | 0 | 0 | — | 3 |
| | 0.0701 | — | — | 2 | — | 3 | — | — | — | — | 3 | — | — | — | 3 | — | — | — | 3 | — | — | — | 3 | 3 | 1 | 0 | — | 3 |
| | 0.0701 | 0 | 0 | 0 | 0 | 2 | 0 | 1 | — | 0 | 0 | 0 | 2 | 0 | 3 | 3 | 3 | 3 | 2 | — | — | — | 3 | — | — | — | — | — |
| | 0.0701 | 0 | 0 | 0 | 0 | 0 | 0 | 0 | — | 0 | 1 | 1 | 1 | 0 | 1 | 3 | 3 | 3 | 3 | — | — | — | 2 | — | — | — | — | — |
| | 0.0701 | 0 | 0 | 0 | 0 | 1 | 0 | 0 | — | 0 | 0 | 2 | 0 | 0 | 3 | 3 | 3 | 3 | 3 | — | — | — | 3 | — | — | — | — | — |
| | 0.0701 | N | N | — | 0 | — | 0 | — | — | 0 | — | 1 | — | 0 | — | — | 3 | 3 | — | — | — | — | — | — | — | — | 3 | — |
| | 0.0701 | 0 | 0 | 0 | 0 | 0 | 0 | 0 | — | 0 | 3 | 0 | 2 | 1 | 3 | 3 | 3 | 3 | 3 | — | — | — | 0 | — | — | — | — | — |
| | 0.0701 | 0 | 0 | — | 0 | — | 0 | — | — | 2 | — | 3 | — | 2 | — | — | 3 | 3 | — | — | — | — | — | — | — | — | 3 | — |
| | 0.0701 | 0 | N | — | 0 | — | 1 | — | — | 1 | — | 3 | — | 1 | — | — | 3 | 3 | — | — | — | — | — | — | — | — | 3 | — |
| | 0.0175 | 0 | 1 | 0 | 0 | 0 | 0 | 0 | — | 0 | 1 | 0 | 1 | 0 | 0 | 1 | 2 | 3 | 1 | — | — | — | 0 | — | — | — | — | — |
| | 0.0175 | 0 | 0 | 0 | 0 | 0 | 0 | 0 | — | 0 | 1 | 0 | 0 | 0 | 1 | 3 | 1 | 3 | 2 | — | — | — | 2 | — | — | — | — | — |
| | 0.0175 | 0 | 0 | 0 | 0 | 0 | 0 | 0 | — | 0 | 2 | 2 | 1 | 0 | 2 | 3 | 3 | 3 | 3 | — | — | — | 0 | — | — | — | — | — |
| | 0.0175 | 1 | 0 | — | 0 | — | 0 | — | — | 0 | — | 2 | — | 1 | — | — | 3 | 3 | — | — | — | — | — | — | — | — | 3 | — |
| | 0.0175 | 0 | N | 0 | 0 | 0 | 0 | 1 | — | 1 | 0 | 1 | 0 | 0 | 0 | 1 | 0 | 3 | 0 | — | — | — | 2 | — | — | — | — | — |
| | 0.0175 | — | — | 0 | — | 0 | — | — | — | — | 1 | — | — | — | 0 | — | — | — | 3 | — | — | — | 3 | 3 | 0 | 0 | — | 3 |
| | 0.0175 | 0 | 0 | 0 | 0 | 0 | 0 | 0 | — | 0 | 1 | 0 | 0 | 0 | 0 | 1 | 1 | 2 | 2 | — | — | — | 2 | — | — | — | — | — |
| | 0.0175 | 0 | 0 | — | 0 | — | 0 | — | — | 0 | — | 0 | — | 0 | — | — | 3 | 2 | — | — | — | — | — | — | — | — | 1 | — |
| | 0.0175 | 0 | 1 | 0 | 0 | 0 | 0 | 0 | — | 0 | 1 | 0 | 1 | 1 | 2 | 1 | 3 | 3 | 3 | — | — | — | 1 | — | — | — | — | — |
| | 0.0175 | 0 | N | — | 0 | — | 1 | — | — | 0 | — | 1 | — | 0 | — | — | 2 | 3 | — | — | — | — | — | — | — | — | 2 | — |
| | 0.0175 | 0 | 0 | 0 | 0 | 0 | 0 | 0 | — | 0 | 0 | 0 | 2 | 0 | 1 | 1 | 2 | 3 | — | — | — | — | 3 | — | — | — | — | — |
| | 0.0175 | 0 | 0 | 0 | 0 | 0 | 0 | 0 | — | 0 | 1 | 0 | 1 | 0 | 3 | 1 | 3 | 3 | 2 | — | — | — | 1 | — | — | — | — | — |
| | 0.0175 | 1 | 0 | 0 | 0 | 0 | 0 | 0 | — | 0 | 2 | 1 | 3 | 1 | 2 | 3 | 3 | 3 | 3 | — | — | — | 0 | — | — | — | — | — |
| | 0.0175 | 1 | N | 0 | 0 | 3 | 0 | 1 | — | 1 | 0 | 2 | 3 | 1 | 2 | 2 | 3 | 3 | 2 | — | — | — | 0 | — | — | — | — | — |
| | 0.0175 | 0 | 0 | 0 | 0 | 1 | 0 | 0 | — | 0 | 0 | 1 | — | N | 2 | 2 | 2 | 3 | 2 | — | — | — | 0 | — | — | — | — | — |
| | 0.0175 | 0 | 1 | 0 | N | 0 | 0 | 0 | 0 | 0 | 0 | 2 | 1 | 0 | 0 | 0 | 3 | 3 | 2 | — | — | — | — | — | — | — | — | — |
| | 0.0175 | 0 | 0 | 0 | 0 | 0 | 0 | 0 | — | 0 | 0 | 1 | 0 | 0 | 2 | 3 | 1 | 3 | 0 | — | — | — | 0 | — | — | — | — | — |
| | 0.0175 | 0 | N | 0 | 0 | 1 | 0 | 0 | — | 0 | 0 | 2 | 0 | 1 | 2 | 3 | 3 | 3 | 3 | — | — | — | N | — | — | — | — | — |
| | 0.0175 | 1 | 0 | 0 | 0 | 0 | 0 | 0 | — | 0 | 0 | 0 | 0 | 0 | 0 | 2 | 3 | 3 | 2 | — | — | — | 1 | — | — | — | — | — |

TABLE B-continued

| Compound No. | Rate kg/ha | Sobe | Cotz | Rape | Cobu | Wibw | Mogl | Kese | Jewe | Viel | Whez | Rice | Gron | Cobr | Drmi | Pygr | Bact | Lrft | Gblq | Sclw | Ccww | Pnbg | Abaz | Brut | Rejg | Wioa |
|---|---|---|---|---|---|---|---|---|---|---|---|---|---|---|---|---|---|---|---|---|---|---|---|---|---|---|
| | 0.0175 | 0 | N | 0 | 0 | N | 0 | 2 | — | 2 | 0 | 1 | 0 | 0 | 2 | 3 | 1 | 3 | 1 | — | — | — | 3 | — | — | — |
| | 0.0175 | 0 | 0 | 0 | 0 | 0 | 0 | 0 | — | 0 | 1 | 0 | 2 | 0 | 2 | 1 | 2 | 3 | 2 | — | — | — | 0 | — | — | — |
| | 0.0175 | N | 0 | 0 | 0 | 0 | 0 | 0 | — | 0 | 0 | 0 | 0 | 0 | 0 | 0 | 0 | 1 | 0 | — | — | — | 0 | — | — | — |
| | 0.0175 | 0 | 1 | 0 | 0 | 1 | 0 | 0 | — | 0 | 0 | 2 | 0 | 1 | 3 | 1 | 3 | 3 | 2 | — | — | — | 0 | — | — | — |
| | 0.0175 | 0 | 1 | 0 | 0 | 1 | 0 | 0 | — | 0 | 0 | 2 | 0 | 0 | 1 | 3 | 2 | 3 | 3 | — | — | — | 0 | — | — | — |
| | 0.0175 | — | — | 1 | — | 2 | — | — | — | — | 1 | — | — | — | 2 | — | — | — | 3 | — | — | — | 3 | 3 | 0 | 0 | — | 1 |
| | 0.0175 | 0 | 0 | 0 | 0 | 0 | 0 | 0 | — | 0 | 2 | 0 | 1 | 0 | 1 | 2 | 3 | 3 | 2 | — | — | — | N | — | — | — |
| | 0.0175 | 0 | 0 | 0 | 0 | 0 | 0 | 0 | — | 0 | 0 | 0 | 0 | 0 | 0 | 0 | 2 | 3 | 2 | — | — | — | 2 | — | — | — |
| | 0.0175 | — | — | 0 | — | 0 | — | — | — | — | 0 | — | — | — | 0 | — | — | — | 3 | — | — | — | 0 | 3 | 0 | 0 | — | 0 |
| | 0.0175 | 0 | 0 | 0 | 0 | 0 | 0 | 0 | — | 1 | 0 | 0 | 0 | 0 | 2 | 1 | 1 | 3 | 1 | — | — | — | 0 | — | — | — |
| | 0.0087 | 0 | 0 | 0 | 0 | 0 | 0 | 0 | — | 0 | 0 | 0 | 0 | 0 | 0 | 0 | 1 | 2 | 1 | — | — | — | 0 | — | — | — |
| | 0.0087 | 0 | N | — | 0 | — | 0 | — | — | 0 | — | 1 | — | 0 | — | — | 0 | 2 | — | — | — | — | — | — | — | 1 | — |
| | 0.0087 | 0 | 1 | 0 | 0 | 0 | 0 | 1 | — | 2 | 0 | 0 | 0 | 0 | 1 | 0 | 0 | 2 | 0 | — | — | — | 0 | — | — | — |
| | 0.0087 | 0 | — | 0 | — | 0 | — | — | 0 | — | 0 | — | 0 | — | — | 0 | 2 | — | — | — | — | — | — | — | 1 | — |
| | 0.0087 | — | — | 0 | — | 0 | — | — | — | — | 1 | — | — | — | 1 | — | — | — | 3 | — | — | — | 1 | 3 | 0 | 0 | — | 3 |
| | 0.0087 | 0 | 0 | 0 | 0 | 0 | 0 | 0 | — | 2 | 0 | 0 | 1 | 0 | 0 | 0 | 1 | 3 | 2 | — | — | — | 0 | — | — | — |
| | 0.0087 | — | — | 0 | — | 0 | — | — | — | — | 0 | — | — | — | 0 | — | — | — | 3 | — | — | — | 0 | 3 | 0 | 0 | — | 0 |
| | 0.0087 | 0 | 0 | 0 | 0 | 0 | 0 | 2 | — | 0 | 0 | 0 | 0 | 0 | 0 | 1 | 0 | 3 | 1 | — | — | — | 1 | — | — | — |
| | 0.0087 | 0 | 0 | 0 | 0 | 0 | 0 | 0 | — | 0 | 0 | 0 | 0 | 0 | 0 | 0 | 0 | 3 | 0 | — | — | — | 0 | — | — | — |
| | 0.0087 | N | 1 | 0 | 0 | N | 0 | 1 | — | N | N | N | 0 | 0 | 0 | 0 | 0 | 2 | 0 | — | — | — | 0 | — | — | — |
| | 0.0087 | 0 | 0 | 0 | 0 | 1 | 0 | 0 | — | 0 | 0 | 1 | 1 | 0 | 0 | 1 | 2 | 2 | 2 | — | — | — | 1 | — | — | — |
| | 0.0087 | 0 | 0 | 0 | N | 0 | 0 | 0 | 0 | 0 | 0 | 0 | 0 | 0 | 0 | 0 | 0 | 1 | 3 | 2 | — | — | — | 0 | — | — | — |
| | 0.0087 | 0 | 0 | 0 | 0 | N | 0 | 0 | — | 0 | 0 | 0 | 2 | 0 | 1 | 0 | 0 | 3 | 1 | — | — | — | 0 | — | — | — |
| | 0.0087 | 0 | 0 | 0 | 0 | 0 | 0 | 0 | — | 0 | 0 | 0 | 1 | 0 | 0 | 0 | 2 | 3 | 0 | — | — | — | 0 | — | — | — |
| | 0.0087 | 0 | 0 | 0 | 0 | 0 | 0 | 0 | — | 0 | 0 | 0 | 0 | 0 | 0 | 0 | 0 | 1 | 0 | — | — | — | 0 | — | — | — |
| | 0.0087 | 0 | 1 | 0 | 0 | 0 | 0 | 1 | — | N | 0 | 1 | 0 | 0 | 1 | 2 | 0 | 3 | 1 | — | — | — | 0 | — | — | — |
| | 0.0044 | 0 | 0 | 0 | 0 | 1 | 0 | 0 | — | 0 | 0 | 0 | 0 | 0 | 0 | 0 | 0 | 1 | 0 | — | — | — | 0 | — | — | — |
| | 0.0044 | 0 | 0 | 0 | 0 | N | 0 | 0 | — | 0 | 0 | 0 | 0 | 0 | 0 | 0 | 0 | 0 | 0 | — | — | — | 0 | — | — | — |
| | 0.0044 | 0 | 1 | 0 | 0 | 1 | 0 | 0 | — | 0 | 0 | 0 | 0 | 1 | 0 | 1 | 1 | 3 | 0 | — | — | — | 0 | — | — | — |
| | 0.0044 | 0 | 0 | 0 | 0 | 1 | 0 | 0 | — | 0 | 0 | 0 | 0 | 0 | 0 | 0 | 1 | 0 | — | — | — | — | 0 | — | — | — |
| | 0.0044 | 0 | 0 | 0 | 0 | 0 | 0 | 0 | N | — | 0 | 0 | 0 | 0 | 0 | 0 | 0 | 0 | 0 | — | — | — | 0 | — | — | — |
| | 0.0044 | 1 | 0 | 0 | 0 | 0 | 0 | 0 | — | 0 | 0 | 0 | 0 | 0 | 0 | 0 | 3 | 1 | — | — | — | — | 0 | — | — | — |
| | 0.0044 | — | — | 0 | — | 1 | — | — | — | — | 0 | — | — | — | 0 | — | — | — | 2 | — | — | — | 2 | 0 | 0 | 0 | — | 0 |
| | 0.0044 | 0 | 0 | — | 0 | — | 0 | — | — | 0 | — | 0 | — | 0 | — | — | 3 | 2 | — | — | — | — | — | — | — | 1 | — |
| 110 | 5.6050 | 3 | 3 | 3 | N | 3 | 3 | 3 | 3 | 3 | 3 | 3 | 3 | 3 | 3 | 3 | 3 | 3 | 3 | — | — | — | — | — | — | — |
| | 1.1210 | 2 | 2 | 3 | N | 3 | 3 | 3 | 3 | 3 | 3 | 3 | 3 | 3 | 3 | 3 | 3 | 3 | 3 | — | — | — | — | — | — | — |

TABLE B-continued

| Compound No. | Rate kg/ha | Sobe | Cotz | Rape | Cbuu | Wibw | Mogl | Kese | Jiwe | Vile | Whez | Rice | Gron | Cobr | Dbri | Pmi | Bygr | Lact | Grft | Sube | Colq | Pecw | Conw | Anbg | Babz | Ruth | Sejg | Wioa |
|---|---|---|---|---|---|---|---|---|---|---|---|---|---|---|---|---|---|---|---|---|---|---|---|---|---|---|---|---|
|  | 0.2803 | 3 | 1 | 2 | N | 3 | 3 | 1 | 3 | 2 | 3 | 3 | 3 | 2 | 3 | 3 | 3 | 3 | 3 | — | — | — | — | — | — | — | — | — |
|  | 0.0701 | 1 | 2 | 0 | N | 1 | 0 | 1 | 1 | 2 | 0 | 3 | 2 | 1 | 3 | 3 | 3 | 3 | 3 | — | — | — | — | — | — | — | — | — |
|  | 0.0175 | 0 | 2 | 0 | N | 0 | 0 | 1 | 0 | 0 | 0 | 1 | 1 | 1 | 0 | 1 | 1 | 2 | 0 | — | — | — | — | — | — | — | — | — |
|  | 0.0087 | 0 | 1 | 0 | N | 0 | 0 | 0 | 1 | 0 | 0 | 1 | 1 | 0 | 0 | 1 | 1 | 1 | 1 | — | — | — | — | — | — | — | — | — |
| 111 | 5.6050 | 3 | 2 | 3 | N | 3 | 3 | 3 | 3 | 3 | 3 | 3 | 3 | 3 | 3 | 3 | 3 | 3 | 3 | — | — | — | — | — | — | — | — | — |
|  | 1.1210 | 2 | 1 | 3 | N | 3 | 2 | 2 | 3 | 3 | 3 | 3 | 3 | 2 | 3 | 3 | 3 | 3 | 3 | — | — | — | — | — | — | — | — | — |
|  | 0.2803 | 1 | 0 | 3 | N | 2 | 1 | 2 | 2 | 0 | 1 | 3 | 2 | 0 | 1 | 3 | 3 | 3 | 3 | — | — | — | — | — | — | — | — | — |
|  | 0.0701 | 0 | N | 0 | N | 0 | 0 | 0 | 0 | 0 | 0 | 0 | 0 | 0 | 0 | 0 | 1 | 3 | 1 | — | — | — | — | — | — | — | — | — |
| 112 | 5.6050 | 3 | 0 | 3 | 0 | 3 | 1 | 2 | 2 | 1 | 3 | 3 | 3 | 3 | 3 | 3 | 3 | 3 | 3 | — | — | — | — | — | — | — | — | — |
|  | 1.1210 | 2 | 0 | 0 | 0 | 3 | 0 | 0 | 3 | 0 | 2 | 3 | 3 | 2 | 3 | 3 | 3 | 3 | 3 | — | — | — | — | — | — | — | — | — |
|  | 0.2803 | 0 | 0 | 0 | N | 1 | 0 | 0 | 1 | 0 | 0 | 2 | 2 | 0 | 1 | 0 | 3 | 3 | 2 | — | — | — | — | — | — | — | — | — |
|  | 0.0701 | 0 | 0 | 0 | 0 | 2 | 0 | 0 | 1 | 0 | 0 | 0 | 0 | 0 | 0 | 0 | 0 | 1 | 0 | — | — | — | — | — | — | — | — | — |
|  | 0.0175 | 0 | 0 | 0 | 0 | N | 0 | 0 | N | 0 | 0 | 0 | 0 | 0 | 0 | 0 | 0 | 0 | 0 | — | — | — | — | — | — | — | — | — |
| 113 | 5.6050 | 0 | 2 | 1 | 0 | 3 | 0 | 0 | — | 1 | 3 | 2 | 3 | 3 | 3 | 3 | 3 | 3 | 3 | — | — | — | — | — | — | — | — | — |
|  | 1.1210 | 1 | 0 | 0 | 0 | 0 | 0 | 0 | — | 0 | 0 | 1 | 3 | 0 | 0 | 0 | 2 | 3 | 3 | — | — | — | 0 | — | — | — | — | — |
|  | 0.2803 | 0 | 0 | 0 | 0 | 0 | 0 | 0 | — | 0 | 0 | 0 | 1 | 0 | 0 | 0 | 0 | 1 | 0 | — | — | — | 0 | — | — | — | — | — |
|  | 0.0701 | 0 | 1 | 0 | 0 | 0 | 0 | 0 | — | 0 | 0 | 0 | 1 | 0 | 0 | 0 | 0 | 0 | 0 | — | — | — | 0 | — | — | — | — | — |
| 114 | 5.6050 | 3 | 0 | 3 | N | 3 | 3 | 3 | 3 | 3 | 3 | 3 | 3 | 3 | 3 | 3 | 3 | 3 | 3 | — | — | — | — | — | — | — | — | — |
|  | 1.1210 | 0 | 0 | 3 | N | 3 | 1 | 1 | 3 | 1 | 3 | 3 | 3 | 3 | 3 | 3 | 3 | 3 | 3 | — | — | — | — | — | — | — | — | — |
|  | 0.2803 | 0 | 0 | 0 | N | 1 | 0 | 0 | 1 | 0 | 2 | 3 | 1 | 0 | 3 | 3 | 3 | 3 | 2 | — | — | — | — | — | — | — | — | — |
|  | 0.0701 | 0 | 0 | 0 | N | 0 | 0 | 0 | 1 | 1 | 0 | 1 | 1 | 1 | 0 | 1 | 0 | 2 | 0 | — | — | — | — | — | — | — | — | — |
|  | 0.0175 | 1 | 0 | 0 | N | 0 | 0 | 0 | 0 | 0 | 0 | 0 | 0 | 0 | 0 | 0 | 0 | 0 | 0 | — | — | — | — | — | — | — | — | — |
| 115 | 5.6050 | 3 | 3 | 3 | 1 | 2 | 3 | 2 | 2 | 1 | 1 | 3 | 3 | 3 | 3 | 3 | 3 | 3 | 3 | — | — | — | — | — | — | — | — | — |
|  | 1.1210 | 1 | 1 | 2 | 0 | 1 | 1 | 0 | 1 | 1 | 0 | 2 | 3 | 3 | 3 | 3 | 3 | 3 | 2 | — | — | — | — | — | — | — | — | — |
|  | 0.2803 | 0 | 1 | 0 | 0 | 0 | 0 | 0 | 0 | 0 | 0 | 1 | 0 | 0 | 0 | 1 | 0 | 1 | 0 | — | — | — | — | — | — | — | — | — |
|  | 0.0701 | 0 | N | 0 | 0 | 0 | 0 | 0 | 0 | 0 | 0 | 0 | 0 | 1 | 0 | 0 | 0 | 0 | 0 | — | — | — | — | — | — | — | — | — |
|  | 0.0175 | 0 | N | 0 | 0 | 0 | 0 | N | 0 | N | 0 | 0 | 0 | 0 | 0 | 0 | 0 | 0 | 0 | — | — | — | — | — | — | — | — | — |
| 116 | 5.6050 | 3 | 3 | 3 | 2 | 3 | 3 | 3 | 3 | 3 | 3 | 3 | 3 | 3 | 3 | 3 | 3 | 3 | 3 | — | — | — | — | — | — | — | — | — |
|  | 1.1210 | 3 | 3 | 3 | 1 | 3 | 3 | 3 | 3 | 3 | 3 | 3 | 3 | 3 | 3 | 3 | 3 | 3 | 3 | — | — | — | — | — | — | — | — | — |
|  | 0.2803 | 3 | 1 | 3 | 0 | 3 | 3 | 3 | 2 | 3 | 3 | 3 | 3 | 3 | 3 | 3 | 3 | 3 | 3 | — | — | — | — | — | — | — | — | — |
|  | 0.0701 | 2 | N | 3 | 0 | 3 | 2 | 2 | 2 | 1 | 2 | 3 | 3 | 1 | 3 | 3 | 3 | 3 | 3 | — | — | — | — | — | — | — | — | — |
|  | 0.0175 | 0 | N | 2 | 0 | 2 | 1 | 1 | 2 | 1 | 1 | 1 | 1 | 0 | 2 | 3 | 3 | 3 | 3 | — | — | — | — | — | — | — | — | — |
|  | 0.0087 | 0 | 0 | 2 | 0 | 0 | 0 | 0 | 0 | 1 | 0 | 1 | 0 | 0 | 3 | 3 | 3 | 3 | | — | — | — | — | — | — | — | — | — |
| 117 | 5.6050 | 3 | 2 | 3 | 2 | 3 | 3 | 3 | 2 | 3 | 3 | 3 | 3 | 3 | 3 | 3 | 3 | 3 | 3 | — | — | — | — | — | — | — | — | — |
|  | 1.1210 | 1 | 0 | 1 | 0 | 2 | 1 | 1 | 2 | 0 | 2 | 2 | 3 | 3 | 3 | 3 | 1 | 3 | 1 | — | — | — | — | — | — | — | — | — |
|  | 0.2803 | 1 | 1 | 0 | 0 | 0 | 0 | 0 | 0 | 0 | 0 | 0 | 1 | 0 | 0 | 0 | 0 | 2 | 0 | — | — | — | — | — | — | — | — | — |

TABLE B-continued

| Compound No. | Rate kg/ha | Sobe | Cotz | Rape | Cbuu | Wibw | Mogl | Kese | Jiwe | Vile | Whez | Rceo | Gron | Cbnr | Dmi | Prgr | Byct | Laft | Grbe | Sulq | Cocw | Pcbw | Cnbg | Abrz | Brth | Rsjg | Wioa |
|---|---|---|---|---|---|---|---|---|---|---|---|---|---|---|---|---|---|---|---|---|---|---|---|---|---|---|---|
| | 0.0701 | 0 | 0 | 0 | 0 | 0 | 0 | 0 | 0 | 0 | 0 | 0 | 0 | 0 | 0 | 0 | 0 | 0 | — | — | — | — | — | — | — | — |
| 118 | 5.6050 | 3 | 2 | 3 | 2 | 3 | 3 | 3 | 3 | 3 | 3 | 3 | 3 | 3 | 3 | 3 | 3 | 3 | — | — | — | — | — | — | — | — |
| | 1.1210 | 3 | 3 | 3 | 1 | 3 | 3 | 3 | 3 | 3 | 3 | 3 | 3 | 3 | 3 | 3 | 3 | 3 | — | — | — | — | — | — | — | — |
| | 1.1210 | 3 | 0 | 3 | 0 | 3 | 3 | 3 | — | 3 | 3 | 3 | 3 | 3 | 3 | 3 | 3 | 3 | — | — | — | 3 | — | — | — | — |
| | 0.2803 | 3 | N | 3 | 0 | 3 | 1 | 3 | — | 3 | 3 | 2 | 3 | 3 | 3 | 3 | 3 | 3 | — | — | — | 3 | — | — | — | — |
| | 0.2803 | 2 | 3 | 2 | 1 | 3 | 3 | 3 | 3 | 3 | 3 | 3 | 3 | 3 | 3 | 3 | 3 | 3 | — | — | — | — | — | — | — | — |
| | 0.0701 | 1 | 0 | 0 | 0 | 2 | 0 | 3 | — | 1 | 1 | 2 | 3 | 1 | 3 | 3 | 3 | 3 | — | — | — | 3 | — | — | — | — |
| | 0.0701 | 2 | 0 | 0 | 1 | 1 | 2 | 2 | 2 | 1 | 2 | 2 | 3 | 1 | 2 | 3 | 3 | 3 | — | — | — | — | — | — | — | — |
| | 0.0175 | 0 | 0 | 0 | 0 | 1 | 0 | 1 | — | 0 | 0 | 0 | 3 | 0 | 2 | 3 | 3 | 2 | 3 | — | — | 2 | — | — | — | — |
| | 0.0175 | 0 | N | 0 | 0 | 1 | 0 | 0 | 1 | 0 | 1 | 1 | 1 | 0 | 1 | 2 | 2 | 3 | 3 | — | — | — | — | — | — | — |
| | 0.0087 | 0 | 0 | 0 | 0 | 0 | 0 | 0 | 1 | 0 | 0 | 1 | 0 | 0 | 1 | 0 | 0 | 1 | 0 | — | — | — | — | — | — | — |
| 119 | 5.6050 | 3 | 3 | 3 | 3 | 3 | 3 | 3 | 3 | 3 | 3 | 3 | 3 | 3 | 3 | 3 | 3 | 3 | — | — | — | — | — | — | — | — |
| | 1.1210 | 3 | 2 | 3 | 2 | 3 | 3 | 3 | 3 | 3 | 3 | 3 | 3 | 3 | 3 | 3 | 3 | 3 | — | — | — | — | — | — | — | — |
| | 0.2803 | 3 | 1 | 3 | 0 | 3 | 3 | 3 | 3 | 3 | 3 | 3 | 3 | 3 | 3 | 3 | 3 | 3 | — | — | — | — | — | — | — | — |
| | 0.0701 | 1 | N | 3 | 0 | 2 | 1 | 3 | 3 | 2 | 3 | 1 | 3 | 2 | 3 | 3 | 3 | 3 | — | — | — | — | — | — | — | — |
| | 0.0175 | 1 | 1 | 2 | 0 | 2 | 0 | 1 | 1 | 1 | 1 | 1 | 3 | 0 | 3 | 2 | 3 | 3 | — | — | — | — | — | — | — | — |
| 120 | 5.6050 | 3 | 0 | 3 | 0 | 3 | 2 | 3 | — | 3 | 3 | 3 | 3 | 3 | 3 | 3 | 3 | 3 | — | — | — | 3 | — | — | — | — |
| | 1.1210 | 3 | 0 | 2 | 0 | 3 | 2 | 2 | — | 3 | 3 | 3 | 3 | 3 | 3 | 3 | 3 | 3 | — | — | — | 3 | — | — | — | — |
| | 0.2803 | 0 | 0 | 2 | 0 | 3 | 0 | 2 | — | 2 | 3 | 3 | 3 | 3 | 3 | 3 | 3 | 3 | — | — | — | 3 | — | — | — | — |
| | 0.0701 | 0 | 0 | 0 | 0 | 2 | 1 | 0 | — | 1 | 1 | 0 | 3 | 0 | 2 | 3 | 3 | 3 | — | — | — | 3 | — | — | — | — |
| | 0.0175 | 0 | 0 | 0 | 0 | 2 | 0 | 0 | — | 0 | 2 | 0 | 2 | 1 | 1 | 3 | 3 | 3 | — | — | — | 1 | — | — | — | — |
| | 0.0087 | 0 | 0 | 0 | 0 | 1 | 0 | 0 | — | 0 | 0 | 0 | 1 | 0 | 1 | 1 | 3 | 2 | — | — | — | 0 | — | — | — | — |
| 121 | 5.6050 | 3 | 2 | 3 | 3 | 3 | 3 | 3 | — | 3 | 3 | 3 | 3 | 3 | 3 | 3 | 3 | 3 | — | — | — | 3 | — | — | — | — |
| | 1.1210 | 3 | 1 | 3 | 1 | 3 | 3 | 3 | — | 3 | 3 | 3 | 3 | 3 | 3 | 3 | 3 | 3 | — | — | — | 3 | — | — | — | — |
| | 0.2803 | 2 | 0 | 3 | 0 | 3 | 2 | 2 | — | 2 | 3 | 3 | 3 | 2 | 3 | 3 | 3 | 3 | — | — | — | 3 | — | — | — | — |
| | 0.0701 | 0 | 1 | 3 | 0 | 3 | 2 | 2 | — | 1 | 3 | 2 | 3 | 0 | 2 | 3 | 3 | 3 | — | — | — | 0 | — | — | — | — |
| | 0.0175 | 0 | 1 | 1 | 0 | 2 | 0 | 0 | — | 1 | 0 | 1 | 1 | 1 | 1 | 2 | 2 | 3 | 1 | — | — | 0 | — | — | — | — |
| | 0.0087 | 1 | 1 | 0 | 0 | 1 | 0 | 1 | — | 0 | 0 | 1 | 0 | 0 | 1 | 0 | 0 | 3 | 0 | — | — | 0 | — | — | — | — |
| 122 | 5.6050 | 3 | 2 | 3 | 1 | 3 | 3 | 3 | 3 | 3 | 3 | 3 | 3 | 3 | 3 | 3 | 3 | 3 | — | — | — | — | — | — | — | — |
| | 1.1210 | 3 | 0 | 3 | 0 | 3 | 3 | 3 | 3 | 2 | 3 | 3 | 3 | 3 | 3 | 3 | 3 | 3 | — | — | — | — | — | — | — | — |
| | 0.2803 | 0 | 0 | 2 | 0 | 3 | 1 | 1 | 3 | 2 | 3 | 3 | 3 | 2 | 3 | 3 | 3 | 3 | — | — | — | — | — | — | — | — |
| | 0.0701 | 1 | 0 | 0 | 0 | 0 | 0 | 1 | 1 | 0 | 1 | 3 | 3 | 1 | 2 | 2 | 3 | 3 | — | — | — | — | — | — | — | — |
| | 0.0175 | 0 | 0 | 0 | 0 | 1 | 0 | 0 | 2 | 0 | 0 | 1 | 0 | 0 | 0 | 2 | 0 | 3 | 1 | — | — | — | — | — | — | — |
| | 0.0087 | 0 | 0 | 0 | 0 | 0 | 0 | 0 | 0 | 0 | 0 | 0 | 0 | 0 | 0 | 0 | 2 | 0 | — | — | — | — | — | — | — | — |
| 123 | 5.6050 | 2 | 2 | 3 | 0 | 2 | 2 | 1 | 2 | 0 | 3 | 3 | 3 | 3 | 3 | 3 | 3 | 3 | — | — | — | — | — | — | — | — |
| | 1.1210 | 1 | 1 | 0 | 0 | 0 | 0 | 0 | 0 | 0 | 0 | 0 | 1 | 2 | 0 | 3 | 1 | 1 | 0 | — | — | — | — | — | — | — |

TABLE B-continued

| Compound No. | Rate kg/ha | Sobe | Cotz | Rape | Cobu | Wibw | Mogl | Kese | Jiwe | Vile | Whez | Rico | Gron | Cobr | Domi | Pyrg | Blart | Lcft | Grbe | Suq | Colw | Pecw | Cong | Abuz | Brrh | Rutj | Siog | Wioa |
|---|---|---|---|---|---|---|---|---|---|---|---|---|---|---|---|---|---|---|---|---|---|---|---|---|---|---|---|---|
| | 0.2803 | 0 | 0 | 0 | 0 | 0 | 0 | 0 | 0 | 0 | 0 | 0 | 0 | 1 | 0 | 0 | 0 | 0 | — | — | — | — | — | — | — | — | — |
| | 0.0701 | 0 | N | 0 | 0 | 0 | 0 | 0 | 0 | 0 | 0 | 0 | 0 | 1 | 0 | N | 0 | 0 | 0 | — | — | — | — | — | — | — | — |
| 125 | 5.6050 | 2 | 0 | 3 | 0 | 3 | 3 | 2 | 3 | 3 | 3 | 3 | 3 | 3 | 3 | 3 | 3 | 3 | 3 | — | — | — | — | — | — | — | — |
| | 1.1210 | 1 | 1 | 3 | 0 | 2 | 1 | 2 | 2 | 2 | 2 | 2 | 3 | 1 | 1 | 3 | 3 | 3 | 3 | — | — | — | — | — | — | — | — |
| | 0.2803 | 0 | 1 | 2 | N | 2 | 1 | 2 | 1 | 1 | 2 | 3 | 1 | 1 | 2 | 3 | 2 | 3 | 3 | — | — | — | — | — | — | — | — |
| | 0.0701 | 0 | 0 | 1 | 0 | 0 | 0 | 0 | 0 | 0 | 1 | 0 | 0 | 0 | 0 | 0 | 0 | 2 | 0 | — | — | — | — | — | — | — | — |
| 126 | 5.6050 | 3 | 0 | 3 | 0 | 3 | 3 | 3 | 3 | 3 | 3 | 3 | 3 | 3 | 3 | 3 | 3 | 3 | 3 | — | — | — | — | — | — | — | — |
| | 1.1210 | 0 | 0 | 3 | 0 | 3 | 1 | 2 | 2 | 2 | 3 | 2 | 3 | 3 | 3 | 3 | 3 | 3 | 3 | — | — | — | — | — | — | — | — |
| | 0.2803 | 1 | 1 | 1 | 0 | 0 | 0 | 0 | 0 | 0 | 0 | 0 | 0 | 0 | 1 | 3 | 1 | 3 | 2 | — | — | — | — | — | — | — | — |
| | 0.0701 | 1 | 1 | 1 | N | 0 | 1 | 1 | 0 | 0 | 1 | 0 | 1 | 1 | 0 | 0 | 1 | 1 | 1 | — | — | — | — | — | — | — | — |
| | 0.0175 | 0 | 0 | 0 | 0 | 0 | 0 | 0 | 0 | 0 | 0 | 0 | 0 | 0 | 0 | 0 | 0 | 0 | 0 | — | — | — | — | — | — | — | — |
| 127 | 5.6050 | 2 | 0 | 1 | 1 | 1 | 1 | 0 | 1 | 0 | 2 | 3 | 3 | 3 | 3 | 3 | 3 | 3 | 1 | — | — | — | — | — | — | — | — |
| | 1.1210 | 1 | N | 0 | 0 | 0 | 0 | 0 | 0 | 1 | 0 | 1 | 1 | 1 | 2 | 2 | 0 | 2 | 0 | — | — | — | — | — | — | — | — |
| | 0.2803 | N | 0 | 0 | 0 | 0 | 0 | 0 | 0 | N | 0 | 0 | 0 | 1 | 0 | 1 | 0 | 0 | 0 | — | — | — | — | — | — | — | — |
| | 0.0701 | 0 | 1 | 0 | 0 | 0 | 0 | 0 | 0 | 0 | 0 | 0 | 0 | 0 | 0 | 0 | 0 | 0 | 0 | — | — | — | — | — | — | — | — |
| 128 | 5.6050 | 3 | 2 | 0 | 1 | 0 | 1 | 1 | 1 | 0 | 1 | 3 | 3 | 3 | 3 | 3 | 3 | 3 | 3 | — | — | — | — | — | — | — | — |
| | 1.1210 | 1 | 1 | 0 | 0 | 1 | 0 | 1 | 1 | 0 | 0 | 2 | 3 | 1 | 3 | 3 | 2 | 3 | 0 | — | — | — | — | — | — | — | — |
| | 0.2803 | 0 | 0 | 0 | 0 | 0 | 0 | 0 | 0 | N | 0 | 1 | 0 | 0 | 1 | 1 | 0 | 1 | 0 | — | — | — | — | — | — | — | — |
| | 0.0701 | 0 | N | 0 | 0 | N | 0 | 0 | N | 0 | 0 | N | 0 | 0 | N | 0 | 0 | 1 | 0 | — | — | — | — | — | — | — | — |
| | 0.0175 | 0 | 0 | 0 | 0 | 0 | 0 | 0 | 0 | N | 0 | N | 0 | 0 | 0 | 0 | 0 | 0 | 0 | — | — | — | — | — | — | — | — |
| 129 | 5.6050 | 3 | 3 | 3 | 3 | 3 | 3 | 3 | 3 | 3 | 3 | 3 | 3 | 3 | 3 | 3 | 3 | 3 | 3 | — | — | — | — | — | — | — | — |
| | 1.1210 | 3 | 3 | 3 | 1 | 3 | 3 | 3 | 3 | 3 | 3 | 3 | 3 | 3 | 3 | 3 | 3 | 3 | 3 | — | — | — | — | — | — | — | — |
| | 0.2803 | 3 | 1 | 3 | 1 | 1 | 3 | 2 | 0 | 2 | 3 | 3 | 3 | 3 | 3 | 3 | 3 | 3 | 3 | — | — | — | — | — | — | — | — |
| | 0.0701 | 2 | 1 | 1 | 0 | 2 | 0 | 1 | 2 | 0 | 2 | 3 | 2 | 1 | 3 | 3 | 3 | 3 | 3 | — | — | — | — | — | — | — | — |
| | 0.0176 | 0 | N | 0 | N | 1 | 0 | 0 | 0 | 0 | 0 | 2 | 1 | 2 | 0 | 1 | 2 | 3 | 3 | — | — | — | — | — | — | — | — |
| | 0.0087 | 1 | 1 | 0 | 0 | 0 | 0 | 0 | 0 | 0 | 0 | 0 | 0 | 0 | 1 | 1 | 2 | 3 | 3 | — | — | — | — | — | — | — | — |
| 130 | 5.6050 | 3 | 2 | 3 | 2 | 3 | 3 | 3 | 3 | 3 | 3 | 3 | 3 | 3 | 3 | 3 | 3 | 3 | 3 | — | — | — | — | — | — | — | — |
| | 1.1210 | 3 | 1 | 3 | 0 | 3 | 3 | 3 | 3 | 3 | 3 | 3 | 3 | 3 | 3 | 3 | 3 | 3 | 3 | — | — | — | — | — | — | — | — |
| | 0.2803 | 2 | 2 | 3 | 1 | 3 | 3 | 3 | 3 | 3 | 3 | 3 | 3 | 3 | 3 | 3 | 3 | 3 | 3 | — | — | — | — | — | — | — | — |
| | 0.0701 | 0 | 1 | 1 | 1 | 1 | 0 | 0 | 2 | 1 | 1 | 1 | 3 | 1 | 2 | 2 | 3 | 3 | 3 | — | — | — | — | — | — | — | — |
| | 0.0175 | 0 | N | 0 | 0 | 0 | 0 | 0 | 0 | 0 | 0 | 0 | 0 | 0 | 1 | 0 | 1 | 3 | 3 | — | — | — | — | — | — | — | — |
| | 0.0087 | 0 | 0 | 0 | 0 | 0 | 0 | 0 | 0 | 0 | 1 | 0 | 0 | 0 | 0 | 0 | 1 | 0 | — | — | — | — | — | — | — | — | — |
| 131 | 5.6050 | 3 | 3 | 3 | 1 | 3 | 3 | 3 | — | 3 | 3 | 3 | 3 | 3 | 3 | 3 | 3 | 3 | 3 | — | — | — | — | 3 | — | — | — |
| | 1.1210 | 3 | 3 | 3 | 1 | 3 | 3 | 3 | — | 3 | 3 | 3 | 3 | 3 | 3 | 3 | 3 | 3 | 3 | — | — | — | — | 3 | — | — | — |
| | 0.2803 | 1 | 0 | 3 | 0 | 3 | 3 | 3 | — | 3 | 3 | 3 | 3 | 2 | 3 | 3 | 3 | 3 | 3 | — | — | — | — | 3 | — | — | — |
| | 0.0701 | 1 | 0 | 1 | 1 | 2 | 1 | 1 | — | 1 | 1 | 2 | 1 | 0 | 3 | 3 | 3 | 3 | 3 | — | — | — | — | 2 | — | — | — |

TABLE B-continued

| Compound No. | Rate kg/ha | Sobe | Cotz | Rape | Cobu | Wibw | Mogl | Kese | Jiwe | Vile | Whez | Riceo | Gron | Cobr | Dobri | Pyrmi | Byagr | Larct | Grte | Subeq | Coslw | Pelcw | Cocwg | Anbrz | Baruth | Ruejg | Wioa |
|---|---|---|---|---|---|---|---|---|---|---|---|---|---|---|---|---|---|---|---|---|---|---|---|---|---|---|---|
| | 0.0175 | 0 | 0 | N | 0 | N | 0 | 0 | — | 2 | 0 | 0 | 1 | 0 | 2 | 1 | 3 | 3 | 3 | — | — | — | N | — | — | — | — |
| | 0.0087 | 0 | 0 | 0 | 0 | 0 | 0 | 0 | — | 0 | 0 | 1 | 0 | 0 | 1 | 0 | 0 | 2 | 2 | — | — | — | 0 | — | — | — | — |
| 132 | 5.6050 | 3 | 3 | 3 | 2 | 3 | 3 | 3 | — | 3 | 3 | 3 | 3 | 3 | 3 | 3 | 3 | 3 | 3 | — | — | — | 3 | — | — | — | — |
| | 1.1210 | 3 | 0 | 3 | 1 | 3 | 3 | 3 | — | 3 | 3 | 3 | 3 | 3 | 3 | 3 | 3 | 3 | 3 | — | — | — | 3 | — | — | — | — |
| | 0.2803 | 1 | 0 | 3 | 0 | 3 | 2 | 2 | — | 2 | 1 | 3 | 2 | 1 | 3 | 3 | 3 | 3 | 3 | — | — | — | 3 | — | — | — | — |
| | 0.0701 | 1 | 0 | 0 | 0 | 1 | 3 | 1 | — | 1 | 0 | 1 | 1 | 0 | 2 | 3 | 3 | 3 | 1 | — | — | — | 2 | — | — | — | — |
| 133 | 5.6050 | 3 | 1 | 3 | 1 | 3 | 3 | 3 | — | 3 | 3 | 3 | 3 | 3 | 3 | 3 | 3 | 3 | 3 | — | — | — | 3 | — | — | — | — |
| | 1.1210 | 2 | 0 | 3 | 0 | 3 | 3 | 3 | — | 3 | 3 | 3 | 3 | 3 | 3 | 3 | 3 | 3 | 3 | — | — | — | 3 | — | — | — | — |
| | 0.2803 | 0 | 1 | 1 | 0 | 0 | 1 | 0 | — | 0 | 2 | 2 | 3 | 0 | 3 | 3 | 3 | 3 | 3 | — | — | — | 3 | — | — | — | — |
| | 0.0701 | N | 1 | 0 | 0 | 0 | 0 | 0 | — | 0 | 0 | 1 | 2 | 0 | 1 | 1 | 0 | 3 | 1 | — | — | — | 2 | — | — | — | — |
| | 0.0175 | 0 | 0 | 0 | 0 | 0 | 1 | 0 | — | 0 | 0 | 0 | 1 | 1 | 1 | 0 | 0 | 2 | 0 | — | — | — | 0 | — | — | — | — |
| | 0.0087 | 1 | 0 | 0 | 0 | N | N | 0 | — | 0 | 0 | 0 | 0 | 0 | 0 | 0 | 0 | 1 | 0 | — | — | — | N | — | — | — | — |
| 134 | 5.6050 | 1 | 0 | 3 | 0 | 3 | 2 | 3 | — | 3 | 2 | 3 | 1 | 3 | 3 | 3 | 3 | 3 | 3 | — | — | — | 3 | — | — | — | — |
| | 1.1210 | 0 | 0 | 1 | 0 | 0 | 0 | 0 | — | 0 | 0 | 0 | 0 | 0 | 2 | 3 | 3 | 3 | 1 | — | — | — | 3 | — | — | — | — |
| | 0.2803 | 0 | 0 | 0 | 0 | 0 | 0 | 0 | — | 0 | 0 | 0 | 0 | 1 | 1 | 1 | 0 | 0 | 0 | — | — | — | 0 | — | — | — | — |
| 135 | 5.6050 | 0 | 1 | 3 | 0 | 2 | 1 | 2 | — | 2 | 1 | 2 | 0 | 3 | 3 | 3 | 3 | 3 | 3 | — | — | — | 3 | — | — | — | — |
| | 1.1210 | 0 | 0 | 1 | 0 | 0 | 0 | 0 | — | 0 | 0 | 0 | 0 | 0 | 2 | 3 | 3 | 3 | 0 | — | — | — | 2 | — | — | — | — |
| | 0.2803 | 0 | 0 | 0 | 0 | 0 | 0 | 0 | — | 0 | 0 | 0 | 0 | 0 | 0 | 0 | 0 | 2 | 0 | — | — | — | 2 | — | — | — | — |
| | 0.0701 | 0 | 0 | 0 | 0 | 1 | 0 | 1 | — | N | 0 | 0 | 0 | 0 | 0 | 0 | 0 | N | N | — | — | — | 2 | — | — | — | — |
| 136 | 5.6050 | 3 | 2 | 3 | 2 | 3 | 3 | 3 | — | 3 | 3 | 3 | 3 | 3 | 3 | 3 | 3 | 3 | 3 | — | — | — | 3 | — | — | — | — |
| | 1.1210 | 2 | 0 | 3 | 1 | 3 | 3 | 3 | — | 3 | 3 | 3 | 3 | 3 | 3 | 3 | 3 | 3 | 3 | — | — | — | 3 | — | — | — | — |
| | 0.2803 | 1 | 0 | 2 | 1 | 2 | 3 | 3 | — | 2 | 3 | 1 | 3 | 1 | 3 | 3 | 3 | 3 | 3 | — | — | — | 3 | — | — | — | — |
| | 0.0701 | 0 | 1 | 0 | 0 | 2 | 0 | 0 | — | 0 | 1 | 0 | 1 | 1 | 1 | 2 | 3 | 3 | 3 | — | — | — | 2 | — | — | — | — |
| | 0.0175 | 0 | 0 | 1 | N | 0 | 0 | 0 | — | 0 | 1 | 0 | 1 | 0 | 0 | 0 | 0 | 3 | 1 | — | — | — | 0 | — | — | — | — |
| 137 | 5.6050 | 3 | 3 | 3 | 3 | 3 | 3 | 3 | — | 3 | 3 | 3 | 3 | 3 | 3 | 3 | 3 | 3 | 3 | — | — | — | 3 | — | — | — | — |
| | 1.1210 | 3 | 2 | 3 | 1 | 3 | 2 | 3 | — | 3 | 3 | 3 | 3 | 3 | 3 | 3 | 3 | 3 | 3 | — | — | — | 3 | — | — | — | — |
| | 0.2803 | 3 | 1 | 3 | 0 | 3 | 1 | 3 | — | 3 | 3 | 3 | 3 | 3 | 3 | 3 | 3 | 3 | 3 | — | — | — | 3 | — | — | — | — |
| | 0.0701 | 0 | 0 | 3 | 0 | 1 | 0 | 1 | — | 2 | 3 | 3 | 1 | 3 | 3 | 3 | 3 | 3 | 3 | — | — | — | 3 | — | — | — | — |
| | 0.0175 | 0 | 0 | 2 | 0 | 0 | 0 | 0 | — | 1 | 2 | 3 | 2 | 0 | 3 | 2 | 3 | 3 | 3 | — | — | — | 3 | — | — | — | — |
| | 0.0044 | 0 | 0 | 0 | 0 | 1 | 0 | 0 | — | 0 | 0 | 1 | 1 | 0 | 0 | 0 | 0 | 1 | 0 | — | — | — | 1 | — | — | — | — |
| 139 | 5.6050 | 2 | 0 | 3 | 0 | 3 | 3 | 3 | — | 3 | 3 | 3 | 3 | 3 | 3 | 3 | 3 | 3 | 3 | — | — | — | 3 | — | — | — | — |
| | 1.1210 | 0 | N | 1 | 0 | 1 | 0 | 0 | — | 1 | 1 | 3 | 3 | 1 | 3 | 3 | 3 | 3 | 1 | — | — | — | 1 | — | — | — | — |
| | 0.2803 | 0 | 1 | 0 | 0 | 0 | 0 | 0 | — | 0 | 0 | 1 | 2 | 1 | 0 | 3 | 0 | 2 | 0 | — | — | — | 0 | — | — | — | — |
| | 0.0701 | 0 | 1 | 0 | 0 | 0 | 0 | 0 | — | 0 | 0 | 0 | 0 | 1 | 0 | 2 | 0 | 0 | 0 | — | — | — | 1 | — | — | — | — |
| | 0.0175 | 0 | 0 | 0 | 0 | 0 | 1 | 0 | — | 0 | 0 | 0 | 0 | 0 | 0 | 0 | 0 | 0 | 0 | — | — | — | 0 | — | — | — | — |
| 140 | 5.6050 | 3 | 1 | 3 | 1 | 3 | 3 | 3 | — | 3 | 3 | 3 | 3 | 3 | 3 | 3 | 3 | 3 | 3 | — | — | — | 3 | — | — | — | — |

TABLE B-continued

| Compound No. | Rate kg/ha | Sobe | Cotz | Rape | Cobu | Wibw | Mogl | Kese | Jiwe | Vele | Whez | Rice | Grso | Corn | Dobr | Pymi | Brag | Lact | Grft | Subqe | Colw | Peqw | Cnbg | Anbz | Bart | Rutj | Swiga | Wioa |
|---|---|---|---|---|---|---|---|---|---|---|---|---|---|---|---|---|---|---|---|---|---|---|---|---|---|---|---|---|
| | 1.1210 | 3 | 2 | 3 | 1 | 3 | 3 | 3 | — | 3 | 3 | 3 | 3 | 3 | 3 | 3 | 3 | 3 | 3 | — | — | — | 3 | — | — | — | — | — |
| | 0.2803 | 2 | 2 | 3 | 0 | 3 | 3 | 3 | — | 3 | 3 | 3 | 3 | 3 | 2 | 3 | 3 | 3 | 3 | — | — | — | 3 | — | — | — | — | — |
| | 0.0701 | 3 | 2 | 2 | 0 | 3 | 1 | 2 | — | 1 | 2 | 3 | 3 | 1 | 3 | 3 | 3 | 3 | 3 | — | — | — | 3 | — | — | — | — | — |
| | 0.0175 | 1 | 1 | 1 | 0 | 2 | 0 | 0 | — | 0 | 1 | 2 | 1 | 0 | 1 | 3 | 3 | 3 | 3 | — | — | — | 2 | — | — | — | — | — |
| 141 | 5.6050 | 3 | 2 | 3 | 0 | 3 | 3 | 3 | — | 3 | 3 | 3 | 3 | 2 | 3 | 3 | 3 | 3 | 3 | — | — | — | 3 | — | — | — | — | — |
| | 1.1210 | 2 | 2 | 3 | 0 | 2 | 2 | 0 | — | 0 | 3 | 3 | 3 | 0 | 2 | 3 | 3 | 3 | 3 | — | — | — | 3 | — | — | — | — | — |
| | 0.2803 | 1 | 1 | 0 | 0 | 1 | 0 | 0 | — | 0 | 1 | 3 | 2 | 1 | 1 | 1 | 3 | 3 | 2 | — | — | — | 2 | — | — | — | — | — |
| | 0.0701 | 0 | 1 | 0 | 0 | 2 | 0 | 0 | — | 0 | 0 | 0 | 0 | 0 | 1 | 0 | 0 | 3 | 0 | — | — | — | 1 | — | — | — | — | — |
| | 0.0175 | 0 | 1 | 0 | 0 | 0 | 0 | 0 | — | 0 | 0 | 0 | 0 | 1 | 0 | 0 | 0 | 0 | 0 | — | — | — | 0 | — | — | — | — | — |

POST-EMERGENT HERBICIDE ACTIVITY ON PLANTS

Although, as has been stated above, the compounds of this invention exhibit predominantly pre-emergence activity in greenhouse testing, nevertheless many of these compounds are active post-emergent herbicides. The post-emergent activity is best seen on younger plants treated at the 1½ to 2 leaf stage. In the tests which follow, larger and more developed plants were used.

The post-emergence herbicidal activity of compounds of this invention was demonstrated by greenhouse testing, and the results are shown in the following Table C. The post-emergent herbicidal activity index used in Table C is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — or a blank |
| Species planted, no data | N |

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/ha. The pans were returned to the greenhouse and watered as before and the injury to the plants as compared to those in control pans was observed at approximately 10–14 days (usually 11 days). The plant identifying codes in Table C are the same as above defined.

TABLE C

Herbicide Primary Postemergence

| Compound | Yens | Anbg | Sejg | Dobr | Bygr | Mogl | Cobu | Vele | Inmu | Wibw | Cabh | Colsq | Pehw | Rhqg | Rhjg |
|---|---|---|---|---|---|---|---|---|---|---|---|---|---|---|---|
| 1 | 0 | — | — | 0 | 0 | 0 | 0 | 0 | — | — | 0 | 0 | 0 | 0 | 0 |
| 2 | 0 | — | — | 0 | 0 | 1 | 0 | 0 | — | — | 0 | 1 | 1 | 0 | 0 |
| 3 | 0 | — | — | 0 | 0 | 0 | 0 | 0 | — | — | 0 | 2 | 0 | 0 | 0 |
| 4 | 0 | — | — | 0 | 0 | 0 | 0 | 0 | — | — | 0 | 0 | 0 | 0 | 0 |
| 5 | 0 | — | — | — | 0 | 0 | 1 | 0 | — | — | 0 | 0 | 0 | 0 | 0 |
| 6 | 0 | — | — | 0 | 0 | 0 | 0 | 0 | — | — | 0 | 0 | 0 | 0 | 0 |
| 7 | 0 | — | — | 0 | 0 | 0 | 0 | 0 | — | — | 0 | 0 | 0 | 0 | 0 |
| 8 | 0 | — | — | 0 | 0 | 0 | 0 | 0 | — | — | 0 | 0 | 0 | 0 | N |
| 9 | 0 | — | — | 0 | 0 | 0 | 0 | 0 | — | — | 0 | 0 | 0 | 0 | 0 |

TABLE C-continued

Herbicide Primary Postemergence

| Compound | Yens | Abng | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|
| 10 | 0 | — | — | 0 | 0 | 0 | 0 | 0 | — | — | 0 | 0 | 0 | 0 | 0 |
| 11 | 0 | — | — | 0 | 0 | 0 | 0 | 0 | — | — | 0 | 0 | 0 | 0 | 0 |
| 12 | 0 | — | — | 0 | 1 | 0 | 0 | 0 | — | — | 0 | 0 | 0 | 0 | 0 |
| 13 | 0 | — | — | 0 | 0 | 0 | 0 | 0 | — | — | 0 | 2 | 0 | 0 | 0 |
| 14 | 0 | — | — | 0 | 2 | 0 | 0 | 0 | — | — | — | 1 | 0 | 0 | 0 |
| 15 | 0 | — | — | 0 | 0 | 0 | 0 | 1 | — | — | — | 1 | 0 | 0 | 0 |
| 16 | 0 | — | — | 0 | 0 | 0 | 1 | 1 | — | — | — | 1 | 0 | 0 | 0 |
| 17 | 0 | — | — | 0 | 0 | 1 | 0 | 0 | — | — | 0 | 0 | 0 | 0 | N |
| 18 | 0 | — | — | — | 0 | 1 | 1 | 0 | — | — | 0 | N | 0 | 2 | 1 |
| 19 | 0 | — | — | — | 0 | 0 | 0 | 0 | — | — | 0 | 1 | 0 | 0 | 0 |
| 20 | 0 | — | — | — | 1 | 0 | 0 | 0 | — | — | 0 | 0 | 0 | 0 | 0 |
| 21 | 0 | — | — | — | 0 | 0 | 0 | 0 | — | — | N | 0 | 0 | 0 | 0 |
| 22 | 0 | — | — | — | 0 | 0 | 0 | 0 | — | — | 0 | 1 | N | 0 | 0 |
| 23 | 0 | — | — | — | 0 | 0 | 0 | 0 | — | — | 0 | 1 | 0 | 0 | N |
| 24 | 0 | — | — | 0 | 0 | 0 | 0 | 0 | — | — | 0 | 1 | 0 | 0 | 0 |
| 25 | 0 | — | — | 0 | 1 | 0 | 0 | 0 | — | — | 0 | 0 | 0 | 0 | 0 |
| 26 | 0 | — | — | 0 | 0 | 1 | 0 | 0 | — | — | N | 0 | 0 | 0 | 0 |
| 27 | 0 | — | — | 0 | 0 | 1 | 0 | 0 | — | — | 0 | 0 | 0 | 0 | 0 |
| 28 | 0 | — | — | 0 | 0 | 0 | N | 0 | — | — | 0 | 0 | 0 | 0 | 0 |
| 29 | 0 | — | — | 0 | N | 1 | 1 | 0 | — | — | 0 | 1 | 1 | 0 | 0 |
| 30 | 0 | — | — | 0 | N | 3 | 3 | 1 | — | — | 3 | 3 | 2 | 0 | 0 |
| 31 | 0 | — | — | 0 | 0 | 0 | 0 | 0 | — | — | 1 | 0 | 0 | 0 | 0 |
| 32 | 0 | — | — | 0 | 0 | 0 | 0 | 0 | — | — | N | 0 | 0 | 0 | N |
| 33 | 0 | — | — | 0 | 0 | 0 | 0 | 0 | — | — | 0 | 0 | 0 | 0 | 0 |
| 34 | 0 | — | — | 0 | 1 | 0 | 0 | 0 | — | — | 0 | 0 | 0 | 0 | 0 |
| 35 | 0 | — | — | 0 | 0 | 0 | 0 | 0 | — | — | 0 | 0 | 0 | 0 | 0 |
| 36 | 0 | — | — | 0 | 0 | 0 | 0 | 0 | — | — | 0 | 1 | 0 | 0 | 0 |
| 37 | 0 | — | — | 0 | 0 | 0 | 0 | 0 | — | — | 0 | 0 | 0 | 0 | 0 |
| 38 | 0 | — | — | 0 | 0 | 0 | 0 | 0 | — | — | 0 | 0 | 0 | 0 | 0 |
| 39 | 0 | — | — | 0 | 0 | 0 | 0 | 0 | — | — | 0 | 1 | 0 | 0 | 0 |
| 40 | 0 | — | — | 0 | 0 | 0 | 0 | 0 | — | — | 0 | 0 | 0 | 0 | 0 |
| 41 | 0 | — | — | 0 | 0 | 0 | 0 | 0 | — | — | 0 | 2 | 0 | 0 | 0 |
| 42 | 0 | — | — | 0 | 1 | 0 | 0 | 0 | — | — | 0 | 0 | 0 | 0 | 0 |
| 43 | 0 | — | — | 0 | 1 | 1 | 1 | 0 | — | — | 0 | 2 | 2 | 0 | 0 |
| 44 | 0 | — | — | 0 | 0 | 0 | 0 | 0 | — | — | 0 | 0 | 0 | 0 | 0 |
| 45 | 0 | — | — | 0 | 1 | 0 | 0 | 0 | — | — | 0 | 0 | 0 | 0 | 0 |
| 46 | 0 | — | — | 0 | 0 | 0 | 0 | 0 | — | — | 0 | 0 | 0 | 0 | 0 |
| 47 | 0 | — | — | 0 | 0 | 0 | 0 | 1 | — | — | 0 | 1 | 0 | 0 | 0 |
| 48 | 0 | — | — | 0 | 0 | 0 | 0 | 0 | — | — | 0 | 0 | 0 | 0 | 0 |
| 49 | 0 | — | — | 0 | 0 | 0 | 0 | 0 | — | — | 0 | 0 | 0 | 0 | 0 |
| 50 | 0 | — | — | 0 | 2 | 0 | 1 | 0 | — | — | 0 | 1 | 1 | 0 | 0 |
| 51 | 0 | — | — | 0 | 1 | 1 | 1 | 0 | — | — | 0 | 0 | 0 | 0 | 0 |
| 52 | 0 | — | — | 0 | 1 | 1 | 0 | 0 | — | — | 0 | N | 0 | 0 | 0 |
| 53 | 0 | — | — | 0 | 0 | 0 | 0 | 0 | — | — | 0 | 0 | 0 | 0 | 0 |
| 54 | 0 | — | — | 0 | 0 | 0 | 0 | 0 | — | — | 0 | 0 | 0 | 0 | 0 |
| 55 | 0 | — | — | 0 | 0 | 0 | 0 | 0 | — | — | 0 | 0 | 0 | 0 | 0 |
| 56 | 0 | — | — | 0 | 0 | 0 | 0 | 0 | — | — | 0 | 0 | 0 | 0 | 0 |
| 57 | 0 | — | — | 0 | 0 | 0 | 0 | 0 | — | — | 0 | 0 | 0 | 0 | 0 |
| 58 | 0 | — | — | 0 | 0 | 0 | 0 | 0 | — | — | 0 | 0 | 0 | 0 | 0 |
| 59 | 0 | — | — | 0 | 0 | 0 | 0 | 0 | — | — | 0 | 0 | 0 | 0 | 0 |
| 60 | 0 | — | — | 0 | 0 | 0 | 0 | 0 | — | — | 0 | 0 | 0 | 0 | 0 |
| 61 | 0 | — | — | 0 | 0 | 0 | 0 | 0 | — | — | 0 | 1 | 0 | 0 | 0 |
| 62 | 0 | — | — | 0 | 0 | 0 | 0 | 0 | — | — | 0 | N | 0 | 0 | 0 |
| 63 | 0 | — | — | 0 | 0 | 0 | 0 | 0 | — | — | 0 | 0 | 0 | 0 | 0 |
| 64 | 0 | — | — | 0 | 0 | 0 | 0 | 0 | — | — | 0 | 0 | 0 | 0 | 0 |
| 65 | 0 | — | — | 0 | 0 | 0 | 0 | 0 | — | — | 0 | 0 | 0 | 0 | 0 |
| 66 | 0 | — | — | 0 | 0 | 0 | 0 | 0 | — | — | 0 | N | 0 | 0 | 0 |
| 67 | 0 | — | — | 0 | 0 | 0 | 0 | 0 | — | — | 0 | 0 | 0 | 0 | 0 |
| 68 | 0 | — | — | 0 | 0 | 0 | 0 | 0 | — | — | 0 | 0 | 0 | 0 | 0 |
| 69 | 0 | — | — | 0 | 0 | 0 | 0 | 0 | — | — | 0 | 3 | 0 | 0 | 0 |
| 70 | 0 | — | — | 0 | 0 | 0 | 0 | 0 | — | — | 0 | 0 | 0 | 0 | 0 |
| 71 | 0 | — | — | 0 | 0 | 0 | 0 | 0 | — | — | 0 | 0 | 0 | 0 | 0 |
| 72 | 0 | — | — | 0 | 1 | 0 | 1 | 0 | — | — | 0 | 0 | 0 | 0 | 0 |
| 73 | 0 | — | — | 0 | 0 | 0 | 0 | 0 | — | — | 0 | 0 | 0 | 0 | 0 |
| 74 | 0 | — | — | 0 | 1 | 0 | 1 | 1 | — | — | 0 | N | 0 | 0 | 0 |
| 75 | 0 | — | — | 0 | 2 | 2 | 1 | 2 | — | — | — | 2 | 1 | 0 | N |
| 76 | 0 | — | — | 0 | 2 | 0 | 1 | 0 | — | — | 0 | 1 | 0 | 0 | 0 |
| 77 | 0 | — | — | 0 | 3 | 2 | 0 | 1 | — | — | 0 | N | N | 0 | 0 |
| 78 | 0 | — | — | 0 | 0 | 1 | 1 | 2 | — | — | 0 | N | N | 0 | 0 |
| 79 | 0 | — | — | 0 | 0 | 0 | 0 | 0 | — | — | 0 | 1 | 0 | 0 | 0 |
| 80 | 0 | — | — | 0 | 1 | 2 | 0 | 1 | — | — | 0 | 0 | N | 0 | 0 |
| 81 | 0 | — | — | 0 | 1 | 1 | 2 | 2 | — | — | 0 | 2 | N | 0 | 0 |

TABLE C-continued

Herbicide Primary Postemergence

| Compound | Yens | Abg | Sjg | Dbr | Byg | Mogl | Cobu | Vele | Imnu | Wibw | Cath | Colq | Pesw | Rhqg | Rhjg |
|---|---|---|---|---|---|---|---|---|---|---|---|---|---|---|---|
| 82 | 0 | — | — | 0 | 0 | 1 | 1 | 1 | — | — | 0 | N | N | 0 | 0 |
| 83 | 0 | — | — | 0 | 0 | 0 | 1 | 1 | — | — | 2 | 0 | 0 | 0 | — |
| 84 | 0 | — | — | 0 | 0 | 0 | 0 | 0 | — | — | 0 | 0 | N | 0 | 0 |
| 85 | 0 | 0 | 0 | 0 | 0 | 0 | 0 | 1 | 1 | 0 | — | — | — | — | — |
| 86 | 0 | — | — | 0 | 1 | 0 | 0 | 0 | — | — | 0 | 1 | 0 | 0 | 0 |
| 87 | 0 | — | — | 0 | 0 | 0 | 0 | 0 | — | — | 0 | 0 | 0 | 0 | 0 |
| 88 | 0 | — | — | 0 | 0 | 0 | 0 | 0 | — | — | 0 | 0 | 0 | 0 | 0 |
| 89 | 0 | — | — | 0 | 0 | 1 | 0 | 0 | — | — | 0 | 3 | 0 | 0 | 0 |
| 90 | 0 | 0 | 1 | 0 | 0 | 0 | 0 | 0 | 1 | 0 | — | — | — | — | — |
| 91 | 0 | — | — | 0 | 0 | 1 | 0 | 0 | — | — | 0 | 3 | 0 | 0 | 0 |
| 92 | 0 | — | — | 0 | 1 | 2 | 0 | 1 | — | — | 0 | 3 | 0 | 0 | 0 |
| 93 | 0 | 0 | 2 | 0 | 2 | 2 | 1 | 2 | 2 | 2 | — | — | — | — | — |
| 94 | 0 | 2 | 1 | 0 | 2 | 2 | 2 | 2 | 2 | 2 | — | — | — | — | — |
| 95 | 0 | 0 | 0 | 0 | 0 | 0 | 0 | 0 | 0 | 0 | — | — | — | — | — |
| 96 | 0 | 0 | 0 | 0 | 0 | 1 | 0 | 0 | 2 | 1 | — | — | — | — | — |
| 97 | 0 | 0 | 2 | 0 | 2 | 2 | 1 | 2 | 2 | 2 | — | — | — | — | — |
| 98 | 0 | 0 | 3 | 0 | 2 | 1 | 1 | 2 | 3 | 2 | — | — | — | — | — |
| 99 | 0 | 0 | 2 | 0 | 1 | 2 | 0 | 2 | 1 | 2 | — | — | — | — | — |
| 100 | 0 | 0 | 0 | 0 | 0 | 0 | 0 | 1 | 0 | 0 | — | — | — | — | — |
| 101 | 0 | 0 | 2 | 0 | 0 | 0 | 0 | 0 | 2 | 1 | — | — | — | — | — |
| 102 | 0 | 0 | 2 | 0 | 2 | 2 | 2 | 2 | 2 | 2 | — | — | — | — | — |
| 103 | 0 | 0 | 2 | 0 | 2 | 2 | 2 | 2 | 2 | 2 | — | — | — | — | — |
| 104 | 0 | 0 | 1 | 0 | 2 | 2 | 2 | 2 | 1 | 2 | — | — | — | — | — |
| 105 | 0 | 0 | 0 | 0 | 0 | 0 | 0 | 0 | 0 | 1 | — | — | — | — | — |
| 106 | 0 | 0 | 2 | 0 | 0 | 0 | 0 | 0 | 0 | 1 | — | — | — | — | — |
| 107 | 0 | 0 | 0 | 0 | 0 | 0 | 1 | 2 | 0 | 2 | — | — | — | — | — |
| 108 | 0 | 0 | 0 | 0 | 0 | 0 | 0 | 0 | 0 | 0 | — | — | — | — | — |
| 109 | 0 | 0 | 2 | 0 | 2 | 2 | 2 | 2 | 2 | 2 | — | — | — | — | — |
| 110 | 0 | 0 | 2 | 0 | 2 | 2 | 2 | 2 | 2 | 2 | — | — | — | — | — |
| 111 | 0 | 0 | 2 | 0 | 2 | 2 | 2 | 2 | 2 | 2 | — | — | — | — | — |
| 112 | 0 | 0 | 1 | 0 | 0 | 0 | 0 | 1 | 2 | 2 | — | — | — | — | — |
| 113 | 0 | 1 | 3 | 0 | 0 | 0 | 0 | 0 | 1 | 2 | — | — | — | — | — |
| 114 | 0 | 0 | 2 | 0 | 2 | 2 | 0 | 2 | 1 | 2 | — | — | — | — | — |
| 115 | 0 | 0 | 0 | 0 | 0 | 1 | 1 | 1 | 1 | 0 | — | — | — | — | — |
| 116 | 0 | 0 | 2 | 0 | 2 | 1 | 0 | 1 | 2 | 0 | — | — | — | — | — |
| 117 | 0 | 0 | 0 | 0 | 0 | 0 | 0 | 2 | 2 | 1 | — | — | — | — | — |
| 118 | 0 | 0 | 0 | 0 | 1 | 0 | 0 | 0 | 1 | 1 | — | — | — | — | — |
| 119 | 0 | 0 | 1 | 0 | 2 | 0 | 1 | 1 | 2 | 2 | — | — | — | — | — |
| 120 | 0 | 0 | 2 | 0 | 2 | 1 | 1 | 0 | 1 | 2 | — | — | — | — | — |
| 121 | 0 | 0 | 2 | 1 | 2 | 2 | N | 1 | 0 | 2 | — | — | — | — | — |
| 122 | 0 | 0 | 0 | 0 | 0 | 0 | 0 | 0 | 0 | 0 | — | — | — | — | — |
| 123 | 0 | 0 | 0 | 0 | 0 | 0 | 0 | 0 | 0 | 0 | — | — | — | — | — |
| 124 | 0 | 0 | 0 | 0 | 0 | 0 | 0 | 0 | 0 | 0 | — | — | — | — | — |
| 125 | 0 | 0 | 1 | 0 | 1 | 0 | 0 | 0 | 0 | 0 | — | — | — | — | — |
| 126 | 0 | 0 | 0 | 0 | 0 | 0 | 0 | 0 | 0 | 0 | — | — | — | — | — |
| 127 | 0 | 0 | 0 | 0 | 0 | 0 | 0 | 0 | 0 | 0 | — | — | — | — | — |
| 128 | 0 | 0 | 0 | 0 | 0 | 1 | 0 | 0 | 0 | 0 | — | — | — | — | — |
| 129 | 0 | 0 | 2 | 0 | 2 | 0 | 2 | 1 | 2 | 2 | — | — | — | — | — |
| 130 | 0 | 1 | 0 | 0 | 2 | 1 | 1 | 0 | 2 | 1 | — | — | — | — | — |
| 131 | 0 | 0 | 0 | 0 | 0 | 0 | 0 | 0 | 0 | 0 | — | — | — | — | — |
| 132 | 0 | 0 | 0 | 0 | 0 | 0 | 0 | 0 | 0 | 0 | — | — | — | — | — |
| 133 | 0 | 0 | 0 | 0 | 0 | 0 | 0 | 0 | 0 | 0 | — | — | — | — | — |
| 134 | 0 | 0 | 0 | 0 | 0 | 1 | 0 | 0 | 0 | 0 | — | — | — | — | — |
| 135 | 0 | 0 | 0 | 0 | 0 | 0 | 0 | 0 | 0 | 0 | — | — | — | — | — |
| 136 | 0 | 0 | 0 | 0 | 0 | 0 | 0 | 0 | 0 | 0 | — | — | — | — | — |
| 137 | 0 | 1 | 2 | 0 | 2 | 1 | 2 | 1 | 0 | 2 | — | — | — | — | — |
| 138 | 0 | 0 | 0 | 0 | 0 | 1 | 1 | 2 | 2 | 2 | — | — | — | — | — |
| 139 | 0 | 0 | 1 | 0 | 0 | 2 | 0 | 1 | 2 | 2 | — | — | — | — | — |
| 140 | 0 | 0 | 2 | 0 | 1 | 2 | 2 | 2 | 2 | 2 | — | — | — | — | — |
| 141 | 0 | 0 | 2 | 0 | 0 | 1 | 1 | 2 | 2 | 2 | — | — | — | — | - |

Compounds of this invention were also tested for herbicidal activity on weed plants in the presence of crop plants according to the following procedure:

Topsoil (silt loam) is sieved through a screen having 1.27 cm openings. In some of the tests the soil was mixed with fertilizer (1225 g/cu. m of 12/5/9 containing isobutylidene diurea), while in other tests the fertilizer was omitted. This mixture is steam sterilized and then placed in aluminum pans 6.985 cm deep having ten holes in the bottom each 0.635 cm in diameter. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with 1.27 cm of a mixture of 50% topsoil and 50% of a mixture of Canadian sphagnum peat moss, vermiculite and a wetting agent. The pans are then placed on a capillary mat on a greenhouse bench and subirrigated as needed. After the plants reach the desired stage (9 to 14 days, 1 to 3 true leaf stage), each pan (except the control pans) is removed to a spraying chamber and sprayed by means of an atomizer, operating at a spray pressure of 170.3 kPa (10 psig) at the application rates noted in Table D. In the spray solution is an amount of an emulsifying agent mixture (35% butylamine salt of dodecylbenzenesulfonic acid and 65% tall oil condensed with ethylene oxide in the ratio of 11 mols of ethylene oxide/mol of tall oil) to give a spray solution or suspension. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered as before and the injury to the plants as compared to the control pans is observed at approximately 10–14 days (usually 11 days).

In the following Table D the legends used to identify the plant species are the same as those used in the preceding Table B.

TABLE D

| Compound | Rate kg/ha | Soybe | Cotz | Rape | Cbuw | Wibw | Mogsl | Hewee | Jiwee | Vhecz | Whcse | Rron | Gobn | Cbmr | Dogri | Pbyct | Bargt | Lrufte | Guobleq | Sceslw | Poesw | Coccw |
|---|---|---|---|---|---|---|---|---|---|---|---|---|---|---|---|---|---|---|---|---|---|---|
| 2 | 5.3808 | 3 | 3 | 3 | 4 | 3 | 2 | 4 | 4 | 4 | 0 | 1 | 2 | 2 | 0 | 3 | 3 | 3 | — | — | — | — |
|  | 5.3808 | 3 | 2 | 2 | 4 | 2 | 1 | 3 | 3 | 2 | 0 | 0 | 1 | 2 | 0 | 3 | 2 | 3 | 2 | — | — | — | — |
|  | 1.1210 | 1 | 2 | 0 | 0 | 2 | 1 | 2 | 2 | 2 | 0 | 0 | 0 | 2 | 0 | 2 | 1 | 3 | 2 | — | — | — | — |
|  | 1.1210 | 1 | 1 | 1 | 0 | 2 | 1 | 2 | 2 | 2 | 0 | 0 | 0 | 2 | 0 | 2 | 1 | 3 | 1 | — | — | — | — |
|  | 0.2803 | 2 | 1 | 1 | 0 | 1 | 2 | 2 | 2 | 2 | 0 | 0 | 0 | 0 | 0 | 0 | 0 | 3 | 0 | — | — | — | — |
|  | 0.2803 | 2 | 2 | 2 | 0 | 1 | 1 | 2 | 1 | 2 | 0 | 0 | 0 | 0 | 0 | 0 | 0 | 3 | 0 | — | — | — | — |
|  | 0.0701 | 0 | 0 | 1 | 0 | 0 | 1 | 1 | 0 | 1 | 0 | 0 | 0 | 0 | 0 | 0 | 0 | 3 | 0 | — | — | — | — |
|  | 0.0701 | 1 | 0 | 1 | 0 | 0 | 2 | 1 | 0 | 1 | 0 | 0 | 0 | 0 | 0 | 0 | 0 | 3 | 0 | — | — | — | — |
| 30 | 11.2100 | 1 | — | — | 2 | 2 | 2 | 1 | — | 1 | 0 | 0 | 1 | 2 | 0 | 0 | 1 | 1 | 1 | 1 | 2 | 1 | — |
|  | 8.4075 | 1 | — | — | 2 | 1 | 1 | 2 | — | 2 | 0 | 0 | 1 | 1 | 0 | 0 | 1 | 1 | 1 | 1 | 1 | 1 | — |
|  | 5.6050 | 1 | — | — | 1 | 1 | 1 | 1 | — | 1 | 0 | 0 | 1 | 1 | 0 | 0 | 1 | 2 | 2 | 1 | 1 | 1 | — |
|  | 2.8025 | 1 | — | — | 1 | 1 | 1 | 1 | — | 1 | 0 | 0 | 1 | 2 | 0 | 1 | 2 | 2 | 2 | 1 | 1 | 1 | — |
|  | 1.1210 | 1 | — | — | 0 | 1 | 1 | 1 | — | 1 | 0 | 0 | 0 | 1 | 0 | 0 | 0 | 0 | 1 | 0 | 0 | — |
|  | 0.5605 | 0 | — | — | 0 | 1 | 1 | 1 | — | 1 | 0 | 0 | 0 | 1 | 0 | 0 | 0 | 1 | 1 | 0 | 0 | 0 | — |
| 50 | 5.3808 | 3 | 3 | 3 | 3 | 3 | 3 | 3 | 3 | 3 | 0 | 0 | 1 | 2 | 0 | 2 | 2 | 3 | 2 | — | — | — | — |
|  | 5.3808 | 3 | 3 | 3 | 3 | 3 | 3 | 3 | 3 | 3 | 0 | 0 | 2 | 1 | 0 | 1 | 3 | 3 | 2 | — | — | — | — |
|  | 1.1210 | 2 | 2 | 3 | 2 | 2 | 2 | 2 | 2 | 2 | 0 | 1 | 0 | 2 | 0 | 1 | 1 | 3 | 1 | — | — | — | — |
|  | 1.1210 | 2 | 3 | 3 | 2 | 3 | 2 | 3 | 3 | 3 | 0 | 1 | 0 | 1 | 0 | 2 | 1 | 3 | 1 | — | — | — | — |
|  | 0.2803 | 1 | 2 | 2 | 1 | 3 | 2 | 2 | 2 | 2 | 0 | 0 | 0 | 0 | 0 | 1 | 0 | 3 | 1 | — | — | — | — |
|  | 0.2803 | 1 | 2 | 3 | 1 | 3 | 2 | 3 | 2 | 3 | 0 | 0 | 0 | 0 | 1 | 1 | 0 | 3 | 1 | — | — | — | — |
|  | 0.0701 | 0 | 1 | 1 | 0 | 1 | 1 | 2 | 2 | 2 | 0 | 0 | 0 | 0 | 0 | 0 | 0 | 3 | 0 | — | — | — | — |
|  | 0.0701 | 0 | 1 | 2 | 0 | 1 | 1 | 2 | 2 | 2 | 0 | 0 | 0 | 0 | 0 | 0 | 0 | 2 | 0 | — | — | — | — |
| 77 | 11.2100 | 2 | — | — | 3 | 3 | 3 | 1 | — | 2 | 1 | 0 | 1 | 3 | 0 | 1 | 3 | 3 | 2 | 2 | 2 | 2 | — |
|  | 11.2100 | 3 | — | — | 3 | 2 | 3 | 3 | — | 3 | 0 | 0 | 1 | 3 | 0 | 2 | 3 | 3 | 3 | 2 | 3 | 1 | — |
|  | 5.6050 | 2 | — | — | 2 | 2 | 2 | 0 | — | 2 | 0 | 0 | 1 | 2 | 0 | 0 | 2 | 3 | 1 | 2 | 2 | 0 | — |
|  | 5.6050 | 3 | — | — | 0 | 3 | 2 | 3 | — | 3 | 0 | 0 | 0 | 2 | 1 | 0 | 2 | 3 | 2 | 1 | 3 | 0 | — |
|  | 2.8025 | 1 | — | — | 1 | 2 | 2 | 3 | — | 3 | 0 | 0 | 1 | 2 | 0 | 0 | 1 | 3 | 1 | 2 | 3 | 0 | — |
|  | 2.8025 | 1 | — | — | 1 | 1 | 2 | 1 | — | 2 | 0 | 0 | 1 | 2 | 0 | 0 | 2 | 3 | 1 | 2 | 2 | 0 | — |
|  | 1.1210 | 1 | — | — | 1 | 0 | 1 | 2 | — | 3 | 0 | 0 | 0 | 0 | 0 | 0 | 0 | 2 | 0 | 1 | 3 | 0 | — |
|  | 1.1210 | 1 | — | — | 0 | 1 | 1 | 0 | — | 1 | 0 | 0 | 1 | 1 | 0 | 0 | 0 | 2 | 0 | 1 | 2 | 0 | — |
| 93 | 5.6050 | 3 | 2 | 3 | 3 | 0 | 3 | 3 | 3 | 3 | 0 | 0 | 2 | 3 | 0 | 0 | 2 | 3 | 1 | — | — | — | — |
|  | 1.1210 | 2 | 0 | 3 | 2 | 0 | 2 | 3 | 3 | 2 | 0 | 0 | 0 | 3 | 0 | 0 | 0 | 3 | 0 | — | — | — | — |
|  | 0.2803 | 1 | 0 | 2 | 0 | 0 | 2 | 3 | 2 | 0 | 0 | 0 | 0 | 3 | 0 | 0 | 0 | 2 | 0 | — | — | — | — |
|  | 0.0701 | 0 | 0 | 0 | 0 | 0 | 0 | 1 | 2 | 0 | 0 | 0 | 0 | 0 | 0 | 0 | 0 | N | 0 | — | — | — | — |
| 97 | 5.6050 | 0 | 0 | 0 | 0 | 0 | 0 | 0 | 1 | 0 | 0 | 0 | 0 | 0 | 0 | 0 | 0 | 0 | 0 | — | — | — | — |
|  | 1.1210 | 0 | 0 | 0 | 0 | 0 | 0 | 0 | 0 | 0 | 0 | 0 | 0 | 0 | 0 | 0 | 0 | 2 | 0 | — | — | — | — |
|  | 0.2803 | 0 | 0 | 0 | 0 | 0 | 0 | 0 | 0 | 0 | 0 | 0 | 0 | 0 | 0 | 0 | 0 | 0 | 0 | — | — | — | — |
|  | 0.0701 | 0 | 0 | 0 | 0 | 0 | 0 | 0 | 0 | 0 | 0 | 0 | 0 | 0 | 0 | 0 | 0 | 0 | 0 | — | — | — | — |
| 98 | 5.6050 | 2 | 2 | 3 | 2 | 3 | 2 | 3 | 3 | 3 | 0 | 0 | 1 | 2 | 0 | 2 | 0 | 3 | 1 | — | — | — | — |
|  | 1.1210 | 0 | 1 | 1 | 1 | 1 | 1 | 2 | 3 | 2 | 0 | 0 | 0 | 0 | N | 0 | 3 | 0 | — | — | — | — |
|  | 0.2803 | 0 | 0 | 0 | 1 | 0 | 0 | 2 | 2 | 2 | 0 | 0 | 0 | 0 | 1 | 0 | 2 | 0 | — | — | — | — |
|  | 0.0701 | 0 | 0 | 0 | 0 | 0 | 0 | 1 | 2 | 1 | 0 | 0 | 0 | 0 | 0 | 0 | 0 | 0 | — | — | — | — |
| 103 | 5.6050 | 2 | 0 | 3 | 0 | 2 | 2 | 3 | 2 | 2 | 0 | 0 | 2 | 3 | 0 | 0 | 0 | 2 | 0 | — | — | — | — |
|  | 1.1219 | 0 | 0 | 1 | 0 | 1 | 1 | 1 | 2 | 0 | 0 | 0 | 0 | 3 | 0 | 0 | 0 | 0 | 0 | — | — | — | — |
|  | 0.2803 | 0 | 0 | 0 | 0 | 0 | 1 | 0 | 0 | 0 | 0 | 0 | 0 | 0 | 0 | 0 | 0 | 0 | 0 | — | — | — | — |
|  | 0.0701 | 0 | 0 | 0 | 0 | 0 | 0 | 0 | 0 | 0 | 0 | 0 | 0 | 0 | 0 | 0 | 0 | 0 | 0 | — | — | — | — |
| 113 | 5.6050 | 1 | 0 | 1 | 0 | 1 | 1 | 1 | — | 1 | 0 | 0 | 0 | 0 | 0 | 0 | 0 | 2 | 0 | — | — | — | 0 |
|  | 1.1210 | 0 | 0 | 0 | 0 | 0 | 0 | 0 | — | 0 | 0 | 0 | 0 | 0 | 0 | 0 | 0 | 0 | 0 | — | — | — | N |
|  | 0.2803 | 0 | 0 | 0 | 0 | 0 | 0 | 0 | — | 0 | 0 | 0 | 0 | 0 | 0 | 0 | 0 | 0 | 0 | — | — | — | 0 |
| 116 | 5.6050 | 2 | 1 | 3 | 2 | 2 | 2 | 2 | — | 2 | 0 | 0 | 1 | 2 | 0 | 0 | 1 | 2 | 1 | — | — | — | 2 |
|  | 1.1210 | 2 | 1 | 3 | 2 | 2 | 2 | 2 | — | 3 | 0 | 0 | 0 | 2 | 0 | 0 | 0 | 2 | 0 | — | — | — | 2 |
|  | 0.2803 | 1 | 0 | 2 | 1 | 1 | 1 | 1 | — | 2 | 0 | 0 | 0 | 0 | 0 | 0 | 0 | 2 | 0 | — | — | — | 1 |
|  | 0.0701 | 1 | 0 | 1 | 0 | 1 | 2 | 1 | — | 1 | 0 | 0 | N | 0 | 0 | 0 | 0 | 2 | 0 | — | — | — | 0 |
| 137 | 5.6050 | 2 | 2 | 3 | 3 | 2 | 2 | 3 | — | 2 | 0 | 1 | 2 | 1 | 1 | 1 | 2 | 3 | 2 | — | — | — | 3 |
|  | 1.1210 | 2 | 2 | 3 | 1 | 3 | 1 | 3 | — | 3 | 0 | 1 | 0 | 0 | 1 | 0 | 2 | 3 | 2 | — | — | — | 3 |
|  | 0.2803 | 0 | 1 | 3 | 0 | 0 | 1 | 1 | — | 3 | 0 | 0 | 0 | 0 | 0 | 0 | 1 | 3 | 2 | — | — | — | 2 |
| 140 | 5.6050 | 2 | 1 | 3 | 3 | 1 | 2 | 3 | — | 3 | 0 | 0 | 2 | 0 | 0 | 0 | 3 | 0 | — | — | — | 3 |
|  | 1.1210 | 2 | 1 | 3 | 3 | 31 | 2 | 3 | — | 2 | 0 | 0 | 1 | 0 | 0 | 0 | 2 | 0 | — | — | — | 2 |
|  | 0.2803 | 1 | 1 | 3 | 1 | 0 | 2 | 3 | — | 3 | 0 | 0 | 0 | 2 | 0 | 0 | 2 | 0 | — | — | — | 2 |

5,877,119

TABLE D-continued

| Compound | Rate kg/ha | S o b e | C o t z | R a p e | C o b u | W i b w | M o g l | H e s e | J i w e | V l e e | W h e c | R i z e | G r o n | C o b n r | D o m r i | P r g i r | B y c g t | L a f g t | G r t e | S r b l e | C u s q w | P e s w | C c w |
|---|---|---|---|---|---|---|---|---|---|---|---|---|---|---|---|---|---|---|---|---|---|---|---|
| 151 | 5.6050 | 2 | 1 | 3 | 2 | 1 | 2 | 1 | — | 2 | 0 | 0 | 0 | 2 | 0 | 0 | 0 | 0 | 0 | — | — | — | 1 |
|  | 1.1210 | 1 | 1 | 3 | 2 | 0 | 1 | 2 | — | 2 | 0 | 0 | 0 | 0 | 0 | 0 | 0 | 0 | 0 | — | — | — | 0 |
|  | 0.2803 | 0 | 1 | 2 | 1 | 0 | 1 | 1 | — | 1 | 0 | 0 | 0 | 0 | 0 | 0 | 0 | 0 | 0 | — | — | — | 0 |

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or antifoaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include N,-N-dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particules such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclic Nitrogen/Sulfur Derivatives

2-Chloro-4-ethylamino-6-isopropylamino-s-triazine
2-Chloro-4,6-bis(isopropylamino)-s-triazine 2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-d:α',1'-c)-pyrazidiinium salt
5-Bromo-3-isopropyl-6-methyluracil 1,1'-dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

Ureas

N-(4-chlorophenoxy)phenyl-N,N-dimethylurea
N,N-dimethyl-N'-(3-chloro-4-methylphenyl)urea
3-(3,4-Dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)carbonyl) amino)sulfonyl)benzoate
Ethyl 2-[methyl 2-(((((4,6-dimethyl-2-pyrimidinyl)amino) carbonyl)amino)sulfonyl)]benzoate
Methyl-2((4,6-dimethoxy pyrimidin-2-yl)aminocarbonyl) amino sulfonyl methyl)benzoate
Methyl 2-(((((4-methoxy-6-methyl-1,3,5-triazin-2-yl) amino)carbonyl)amino)sulfonyl)benzoate

Carbamates/Thiolcarbamates

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[(trifluoromethyl)sulfonyl]amino] phenyl]acetamide N-Isopropyl-2-chloroacetanilide
2',6'-Diethyl-N-methoxymethyl-2-chloroacetanilide
2'-Methyl-6'-ethyl-N-(2-methoxypropyl-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts.
Butyl 2-[4-[(5-(trifluoromethyl)-2-pyridinyl)oxy]-phenoxy]-propanoate

Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methyl sulfonyl 2-nitrobenzamide
1'-(Carboethoxy)ethyl 5-[2-chloro-4-(trifluoromethyl) phenoxy]-2-nitrobenzoate

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo(2.2.1)heptane, 1-methyl-4-(1-methyl ethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | | Weight Percent |
|---|---|---|
| I. Emulsifiable Concentrates | | |
| A. | Compound of Example No. 2 | 11.0 |
| | Free acid of complex organic phosphate or aromatic or aliphatic hydrophobe base (e.g., GAFAC RE-610 registered trademark of GAF Corp.) | 5.59 |
| | Polyoxyethylene/polyoxypropylene block copolymer with butanol (e.g., Tergitol XH registered trademark of Union Carbide Corp.) | 1.11 |
| | Phenol | 5.34 |
| | Monochlorobenzene | 76.96 |
| | | 100.00 |
| B. | Compound of Example No. 13 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |
| II. Flowables | | |
| A. | Compound of Example No. 23 | 25.00 |
| | Methyl cellulose | 0.3 |
| | Silica Aerogel | 1.5 |
| | Sodium lignosulfonate | 3.5 |
| | Sodium N-methyl-N-oleyl taurate | 2.0 |
| | Water | 67.7 |
| | | 100.00 |
| B. | Compound of Example No. 17 | 45.0 |
| | Methyl cellulose | .3 |
| | Silica aerogel | 1.5 |
| | Sodium lignosulfonate | 3.5 |
| | Sodium N-methyl-N-oleyl taurate | 2.0 |
| | Water | 47.7 |
| | | 100.00 |

| | | Weight Percent |
|---|---|---|
| III. Wettable Powders | | |
| A. | Compound of Example No. 4 | 25.0 |
| | Sodium lignosulfonate | 3.0 |
| | Sodium N-methyl-N-oleyl-taurate | 1.0 |
| | Amorphous silica (synthetic) | 71.0 |
| | | 100.00 |
| B. | Compound of Example 20 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 5 | 10.0 |
| | Sodium lignosulfonate | 3.0 |
| | Sodium N-methyl-N-oleyl-taurate | 1.0 |
| | Kaolinite clay | 86.0 |
| | | 100.00 |
| IV. Dusts | | |
| A. | Compound of Example No. 12 | 2.0 |
| | Attapulgite | 98.0 |
| | | 100.00 |
| B. | Compound of Example No. 9 | 60.0 |
| | Montmorillonite | 40.0 |
| | | 100.00 |
| C. | Compound of Example No. 53 | 30.0 |
| | Ethylene glycol | 1.0 |
| | Bentonite | 69.0 |
| | | 100.00 |
| D. | Compound of Example No. 61 | 1.0 |
| | Diatomaceous earth | 99.0 |
| | | 100.00 |
| V. Granules | | |
| A. | Compound of Example No. 51 | 15.0 |
| | Granular attapulgite (20/40 mesh) | 85.0 |
| | | 100.00 |
| B. | Compound of Example No. 69 | 30.0 |
| | Diatomaceous earth (20/40) | 70.0 |
| | | 100.00 |
| C. | Compound of Example No. 57 | 1.0 |
| | Ethylene glycol | 5.0 |
| | Methylene blue | 0.1 |
| | Pyrophyllite | 93.9 |
| | | 100.00 |
| D. | Compound of Example No. 45 | 5.0 |
| | Pyrophyllite (20/40) | 95.0 |
| | | 100.00 |

When operating in accordance with the present invention, effective amounts of the compounds of this invention are applied to the soil containing the seeds, or vegetative propagules or may be incorporated into soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective pre-emergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or medium in which vegetation may take root and grow, and includes not only earth but also compost, manure, muck, humus, sand, and the like, adapted to support plant growth.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skills in the art to which the invention pertains.

What is claimed is:

1. A compound represented by the formula

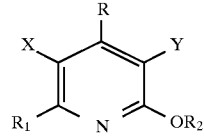

wherein:

$R_1$ is fluorinated methyl, chlorofluorinated methyl or fluorinated ethyl;

$R_2$ is hydrogen, C1–C7 alkyl, trichloromethyl, C2–C8 cyanoalkyl, C3–C7 alkenyl, or C3–C7 alkynyl;

R is C1–C6 straight or branched alkyl, C1–C7 haloalkyl, C2–C14 alkylthioalkyl, C2–C14 alkoxyalkyl, C2–C8 carboxyalkyl, C3–C4 cycloalkyl, or cyclopropylmethyl; and X and Y are independently selected from

where $Z_1$ is oxygen or $NR_3$ where $R_3$ is lower alkyl and where Z is selected from 1-pyrazolyl; 1-imidazolyl; 1,2,4-triazolyl; 1-pyrrolidinyl; 1-piperidinyl; 1-azetidinyl; 4-morpholinyl; 4-thiomorpholinyl; 3-thiazolidinyl; 1-aziridinyl; hexahydro-1-azepinyl; and 2-isoxazolidinyl.

2. A compound according to claim 1 wherein $R_1$ is $CF_3$ and $R_2$ is $CH_3$.

3. A compound according to claim 2 wherein R is $C_1$–$C_4$ straight or branched chain alkyl.

4. A compound according to claim 2 wherein R is selected from cyclobutyl and cyclopropylmethyl.

5. An herbicidal composition comprising an adjuvant and an effective amount of a compound represented by the formula

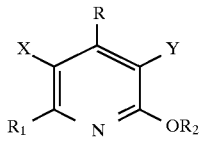

wherein:
R₁ is fluorinated methyl, chlorofluorinated methyl or fluorinated ethyl;
R₂ is hydrogen, C1–C7 alkyl, trichloromethyl, C2–C8 cyanoalkyl, C3–C7 alkenyl, or C3–C7 alkynyl;
R is C1–C6 straight or branched alkyl, C1–C7 haloalkyl, C2–C14 alkylthioalkyl, C2–C14 alkoxyalkyl, C2–C8 carboxyalkyl, C3–C4 cycloalkyl, or cyclopropylmethyl; and
X and Y are independently selected from

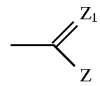

where $Z_1$ is oxygen or $NR_3$ where $R_3$ is lower alkyl and where Z is selected from 1-pyrazolyl; 1-imidazolyl; 1,2,4-triazolyl; 1-pyrrolidinyl; 1-piperidinyl; 1-azetidinyl; 4-morpholinyl; 4-thiomorpholinyl; 3-thiazolidinyl; 1-aziridinyl; hexahydro-1-azepinyl; and 2-isoxazolidinyl.

6. A composition according to claim 5 wherein $R_1$ is $CF_3$ and $R_2$ is $CH_3$.

7. A composition according to claim 6 wherein R is $C_1$–$C_4$ straight or branched chain alkyl.

8. A composition according to claim 6 wherein R is selected from cyclobutyl and cyclopropylmethyl.

9. A method of controlling undesirable vegetation comprising applying to the soil an effective herbicidal amount of a compound represented by the formula

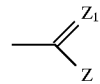

wherein:
R₁ is fluorinated methyl, chlorofluorinated methyl or fluorinated ethyl;
R₂ is hydrogen, C1–C7 alkyl, trichloromethyl, C2–C8 cyanoalkyl, C3–C7 alkenyl, or C3–C7 alkynyl;
R is C1–C6 straight or branched alkyl, C1–C7 haloalkyl, C2–C14 alkylthioalkyl, C2–C14 alkoxyalkyl, C2–C8 carboxyalkyl, C3–C4 cycloalkyl, or cyclopropylmethyl; and
X and Y are independently selected from where $Z_1$ is oxygen or $NR_3$ where $R_3$ is lower alkyl and where Z is selected from 1-pyrazolyl; 1-imidazolyl; 1,2,4-triazolyl; 1-pyrrolidinyl; 1-piperidinyl; 1-azetidinyl; 4-morpholinyl; 4-thiomorpholinyl; 3-thiazolidinyl; 1-aziridinyl; hexahydro-1-azepinyl; and 2-isoxazolidinyl.

10. A method according to claim 9 wherein $R_1$ is $CF_3$ and $R_2$ is $CH_3$.

11. A method according to claim 10 wherein R is $C_1$–$C_4$ straight or branched chain alkyl.

12. A method according to claim 10 wherein R is elected from cyclobutyl and cyclopropylmethyl.

* * * * *